US011230582B2

(12) United States Patent
Sommerfeld et al.

(10) Patent No.: US 11,230,582 B2
(45) Date of Patent: Jan. 25, 2022

(54) FGF21 VARIANTS

(71) Applicant: SANOFI, Paris (FR)

(72) Inventors: Mark Sommerfeld, Frankfurt (DE);
Thomas Langer, Frankfurt (DE);
Oliver Boscheinen, Frankfurt (DE);
Matthias Dreyer, Frankfurt (DE);
Werner Dittrich, Frankfurt (DE); Paul Habermann, Frankfurt (DE)

(73) Assignee: SANOFI, Paris (FR)

( * ) Notice: Subject to any disclaimer, the term of this patent is extended or adjusted under 35 U.S.C. 154(b) by 517 days.

(21) Appl. No.: 15/776,726

(22) PCT Filed: Dec. 2, 2016

(86) PCT No.: PCT/EP2016/079551
§ 371 (c)(1),
(2) Date: May 16, 2018

(87) PCT Pub. No.: WO2017/093465
PCT Pub. Date: Jun. 8, 2017

(65) Prior Publication Data
US 2018/0371041 A1 Dec. 27, 2018

(30) Foreign Application Priority Data

Dec. 2, 2015 (EP) .................................... 15306913

(51) Int. Cl.
| *A61K 38/18* | (2006.01) |
| *C07K 14/50* | (2006.01) |
| *A61K 47/60* | (2017.01) |
| *A61K 45/06* | (2006.01) |
| *C07K 14/78* | (2006.01) |
| *A61K 38/00* | (2006.01) |
| *A61K 47/61* | (2017.01) |
| *C07K 14/765* | (2006.01) |

(52) U.S. Cl.
CPC .......... *C07K 14/50* (2013.01); *A61K 38/1825* (2013.01); *A61K 45/06* (2013.01); *A61K 47/60* (2017.08); *C07K 14/78* (2013.01); *A61K 38/00* (2013.01); *A61K 47/61* (2017.08); *C07K 14/765* (2013.01); *C07K 2319/20* (2013.01); *C07K 2319/21* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| 7,459,540 B1 | 12/2008 | Thomason et al. |
| 7,491,697 B2 | 2/2009 | Beals et al. |
| 7,582,607 B2 | 9/2009 | Frye et al. |
| 8,034,770 B2 * | 10/2011 | Belouski ................... A61P 3/00 514/9.1 |
| 9,006,400 B2 * | 4/2015 | Boettcher ................. A61P 3/08 530/399 |
| 2009/0018076 A1 | 1/2009 | Thomason et al. |
| 2010/0226921 A1 | 9/2010 | Thomason et al. |
| 2013/0079500 A1 | 3/2013 | Boettcher et al. |
| 2015/0166622 A1 | 6/2015 | Boettcher et al. |

FOREIGN PATENT DOCUMENTS

| JP | 2011-523561 A | 8/2011 |
| JP | 2013-533227 A | 8/2013 |
| JP | 2014-530220 A | 11/2014 |
| WO | WO 2008/121563 A2 | 10/2008 |
| WO | WO 2008/121563 A3 | 10/2008 |
| WO | 2009/149171 A2 | 12/2009 |
| WO | 2010/042747 A2 | 4/2010 |
| WO | 2010/129503 A2 | 11/2010 |
| WO | 2010/129600 A2 | 11/2010 |
| WO | 2013/188182 A1 | 12/2013 |

OTHER PUBLICATIONS

International Preliminary Report on Patentability of PCT/EP2016/079551 dated Jun. 14, 2018, 20 pp.
Database Geneseq [Online] Aug. 13, 2015 (Aug. 13, 2015), "Human mutant FGF21 protein (Q55C/N149C)." XP55340105, retrieved from EBI accession No. GSP:BCB15029, Database accession No. BCB15029. The Written Opinion of the International Searching Authority for PCT/EP2016/079551, dated Jun. 14, 2018; however, the sequence is not obtainable publicly under the above accession numbers.
European Search Report for European Patent Application No. 20150761.3, dated May 15, 2020, 5 pages.
Adams et al., "LY2405319, an Engineered FGF21 Variant, Improves the Metabolic Status of Diabetic Monkeys", PLoS One, 2013, 8(6): e65763.
Lu et al., "Study on the Correlation of Serum FGF21 with Insulin Resistance and Pancreatic Islet Cell Function in Patients with Gestational Diabetes", Acta Universitatis Medicinalis Anhui, 2013, 48(12): 1495-1498.

\* cited by examiner

Primary Examiner — Christine J Saoud
(74) Attorney, Agent, or Firm — Lathrop GPM LLP; James H. Velema, Esq.

(57) ABSTRACT

The present invention relates to polypeptide variants of human fibroblast growth factor 21 (FGF21) and fusion molecules thereof, as well as to nucleic acid molecules encoding the same. It further relates to their use as medicaments, in particular for the treatment of obesity, overweight, metabolic syndrome, diabetes mellitus, hyperglycemia, dyslipidemia, non-alcoholic steatohepatitis (NASH) and/or atherosclerosis.

6 Claims, 30 Drawing Sheets
Specification includes a Sequence Listing.

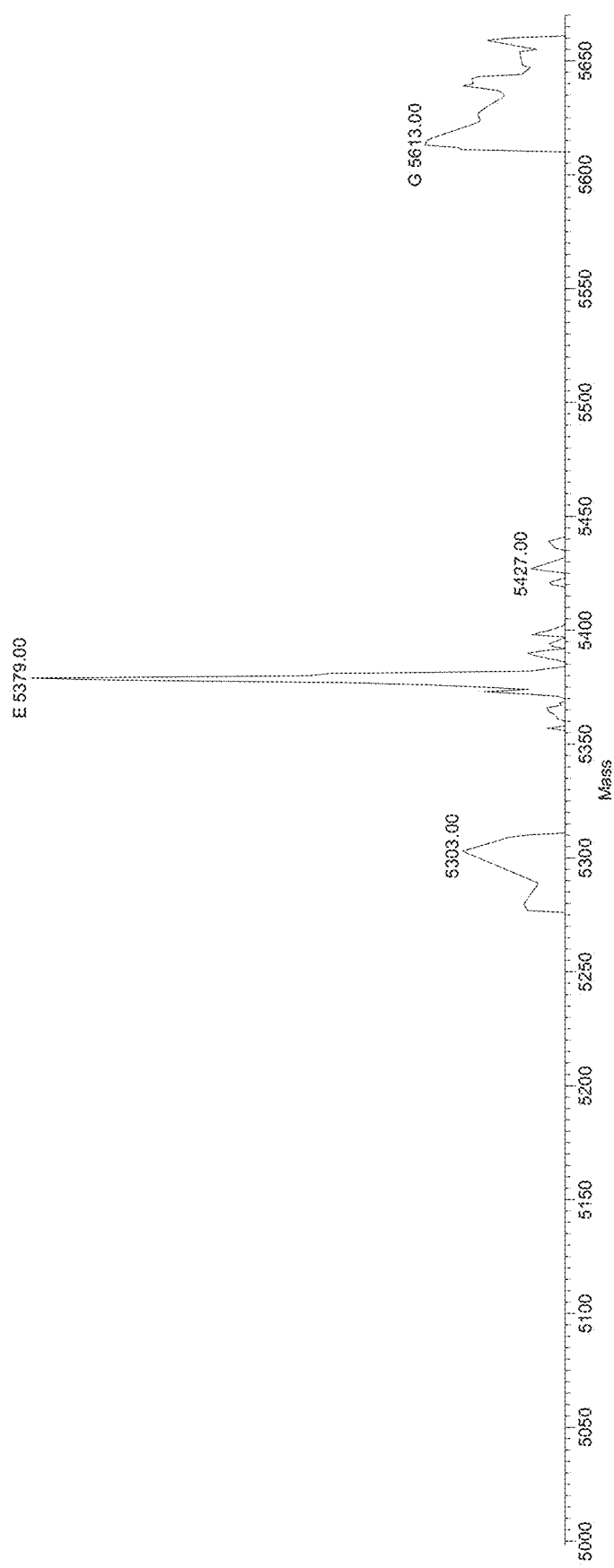

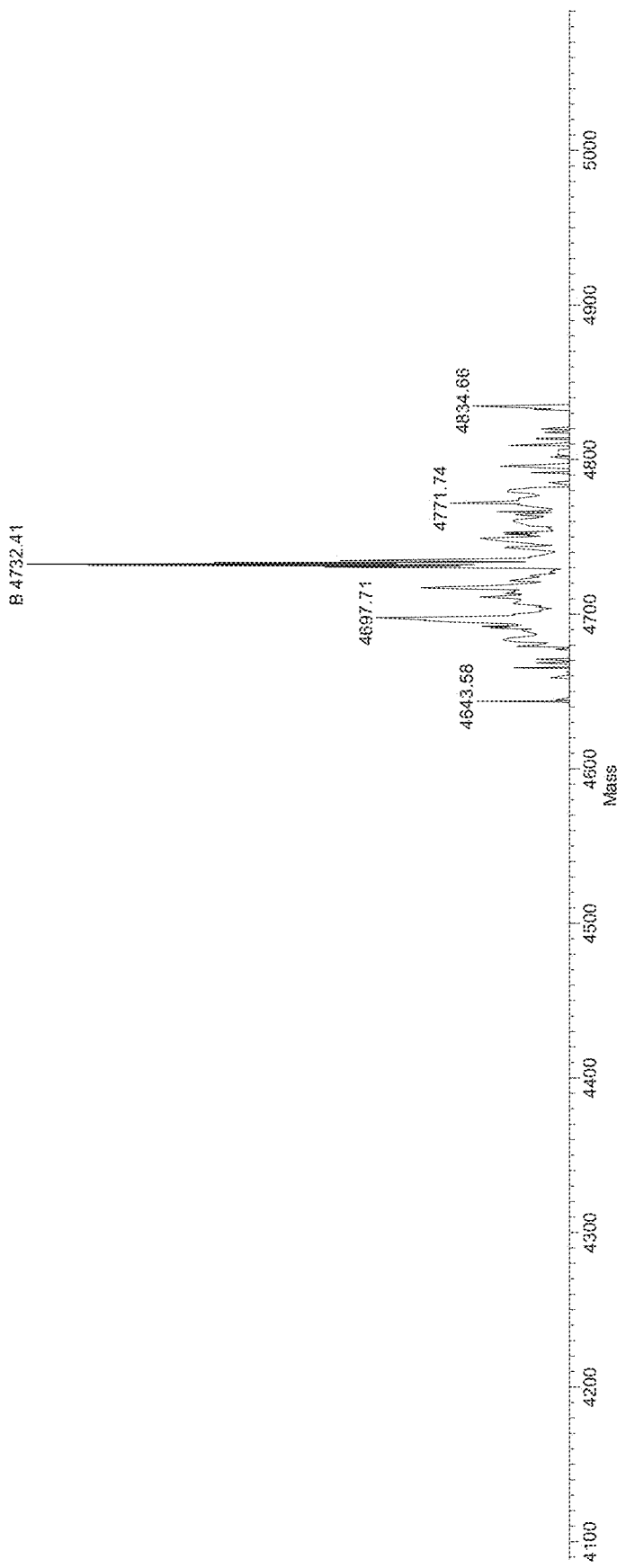

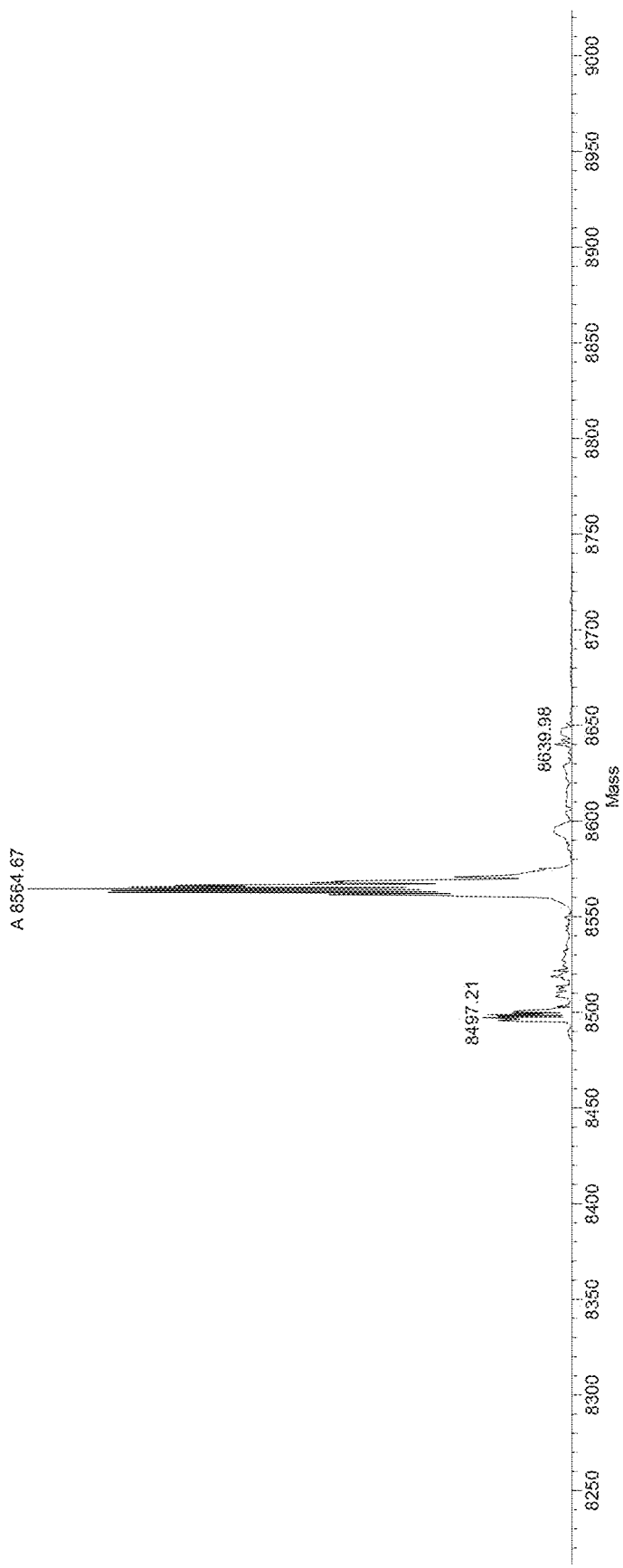

Figure 6B                    Figure 6C

SEQUENCE LISTING

<160> NUMBER OF SEQ ID NOS: 328

<210> SEQ ID NO 1
<211> LENGTH: 209
<212> TYPE: PRT
<213> ORGANISM: Homo sapiens

<400> SEQUENCE: 1

```
Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175
```

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
            195                 200                 205

Ser

<210> SEQ ID NO 2
<211> LENGTH: 181
<212> TYPE: PRT
<213> ORGANISM: Homo sapiens

<400> SEQUENCE: 2

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 3
<211> LENGTH: 182
<212> TYPE: PRT
<213> ORGANISM: Artificial Sequence
<220> FEATURE:
<223> OTHER INFORMATION: G-FGF21

<400> SEQUENCE: 3

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

```
Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 4
<211> LENGTH: 21
<212> TYPE: PRT
<213> ORGANISM: Artificial Sequence
<220> FEATURE:
<223> OTHER INFORMATION: IL2 signal sequence

<400> SEQUENCE: 4

Met Tyr Arg Met Gln Leu Leu Ser Cys Ile Ala Leu Leu Ser Leu Ala
1               5                   10                  15

Leu Val Thr Asn Ser
            20

<210> SEQ ID NO 5
<211> LENGTH: 28
<212> TYPE: PRT
<213> ORGANISM: Artificial Sequence
<220> FEATURE:
<223> OTHER INFORMATION: His-tag

<400> SEQUENCE: 5

Asp Ile Gln Thr Gly Gly Ser His Ala His Gly His Gly His Ala His
1               5                   10                  15

Gly His Gly Gly Ser Gly Glu Asn Leu Tyr Phe Gln
            20                  25

<210> SEQ ID NO 6
<211> LENGTH: 20
<212> TYPE: PRT
<213> ORGANISM: Artificial Sequence
<220> FEATURE:
<223> OTHER INFORMATION: His-tag

<400> SEQUENCE: 6

Met Gly His His His His His His His His Gly Gly Gly Glu Asn Leu
1               5                   10                  15

Tyr Phe Gln Gly
            20

<210> SEQ ID NO 7
<211> LENGTH: 108
<212> TYPE: PRT
<213> ORGANISM: Artificial Sequence
<220> FEATURE:
<223> OTHER INFORMATION: His-tag + SUMO-tag

<400> SEQUENCE: 7

Met Gly His His His His His His Gly Ser Leu Gln Asp Ser Glu Val
1               5                   10                  15
```

```
Asn Gln Glu Ala Lys Pro Glu Val Lys Pro Glu Val Lys Pro Glu Thr
                20                  25                  30

His Ile Asn Leu Lys Val Ser Asp Gly Ser Ser Glu Ile Phe Phe Lys
            35                  40                  45

Ile Lys Lys Thr Thr Pro Leu Arg Arg Leu Met Glu Ala Phe Ala Lys
 50                  55                  60

Arg Gln Gly Lys Glu Met Asp Ser Leu Arg Phe Leu Tyr Asp Gly Ile
 65                  70                  75                  80

Arg Ile Gln Ala Asp Gln Ala Pro Glu Asp Leu Asp Met Glu Asp Asn
                85                  90                  95

Asp Ile Ile Glu Ala His Arg Glu Gln Ile Gly Gly
            100                 105

<210> SEQ ID NO 8
<211> LENGTH: 182
<212> TYPE: PRT
<213> ORGANISM: Artificial Sequence
<220> FEATURE:
<223> OTHER INFORMATION: G-FGF21 S195C, S200C

<400> SEQUENCE: 8

Gly His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Cys Met Val Gly Pro Cys Gln Gly Arg
                165                 170                 175

Ser Pro Ser Tyr Ala Ser
            180

<210> SEQ ID NO 9
<211> LENGTH: 182
<212> TYPE: PRT
<213> ORGANISM: Artificial Sequence
<220> FEATURE:
<223> OTHER INFORMATION: G-FGF21 P199S, S200P

<400> SEQUENCE: 9

Gly His Pro Ile Pro Asp Ser Ser Pro Leu Leu Gln Phe Gly Gly Gln
 1               5                  10                  15
```

```
Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Ser Pro Gln Gly Arg
                165                 170                 175

Ser Pro Ser Tyr Ala Ser
                180
```

<210> SEQ ID NO 10
<211> LENGTH: 182
<212> TYPE: PRT
<213> ORGANISM: Artificial Sequence
<220> FEATURE:
<223> OTHER INFORMATION: G-FGF21 P199Q, Q201P

<400> SEQUENCE: 10

```
Gly His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Gln Ser Pro Gly Arg
                165                 170                 175

Ser Pro Ser Tyr Ala Ser
                180
```

<210> SEQ ID NO 11
<211> LENGTH: 181
<212> TYPE: PRT
<213> ORGANISM: Artificial Sequence
<220> FEATURE:
<223> OTHER INFORMATION: G-FGF21 P199 deleted

<400> SEQUENCE: 11

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Ser Gln Gly Arg Ser
                165                 170                 175

Pro Ser Tyr Ala Ser
            180
```

<210> SEQ ID NO 12
<211> LENGTH: 182
<212> TYPE: PRT
<213> ORGANISM: Artificial Sequence
<220> FEATURE:
<223> OTHER INFORMATION: G-FGF21 M196P, V197G, G198V, P199M

<400> SEQUENCE: 12

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110
```

His Gly Leu Pro Leu His Leu Pro Gly Asn Lys Ser Pro His Arg Asp
         115                 120                 125

Pro Ala Pro Arg Gly Pro Ala Arg Phe Leu Pro Leu Pro Gly Leu Pro
         130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Pro Gly Val Met Ser Gln Gly Arg
                165                 170                 175

Ser Pro Ser Tyr Ala Ser
         180

<210> SEQ ID NO 13
<211> LENGTH: 182
<212> TYPE: PRT
<213> ORGANISM: Artificial Sequence
<220> FEATURE:
<223> OTHER INFORMATION: G-FGF21 M196V, V197M

<400> SEQUENCE: 13

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
         35                  40                  45

Ser Pro Glu Ser Leu Leu Gln Leu Lys Ala Leu Lys Pro Gly Val Ile
     50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
         115                 120                 125

Pro Ala Pro Arg Gly Pro Ala Arg Phe Leu Pro Leu Pro Gly Leu Pro
         130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Val Met Gly Pro Ser Gln Gly Arg
                165                 170                 175

Ser Pro Ser Tyr Ala Ser
         180

<210> SEQ ID NO 14
<211> LENGTH: 182
<212> TYPE: PRT
<213> ORGANISM: Artificial Sequence
<220> FEATURE:
<223> OTHER INFORMATION: G-FGF V197E

<400> SEQUENCE: 14

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Glu Gly Pro Ser Gln Gly Arg
                165                 170                 175

Ser Pro Ser Tyr Ala Ser
            180

<210> SEQ ID NO 15
<211> LENGTH: 187
<212> TYPE: PRT
<213> ORGANISM: Artificial Sequence
<220> FEATURE:
<223> OTHER INFORMATION: G-FGF21 GGGGS inserted between G198 and P199

<400> SEQUENCE: 15

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Gly Gly Gly Ser
                165                 170                 175

Pro Ser Gln Gly Arg Ser Pro Ser Tyr Ala Ser
            180                 185

<210> SEQ ID NO 16
<211> LENGTH: 182
<212> TYPE: PRT
<213> ORGANISM: Artificial Sequence
<220> FEATURE:
<223> OTHER INFORMATION: G-FGF21 G198E

<400> SEQUENCE: 16

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Glu Pro Ser Gln Gly Arg
                165                 170                 175

Ser Pro Ser Tyr Ala Ser
            180
```

<210> SEQ ID NO 17
<211> LENGTH: 182
<212> TYPE: PRT
<213> ORGANISM: Artificial Sequence
<220> FEATURE:
<223> OTHER INFORMATION: G-FGF21 G198D

<400> SEQUENCE: 17

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110
```

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Asp Pro Ser Gln Gly Arg
                165                 170                 175

Ser Pro Ser Tyr Ala Ser
            180

<210> SEQ ID NO 18
<211> LENGTH: 182
<212> TYPE: PRT
<213> ORGANISM: Artificial Sequence
<220> FEATURE:
<223> OTHER INFORMATION: G-FGF21 G198R

<400> SEQUENCE: 18

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Arg Pro Ser Gln Gly Arg
                165                 170                 175

Ser Pro Ser Tyr Ala Ser
            180

<210> SEQ ID NO 19
<211> LENGTH: 182
<212> TYPE: PRT
<213> ORGANISM: Artificial Sequence
<220> FEATURE:
<223> OTHER INFORMATION: G-FGF21 G198K

<400> SEQUENCE: 19

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

```
His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Lys Pro Ser Gln Gly Arg
                165                 170                 175

Ser Pro Ser Tyr Ala Ser
            180

<210> SEQ ID NO 20
<211> LENGTH: 182
<212> TYPE: PRT
<213> ORGANISM: Artificial Sequence
<220> FEATURE:
<223> OTHER INFORMATION: G-FGF21 G198Y

<400> SEQUENCE: 20

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Tyr Pro Ser Gln Gly Arg
                165                 170                 175

Ser Pro Ser Tyr Ala Ser
            180
```

<210> SEQ ID NO 21
<211> LENGTH: 182
<212> TYPE: PRT
<213> ORGANISM: Artificial Sequence
<220> FEATURE:
<223> OTHER INFORMATION: G-FGF21 P199G

<400> SEQUENCE: 21

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Gly Ser Gln Gly Arg
                165                 170                 175

Ser Pro Ser Tyr Ala Ser
            180
```

<210> SEQ ID NO 22
<211> LENGTH: 182
<212> TYPE: PRT
<213> ORGANISM: Artificial Sequence
<220> FEATURE:
<223> OTHER INFORMATION: G-FGF21 P199R

<400> SEQUENCE: 22

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110
```

-continued

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Arg Ser Gln Gly Arg
                165                 170                 175

Ser Pro Ser Tyr Ala Ser
            180

<210> SEQ ID NO 23
<211> LENGTH: 182
<212> TYPE: PRT
<213> ORGANISM: Artificial Sequence
<220> FEATURE:
<223> OTHER INFORMATION: G-FGF21 P199T

<400> SEQUENCE: 23

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Thr Ser Gln Gly Arg
                165                 170                 175

Ser Pro Ser Tyr Ala Ser
            180

<210> SEQ ID NO 24
<211> LENGTH: 182
<212> TYPE: PRT
<213> ORGANISM: Artificial Sequence
<220> FEATURE:
<223> OTHER INFORMATION: G-FGF21 G198P, P199G

<400> SEQUENCE: 24

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
            130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Pro Gly Ser Gln Gly Arg
                165                 170                 175

Ser Pro Ser Tyr Ala Ser
            180

<210> SEQ ID NO 25
<211> LENGTH: 182
<212> TYPE: PRT
<213> ORGANISM: Artificial Sequence
<220> FEATURE:
<223> OTHER INFORMATION: G-FGF21 S200Q, Q201S

<400> SEQUENCE: 25

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
            130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Pro Gly Ser Gln Gly Arg
                165                 170                 175

Ser Pro Ser Tyr Ala Ser
            180

<210> SEQ ID NO 26

<211> LENGTH: 182
<212> TYPE: PRT
<213> ORGANISM: Artificial Sequence
<220> FEATURE:
<223> OTHER INFORMATION: G-FGF21 V197D, G198V, P199D, S200H

<400> SEQUENCE: 26

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Asp Val Asp His Gln Gly Arg
                165                 170                 175

Ser Pro Ser Tyr Ala Ser
            180
```

<210> SEQ ID NO 27
<211> LENGTH: 185
<212> TYPE: PRT
<213> ORGANISM: Artificial Sequence
<220> FEATURE:
<223> OTHER INFORMATION: G-FGF21 V197-R203 deleted and replaced by
      GHRSHLQTVF

<400> SEQUENCE: 27

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125
```

```
Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Gly His Arg Ser His Leu Gln
                165                 170                 175

Thr Val Phe Ser Pro Ser Tyr Ala Ser
            180                 185

<210> SEQ ID NO 28
<211> LENGTH: 181
<212> TYPE: PRT
<213> ORGANISM: Artificial Sequence
<220> FEATURE:
<223> OTHER INFORMATION: G-FGF21 V197-R203 deleted and replaced by
      GLNSMV

<400> SEQUENCE: 28

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Gly Leu Asn Ser Met Val Ser
                165                 170                 175

Pro Ser Tyr Ala Ser
            180

<210> SEQ ID NO 29
<211> LENGTH: 181
<212> TYPE: PRT
<213> ORGANISM: Artificial Sequence
<220> FEATURE:
<223> OTHER INFORMATION: G-FGF21 G198 deleted

<400> SEQUENCE: 29

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45
```

```
Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
               100                 105                 110

His Gly Leu Pro Leu His Leu Pro Gly Asn Lys Ser Pro His Arg Asp
               115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Pro Ser Gln Gly Arg Ser
                165                 170                 175

Pro Ser Tyr Ala Ser
        180
```

<210> SEQ ID NO 30
<211> LENGTH: 180
<212> TYPE: PRT
<213> ORGANISM: Artificial Sequence
<220> FEATURE:
<223> OTHER INFORMATION: G-FGF21 G198-P199 deleted

<400> SEQUENCE: 30

```
Gly His Pro Ile Pro Asp Ser Ser Pro Leu Leu Gln Phe Gly Gly Gln
 1                   5                  10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
               100                 105                 110

His Gly Leu Pro Leu His Leu Pro Gly Asn Lys Ser Pro His Arg Asp
               115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Ser Gln Gly Arg Ser Pro
                165                 170                 175

Ser Tyr Ala Ser
        180
```

<210> SEQ ID NO 31
<211> LENGTH: 181
<212> TYPE: PRT
<213> ORGANISM: Artificial Sequence
<220> FEATURE:
<223> OTHER INFORMATION: G-FGF21 G198 deleted, P199F

<400> SEQUENCE: 31

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Phe Ser Gln Gly Arg Ser
                165                 170                 175

Pro Ser Tyr Ala Ser
            180

<210> SEQ ID NO 32
<211> LENGTH: 181
<212> TYPE: PRT
<213> ORGANISM: Artificial Sequence
<220> FEATURE:
<223> OTHER INFORMATION: G-FGF21 G198 deleted, P199L

<400> SEQUENCE: 32

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

-continued

```
Pro Ala Pro Pro Glu Pro Pro Gly Ile Leu Ala Pro Gln Pro Asp
145                 150                 155                 160

Val Gly Ser Ser Asp Pro Leu Ser Met Val Leu Ser Gln Gly Arg Ser
                165                 170                 175

Pro Ser Tyr Ala Ser
            180
```

<210> SEQ ID NO 33
<211> LENGTH: 181
<212> TYPE: PRT
<213> ORGANISM: Artificial Sequence
<220> FEATURE:
<223> OTHER INFORMATION: G-FGF21 G198 deleted, P199L, S200N

<400> SEQUENCE: 33

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Asp
145                 150                 155                 160

Val Gly Ser Ser Asp Pro Leu Ser Met Val Leu Asn Gln Gly Arg Ser
                165                 170                 175

Pro Ser Tyr Ala Ser
            180
```

<210> SEQ ID NO 34
<211> LENGTH: 181
<212> TYPE: PRT
<213> ORGANISM: Artificial Sequence
<220> FEATURE:
<223> OTHER INFORMATION: G-FGF21 V197 deleted

<400> SEQUENCE: 34

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60
```

```
Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
             85                   90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Gly Pro Ser Gln Gly Arg Ser
            165                 170                 175

Pro Ser Tyr Ala Ser
            180

<210> SEQ ID NO 35
<211> LENGTH: 182
<212> TYPE: PRT
<213> ORGANISM: Artificial Sequence
<220> FEATURE:
<223> OTHER INFORMATION: G-FGF21 L146C, A162C

<400> SEQUENCE: 35

Gly His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
             85                   90                  95

Arg Glu Leu Leu Leu Glu Asp Gly Tyr Asn Val Tyr Gln Ser Glu Ala
            100                 105                 110

His Gly Leu Pro Leu His Cys Pro Gly Asn Lys Ser Pro His Arg Asp
            115                 120                 125

Pro Ala Pro Arg Gly Pro Cys Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
            165                 170                 175

Ser Pro Ser Tyr Ala Ser
            180

<210> SEQ ID NO 36
<211> LENGTH: 181
<212> TYPE: PRT
<213> ORGANISM: Artificial Sequence
<220> FEATURE:
<223> OTHER INFORMATION: G-FGF21 A59C, G71C, P199 deleted
```

<400> SEQUENCE: 36

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Cys
            20                  25                  30

His Leu Glu Ile Arg Glu Asp Gly Thr Val Gly Cys Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Ser Gln Gly Arg Ser
                165                 170                 175

Pro Ser Tyr Ala Ser
            180
```

<210> SEQ ID NO 37
<211> LENGTH: 182
<212> TYPE: PRT
<213> ORGANISM: Artificial Sequence
<220> FEATURE:
<223> OTHER INFORMATION: G-FGF21 A59C, G71C, G198Y

<400> SEQUENCE: 37

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Cys
            20                  25                  30

His Leu Glu Ile Arg Glu Asp Gly Thr Val Gly Cys Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160
```

Val Gly Ser Ser Asp Pro Leu Ser Met Val Tyr Pro Ser Gln Gly Arg
            165                 170                 175

Ser Pro Ser Tyr Ala Ser
            180

<210> SEQ ID NO 38
<211> LENGTH: 181
<212> TYPE: PRT
<213> ORGANISM: Artificial Sequence
<220> FEATURE:
<223> OTHER INFORMATION: G-FGF21 S76C, S79C, P199 deleted

<400> SEQUENCE: 38

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Cys Pro Glu Cys Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Ser Gln Gly Arg Ser
                165                 170                 175

Pro Ser Tyr Ala Ser
            180

<210> SEQ ID NO 39
<211> LENGTH: 182
<212> TYPE: PRT
<213> ORGANISM: Artificial Sequence
<220> FEATURE:
<223> OTHER INFORMATION: G-FGF21 S76C, S79C, G198Y

<400> SEQUENCE: 39

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Cys Pro Glu Cys Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

```
Gly Ala Leu Tyr Gly Ser Leu His Phe Asp Pro Glu Ala Cys Ser Phe
            85                  90                  95

Arg Glu Leu Leu Leu Glu Asp Gly Tyr Asn Val Tyr Gln Ser Glu Ala
           100                 105                 110

His Gly Leu Pro Leu His Leu Pro Gly Asn Lys Ser Pro His Arg Asp
           115                 120                 125

Pro Ala Pro Arg Gly Pro Ala Arg Phe Leu Pro Leu Pro Gly Leu Pro
           130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Tyr Pro Ser Gln Gly Arg
               165                  170                 175

Ser Pro Ser Tyr Ala Ser
            180

<210> SEQ ID NO 40
<211> LENGTH: 181
<212> TYPE: PRT
<213> ORGANISM: Artificial Sequence
<220> FEATURE:
<223> OTHER INFORMATION: G-FGF21 G108C, L142C, P199 deleted

<400> SEQUENCE: 40

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Cys Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
           100                 105                 110

His Gly Cys Pro Leu His Leu Pro Gly Asn Lys Ser Pro His Arg Asp
           115                 120                 125

Pro Ala Pro Arg Gly Pro Ala Arg Phe Leu Pro Leu Pro Gly Leu Pro
           130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Ser Gln Gly Arg Ser
                165                 170                 175

Pro Ser Tyr Ala Ser
            180

<210> SEQ ID NO 41
<211> LENGTH: 182
<212> TYPE: PRT
<213> ORGANISM: Artificial Sequence
<220> FEATURE:
<223> OTHER INFORMATION: G-FGF21 G108C, L142C, G198Y
```

<400> SEQUENCE: 41

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Cys Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Cys Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Tyr Pro Ser Gln Gly Arg
                165                 170                 175

Ser Pro Ser Tyr Ala Ser
            180
```

<210> SEQ ID NO 42
<211> LENGTH: 181
<212> TYPE: PRT
<213> ORGANISM: Artificial Sequence
<220> FEATURE:
<223> OTHER INFORMATION: G-FGF21 D107C, D155C, P199 deleted

<400> SEQUENCE: 42

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Cys
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Cys
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160
```

```
Val Gly Ser Ser Asp Pro Leu Ser Met Val Gly Ser Gln Gly Arg Ser
                165                 170                 175

Pro Ser Tyr Ala Ser
            180

<210> SEQ ID NO 43
<211> LENGTH: 182
<212> TYPE: PRT
<213> ORGANISM: Artificial Sequence
<220> FEATURE:
<223> OTHER INFORMATION: G-FGF21 D107C, D155C, G198Y

<400> SEQUENCE: 43

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Cys
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Cys
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Tyr Pro Ser Gln Gly Arg
                165                 170                 175

Ser Pro Ser Tyr Ala Ser
            180

<210> SEQ ID NO 44
<211> LENGTH: 181
<212> TYPE: PRT
<213> ORGANISM: Artificial Sequence
<220> FEATURE:
<223> OTHER INFORMATION: G-FGF21 Q55C, P147C, P199 deleted

<400> SEQUENCE: 44

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Cys Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95
```

```
Arg Glu Leu Leu Leu Glu Asp Gly Tyr Asn Val Tyr Gln Ser Glu Ala
            100                 105                 110

His Gly Leu Pro Leu His Leu Cys Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Ser Gln Gly Arg Ser
            165                 170                 175

Pro Ser Tyr Ala Ser
            180

<210> SEQ ID NO 45
<211> LENGTH: 182
<212> TYPE: PRT
<213> ORGANISM: Artificial Sequence
<220> FEATURE:
<223> OTHER INFORMATION: G-FGF21 Q55C, P147C, G198Y

<400> SEQUENCE: 45

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Cys Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Cys Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Tyr Pro Ser Gln Gly Arg
            165                 170                 175

Ser Pro Ser Tyr Ala Ser
            180

<210> SEQ ID NO 46
<211> LENGTH: 181
<212> TYPE: PRT
<213> ORGANISM: Artificial Sequence
<220> FEATURE:
<223> OTHER INFORMATION: G-FGF21 Q55C, N149C, P199 deleted

<400> SEQUENCE: 46

Gly His Pro Ile Pro Asp Ser Ser Pro Leu Leu Gln Phe Gly Gly Gln
1               5                   10                  15
```

```
Val Arg Gln Arg Tyr Leu Tyr Thr Asp Asp Ala Cys Gln Thr Glu Ala
         20                  25                  30

His Leu Glu Ile Arg Glu Asp Gly Thr Val Gly Gly Ala Ala Asp Gln
         35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Cys Lys Ser Pro His Arg Asp
                115                 120                 125

Pro Ala Pro Arg Gly Pro Ala Arg Phe Leu Pro Leu Pro Gly Leu Pro
                130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Ser Gln Gly Arg Ser
                165                 170                 175

Pro Ser Tyr Ala Ser
            180

<210> SEQ ID NO 47
<211> LENGTH: 182
<212> TYPE: PRT
<213> ORGANISM: Artificial Sequence
<220> FEATURE:
<223> OTHER INFORMATION: G-FGF21 Q55C, N149C, G198Y

<400> SEQUENCE: 47

Gly His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Cys Gln Thr Glu Ala
         20                  25                  30

His Leu Glu Ile Arg Glu Asp Gly Thr Val Gly Gly Ala Ala Asp Gln
         35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Cys Lys Ser Pro His Arg Asp
                115                 120                 125

Pro Ala Pro Arg Gly Pro Ala Arg Phe Leu Pro Leu Pro Gly Leu Pro
                130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Tyr Pro Ser Gln Gly Arg
                165                 170                 175

Ser Pro Ser Tyr Ala Ser
            180
```

-continued

<210> SEQ ID NO 48
<211> LENGTH: 181
<212> TYPE: PRT
<213> ORGANISM: Artificial Sequence
<220> FEATURE:
<223> OTHER INFORMATION: G-FGF21 M196 deleted

<400> SEQUENCE: 48

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Val Gly Pro Ser Gln Gly Arg Ser
                165                 170                 175

Pro Ser Tyr Ala Ser
            180
```

<210> SEQ ID NO 49
<211> LENGTH: 181
<212> TYPE: PRT
<213> ORGANISM: Artificial Sequence
<220> FEATURE:
<223> OTHER INFORMATION: G-FGF21 S195 deleted

<400> SEQUENCE: 49

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110
```

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Asp
145                 150                 155                 160

Val Gly Ser Ser Asp Pro Leu Met Val Gly Pro Ser Gln Gly Arg Ser
                165                 170                 175

Pro Ser Tyr Ala Ser
        180

<210> SEQ ID NO 50
<211> LENGTH: 181
<212> TYPE: PRT
<213> ORGANISM: Artificial Sequence
<220> FEATURE:
<223> OTHER INFORMATION: G-FGF21 L194 deleted

<400> SEQUENCE: 50

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Asp
145                 150                 155                 160

Val Gly Ser Ser Asp Pro Ser Met Val Gly Pro Ser Gln Gly Arg Ser
                165                 170                 175

Pro Ser Tyr Ala Ser
        180

<210> SEQ ID NO 51
<211> LENGTH: 181
<212> TYPE: PRT
<213> ORGANISM: Artificial Sequence
<220> FEATURE:
<223> OTHER INFORMATION: G-FGF21 P193 deleted

<400> SEQUENCE: 51

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
            130                 135                 140

Pro Ala Pro Pro Glu Pro Pro Gly Ile Leu Ala Pro Gln Pro Pro Asp
145                 150                 155                 160

Val Gly Ser Ser Asp Leu Ser Met Val Gly Pro Ser Gln Gly Arg Ser
                165                 170                 175

Pro Ser Tyr Ala Ser
            180

<210> SEQ ID NO 52
<211> LENGTH: 181
<212> TYPE: PRT
<213> ORGANISM: Artificial Sequence
<220> FEATURE:
<223> OTHER INFORMATION: G-FGF21 D192 deleted

<400> SEQUENCE: 52

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
            130                 135                 140

Pro Ala Pro Pro Glu Pro Pro Gly Ile Leu Ala Pro Gln Pro Pro Asp
145                 150                 155                 160

Val Gly Ser Ser Pro Leu Ser Met Val Gly Pro Ser Gln Gly Arg Ser
                165                 170                 175

Pro Ser Tyr Ala Ser
            180

-continued

```
<210> SEQ ID NO 53
<211> LENGTH: 181
<212> TYPE: PRT
<213> ORGANISM: Artificial Sequence
<220> FEATURE:
<223> OTHER INFORMATION: G-FGF21 S191 deleted

<400> SEQUENCE: 53

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Asp Pro Leu Ser Met Val Gly Pro Ser Gln Gly Arg Ser
                165                 170                 175

Pro Ser Tyr Ala Ser
            180

<210> SEQ ID NO 54
<211> LENGTH: 180
<212> TYPE: PRT
<213> ORGANISM: Artificial Sequence
<220> FEATURE:
<223> OTHER INFORMATION: G-FGF21 S190-S191 deleted

<400> SEQUENCE: 54

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110
```

-continued

```
His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Asp Pro Leu Ser Met Val Gly Pro Ser Gln Gly Arg Ser Pro
                165                 170                 175

Ser Tyr Ala Ser
            180

<210> SEQ ID NO 55
<211> LENGTH: 181
<212> TYPE: PRT
<213> ORGANISM: Artificial Sequence
<220> FEATURE:
<223> OTHER INFORMATION: G-FGF21 G189 deleted

<400> SEQUENCE: 55

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Ser Ser Asp Pro Leu Ser Met Val Gly Pro Ser Gln Gly Arg Ser
                165                 170                 175

Pro Ser Tyr Ala Ser
            180

<210> SEQ ID NO 56
<211> LENGTH: 181
<212> TYPE: PRT
<213> ORGANISM: Artificial Sequence
<220> FEATURE:
<223> OTHER INFORMATION: G-FGF21 V188 deleted

<400> SEQUENCE: 56

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30
```

```
His Leu Glu Ile Arg Glu Asp Gly Thr Val Gly Gly Ala Ala Asp Gln
         35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
                115                 120                 125

Pro Ala Pro Arg Gly Pro Ala Arg Phe Leu Pro Leu Pro Gly Leu Pro
            130                 135                 140

Pro Ala Pro Pro Glu Pro Pro Gly Ile Leu Ala Pro Gln Pro Pro Asp
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 57
<211> LENGTH: 181
<212> TYPE: PRT
<213> ORGANISM: Artificial Sequence
<220> FEATURE:
<223> OTHER INFORMATION: G-FGF21 D187 deleted

<400> SEQUENCE: 57

Gly His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
                 20                  25                  30

His Leu Glu Ile Arg Glu Asp Gly Thr Val Gly Gly Ala Ala Asp Gln
         35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
                115                 120                 125

Pro Ala Pro Arg Gly Pro Ala Arg Phe Leu Pro Leu Pro Gly Leu Pro
            130                 135                 140

Pro Ala Pro Pro Glu Pro Pro Gly Ile Leu Ala Pro Gln Pro Pro Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 58
```

```
<211> LENGTH: 181
<212> TYPE: PRT
<213> ORGANISM: Artificial Sequence
<220> FEATURE:
<223> OTHER INFORMATION: G-FGF21 P186 deleted

<400> SEQUENCE: 58

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 59
<211> LENGTH: 180
<212> TYPE: PRT
<213> ORGANISM: Artificial Sequence
<220> FEATURE:
<223> OTHER INFORMATION: G-FGF21 P185-P186 deleted

<400> SEQUENCE: 59

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125
```

-continued

```
Pro Ala Pro Arg Gly Pro Ala Arg Phe Leu Pro Leu Pro Gly Leu Pro
            130                 135                 140

Pro Ala Pro Pro Glu Pro Pro Gly Ile Leu Ala Pro Gln Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 60
<211> LENGTH: 181
<212> TYPE: PRT
<213> ORGANISM: Artificial Sequence
<220> FEATURE:
<223> OTHER INFORMATION: G-FGF21 Q184 deleted

<400> SEQUENCE: 60

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 61
<211> LENGTH: 181
<212> TYPE: PRT
<213> ORGANISM: Artificial Sequence
<220> FEATURE:
<223> OTHER INFORMATION: G-FGF21 S200 deleted

<400> SEQUENCE: 61

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45
```

```
Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
                115                 120                 125

Pro Ala Pro Arg Gly Pro Ala Arg Phe Leu Pro Leu Pro Gly Leu Pro
                130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Gln Gly Arg Ser
                165                 170                 175

Pro Ser Tyr Ala Ser
                180

<210> SEQ ID NO 62
<211> LENGTH: 181
<212> TYPE: PRT
<213> ORGANISM: Artificial Sequence
<220> FEATURE:
<223> OTHER INFORMATION: G-FGF21 Q201 deleted

<400> SEQUENCE: 62

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
                35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
                115                 120                 125

Pro Ala Pro Arg Gly Pro Ala Arg Phe Leu Pro Leu Pro Gly Leu Pro
                130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gly Arg Ser
                165                 170                 175

Pro Ser Tyr Ala Ser
                180

<210> SEQ ID NO 63
<211> LENGTH: 181
<212> TYPE: PRT
<213> ORGANISM: Artificial Sequence
```

<220> FEATURE:
<223> OTHER INFORMATION: G-FGF21 G202 deleted

<400> SEQUENCE: 63

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Arg Ser
                165                 170                 175

Pro Ser Tyr Ala Ser
            180

<210> SEQ ID NO 64
<211> LENGTH: 181
<212> TYPE: PRT
<213> ORGANISM: Artificial Sequence
<220> FEATURE:
<223> OTHER INFORMATION: G-FGF21 R203 deleted

<400> SEQUENCE: 64

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

```
Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Ser
                165                 170                 175

Pro Ser Tyr Ala Ser
            180

<210> SEQ ID NO 65
<211> LENGTH: 181
<212> TYPE: PRT
<213> ORGANISM: Artificial Sequence
<220> FEATURE:
<223> OTHER INFORMATION: G-FGF21 S204 deleted

<400> SEQUENCE: 65

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Pro Ser Tyr Ala Ser
            180

<210> SEQ ID NO 66
<211> LENGTH: 181
<212> TYPE: PRT
<213> ORGANISM: Artificial Sequence
<220> FEATURE:
<223> OTHER INFORMATION: G-FGF21 P205 deleted

<400> SEQUENCE: 66

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60
```

```
Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
             85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Ser Tyr Ala Ser
            180

<210> SEQ ID NO 67
<211> LENGTH: 181
<212> TYPE: PRT
<213> ORGANISM: Artificial Sequence
<220> FEATURE:
<223> OTHER INFORMATION: G-FGF21 S206 deleted

<400> SEQUENCE: 67

Gly His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
             85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Tyr Ala Ser
            180

<210> SEQ ID NO 68
<211> LENGTH: 181
<212> TYPE: PRT
<213> ORGANISM: Artificial Sequence
<220> FEATURE:
<223> OTHER INFORMATION: G-FGF21 Y207 deleted
```

<400> SEQUENCE: 68

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Ala Ser
            180
```

<210> SEQ ID NO 69
<211> LENGTH: 180
<212> TYPE: PRT
<213> ORGANISM: Artificial Sequence
<220> FEATURE:
<223> OTHER INFORMATION: G-FGF21 V197 deleted, S201 deleted

<400> SEQUENCE: 69

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160
```

```
Val Gly Ser Ser Asp Pro Leu Ser Met Gly Pro Gln Gly Arg Ser Pro
                165                 170                 175

Ser Tyr Ala Ser
            180

<210> SEQ ID NO 70
<211> LENGTH: 180
<212> TYPE: PRT
<213> ORGANISM: Artificial Sequence
<220> FEATURE:
<223> OTHER INFORMATION: G-FGF21 M196 deleted, S201 deleted

<400> SEQUENCE: 70

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Val Gly Pro Gln Gly Arg Ser Pro
                165                 170                 175

Ser Tyr Ala Ser
            180

<210> SEQ ID NO 71
<211> LENGTH: 180
<212> TYPE: PRT
<213> ORGANISM: Artificial Sequence
<220> FEATURE:
<223> OTHER INFORMATION: G-FGF21 M196-V197 deleted

<400> SEQUENCE: 71

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80
```

-continued

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Gly Pro Ser Gln Gly Arg Ser Pro
                165                 170                 175

Ser Tyr Ala Ser
            180

<210> SEQ ID NO 72
<211> LENGTH: 180
<212> TYPE: PRT
<213> ORGANISM: Artificial Sequence
<220> FEATURE:
<223> OTHER INFORMATION: G-FGF21 V197-G198 deleted

<400> SEQUENCE: 72

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Pro Ser Gln Gly Arg Ser Pro
                165                 170                 175

Ser Tyr Ala Ser
            180

<210> SEQ ID NO 73
<211> LENGTH: 180
<212> TYPE: PRT
<213> ORGANISM: Artificial Sequence
<220> FEATURE:
<223> OTHER INFORMATION: G-FGF21 S195-M196 deleted

<400> SEQUENCE: 73

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Val Gly Pro Ser Gln Gly Arg Ser Pro
                165                 170                 175

Ser Tyr Ala Ser
            180
```

<210> SEQ ID NO 74
<211> LENGTH: 180
<212> TYPE: PRT
<213> ORGANISM: Artificial Sequence
<220> FEATURE:
<223> OTHER INFORMATION: G-FGF21 G198 deleted, S200 deleted

<400> SEQUENCE: 74

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160
```

```
Val Gly Ser Ser Asp Pro Leu Ser Met Val Pro Gln Gly Arg Ser Pro
                165                 170                 175

Ser Tyr Ala Ser
        180

<210> SEQ ID NO 75
<211> LENGTH: 182
<212> TYPE: PRT
<213> ORGANISM: Artificial Sequence
<220> FEATURE:
<223> OTHER INFORMATION: G-FGF21 H60C, S79C

<400> SEQUENCE: 75

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

Cys Leu Glu Ile Arg Glu Asp Gly Thr Val Gly Gly Ala Ala Asp Gln
        35                  40                  45

Ser Pro Glu Cys Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 76
<211> LENGTH: 182
<212> TYPE: PRT
<213> ORGANISM: Artificial Sequence
<220> FEATURE:
<223> OTHER INFORMATION: G-FGF21 H145C, L165C

<400> SEQUENCE: 76

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95
```

Arg Glu Leu Leu Leu Glu Asp Gly Tyr Asn Val Tyr Gln Ser Glu Ala
                100                 105                 110

His Gly Leu Pro Leu Cys Leu Pro Gly Asn Lys Ser Pro His Arg Asp
            115                 120                 125

Pro Ala Pro Arg Gly Pro Ala Arg Phe Cys Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 77
<211> LENGTH: 182
<212> TYPE: PRT
<213> ORGANISM: Artificial Sequence
<220> FEATURE:
<223> OTHER INFORMATION: G-FGF21 A59C, G71C

<400> SEQUENCE: 77

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Cys
            20                  25                  30

His Leu Glu Ile Arg Glu Asp Gly Thr Val Gly Cys Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 78
<211> LENGTH: 182
<212> TYPE: PRT
<213> ORGANISM: Artificial Sequence
<220> FEATURE:
<223> OTHER INFORMATION: G-FGF21 H60C, A72C

<400> SEQUENCE: 78

Gly His Pro Ile Pro Asp Ser Ser Pro Leu Leu Gln Phe Gly Gly Gln
1               5                   10                  15

```
Val Arg Gln Arg Tyr Leu Tyr Thr Asp Asp Ala Gln Gln Thr Glu Ala
            20                  25                  30

Cys Leu Glu Ile Arg Glu Asp Gly Thr Val Gly Gly Cys Ala Asp Gln
        35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
 130                 135                 140

Pro Ala Pro Pro Glu Pro Pro Gly Ile Leu Ala Pro Gln Pro Pro Asp
 145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 79
<211> LENGTH: 182
<212> TYPE: PRT
<213> ORGANISM: Artificial Sequence
<220> FEATURE:
<223> OTHER INFORMATION: G-FGF21 I63C, G112C

<400> SEQUENCE: 79

```
Gly His Pro Ile Pro Asp Ser Ser Pro Leu Leu Gln Phe Gly Gly Gln
 1               5                   10                  15

Val Arg Gln Arg Tyr Leu Tyr Thr Asp Asp Ala Gln Gln Thr Glu Ala
            20                  25                  30

His Leu Glu Cys Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Cys Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
 130                 135                 140

Pro Ala Pro Pro Glu Pro Pro Gly Ile Leu Ala Pro Gln Pro Pro Asp
 145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 80
<211> LENGTH: 182
<212> TYPE: PRT
<213> ORGANISM: Artificial Sequence
<220> FEATURE:
<223> OTHER INFORMATION: G-FGF21 L49C, L170C

<400> SEQUENCE: 80

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Cys Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 81
<211> LENGTH: 182
<212> TYPE: PRT
<213> ORGANISM: Artificial Sequence
<220> FEATURE:
<223> OTHER INFORMATION: G-FGF21 T51C, L167C

<400> SEQUENCE: 81

Gly His Pro Ile Pro Asp Ser Ser Pro Leu Leu Gln Phe Gly Gly Gln
1               5                   10                  15

Val Arg Gln Arg Tyr Leu Tyr Cys Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

```
His Gly Leu Pro Leu His Leu Pro Gly Asn Lys Ser Pro His Arg Asp
        115                 120                 125

Pro Ala Pro Arg Gly Pro Ala Arg Phe Leu Pro Cys Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
        180

<210> SEQ ID NO 82
<211> LENGTH: 182
<212> TYPE: PRT
<213> ORGANISM: Artificial Sequence
<220> FEATURE:
<223> OTHER INFORMATION: G-FGF21 H140C, L142C

<400> SEQUENCE: 82

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

Cys Gly Cys Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
        180

<210> SEQ ID NO 83
<211> LENGTH: 182
<212> TYPE: PRT
<213> ORGANISM: Artificial Sequence
<220> FEATURE:
<223> OTHER INFORMATION: G-FGF21 D130C, Y132C

<400> SEQUENCE: 83

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30
```

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Cys Gly Cys Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 84
<211> LENGTH: 182
<212> TYPE: PRT
<213> ORGANISM: Artificial Sequence
<220> FEATURE:
<223> OTHER INFORMATION: G-FGF21 S137C, H140C

<400> SEQUENCE: 84

Gly His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
             20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Cys Glu Ala
            100                 105                 110

Cys Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 85

```
<211> LENGTH: 182
<212> TYPE: PRT
<213> ORGANISM: Artificial Sequence
<220> FEATURE:
<223> OTHER INFORMATION: G-FGF21 S76C, S79C

<400> SEQUENCE: 85

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Cys Pro Glu Cys Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 86
<211> LENGTH: 182
<212> TYPE: PRT
<213> ORGANISM: Artificial Sequence
<220> FEATURE:
<223> OTHER INFORMATION: G-FGF21 G108C, L142C

<400> SEQUENCE: 86

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Cys Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Cys Pro Leu His Leu Pro Gly Asn Lys Ser Pro His Arg Asp
        115                 120                 125
```

-continued

```
Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 87
<211> LENGTH: 182
<212> TYPE: PRT
<213> ORGANISM: Artificial Sequence
<220> FEATURE:
<223> OTHER INFORMATION: G-FGF21 A72C, S79C

<400> SEQUENCE: 87

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Cys Ala Asp Gln
        35                  40                  45

Ser Pro Glu Cys Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 88
<211> LENGTH: 182
<212> TYPE: PRT
<213> ORGANISM: Artificial Sequence
<220> FEATURE:
<223> OTHER INFORMATION: G-FGF21 H60C, S79C, H145C, L165C

<400> SEQUENCE: 88

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

Cys Leu Glu Ile Arg Glu Asp Gly Thr Val Gly Gly Ala Ala Asp Gln
        35                  40                  45
```

Ser Pro Glu Cys Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu Cys Leu Pro Gly Asn Lys Ser Pro His Arg Asp
                115                 120                 125

Pro Ala Pro Arg Gly Pro Ala Arg Phe Cys Pro Leu Pro Gly Leu Pro
                130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 89
<211> LENGTH: 182
<212> TYPE: PRT
<213> ORGANISM: Artificial Sequence
<220> FEATURE:
<223> OTHER INFORMATION: G-FGF21 A72C, S79C, G108C, L142C

<400> SEQUENCE: 89

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Cys Ala Asp Gln
            35                  40                  45

Ser Pro Glu Cys Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Cys Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Cys Pro Leu His Leu Pro Gly Asn Lys Ser Pro His Arg Asp
                115                 120                 125

Pro Ala Pro Arg Gly Pro Ala Arg Phe Leu Pro Leu Pro Gly Leu Pro
                130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 90
<211> LENGTH: 182
<212> TYPE: PRT
<213> ORGANISM: Artificial Sequence

```
<220> FEATURE:
<223> OTHER INFORMATION: G-FGF21 R47C, P174C

<400> SEQUENCE: 90
```

| Gly | His | Pro | Ile | Pro | Asp | Ser | Ser | Pro | Leu | Leu | Gln | Phe | Gly | Gly | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Val Arg Gln Cys Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
    130                 135                 140

Pro Ala Cys Pro Glu Pro Pro Gly Ile Leu Ala Pro Gln Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

```
<210> SEQ ID NO 91
<211> LENGTH: 182
<212> TYPE: PRT
<213> ORGANISM: Artificial Sequence
<220> FEATURE:
<223> OTHER INFORMATION: G-FGF21 M196C, R203C

<400> SEQUENCE: 91
```

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
    130                 135                 140

```
Pro Ala Pro Pro Glu Pro Pro Gly Ile Leu Ala Pro Gln Pro Asp
145                 150                 155                 160

Val Gly Ser Ser Asp Pro Leu Ser Cys Val Gly Pro Ser Gln Gly Cys
                165                 170                 175

Ser Pro Ser Tyr Ala Ser
            180
```

<210> SEQ ID NO 92
<211> LENGTH: 182
<212> TYPE: PRT
<213> ORGANISM: Artificial Sequence
<220> FEATURE:
<223> OTHER INFORMATION: G-FGF21 D107C, D155C

<400> SEQUENCE: 92

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Cys
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Cys
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 93
<211> LENGTH: 182
<212> TYPE: PRT
<213> ORGANISM: Artificial Sequence
<220> FEATURE:
<223> OTHER INFORMATION: G-FGF21 Q55C, G148C

<400> SEQUENCE: 93

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Cys Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60
```

```
Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
            100                 105                 110

His Gly Leu Pro Leu His Leu Pro Cys Asn Lys Ser Pro His Arg Asp
        115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 94
<211> LENGTH: 175
<212> TYPE: PRT
<213> ORGANISM: Artificial Sequence
<220> FEATURE:
<223> OTHER INFORMATION: G-FGF21 Q55C, G148C, N149-R159 deleted and replaced by GSGS

<400> SEQUENCE: 94

```
Gly His Pro Ile Pro Asp Ser Ser Pro Leu Leu Gln Phe Gly Gly Gln
  1               5                  10                  15

Val Arg Gln Arg Tyr Leu Tyr Thr Asp Asp Ala Cys Gln Thr Glu Ala
                 20                  25                  30

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
            100                 105                 110

His Gly Leu Pro Leu His Leu Pro Cys Gly Ser Gly Ser Gly Pro Ala
        115                 120                 125

Arg Phe Leu Pro Leu Pro Gly Leu Pro Pro Ala Pro Pro Glu Pro Pro
130                 135                 140

Gly Ile Leu Ala Pro Gln Pro Pro Asp Val Gly Ser Ser Asp Pro Leu
145                 150                 155                 160

Ser Met Val Gly Pro Ser Gln Gly Arg Ser Pro Ser Tyr Ala Ser
                165                 170                 175
```

<210> SEQ ID NO 95
<211> LENGTH: 177
<212> TYPE: PRT
<213> ORGANISM: Artificial Sequence
<220> FEATURE:
<223> OTHER INFORMATION: G-FGF21 Q55C, G148C, N149-R159 deleted and replaced by GGSGGS

<400> SEQUENCE: 95

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Cys Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Cys Gly Gly Ser Gly Ser Gly
        115                 120                 125

Pro Ala Arg Phe Leu Pro Leu Pro Gly Leu Pro Pro Ala Pro Pro Glu
130                 135                 140

Pro Pro Gly Ile Leu Ala Pro Gln Pro Pro Asp Val Gly Ser Ser Asp
145                 150                 155                 160

Pro Leu Ser Met Val Gly Pro Ser Gln Gly Arg Ser Pro Ser Tyr Ala
                165                 170                 175

Ser
```

<210> SEQ ID NO 96
<211> LENGTH: 182
<212> TYPE: PRT
<213> ORGANISM: Artificial Sequence
<220> FEATURE:
<223> OTHER INFORMATION: G-FGF21 Q55G, Q56C, L146C

<400> SEQUENCE: 96

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gly Cys Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Cys Pro Gly Asn Lys Ser Pro His Arg Asp
        115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160
```

Val Gly Ser Ser Asp Pro Leu Ser Met Val Gly Pro Ser Gln Gly Arg
            165                 170                 175

Ser Pro Ser Tyr Ala Ser
            180

<210> SEQ ID NO 97
<211> LENGTH: 173
<212> TYPE: PRT
<213> ORGANISM: Artificial Sequence
<220> FEATURE:
<223> OTHER INFORMATION: G-FGF21 Q55G, Q56C, L146C, P147-R159 deleted
      and replaced by GSGS

<400> SEQUENCE: 97

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gly Cys Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Cys Gly Ser Gly Ser Gly Pro Ala Arg Phe
        115                 120                 125

Leu Pro Leu Pro Gly Leu Pro Pro Ala Pro Pro Glu Pro Pro Gly Ile
    130                 135                 140

Leu Ala Pro Gln Pro Pro Asp Val Gly Ser Ser Asp Pro Leu Ser Met
145                 150                 155                 160

Val Gly Pro Ser Gln Gly Arg Ser Pro Ser Tyr Ala Ser
                165                 170

<210> SEQ ID NO 98
<211> LENGTH: 175
<212> TYPE: PRT
<213> ORGANISM: Artificial Sequence
<220> FEATURE:
<223> OTHER INFORMATION: G-FGF21 Q55G, Q56C, L146C, P147-R159 deleted
      and replaced by GGSGGS

<400> SEQUENCE: 98

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gly Cys Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Cys Gly Ser Gly Ser Gly Pro Ala
            115                 120                 125

Arg Phe Leu Pro Leu Pro Gly Leu Pro Pro Ala Pro Pro Glu Pro Pro
130                 135                 140

Gly Ile Leu Ala Pro Gln Pro Pro Asp Val Gly Ser Ser Asp Pro Leu
145                 150                 155                 160

Ser Met Val Gly Pro Ser Gln Gly Arg Ser Pro Ser Tyr Ala Ser
            165                 170                 175

<210> SEQ ID NO 99
<211> LENGTH: 182
<212> TYPE: PRT
<213> ORGANISM: Artificial Sequence
<220> FEATURE:
<223> OTHER INFORMATION: G-FGF21 Q55C, P147C

<400> SEQUENCE: 99

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Cys Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Cys Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 100
<211> LENGTH: 182
<212> TYPE: PRT
<213> ORGANISM: Artificial Sequence
<220> FEATURE:
<223> OTHER INFORMATION: G-FGF21 Q55C, N149C

<400> SEQUENCE: 100

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Cys Gln Thr Glu Ala
            20                  25                  30

```
His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Cys Lys Ser Pro His Arg Asp
                115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 101
<211> LENGTH: 182
<212> TYPE: PRT
<213> ORGANISM: Artificial Sequence
<220> FEATURE:
<223> OTHER INFORMATION: G-FGF21 E62C, E78C

<400> SEQUENCE: 101

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Cys Ile Arg Glu Asp Gly Thr Val Gly Gly Ala Ala Asp Gln
        35                  40                  45

Ser Pro Cys Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
                115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 102
```

```
<211> LENGTH: 182
<212> TYPE: PRT
<213> ORGANISM: Artificial Sequence
<220> FEATURE:
<223> OTHER INFORMATION: G-FGF21 E62C, S79C

<400> SEQUENCE: 102
```

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Cys Ile Arg Glu Asp Gly Thr Val Gly Gly Ala Ala Asp Gln
        35                  40                  45

Ser Pro Glu Cys Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65              70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

```
<210> SEQ ID NO 103
<211> LENGTH: 182
<212> TYPE: PRT
<213> ORGANISM: Artificial Sequence
<220> FEATURE:
<223> OTHER INFORMATION: G-FGF21 R100C, L114C

<400> SEQUENCE: 103
```

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Cys Phe Leu Cys Gln Arg Pro Asp
65              70                  75                  80

Gly Ala Leu Tyr Gly Ser Cys His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

```
Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 104
<211> LENGTH: 182
<212> TYPE: PRT
<213> ORGANISM: Artificial Sequence
<220> FEATURE:
<223> OTHER INFORMATION: G-FGF21 L102C, G112C

<400> SEQUENCE: 104

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Cys Cys Gln Arg Pro Asp
65                  70                  75                  80

Gly Ala Leu Tyr Cys Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 105
<211> LENGTH: 182
<212> TYPE: PRT
<213> ORGANISM: Artificial Sequence
<220> FEATURE:
<223> OTHER INFORMATION: G-FGF21 A59C, A73C

<400> SEQUENCE: 105

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Cys
            20                  25                  30

His Leu Glu Ile Arg Glu Asp Gly Thr Val Gly Gly Ala Cys Asp Gln
        35                  40                  45
```

```
Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
                115                 120                 125

Pro Ala Pro Arg Gly Pro Ala Arg Phe Leu Pro Leu Pro Gly Leu Pro
                130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180
```

<210> SEQ ID NO 106
<211> LENGTH: 182
<212> TYPE: PRT
<213> ORGANISM: Artificial Sequence
<220> FEATURE:
<223> OTHER INFORMATION: G-FGF21 E62C, A72C

<400> SEQUENCE: 106

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Cys Ile Arg Glu Asp Gly Thr Val Gly Gly Cys Ala Asp Gln
                35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
                115                 120                 125

Pro Ala Pro Arg Gly Pro Ala Arg Phe Leu Pro Leu Pro Gly Leu Pro
                130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180
```

<210> SEQ ID NO 107
<211> LENGTH: 182
<212> TYPE: PRT
<213> ORGANISM: Artificial Sequence

<220> FEATURE:
<223> OTHER INFORMATION: G-FGF21 Q104C, S137C

<400> SEQUENCE: 107

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Cys Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Cys Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 108
<211> LENGTH: 182
<212> TYPE: PRT
<213> ORGANISM: Artificial Sequence
<220> FEATURE:
<223> OTHER INFORMATION: G-FGF21 Q104C, H140C

<400> SEQUENCE: 108

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Cys Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

Cys Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 109
<211> LENGTH: 182
<212> TYPE: PRT
<213> ORGANISM: Artificial Sequence
<220> FEATURE:
<223> OTHER INFORMATION: G-FGF21 A54C, P161C

<400> SEQUENCE: 109

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Cys Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Cys Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 110
<211> LENGTH: 182
<212> TYPE: PRT
<213> ORGANISM: Artificial Sequence
<220> FEATURE:
<223> OTHER INFORMATION: G-FGF21 Q56C, L146C

<400> SEQUENCE: 110

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Cys Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
50                  55                  60

```
Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Cys His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 111
<211> LENGTH: 182
<212> TYPE: PRT
<213> ORGANISM: Artificial Sequence
<220> FEATURE:
<223> OTHER INFORMATION: G-FGF21 I63C, T98C

<400> SEQUENCE: 111

Gly His Pro Ile Pro Asp Ser Ser Pro Leu Leu Gln Phe Gly Gly Gln
1                5                  10                  15

Val Arg Gln Arg Tyr Leu Tyr Thr Asp Asp Ala Gln Gln Thr Glu Ala
                 20                  25                  30

His Leu Glu Cys Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
 50                  55                  60

Gln Ile Leu Gly Val Lys Cys Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 112
<211> LENGTH: 182
<212> TYPE: PRT
<213> ORGANISM: Artificial Sequence
<220> FEATURE:
<223> OTHER INFORMATION: G-FGF21 G67C, R100C
```

```
<400> SEQUENCE: 112

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Cys Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Cys Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 113
<211> LENGTH: 182
<212> TYPE: PRT
<213> ORGANISM: Artificial Sequence
<220> FEATURE:
<223> OTHER INFORMATION: G-FGF21 V69C, L110C

<400> SEQUENCE: 113

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Cys Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Cys Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160
```

Val Gly Ser Ser Asp Pro Leu Ser Met Val Gly Pro Ser Gln Gly Arg
            165                 170                 175

Ser Pro Ser Tyr Ala Ser
            180

<210> SEQ ID NO 114
<211> LENGTH: 182
<212> TYPE: PRT
<213> ORGANISM: Artificial Sequence
<220> FEATURE:
<223> OTHER INFORMATION: G-FGF21 A120C, A139C

<400> SEQUENCE: 114

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Cys Cys Ser Phe
                85                  90                  95

Arg Glu Leu Leu Leu Glu Asp Gly Tyr Asn Val Tyr Gln Ser Glu Cys
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
            165                 170                 175

Ser Pro Ser Tyr Ala Ser
            180

<210> SEQ ID NO 115
<211> LENGTH: 182
<212> TYPE: PRT
<213> ORGANISM: Artificial Sequence
<220> FEATURE:
<223> OTHER INFORMATION: G-FGF21 R124C, Q136C

<400> SEQUENCE: 115

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

```
Gly Ala Leu Tyr Gly Ser Leu His Phe Asp Pro Glu Ala Cys Ser Phe
                85                  90                  95

Cys Glu Leu Leu Leu Glu Asp Gly Tyr Asn Val Tyr Cys Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 116
<211> LENGTH: 182
<212> TYPE: PRT
<213> ORGANISM: Artificial Sequence
<220> FEATURE:
<223> OTHER INFORMATION: G-FGF21 P143C, A162C

<400> SEQUENCE: 116

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Cys Leu His Leu Pro Gly Asn Lys Ser Pro His Arg Asp
        115                 120                 125

Pro Ala Pro Arg Gly Pro Cys Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 117
<211> LENGTH: 182
<212> TYPE: PRT
<213> ORGANISM: Artificial Sequence
<220> FEATURE:
<223> OTHER INFORMATION: G-FGF21 P77C, K97C
```

<400> SEQUENCE: 117

| Gly | His | Pro | Ile | Pro | Asp | Ser | Ser | Pro | Leu | Leu | Gln | Phe | Gly | Gly | Gln |
|---|---|---|---|---|---|---|---|---|---|---|---|---|---|---|---|
| 1 | | | | 5 | | | | | 10 | | | | | 15 | |

Val Arg Gln Arg Tyr Leu Tyr Thr Asp Asp Ala Gln Gln Thr Glu Ala
    20        25        30

His Leu Glu Ile Arg Glu Asp Gly Thr Val Gly Gly Ala Ala Asp Gln
      35        40        45

Ser Cys Glu Ser Leu Leu Gln Leu Lys Ala Leu Lys Pro Gly Val Ile
50          55         60

Gln Ile Leu Gly Val Cys Thr Ser Arg Phe Leu Cys Gln Arg Pro Asp
65        70         75        80

Gly Ala Leu Tyr Gly Ser Leu His Phe Asp Pro Glu Ala Cys Ser Phe
        85         90        95

Arg Glu Leu Leu Leu Glu Asp Gly Tyr Asn Val Tyr Gln Ser Glu Ala
        100        105        110

His Gly Leu Pro Leu His Leu Pro Gly Asn Lys Ser Pro His Arg Asp
      115        120        125

Pro Ala Pro Arg Gly Pro Ala Arg Phe Leu Pro Leu Pro Gly Leu Pro
130        135         140

Pro Ala Pro Pro Glu Pro Pro Gly Ile Leu Ala Pro Gln Pro Pro Asp
145        150         155        160

Val Gly Ser Ser Asp Pro Leu Ser Met Val Gly Pro Ser Gln Gly Arg
        165        170        175

Ser Pro Ser Tyr Ala Ser
      180

<210> SEQ ID NO 118
<211> LENGTH: 182
<212> TYPE: PRT
<213> ORGANISM: Artificial Sequence
<220> FEATURE:
<223> OTHER INFORMATION: G-FGF21 E78C, T98C

<400> SEQUENCE: 118

Gly His Pro Ile Pro Asp Ser Ser Pro Leu Leu Gln Phe Gly Gly Gln
1        5         10        15

Val Arg Gln Arg Tyr Leu Tyr Thr Asp Asp Ala Gln Gln Thr Glu Ala
    20        25        30

His Leu Glu Ile Arg Glu Asp Gly Thr Val Gly Gly Ala Ala Asp Gln
      35        40        45

Ser Pro Cys Ser Leu Leu Gln Leu Lys Ala Leu Lys Pro Gly Val Ile
50          55         60

Gln Ile Leu Gly Val Lys Cys Ser Arg Phe Leu Cys Gln Arg Pro Asp
65        70         75        80

Gly Ala Leu Tyr Gly Ser Leu His Phe Asp Pro Glu Ala Cys Ser Phe
        85         90        95

Arg Glu Leu Leu Leu Glu Asp Gly Tyr Asn Val Tyr Gln Ser Glu Ala
        100        105        110

His Gly Leu Pro Leu His Leu Pro Gly Asn Lys Ser Pro His Arg Asp
      115        120        125

Pro Ala Pro Arg Gly Pro Ala Arg Phe Leu Pro Leu Pro Gly Leu Pro
130        135         140

Pro Ala Pro Pro Glu Pro Pro Gly Ile Leu Ala Pro Gln Pro Pro Asp
145        150         155        160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 119
<211> LENGTH: 182
<212> TYPE: PRT
<213> ORGANISM: Artificial Sequence
<220> FEATURE:
<223> OTHER INFORMATION: G-FGF21 L80C, V96C

<400> SEQUENCE: 119

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Cys Leu Gln Leu Lys Ala Leu Lys Pro Gly Val Ile
        50                  55                  60

Gln Ile Leu Gly Cys Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 120
<211> LENGTH: 182
<212> TYPE: PRT
<213> ORGANISM: Artificial Sequence
<220> FEATURE:
<223> OTHER INFORMATION: G-FGF21 H145C, P161C

<400> SEQUENCE: 120

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu Cys Leu Pro Gly Asn Lys Ser Pro His Arg Asp
            115                 120                 125

Pro Ala Pro Arg Gly Cys Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 121
<211> LENGTH: 182
<212> TYPE: PRT
<213> ORGANISM: Artificial Sequence
<220> FEATURE:
<223> OTHER INFORMATION: G-FGF21 L81C, G95C

<400> SEQUENCE: 121

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Cys Gln Leu Lys Ala Leu Lys Pro Gly Val Ile
    50                  55                  60

Gln Ile Leu Cys Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 122
<211> LENGTH: 182
<212> TYPE: PRT
<213> ORGANISM: Artificial Sequence
<220> FEATURE:
<223> OTHER INFORMATION: G-FGF21 Q82C, L94C

<400> SEQUENCE: 122

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Cys Leu Lys Ala Leu Lys Pro Gly Val Ile
 50                  55                  60

Gln Ile Cys Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 123
<211> LENGTH: 182
<212> TYPE: PRT
<213> ORGANISM: Artificial Sequence
<220> FEATURE:
<223> OTHER INFORMATION: G-FGF21 L83C, I91C

<400> SEQUENCE: 123

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Cys Lys Ala Leu Lys Pro Gly Val Cys
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 124
<211> LENGTH: 182
<212> TYPE: PRT
<213> ORGANISM: Artificial Sequence
<220> FEATURE:
<223> OTHER INFORMATION: G-FGF21 D155L

<400> SEQUENCE: 124

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Leu
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 125
<211> LENGTH: 182
<212> TYPE: PRT
<213> ORGANISM: Artificial Sequence
<220> FEATURE:
<223> OTHER INFORMATION: G-FGF21 D155K

<400> SEQUENCE: 125

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Lys
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 126
<211> LENGTH: 182
<212> TYPE: PRT
<213> ORGANISM: Artificial Sequence
<220> FEATURE:
<223> OTHER INFORMATION: G-FGF21 D155Y

<400> SEQUENCE: 126

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Tyr
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 127
<211> LENGTH: 182
<212> TYPE: PRT
<213> ORGANISM: Artificial Sequence
<220> FEATURE:
<223> OTHER INFORMATION: G-FGF21 D155P

<400> SEQUENCE: 127

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Pro
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 128
<211> LENGTH: 182
<212> TYPE: PRT
<213> ORGANISM: Artificial Sequence
<220> FEATURE:
<223> OTHER INFORMATION: G-FGF21 D155E

<400> SEQUENCE: 128

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Glu
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 129

```
<211> LENGTH: 182
<212> TYPE: PRT
<213> ORGANISM: Artificial Sequence
<220> FEATURE:
<223> OTHER INFORMATION: G-FGF21 D155N

<400> SEQUENCE: 129
```

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asn
        115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

```
<210> SEQ ID NO 130
<211> LENGTH: 182
<212> TYPE: PRT
<213> ORGANISM: Artificial Sequence
<220> FEATURE:
<223> OTHER INFORMATION: G-FGF21 R154Q, D155L

<400> SEQUENCE: 130
```

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Gln Leu
        115                 120                 125

-continued

```
Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 131
<211> LENGTH: 182
<212> TYPE: PRT
<213> ORGANISM: Artificial Sequence
<220> FEATURE:
<223> OTHER INFORMATION: G-FGF21 R154Q, D155K

<400> SEQUENCE: 131

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Gln Lys
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 132
<211> LENGTH: 182
<212> TYPE: PRT
<213> ORGANISM: Artificial Sequence
<220> FEATURE:
<223> OTHER INFORMATION: G-FGF21 H153Q, R154Q, D155N, A157V, R159K

<400> SEQUENCE: 132

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60
```

```
Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro Gln Gln Asn
            115                 120                 125

Pro Val Pro Lys Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 133
<211> LENGTH: 182
<212> TYPE: PRT
<213> ORGANISM: Artificial Sequence
<220> FEATURE:
<223> OTHER INFORMATION: G-FGF21 P152A, H153K, R154K, D155E, P156A,
      A157S, R159Q

<400> SEQUENCE: 133

Gly His Pro Ile Pro Asp Ser Ser Pro Leu Leu Gln Phe Gly Gly Gln
  1               5                  10                  15

Val Arg Gln Arg Tyr Leu Tyr Thr Asp Asp Ala Gln Gln Thr Glu Ala
             20                  25                  30

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Ala Lys Lys Glu
            115                 120                 125

Ala Ser Pro Gln Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 134
<211> LENGTH: 182
<212> TYPE: PRT
<213> ORGANISM: Artificial Sequence
<220> FEATURE:
<223> OTHER INFORMATION: G-FGF21 H153Y, R154K, D155N, P156K, A157G
```

<400> SEQUENCE: 134

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro Tyr Lys Asn
            115                 120                 125

Lys Gly Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 135
<211> LENGTH: 180
<212> TYPE: PRT
<213> ORGANISM: Artificial Sequence
<220> FEATURE:
<223> OTHER INFORMATION: G-FGF21 P152-H153 deleted

<400> SEQUENCE: 135

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Arg Asp Pro Ala
            115                 120                 125

Pro Arg Gly Pro Ala Arg Phe Leu Pro Leu Pro Gly Leu Pro Pro Ala
130                 135                 140

Pro Pro Glu Pro Pro Gly Ile Leu Ala Pro Gln Pro Pro Asp Val Gly
145                 150                 155                 160

```
Ser Ser Asp Pro Leu Ser Met Val Gly Pro Ser Gln Gly Arg Ser Pro
                165                 170                 175

Ser Tyr Ala Ser
            180

<210> SEQ ID NO 136
<211> LENGTH: 171
<212> TYPE: PRT
<213> ORGANISM: Artificial Sequence
<220> FEATURE:
<223> OTHER INFORMATION: G-FGF21 N149-R163 deleted and replaced by GSGS

<400> SEQUENCE: 136

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gly Ser Gly Ser Phe Leu Pro
        115                 120                 125

Leu Pro Gly Leu Pro Pro Ala Pro Pro Glu Pro Pro Gly Ile Leu Ala
    130                 135                 140

Pro Gln Pro Pro Asp Val Gly Ser Ser Asp Pro Leu Ser Met Val Gly
145                 150                 155                 160

Pro Ser Gln Gly Arg Ser Pro Ser Tyr Ala Ser
                165                 170

<210> SEQ ID NO 137
<211> LENGTH: 173
<212> TYPE: PRT
<213> ORGANISM: Artificial Sequence
<220> FEATURE:
<223> OTHER INFORMATION: G-FGF21 N149-A162 deleted and replaced by GSHSG

<400> SEQUENCE: 137

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110
```

His Gly Leu Pro Leu His Leu Pro Gly Gly Ser His Ser Gly Arg Phe
        115                 120                 125

Leu Pro Leu Pro Gly Leu Pro Pro Ala Pro Pro Glu Pro Pro Gly Ile
130                 135                 140

Leu Ala Pro Gln Pro Pro Asp Val Gly Ser Ser Asp Pro Leu Ser Met
145                 150                 155                 160

Val Gly Pro Ser Gln Gly Arg Ser Pro Ser Tyr Ala Ser
                165                 170

<210> SEQ ID NO 138
<211> LENGTH: 174
<212> TYPE: PRT
<213> ORGANISM: Artificial Sequence
<220> FEATURE:
<223> OTHER INFORMATION: G-FGF21 N149-A162 deleted and replaced by
      GSHSGS

<400> SEQUENCE: 138

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gly Ser His Ser Gly Ser Arg
        115                 120                 125

Phe Leu Pro Leu Pro Gly Leu Pro Pro Ala Pro Pro Glu Pro Pro Gly
    130                 135                 140

Ile Leu Ala Pro Gln Pro Pro Asp Val Gly Ser Ser Asp Pro Leu Ser
145                 150                 155                 160

Met Val Gly Pro Ser Gln Gly Arg Ser Pro Ser Tyr Ala Ser
                165                 170

<210> SEQ ID NO 139
<211> LENGTH: 182
<212> TYPE: PRT
<213> ORGANISM: Artificial Sequence
<220> FEATURE:
<223> OTHER INFORMATION: G-FGF21 K150H

<400> SEQUENCE: 139

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

```
Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn His Ser Pro His Arg Asp
                115                 120                 125

Pro Ala Pro Arg Gly Pro Ala Arg Phe Leu Pro Leu Pro Gly Leu Pro
                130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 140
<211> LENGTH: 182
<212> TYPE: PRT
<213> ORGANISM: Artificial Sequence
<220> FEATURE:
<223> OTHER INFORMATION: G-FGF21 K150H, P152L

<400> SEQUENCE: 140

Gly His Pro Ile Pro Asp Ser Ser Pro Leu Leu Gln Phe Gly Gly Gln
  1               5                  10                  15

Val Arg Gln Arg Tyr Leu Tyr Thr Asp Asp Ala Gln Gln Thr Glu Ala
                 20                  25                  30

His Leu Glu Ile Arg Glu Asp Gly Thr Val Gly Gly Ala Ala Asp Gln
                 35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn His Ser Leu His Arg Asp
                115                 120                 125

Pro Ala Pro Arg Gly Pro Ala Arg Phe Leu Pro Leu Pro Gly Leu Pro
                130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 141
<211> LENGTH: 182
<212> TYPE: PRT
<213> ORGANISM: Artificial Sequence
<220> FEATURE:
<223> OTHER INFORMATION: G-FGF21 R163H
```

<400> SEQUENCE: 141

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
            85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala His Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
            165                 170                 175

Ser Pro Ser Tyr Ala Ser
            180

<210> SEQ ID NO 142
<211> LENGTH: 182
<212> TYPE: PRT
<213> ORGANISM: Artificial Sequence
<220> FEATURE:
<223> OTHER INFORMATION: G-FGF21 P158H, R159H

<400> SEQUENCE: 142

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
            85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala His His Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 143
<211> LENGTH: 179
<212> TYPE: PRT
<213> ORGANISM: Artificial Sequence
<220> FEATURE:
<223> OTHER INFORMATION: G-FGF21 N149-D155 deleted and replaced by GSGS

<400> SEQUENCE: 143

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Gly Ser Gly Ser Pro Ala Pro
        115                 120                 125

Arg Gly Pro Ala Arg Phe Leu Pro Leu Pro Gly Leu Pro Pro Ala Pro
    130                 135                 140

Pro Glu Pro Pro Gly Ile Leu Ala Pro Gln Pro Pro Asp Val Gly Ser
145                 150                 155                 160

Ser Asp Pro Leu Ser Met Val Gly Pro Ser Gln Gly Arg Ser Pro Ser
                165                 170                 175

Tyr Ala Ser

<210> SEQ ID NO 144
<211> LENGTH: 180
<212> TYPE: PRT
<213> ORGANISM: Artificial Sequence
<220> FEATURE:
<223> OTHER INFORMATION: G-FGF21 N149-D155 deleted and replaced by GSHSG

<400> SEQUENCE: 144

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

```
Arg Glu Leu Leu Leu Glu Asp Gly Tyr Asn Val Tyr Gln Ser Glu Ala
            100                 105                 110

His Gly Leu Pro Leu His Leu Pro Gly Ser His Ser Gly Pro Ala
            115                 120                 125

Pro Arg Gly Pro Ala Arg Phe Leu Pro Leu Pro Gly Leu Pro Pro Ala
130                 135                 140

Pro Pro Glu Pro Pro Gly Ile Leu Ala Pro Gln Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 145
<211> LENGTH: 179
<212> TYPE: PRT
<213> ORGANISM: Artificial Sequence
<220> FEATURE:
<223> OTHER INFORMATION: G-FGF21 N149-D155 deleted and replaced by ATTS

<400> SEQUENCE: 145

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Ala Thr Thr Ser Pro Ala Pro
            115                 120                 125

Arg Gly Pro Ala Arg Phe Leu Pro Leu Pro Gly Leu Pro Pro Ala Pro
            130                 135                 140

Pro Glu Pro Pro Gly Ile Leu Ala Pro Gln Pro Pro Asp Val Gly Ser
145                 150                 155                 160

Ser Asp Pro Leu Ser Met Val Gly Pro Ser Gln Gly Arg Ser Pro Ser
                165                 170                 175

Tyr Ala Ser

<210> SEQ ID NO 146
<211> LENGTH: 179
<212> TYPE: PRT
<213> ORGANISM: Artificial Sequence
<220> FEATURE:
<223> OTHER INFORMATION: G-FGF21 R159-R163 deleted and replaced by GA

<400> SEQUENCE: 146

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30
```

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
             100                 105                 110

His Gly Leu Pro Leu His Leu Pro Gly Asn Lys Ser Pro His Arg Asp
             115                 120                 125

Pro Ala Pro Gly Ala Phe Leu Pro Leu Pro Gly Leu Pro Pro Ala Pro
130                 135                 140

Pro Glu Pro Pro Gly Ile Leu Ala Pro Gln Pro Pro Asp Val Gly Ser
145                 150                 155                 160

Ser Asp Pro Leu Ser Met Val Gly Pro Ser Gln Gly Arg Ser Pro Ser
                 165                 170                 175

Tyr Ala Ser

<210> SEQ ID NO 147
<211> LENGTH: 179
<212> TYPE: PRT
<213> ORGANISM: Artificial Sequence
<220> FEATURE:
<223> OTHER INFORMATION: G-FGF21 R159-R163 deleted and replaced by GY

<400> SEQUENCE: 147

Gly His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
             20                  25                  30

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
             100                 105                 110

His Gly Leu Pro Leu His Leu Pro Gly Asn Lys Ser Pro His Arg Asp
             115                 120                 125

Pro Ala Pro Gly Tyr Phe Leu Pro Leu Pro Gly Leu Pro Pro Ala Pro
130                 135                 140

Pro Glu Pro Pro Gly Ile Leu Ala Pro Gln Pro Pro Asp Val Gly Ser
145                 150                 155                 160

Ser Asp Pro Leu Ser Met Val Gly Pro Ser Gln Gly Arg Ser Pro Ser
                 165                 170                 175

Tyr Ala Ser

<210> SEQ ID NO 148
<211> LENGTH: 179
<212> TYPE: PRT
<213> ORGANISM: Artificial Sequence
<220> FEATURE:
<223> OTHER INFORMATION: G-FGF21 R159-R163 deleted and replaced by HH

<400> SEQUENCE: 148

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro His His Phe Leu Pro Leu Pro Gly Leu Pro Pro Ala Pro
    130                 135                 140

Pro Glu Pro Pro Gly Ile Leu Ala Pro Gln Pro Pro Asp Val Gly Ser
145                 150                 155                 160

Ser Asp Pro Leu Ser Met Val Gly Pro Ser Gln Gly Arg Ser Pro Ser
                165                 170                 175

Tyr Ala Ser

<210> SEQ ID NO 149
<211> LENGTH: 179
<212> TYPE: PRT
<213> ORGANISM: Artificial Sequence
<220> FEATURE:
<223> OTHER INFORMATION: G-FGF21 R159-R163 deleted and replaced by GE

<400> SEQUENCE: 149

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Gly Glu Phe Leu Pro Leu Pro Gly Leu Pro Pro Ala Pro
    130                 135                 140

Pro Glu Pro Pro Gly Ile Leu Ala Pro Gln Pro Pro Asp Val Gly Ser
145                 150                 155                 160

Ser Asp Pro Leu Ser Met Val Gly Pro Ser Gln Gly Arg Ser Pro Ser
            165                 170                 175

Tyr Ala Ser

<210> SEQ ID NO 150
<211> LENGTH: 179
<212> TYPE: PRT
<213> ORGANISM: Artificial Sequence
<220> FEATURE:
<223> OTHER INFORMATION: G-FGF21 R159-R163 deleted and replaced by HE

<400> SEQUENCE: 150

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro His Glu Phe Leu Pro Leu Pro Gly Leu Pro Pro Ala Pro
    130                 135                 140

Pro Glu Pro Pro Gly Ile Leu Ala Pro Gln Pro Pro Asp Val Gly Ser
145                 150                 155                 160

Ser Asp Pro Leu Ser Met Val Gly Pro Ser Gln Gly Arg Ser Pro Ser
            165                 170                 175

Tyr Ala Ser

<210> SEQ ID NO 151
<211> LENGTH: 182
<212> TYPE: PRT
<213> ORGANISM: Artificial Sequence
<220> FEATURE:
<223> OTHER INFORMATION: G-FGF21 A162Y

<400> SEQUENCE: 151

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

```
Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Tyr Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 152
<211> LENGTH: 182
<212> TYPE: PRT
<213> ORGANISM: Artificial Sequence
<220> FEATURE:
<223> OTHER INFORMATION: G-FGF21 R159H

<400> SEQUENCE: 152

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro His Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 153
<211> LENGTH: 182
<212> TYPE: PRT
<213> ORGANISM: Artificial Sequence
<220> FEATURE:
<223> OTHER INFORMATION: G-FGF21 S200M

<400> SEQUENCE: 153

```
Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30
```

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Met Gln Gly Arg
                165                 170                 175

Ser Pro Ser Tyr Ala Ser
            180

<210> SEQ ID NO 154
<211> LENGTH: 182
<212> TYPE: PRT
<213> ORGANISM: Artificial Sequence
<220> FEATURE:
<223> OTHER INFORMATION: G-FGF21 G202T

<400> SEQUENCE: 154

Gly His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Thr Arg
                165                 170                 175

Ser Pro Ser Tyr Ala Ser
            180

<210> SEQ ID NO 155

```
<211> LENGTH: 182
<212> TYPE: PRT
<213> ORGANISM: Artificial Sequence
<220> FEATURE:
<223> OTHER INFORMATION: G-FGF21 R203E

<400> SEQUENCE: 155

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Glu
                165                 170                 175

Ser Pro Ser Tyr Ala Ser
            180

<210> SEQ ID NO 156
<211> LENGTH: 182
<212> TYPE: PRT
<213> ORGANISM: Artificial Sequence
<220> FEATURE:
<223> OTHER INFORMATION: G-FGF21 R203H

<400> SEQUENCE: 156

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125
```

```
Pro Ala Pro Arg Gly Pro Ala Arg Phe Leu Pro Leu Pro Gly Leu Pro
            130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly His
                165                 170                 175

Ser Pro Ser Tyr Ala Ser
            180

<210> SEQ ID NO 157
<211> LENGTH: 180
<212> TYPE: PRT
<213> ORGANISM: Artificial Sequence
<220> FEATURE:
<223> OTHER INFORMATION: G-FGF21 G202-R203 deleted

<400> SEQUENCE: 157

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Ser Pro
                165                 170                 175

Ser Tyr Ala Ser
            180

<210> SEQ ID NO 158
<211> LENGTH: 143
<212> TYPE: PRT
<213> ORGANISM: Artificial Sequence
<220> FEATURE:
<223> OTHER INFORMATION: FGF21 (S34-E176), Q55C, N149C

<400> SEQUENCE: 158

Ser Ser Pro Leu Leu Gln Phe Gly Gly Gln Val Arg Gln Arg Tyr Leu
1               5                   10                  15

Tyr Thr Asp Asp Ala Cys Gln Thr Glu Ala His Leu Glu Ile Arg Glu
            20                  25                  30

Asp Gly Thr Val Gly Gly Ala Ala Asp Gln Ser Pro Glu Ser Leu Leu
        35                  40                  45
```

```
Gln Leu Lys Ala Leu Lys Pro Gly Val Ile Gln Ile Leu Gly Val Lys
 50                  55                  60

Thr Ser Arg Phe Leu Cys Gln Arg Pro Asp Gly Ala Leu Tyr Gly Ser
 65                  70                  75                  80

Leu His Phe Asp Pro Glu Ala Cys Ser Phe Arg Glu Leu Leu Leu Glu
                 85                  90                  95

Asp Gly Tyr Asn Val Tyr Gln Ser Glu Ala His Gly Leu Pro Leu His
                100                 105                 110

Leu Pro Gly Cys Lys Ser Pro His Arg Asp Pro Ala Pro Arg Gly Pro
            115                 120                 125

Ala Arg Phe Leu Pro Leu Pro Gly Leu Pro Pro Ala Pro Pro Glu
            130                 135                 140

<210> SEQ ID NO 159
<211> LENGTH: 199
<212> TYPE: PRT
<213> ORGANISM: Artificial Sequence
<220> FEATURE:
<223> OTHER INFORMATION: G-FGF21 PLSMVGPSQGRSPSYAS inserted after S209

<400> SEQUENCE: 159

Gly His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
                 20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
            130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser Pro Leu Ser Met Val Gly Pro Ser Gln Gly
            180                 185                 190

Arg Ser Pro Ser Tyr Ala Ser
            195

<210> SEQ ID NO 160
<211> LENGTH: 198
<212> TYPE: PRT
<213> ORGANISM: Artificial Sequence
<220> FEATURE:
<223> OTHER INFORMATION: G-FGF21 P199 deleted, PLSMVGSQGRSPSYAS inserted
      after S209
```

<400> SEQUENCE: 160

```
Gly His Pro Ile Pro Asp Ser Ser Pro Leu Leu Gln Phe Gly Gln
1               5                  10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser Pro Leu Ser Met Val Gly Ser Gln Gly Arg
                180                 185                 190

Ser Pro Ser Tyr Ala Ser
        195
```

<210> SEQ ID NO 161
<211> LENGTH: 4
<212> TYPE: PRT
<213> ORGANISM: Artificial Sequence
<220> FEATURE:
<223> OTHER INFORMATION: Linker

<400> SEQUENCE: 161

```
Gly Ser Gly Ser
1
```

<210> SEQ ID NO 162
<211> LENGTH: 6
<212> TYPE: PRT
<213> ORGANISM: Artificial Sequence
<220> FEATURE:
<223> OTHER INFORMATION: Linker

<400> SEQUENCE: 162

```
Gly Gly Ser Gly Gly Ser
1               5
```

<210> SEQ ID NO 163
<211> LENGTH: 5
<212> TYPE: PRT
<213> ORGANISM: Artificial Sequence
<220> FEATURE:
<223> OTHER INFORMATION: Linker

```
<400> SEQUENCE: 163

Gly Ser His Ser Gly
1               5

<210> SEQ ID NO 164
<211> LENGTH: 4
<212> TYPE: PRT
<213> ORGANISM: Artificial Sequence
<220> FEATURE:
<223> OTHER INFORMATION: Linker

<400> SEQUENCE: 164

Ala Thr Thr Ser
1

<210> SEQ ID NO 165
<211> LENGTH: 6
<212> TYPE: PRT
<213> ORGANISM: Artificial Sequence
<220> FEATURE:
<223> OTHER INFORMATION: Linker

<400> SEQUENCE: 165

Gly Ser His Ser Gly Ser
1               5

<210> SEQ ID NO 166
<211> LENGTH: 10
<212> TYPE: PRT
<213> ORGANISM: Artificial Sequence
<220> FEATURE:
<223> OTHER INFORMATION: Linker

<400> SEQUENCE: 166

Gly His Arg Ser His Leu Gln Thr Val Phe
1               5                   10

<210> SEQ ID NO 167
<211> LENGTH: 6
<212> TYPE: PRT
<213> ORGANISM: Artificial Sequence
<220> FEATURE:
<223> OTHER INFORMATION: Linker

<400> SEQUENCE: 167

Gly Leu Asn Ser Met Val
1               5

<210> SEQ ID NO 168
<211> LENGTH: 5
<212> TYPE: PRT
<213> ORGANISM: Artificial Sequence
<220> FEATURE:
<223> OTHER INFORMATION: Linker

<400> SEQUENCE: 168

Gly Gly Gly Gly Ser
1               5

<210> SEQ ID NO 169
<211> LENGTH: 17
<212> TYPE: PRT
<213> ORGANISM: Artificial Sequence
<220> FEATURE:
<223> OTHER INFORMATION: C-terminal extension
```

-continued

<400> SEQUENCE: 169

Pro Leu Ser Met Val Gly Pro Ser Gln Gly Arg Ser Pro Ser Tyr Ala
1               5                   10                  15

Ser

<210> SEQ ID NO 170
<211> LENGTH: 16
<212> TYPE: PRT
<213> ORGANISM: Artificial Sequence
<220> FEATURE:
<223> OTHER INFORMATION: C-terminal extension

<400> SEQUENCE: 170

Pro Leu Ser Met Val Gly Ser Gln Gly Arg Ser Pro Ser Tyr Ala Ser
1               5                   10                  15

<210> SEQ ID NO 171
<211> LENGTH: 209
<212> TYPE: PRT
<213> ORGANISM: Artificial Sequence
<220> FEATURE:
<223> OTHER INFORMATION: FGF21 variant, consensus sequence I
<220> FEATURE:
<221> NAME/KEY: misc_feature
<222> LOCATION: (1)..(28)
<223> OTHER INFORMATION: Signal peptide
<220> FEATURE:
<221> NAME/KEY: misc_feature
<222> LOCATION: (55)..(55)
<223> OTHER INFORMATION: Xaa is Q or another amino acid
<220> FEATURE:
<221> NAME/KEY: misc_feature
<222> LOCATION: (147)..(147)
<223> OTHER INFORMATION: Xaa is P or C or deleted
<220> FEATURE:
<221> NAME/KEY: misc_feature
<222> LOCATION: (148)..(148)
<223> OTHER INFORMATION: Xaa is G or C or deleted
<220> FEATURE:
<221> NAME/KEY: misc_feature
<222> LOCATION: (149)..(149)
<223> OTHER INFORMATION: Xaa is N or C or deleted
<220> FEATURE:
<221> NAME/KEY: misc_feature
<222> LOCATION: (150)..(150)
<223> OTHER INFORMATION: Xaa is K or another amino acid or deleted
<220> FEATURE:
<221> NAME/KEY: misc_feature
<222> LOCATION: (151)..(151)
<223> OTHER INFORMATION: Xaa is S or deleted
<220> FEATURE:
<221> NAME/KEY: misc_feature
<222> LOCATION: (152)..(152)
<223> OTHER INFORMATION: Xaa is P or another amino acid or deleted
<220> FEATURE:
<221> NAME/KEY: misc_feature
<222> LOCATION: (153)..(153)
<223> OTHER INFORMATION: Xaa is H or another amino acid or deleted
<220> FEATURE:
<221> NAME/KEY: misc_feature
<222> LOCATION: (154)..(154)
<223> OTHER INFORMATION: Xaa is R or another amino acid or deleted
<220> FEATURE:
<221> NAME/KEY: misc_feature
<222> LOCATION: (155)..(155)
<223> OTHER INFORMATION: Xaa is D or another amino acid or deleted
<220> FEATURE:
<221> NAME/KEY: misc_feature
<222> LOCATION: (156)..(156)
<223> OTHER INFORMATION: Xaa is P or another amino acid or deleted
<220> FEATURE:
<221> NAME/KEY: misc_feature
<222> LOCATION: (157)..(157)
<223> OTHER INFORMATION: Xaa is A or another amino acid or deleted

```
<220> FEATURE:
<221> NAME/KEY: misc_feature
<222> LOCATION: (158)..(158)
<223> OTHER INFORMATION: Xaa is P or another amino acid or deleted
<220> FEATURE:
<221> NAME/KEY: misc_feature
<222> LOCATION: (159)..(159)
<223> OTHER INFORMATION: Xaa is R or another amino acid or deleted
<220> FEATURE:
<221> NAME/KEY: misc_feature
<222> LOCATION: (160)..(160)
<223> OTHER INFORMATION: Xaa is G or deleted
<220> FEATURE:
<221> NAME/KEY: misc_feature
<222> LOCATION: (161)..(161)
<223> OTHER INFORMATION: Xaa is P or C or deleted
<220> FEATURE:
<221> NAME/KEY: misc_feature
<222> LOCATION: (162)..(162)
<223> OTHER INFORMATION: Xaa is A or another amino acid or deleted
<220> FEATURE:
<221> NAME/KEY: misc_feature
<222> LOCATION: (163)..(163)
<223> OTHER INFORMATION: Xaa is R or another amino acid or deleted
<220> FEATURE:
<221> NAME/KEY: misc_feature
<222> LOCATION: (184)..(184)
<223> OTHER INFORMATION: Xaa is Q or deleted
<220> FEATURE:
<221> NAME/KEY: misc_feature
<222> LOCATION: (185)..(185)
<223> OTHER INFORMATION: Xaa is P or deleted
<220> FEATURE:
<221> NAME/KEY: misc_feature
<222> LOCATION: (186)..(186)
<223> OTHER INFORMATION: Xaa is P or deleted
<220> FEATURE:
<221> NAME/KEY: misc_feature
<222> LOCATION: (187)..(187)
<223> OTHER INFORMATION: Xaa is D or deleted
<220> FEATURE:
<221> NAME/KEY: misc_feature
<222> LOCATION: (188)..(188)
<223> OTHER INFORMATION: Xaa is V or deleted
<220> FEATURE:
<221> NAME/KEY: misc_feature
<222> LOCATION: (189)..(189)
<223> OTHER INFORMATION: Xaa is G or deleted
<220> FEATURE:
<221> NAME/KEY: misc_feature
<222> LOCATION: (190)..(190)
<223> OTHER INFORMATION: Xaa is S or deleted
<220> FEATURE:
<221> NAME/KEY: misc_feature
<222> LOCATION: (191)..(191)
<223> OTHER INFORMATION: Xaa is S or deleted
<220> FEATURE:
<221> NAME/KEY: misc_feature
<222> LOCATION: (192)..(192)
<223> OTHER INFORMATION: Xaa is D or deleted
<220> FEATURE:
<221> NAME/KEY: misc_feature
<222> LOCATION: (193)..(193)
<223> OTHER INFORMATION: Xaa is P or deleted
<220> FEATURE:
<221> NAME/KEY: misc_feature
<222> LOCATION: (194)..(194)
<223> OTHER INFORMATION: Xaa is L or deleted
<220> FEATURE:
<221> NAME/KEY: misc_feature
<222> LOCATION: (195)..(195)
<223> OTHER INFORMATION: Xaa is S or C or deleted
<220> FEATURE:
<221> NAME/KEY: misc_feature
<222> LOCATION: (196)..(196)
<223> OTHER INFORMATION: Xaa is M or another amino acid or deleted
<220> FEATURE:
<221> NAME/KEY: misc_feature
<222> LOCATION: (197)..(197)
```

```
<223> OTHER INFORMATION: Xaa is V or another amino acid or deleted
<220> FEATURE:
<221> NAME/KEY: misc_feature
<222> LOCATION: (198)..(198)
<223> OTHER INFORMATION: Xaa is G or another amino acid or deleted
<220> FEATURE:
<221> NAME/KEY: misc_feature
<222> LOCATION: (199)..(199)
<223> OTHER INFORMATION: Xaa is P or another amino acid or deleted
<220> FEATURE:
<221> NAME/KEY: misc_feature
<222> LOCATION: (200)..(200)
<223> OTHER INFORMATION: Xaa is S or another amino acid or deleted
<220> FEATURE:
<221> NAME/KEY: misc_feature
<222> LOCATION: (201)..(201)
<223> OTHER INFORMATION: Xaa is Q or another amino acid or deleted
<220> FEATURE:
<221> NAME/KEY: misc_feature
<222> LOCATION: (202)..(202)
<223> OTHER INFORMATION: Xaa is G or another amino acid or deleted
<220> FEATURE:
<221> NAME/KEY: misc_feature
<222> LOCATION: (203)..(203)
<223> OTHER INFORMATION: Xaa is R or another amino acid or deleted
<220> FEATURE:
<221> NAME/KEY: misc_feature
<222> LOCATION: (204)..(204)
<223> OTHER INFORMATION: Xaa is S or deleted
<220> FEATURE:
<221> NAME/KEY: misc_feature
<222> LOCATION: (205)..(205)
<223> OTHER INFORMATION: Xaa is P or deleted
<220> FEATURE:
<221> NAME/KEY: misc_feature
<222> LOCATION: (206)..(206)
<223> OTHER INFORMATION: Xaa is S or deleted
<220> FEATURE:
<221> NAME/KEY: misc_feature
<222> LOCATION: (207)..(207)
<223> OTHER INFORMATION: Xaa is Y or deleted

<400> SEQUENCE: 171

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Ala Xaa Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu
        115                 120                 125

Glu Asp Gly Tyr Asn Val Tyr Gln Ser Glu Ala His Gly Leu Pro Leu
130                 135                 140

His Leu Xaa Xaa Xaa Xaa Xaa Xaa Xaa Xaa Xaa Xaa Xaa Xaa
145                 150                 155                 160

Xaa Xaa Xaa Phe Leu Pro Leu Pro Gly Leu Pro Pro Ala Pro Pro Glu
                165                 170                 175

Pro Pro Gly Ile Leu Ala Pro Xaa Xaa Xaa Xaa Xaa Xaa Xaa Xaa
            180                 185                 190
```

```
Xaa Xaa Xaa Xaa Xaa Xaa Xaa Xaa Xaa Xaa Xaa Xaa Xaa Ala
        195                 200                 205

Ser

<210> SEQ ID NO 172
<211> LENGTH: 209
<212> TYPE: PRT
<213> ORGANISM: Homo sapiens

<400> SEQUENCE: 172

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Ser Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 173
<211> LENGTH: 209
<212> TYPE: PRT
<213> ORGANISM: Homo sapiens

<400> SEQUENCE: 173

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80
```

```
Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu
        115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 174
<211> LENGTH: 182
<212> TYPE: PRT
<213> ORGANISM: Artificial Sequence
<220> FEATURE:
<223> OTHER INFORMATION: G-FGF21 (L174 variant)

<400> SEQUENCE: 174

Gly His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 175
<211> LENGTH: 181
<212> TYPE: PRT
<213> ORGANISM: Artificial Sequence
<220> FEATURE:
```

```
<223> OTHER INFORMATION: FGF21 variant, consensus sequence II
<220> FEATURE:
<221> NAME/KEY: misc_feature
<222> LOCATION: (27)..(27)
<223> OTHER INFORMATION: Xaa is Q or C
<220> FEATURE:
<221> NAME/KEY: misc_feature
<222> LOCATION: (119)..(119)
<223> OTHER INFORMATION: Xaa is P or C
<220> FEATURE:
<221> NAME/KEY: misc_feature
<222> LOCATION: (120)..(120)
<223> OTHER INFORMATION: Xaa is G or C
<220> FEATURE:
<221> NAME/KEY: misc_feature
<222> LOCATION: (121)..(121)
<223> OTHER INFORMATION: Xaa is N or C
<220> FEATURE:
<221> NAME/KEY: misc_feature
<222> LOCATION: (127)..(127)
<223> OTHER INFORMATION: Xaa is D or C
<220> FEATURE:
<221> NAME/KEY: misc_feature
<222> LOCATION: (133)..(133)
<223> OTHER INFORMATION: Xaa is P or C
<220> FEATURE:
<221> NAME/KEY: misc_feature
<222> LOCATION: (134)..(134)
<223> OTHER INFORMATION: Xaa is A or C
<220> FEATURE:
<221> NAME/KEY: misc_feature
<222> LOCATION: (167)..(167)
<223> OTHER INFORMATION: Xaa is S or C
<220> FEATURE:
<221> NAME/KEY: misc_feature
<222> LOCATION: (168)..(168)
<223> OTHER INFORMATION: Xaa is M or another amino acid or deleted
<220> FEATURE:
<221> NAME/KEY: misc_feature
<222> LOCATION: (169)..(169)
<223> OTHER INFORMATION: Xaa is V or another amino acid or deleted
<220> FEATURE:
<221> NAME/KEY: misc_feature
<222> LOCATION: (170)..(170)
<223> OTHER INFORMATION: Xaa is G or another amino acid or deleted
<220> FEATURE:
<221> NAME/KEY: misc_feature
<222> LOCATION: (171)..(171)
<223> OTHER INFORMATION: Xaa is P or another amino acid or deleted
<220> FEATURE:
<221> NAME/KEY: misc_feature
<222> LOCATION: (172)..(172)
<223> OTHER INFORMATION: Xaa is S or another amino acid or deleted
<220> FEATURE:
<221> NAME/KEY: misc_feature
<222> LOCATION: (173)..(173)
<223> OTHER INFORMATION: Xaa is Q or another amino acid or deleted
<220> FEATURE:
<221> NAME/KEY: misc_feature
<222> LOCATION: (174)..(174)
<223> OTHER INFORMATION: Xaa is G or another amino acid or deleted
<220> FEATURE:
<221> NAME/KEY: misc_feature
<222> LOCATION: (175)..(175)
<223> OTHER INFORMATION: Xaa is R or another amino acid or deleted

<400> SEQUENCE: 175

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Xaa Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60
```

```
Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Xaa Xaa Xaa Lys Ser Pro His Arg Xaa Pro
            115                 120                 125

Ala Pro Arg Gly Xaa Xaa Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Xaa Xaa Xaa Xaa Xaa Xaa Xaa Xaa Xaa Ser
                165                 170                 175

Pro Ser Tyr Ala Ser
            180

<210> SEQ ID NO 176
<211> LENGTH: 181
<212> TYPE: PRT
<213> ORGANISM: Artificial Sequence
<220> FEATURE:
<223> OTHER INFORMATION: FGF21 variant, consensus sequence III
<220> FEATURE:
<221> NAME/KEY: misc_feature
<222> LOCATION: (27)..(27)
<223> OTHER INFORMATION: Xaa is Q or C
<220> FEATURE:
<221> NAME/KEY: misc_feature
<222> LOCATION: (119)..(119)
<223> OTHER INFORMATION: Xaa is P or C
<220> FEATURE:
<221> NAME/KEY: misc_feature
<222> LOCATION: (121)..(121)
<223> OTHER INFORMATION: Xaa is N or C
<220> FEATURE:
<221> NAME/KEY: misc_feature
<222> LOCATION: (127)..(127)
<223> OTHER INFORMATION: Xaa is D or C
<220> FEATURE:
<221> NAME/KEY: misc_feature
<222> LOCATION: (170)..(170)
<223> OTHER INFORMATION: Xaa is G or another amino acid or deleted
<220> FEATURE:
<221> NAME/KEY: misc_feature
<222> LOCATION: (171)..(171)
<223> OTHER INFORMATION: Xaa is P or another amino acid or deleted

<400> SEQUENCE: 176

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Xaa Gln Thr Glu Ala His
                 20                  25                  30

Leu Glu Ile Arg Glu Asp Gly Thr Val Gly Gly Ala Ala Asp Gln Ser
             35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110
```

```
Gly Leu Pro Leu His Leu Xaa Gly Xaa Lys Ser Pro His Arg Xaa Pro
            115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Xaa Xaa Ser Gln Gly Arg Ser
                165                 170                 175

Pro Ser Tyr Ala Ser
            180

<210> SEQ ID NO 177
<211> LENGTH: 181
<212> TYPE: PRT
<213> ORGANISM: Artificial Sequence
<220> FEATURE:
<223> OTHER INFORMATION: FGF21 S195C, S200C

<400> SEQUENCE: 177

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Cys Met Val Gly Pro Cys Gln Gly Arg Ser
                165                 170                 175

Pro Ser Tyr Ala Ser
            180

<210> SEQ ID NO 178
<211> LENGTH: 181
<212> TYPE: PRT
<213> ORGANISM: Artificial Sequence
<220> FEATURE:
<223> OTHER INFORMATION: FGF21 P199S, S200P

<400> SEQUENCE: 178

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30
```

```
Leu Glu Ile Arg Glu Asp Gly Thr Val Gly Gly Ala Ala Asp Gln Ser
         35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Ser Pro Gln Gly Arg Ser
                165                 170                 175

Pro Ser Tyr Ala Ser
            180

<210> SEQ ID NO 179
<211> LENGTH: 181
<212> TYPE: PRT
<213> ORGANISM: Artificial Sequence
<220> FEATURE:
<223> OTHER INFORMATION: FGF21 P199Q, Q201P

<400> SEQUENCE: 179

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
             20                  25                  30

Leu Glu Ile Arg Glu Asp Gly Thr Val Gly Gly Ala Ala Asp Gln Ser
         35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Gln Ser Pro Gly Arg Ser
                165                 170                 175

Pro Ser Tyr Ala Ser
            180

<210> SEQ ID NO 180
```

```
<211> LENGTH: 180
<212> TYPE: PRT
<213> ORGANISM: Artificial Sequence
<220> FEATURE:
<223> OTHER INFORMATION: FGF21 P199 deleted

<400> SEQUENCE: 180

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser Pro
                165                 170                 175

Ser Tyr Ala Ser
            180

<210> SEQ ID NO 181
<211> LENGTH: 181
<212> TYPE: PRT
<213> ORGANISM: Artificial Sequence
<220> FEATURE:
<223> OTHER INFORMATION: FGF21 M196P, V197G, G198V, P199M

<400> SEQUENCE: 181

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125
```

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Pro Gly Val Met Ser Gln Gly Arg Ser
                165                 170                 175

Pro Ser Tyr Ala Ser
            180

<210> SEQ ID NO 182
<211> LENGTH: 181
<212> TYPE: PRT
<213> ORGANISM: Artificial Sequence
<220> FEATURE:
<223> OTHER INFORMATION: FGF21 M196V, V197M

<400> SEQUENCE: 182

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Val Met Gly Pro Ser Gln Gly Arg Ser
                165                 170                 175

Pro Ser Tyr Ala Ser
            180

<210> SEQ ID NO 183
<211> LENGTH: 181
<212> TYPE: PRT
<213> ORGANISM: Artificial Sequence
<220> FEATURE:
<223> OTHER INFORMATION: FGF21 V197E

<400> SEQUENCE: 183

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

```
Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Glu Gly Pro Ser Gln Gly Arg Ser
                165                 170                 175

Pro Ser Tyr Ala Ser
            180

<210> SEQ ID NO 184
<211> LENGTH: 186
<212> TYPE: PRT
<213> ORGANISM: Artificial Sequence
<220> FEATURE:
<223> OTHER INFORMATION: FGF21 GGGGS (SEQ ID NO: 168) inserted between
      G198 and P199

<400> SEQUENCE: 184

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Gly Gly Gly Ser Pro
                165                 170                 175

Ser Gln Gly Arg Ser Pro Ser Tyr Ala Ser
            180                 185

<210> SEQ ID NO 185
<211> LENGTH: 181
<212> TYPE: PRT
```

<213> ORGANISM: Artificial Sequence
<220> FEATURE:
<223> OTHER INFORMATION: FGF21 G198E

<400> SEQUENCE: 185

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Glu Pro Ser Gln Gly Arg Ser
                165                 170                 175

Pro Ser Tyr Ala Ser
            180
```

<210> SEQ ID NO 186
<211> LENGTH: 181
<212> TYPE: PRT
<213> ORGANISM: Artificial Sequence
<220> FEATURE:
<223> OTHER INFORMATION: FGF21 G198D

<400> SEQUENCE: 186

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140
```

```
Ala Pro Pro Glu Pro Pro Gly Ile Leu Ala Pro Gln Pro Pro Asp Val
145                 150                 155                 160

Gly Ser Ser Asp Pro Leu Ser Met Val Asp Pro Ser Gln Gly Arg Ser
                165                 170                 175

Pro Ser Tyr Ala Ser
            180

<210> SEQ ID NO 187
<211> LENGTH: 181
<212> TYPE: PRT
<213> ORGANISM: Artificial Sequence
<220> FEATURE:
<223> OTHER INFORMATION: FGF21 G198R

<400> SEQUENCE: 187

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Arg Pro Ser Gln Gly Arg Ser
                165                 170                 175

Pro Ser Tyr Ala Ser
            180

<210> SEQ ID NO 188
<211> LENGTH: 181
<212> TYPE: PRT
<213> ORGANISM: Artificial Sequence
<220> FEATURE:
<223> OTHER INFORMATION: FGF21 G198K

<400> SEQUENCE: 188

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80
```

```
Ala Leu Tyr Gly Ser Leu His Phe Asp Pro Glu Ala Cys Ser Phe Arg
            85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Lys Pro Ser Gln Gly Arg Ser
            165                 170                 175

Pro Ser Tyr Ala Ser
            180

<210> SEQ ID NO 189
<211> LENGTH: 181
<212> TYPE: PRT
<213> ORGANISM: Artificial Sequence
<220> FEATURE:
<223> OTHER INFORMATION: FGF21 G198Y

<400> SEQUENCE: 189

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
            50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
            85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Tyr Pro Ser Gln Gly Arg Ser
            165                 170                 175

Pro Ser Tyr Ala Ser
            180

<210> SEQ ID NO 190
<211> LENGTH: 181
<212> TYPE: PRT
<213> ORGANISM: Artificial Sequence
<220> FEATURE:
<223> OTHER INFORMATION: FGF21 P199G
```

```
<400> SEQUENCE: 190

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser
                165                 170                 175

Pro Ser Tyr Ala Ser
            180

<210> SEQ ID NO 191
<211> LENGTH: 181
<212> TYPE: PRT
<213> ORGANISM: Artificial Sequence
<220> FEATURE:
<223> OTHER INFORMATION: FGF21 P199R

<400> SEQUENCE: 191

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160
```

```
Gly Ser Ser Asp Pro Leu Ser Met Val Gly Arg Ser Gln Gly Arg Ser
                165                 170                 175

Pro Ser Tyr Ala Ser
            180

<210> SEQ ID NO 192
<211> LENGTH: 181
<212> TYPE: PRT
<213> ORGANISM: Artificial Sequence
<220> FEATURE:
<223> OTHER INFORMATION: FGF21 P199T

<400> SEQUENCE: 192

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Thr Ser Gln Gly Arg Ser
                165                 170                 175

Pro Ser Tyr Ala Ser
            180

<210> SEQ ID NO 193
<211> LENGTH: 181
<212> TYPE: PRT
<213> ORGANISM: Artificial Sequence
<220> FEATURE:
<223> OTHER INFORMATION: FGF21 G198P, P199G

<400> SEQUENCE: 193

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95
```

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Pro Gly Ser Gln Gly Arg Ser
                165                 170                 175

Pro Ser Tyr Ala Ser
        180

<210> SEQ ID NO 194
<211> LENGTH: 181
<212> TYPE: PRT
<213> ORGANISM: Artificial Sequence
<220> FEATURE:
<223> OTHER INFORMATION: FGF21 S200Q, Q201S

<400> SEQUENCE: 194

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Gln Ser Gly Arg Ser
                165                 170                 175

Pro Ser Tyr Ala Ser
        180

<210> SEQ ID NO 195
<211> LENGTH: 181
<212> TYPE: PRT
<213> ORGANISM: Artificial Sequence
<220> FEATURE:
<223> OTHER INFORMATION: FGF21 V197D, G198V, P199D, S200H

<400> SEQUENCE: 195

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Asp Val Asp His Gln Gly Arg Ser
                165                 170                 175

Pro Ser Tyr Ala Ser
            180

<210> SEQ ID NO 196
<211> LENGTH: 184
<212> TYPE: PRT
<213> ORGANISM: Artificial Sequence
<220> FEATURE:
<223> OTHER INFORMATION: FGF21 V197-R203 deleted and replaced by
      GHRSHLQTVF (SEQ ID NO: 166)

<400> SEQUENCE: 196

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Gly His Arg Ser His Leu Gln Thr
                165                 170                 175

<210> SEQ ID NO 197
<211> LENGTH: 180
<212> TYPE: PRT
<213> ORGANISM: Artificial Sequence
<220> FEATURE:
<223> OTHER INFORMATION: FGF21 V197-R203 deleted and replaced by GLNSMV
      (SEQ ID NO: 167)

<400> SEQUENCE: 197

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Gly Leu Asn Ser Met Val Ser Pro
                165                 170                 175

Ser Tyr Ala Ser
            180

<210> SEQ ID NO 198
<211> LENGTH: 180
<212> TYPE: PRT
<213> ORGANISM: Artificial Sequence
<220> FEATURE:
<223> OTHER INFORMATION: FGF21 G198 deleted

<400> SEQUENCE: 198

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Pro Ser Gln Gly Arg Ser Pro
                165                 170                 175

Ser Tyr Ala Ser
        180

<210> SEQ ID NO 199
<211> LENGTH: 179
<212> TYPE: PRT
<213> ORGANISM: Artificial Sequence
<220> FEATURE:
<223> OTHER INFORMATION: FGF21 G198-P199 deleted

<400> SEQUENCE: 199

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Ser Gln Gly Arg Ser Pro Ser
                165                 170                 175

Tyr Ala Ser

<210> SEQ ID NO 200
<211> LENGTH: 180
<212> TYPE: PRT
<213> ORGANISM: Artificial Sequence
<220> FEATURE:
<223> OTHER INFORMATION: FGF21 G198 deleted, P199F

<400> SEQUENCE: 200

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

```
Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Phe Ser Gln Gly Arg Ser Pro
                165                 170                 175

Ser Tyr Ala Ser
            180

<210> SEQ ID NO 201
<211> LENGTH: 180
<212> TYPE: PRT
<213> ORGANISM: Artificial Sequence
<220> FEATURE:
<223> OTHER INFORMATION: FGF21 G198 deleted, P199L

<400> SEQUENCE: 201

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Leu Ser Gln Gly Arg Ser Pro
                165                 170                 175

Ser Tyr Ala Ser
            180

<210> SEQ ID NO 202
<211> LENGTH: 180
```

```
<212> TYPE: PRT
<213> ORGANISM: Artificial Sequence
<220> FEATURE:
<223> OTHER INFORMATION: FGF21 G198 deleted, P199L, S200N

<400> SEQUENCE: 202

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Leu Asn Gln Gly Arg Ser Pro
                165                 170                 175

Ser Tyr Ala Ser
            180

<210> SEQ ID NO 203
<211> LENGTH: 180
<212> TYPE: PRT
<213> ORGANISM: Artificial Sequence
<220> FEATURE:
<223> OTHER INFORMATION: FGF21 V197 deleted

<400> SEQUENCE: 203

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140
```

```
Ala Pro Pro Glu Pro Pro Gly Ile Leu Ala Pro Gln Pro Pro Asp Val
145                 150                 155                 160

Gly Ser Ser Asp Pro Leu Ser Met Gly Pro Ser Gln Gly Arg Ser Pro
                165                 170                 175

Ser Tyr Ala Ser
            180

<210> SEQ ID NO 204
<211> LENGTH: 181
<212> TYPE: PRT
<213> ORGANISM: Artificial Sequence
<220> FEATURE:
<223> OTHER INFORMATION: FGF21 L146C, A162C

<400> SEQUENCE: 204

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Cys Pro Gly Asn Lys Ser Pro His Arg Asp Pro
        115                 120                 125

Ala Pro Arg Gly Pro Cys Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 205
<211> LENGTH: 180
<212> TYPE: PRT
<213> ORGANISM: Artificial Sequence
<220> FEATURE:
<223> OTHER INFORMATION: FGF21 A59C, G71C, P199 deleted

<400> SEQUENCE: 205

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60
```

```
Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser Pro
                165                 170                 175

Ser Tyr Ala Ser
            180

<210> SEQ ID NO 206
<211> LENGTH: 181
<212> TYPE: PRT
<213> ORGANISM: Artificial Sequence
<220> FEATURE:
<223> OTHER INFORMATION: FGF21 A59C, G71C, G198Y

<400> SEQUENCE: 206

His Pro Ile Pro Asp Ser Ser Pro Leu Leu Gln Phe Gly Gly Gln Val
  1               5                  10                  15

Arg Gln Arg Tyr Leu Tyr Thr Asp Asp Ala Gln Gln Thr Glu Cys His
                 20                  25                  30

Leu Glu Ile Arg Glu Asp Gly Thr Val Gly Cys Ala Ala Asp Gln Ser
             35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Tyr Pro Ser Gln Gly Arg Ser
                165                 170                 175

Pro Ser Tyr Ala Ser
            180

<210> SEQ ID NO 207
<211> LENGTH: 180
<212> TYPE: PRT
<213> ORGANISM: Artificial Sequence
<220> FEATURE:
<223> OTHER INFORMATION: FGF21 S76C, S79C, P199 deleted
```

-continued

```
<400> SEQUENCE: 207

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Cys
        35                  40                  45

Pro Glu Cys Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser Pro
                165                 170                 175

Ser Tyr Ala Ser
            180

<210> SEQ ID NO 208
<211> LENGTH: 181
<212> TYPE: PRT
<213> ORGANISM: Artificial Sequence
<220> FEATURE:
<223> OTHER INFORMATION: FGF21 S76C, S79C, G198Y

<400> SEQUENCE: 208

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Cys
        35                  40                  45

Pro Glu Cys Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160
```

Gly Ser Ser Asp Pro Leu Ser Met Val Tyr Pro Ser Gln Gly Arg Ser
                165                 170                 175

Pro Ser Tyr Ala Ser
            180

<210> SEQ ID NO 209
<211> LENGTH: 180
<212> TYPE: PRT
<213> ORGANISM: Artificial Sequence
<220> FEATURE:
<223> OTHER INFORMATION: FGF21 G108C, L142C, P199 deleted

<400> SEQUENCE: 209

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Cys
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Cys Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser Pro
                165                 170                 175

Ser Tyr Ala Ser
            180

<210> SEQ ID NO 210
<211> LENGTH: 181
<212> TYPE: PRT
<213> ORGANISM: Artificial Sequence
<220> FEATURE:
<223> OTHER INFORMATION: FGF21 G108C, L142C, G198Y

<400> SEQUENCE: 210

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Cys
65                  70                  75                  80

Ala Leu Tyr Gly Ser Leu His Phe Asp Pro Glu Ala Cys Ser Phe Arg
            85                  90                  95

Glu Leu Leu Leu Glu Asp Gly Tyr Asn Val Tyr Gln Ser Glu Ala His
        100                 105                 110

Gly Cys Pro Leu His Leu Pro Gly Asn Lys Ser Pro His Arg Asp Pro
    115                 120                 125

Ala Pro Arg Gly Pro Ala Arg Phe Leu Pro Leu Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Tyr Pro Ser Gln Gly Arg Ser
                165                 170                 175

Pro Ser Tyr Ala Ser
            180

<210> SEQ ID NO 211
<211> LENGTH: 180
<212> TYPE: PRT
<213> ORGANISM: Artificial Sequence
<220> FEATURE:
<223> OTHER INFORMATION: FGF21 D107C, D155C, P199 deleted

<400> SEQUENCE: 211

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Cys Gly
65                  70                  75                  80

Ala Leu Tyr Gly Ser Leu His Phe Asp Pro Glu Ala Cys Ser Phe Arg
            85                  90                  95

Glu Leu Leu Leu Glu Asp Gly Tyr Asn Val Tyr Gln Ser Glu Ala His
        100                 105                 110

Gly Leu Pro Leu His Leu Pro Gly Asn Lys Ser Pro His Arg Cys Pro
    115                 120                 125

Ala Pro Arg Gly Pro Ala Arg Phe Leu Pro Leu Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser Pro
                165                 170                 175

Ser Tyr Ala Ser
            180

<210> SEQ ID NO 212
<211> LENGTH: 181
<212> TYPE: PRT
<213> ORGANISM: Artificial Sequence
<220> FEATURE:
<223> OTHER INFORMATION: FGF21 D107C, D155C, G198Y

<400> SEQUENCE: 212

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Cys Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Cys Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Tyr Pro Ser Gln Gly Arg Ser
                165                 170                 175

Pro Ser Tyr Ala Ser
            180
```

<210> SEQ ID NO 213
<211> LENGTH: 180
<212> TYPE: PRT
<213> ORGANISM: Artificial Sequence
<220> FEATURE:
<223> OTHER INFORMATION: FGF21 Q55C, P147C, P199 deleted

<400> SEQUENCE: 213

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Cys Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160
```

```
Gly Ser Ser Asp Pro Leu Ser Met Val Gly Ser Gln Gly Arg Ser Pro
                165                 170                 175

Ser Tyr Ala Ser
            180

<210> SEQ ID NO 214
<211> LENGTH: 181
<212> TYPE: PRT
<213> ORGANISM: Artificial Sequence
<220> FEATURE:
<223> OTHER INFORMATION: FGF21 Q55C, P147C, G198Y

<400> SEQUENCE: 214

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Cys Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Tyr Pro Ser Gln Gly Arg Ser
                165                 170                 175

Pro Ser Tyr Ala Ser
            180

<210> SEQ ID NO 215
<211> LENGTH: 180
<212> TYPE: PRT
<213> ORGANISM: Artificial Sequence
<220> FEATURE:
<223> OTHER INFORMATION: FGF21 Q55C, N149C, P199 deleted

<400> SEQUENCE: 215

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95
```

Glu Leu Leu Leu Glu Asp Gly Tyr Asn Val Tyr Gln Ser Glu Ala His
            100                 105                 110

Gly Leu Pro Leu His Leu Pro Gly Cys Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser Pro
                165                 170                 175

Ser Tyr Ala Ser
            180

<210> SEQ ID NO 216
<211> LENGTH: 181
<212> TYPE: PRT
<213> ORGANISM: Artificial Sequence
<220> FEATURE:
<223> OTHER INFORMATION: FGF21 Q55C, N149C, G198Y

<400> SEQUENCE: 216

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Cys Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Tyr Pro Ser Gln Gly Arg Ser
                165                 170                 175

Pro Ser Tyr Ala Ser
            180

<210> SEQ ID NO 217
<211> LENGTH: 180
<212> TYPE: PRT
<213> ORGANISM: Artificial Sequence
<220> FEATURE:
<223> OTHER INFORMATION: FGF21 M196 deleted

<400> SEQUENCE: 217

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
            85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Val Gly Pro Ser Gln Gly Arg Ser Pro
                165                 170                 175

Ser Tyr Ala Ser
            180

<210> SEQ ID NO 218
<211> LENGTH: 180
<212> TYPE: PRT
<213> ORGANISM: Artificial Sequence
<220> FEATURE:
<223> OTHER INFORMATION: FGF21 S195 deleted

<400> SEQUENCE: 218

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
            85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Met Val Gly Pro Ser Gln Gly Arg Ser Pro
                165                 170                 175

Ser Tyr Ala Ser
            180

<210> SEQ ID NO 219
<211> LENGTH: 180
<212> TYPE: PRT
<213> ORGANISM: Artificial Sequence
<220> FEATURE:
<223> OTHER INFORMATION: FGF21 L194 deleted

<400> SEQUENCE: 219

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Ser Met Val Gly Pro Ser Gln Gly Arg Ser Pro
                165                 170                 175

Ser Tyr Ala Ser
            180

<210> SEQ ID NO 220
<211> LENGTH: 180
<212> TYPE: PRT
<213> ORGANISM: Artificial Sequence
<220> FEATURE:
<223> OTHER INFORMATION: FGF21 P193 deleted

<400> SEQUENCE: 220

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

```
Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Leu Ser Met Val Gly Pro Ser Gln Gly Arg Ser Pro
            165                 170                 175

Ser Tyr Ala Ser
            180

<210> SEQ ID NO 221
<211> LENGTH: 180
<212> TYPE: PRT
<213> ORGANISM: Artificial Sequence
<220> FEATURE:
<223> OTHER INFORMATION: FGF21 D192 deleted

<400> SEQUENCE: 221

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Pro Leu Ser Met Val Gly Pro Ser Gln Gly Arg Ser Pro
            165                 170                 175

Ser Tyr Ala Ser
            180

<210> SEQ ID NO 222
<211> LENGTH: 180
<212> TYPE: PRT
<213> ORGANISM: Artificial Sequence
<220> FEATURE:
<223> OTHER INFORMATION: FGF21 S191 deleted

<400> SEQUENCE: 222

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30
```

```
Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Asp Val
145                 150                 155                 160

Gly Ser Asp Pro Leu Ser Met Val Gly Pro Ser Gln Gly Arg Ser Pro
                165                 170                 175

Ser Tyr Ala Ser
            180

<210> SEQ ID NO 223
<211> LENGTH: 179
<212> TYPE: PRT
<213> ORGANISM: Artificial Sequence
<220> FEATURE:
<223> OTHER INFORMATION: FGF21 S190-S191 deleted

<400> SEQUENCE: 223

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Asp Val
145                 150                 155                 160

Gly Asp Pro Leu Ser Met Val Gly Pro Ser Gln Gly Arg Ser Pro Ser
                165                 170                 175

Tyr Ala Ser

<210> SEQ ID NO 224
<211> LENGTH: 180
```

```
<212> TYPE: PRT
<213> ORGANISM: Artificial Sequence
<220> FEATURE:
<223> OTHER INFORMATION: FGF21 G189 deleted

<400> SEQUENCE: 224

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 225
<211> LENGTH: 180
<212> TYPE: PRT
<213> ORGANISM: Artificial Sequence
<220> FEATURE:
<223> OTHER INFORMATION: FGF21 V188 deleted

<400> SEQUENCE: 225

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140
```

```
Ala Pro Pro Glu Pro Pro Gly Ile Leu Ala Pro Gln Pro Pro Asp Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 226
<211> LENGTH: 180
<212> TYPE: PRT
<213> ORGANISM: Artificial Sequence
<220> FEATURE:
<223> OTHER INFORMATION: FGF21 D187 deleted

<400> SEQUENCE: 226

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 227
<211> LENGTH: 180
<212> TYPE: PRT
<213> ORGANISM: Artificial Sequence
<220> FEATURE:
<223> OTHER INFORMATION: FGF21 P186 deleted

<400> SEQUENCE: 227

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60
```

```
Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 228
<211> LENGTH: 179
<212> TYPE: PRT
<213> ORGANISM: Artificial Sequence
<220> FEATURE:
<223> OTHER INFORMATION: FGF21 P185-P186 deleted

<400> SEQUENCE: 228

His Pro Ile Pro Asp Ser Ser Pro Leu Leu Gln Phe Gly Gly Gln Val
  1               5                  10                  15

Arg Gln Arg Tyr Leu Tyr Thr Asp Asp Ala Gln Gln Thr Glu Ala His
                 20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Asp Val Gly Ser
145                 150                 155                 160

Ser Asp Pro Leu Ser Met Val Gly Pro Ser Gln Gly Arg Ser Pro Ser
                165                 170                 175

Tyr Ala Ser

<210> SEQ ID NO 229
<211> LENGTH: 180
<212> TYPE: PRT
<213> ORGANISM: Artificial Sequence
<220> FEATURE:
<223> OTHER INFORMATION: FGF21 Q184 deleted
```

<400> SEQUENCE: 229

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Pro Asp Val Gly
145                 150                 155                 160

Ser Ser Asp Pro Leu Ser Met Val Gly Pro Ser Gln Gly Arg Ser Pro
                165                 170                 175

Ser Tyr Ala Ser
            180

<210> SEQ ID NO 230
<211> LENGTH: 180
<212> TYPE: PRT
<213> ORGANISM: Artificial Sequence
<220> FEATURE:
<223> OTHER INFORMATION: FGF21 S200 deleted

<400> SEQUENCE: 230

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

```
Gly Ser Ser Asp Pro Leu Ser Met Val Gly Pro Gln Gly Arg Ser Pro
                165                 170                 175
Ser Tyr Ala Ser
            180

<210> SEQ ID NO 231
<211> LENGTH: 180
<212> TYPE: PRT
<213> ORGANISM: Artificial Sequence
<220> FEATURE:
<223> OTHER INFORMATION: FGF21 Q201 deleted

<400> SEQUENCE: 231

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
            20                  25                  30
Leu Glu Ile Arg Glu Asp Gly Thr Val Gly Gly Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Pro Pro Glu Pro Pro Gly Ile Leu Ala Pro Gln Pro Pro Asp Val
145                 150                 155                 160
Gly Ser Ser Asp Pro Leu Ser Met Val Gly Pro Ser Gly Arg Ser Pro
                165                 170                 175
Ser Tyr Ala Ser
            180

<210> SEQ ID NO 232
<211> LENGTH: 180
<212> TYPE: PRT
<213> ORGANISM: Artificial Sequence
<220> FEATURE:
<223> OTHER INFORMATION: FGF21 G202 deleted

<400> SEQUENCE: 232

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
            20                  25                  30
Leu Glu Ile Arg Glu Asp Gly Thr Val Gly Gly Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
                85                  90                  95
```

```
Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Arg Ser Pro
                165                 170                 175

Ser Tyr Ala Ser
            180

<210> SEQ ID NO 233
<211> LENGTH: 180
<212> TYPE: PRT
<213> ORGANISM: Artificial Sequence
<220> FEATURE:
<223> OTHER INFORMATION: FGF21 R203 deleted

<400> SEQUENCE: 233

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Ser Pro
                165                 170                 175

Ser Tyr Ala Ser
            180

<210> SEQ ID NO 234
<211> LENGTH: 180
<212> TYPE: PRT
<213> ORGANISM: Artificial Sequence
<220> FEATURE:
<223> OTHER INFORMATION: FGF21 S204 deleted

<400> SEQUENCE: 234

His Pro Ile Pro Asp Ser Ser Pro Leu Leu Gln Phe Gly Gly Gln Val
1               5                   10                  15
```

```
Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Pro
                165                 170                 175

Ser Tyr Ala Ser
            180

<210> SEQ ID NO 235
<211> LENGTH: 180
<212> TYPE: PRT
<213> ORGANISM: Artificial Sequence
<220> FEATURE:
<223> OTHER INFORMATION: FGF21 P205 deleted

<400> SEQUENCE: 235

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Ser Tyr Ala Ser
            180
```

<210> SEQ ID NO 236
<211> LENGTH: 180
<212> TYPE: PRT
<213> ORGANISM: Artificial Sequence
<220> FEATURE:
<223> OTHER INFORMATION: FGF21 S206 deleted

<400> SEQUENCE: 236

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Tyr Ala Ser
        180
```

<210> SEQ ID NO 237
<211> LENGTH: 180
<212> TYPE: PRT
<213> ORGANISM: Artificial Sequence
<220> FEATURE:
<223> OTHER INFORMATION: FGF21 Y207 deleted

<400> SEQUENCE: 237

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110
```

-continued

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Ala Ser
            180

<210> SEQ ID NO 238
<211> LENGTH: 179
<212> TYPE: PRT
<213> ORGANISM: Artificial Sequence
<220> FEATURE:
<223> OTHER INFORMATION: FGF21 V197 deleted, S201 deleted

<400> SEQUENCE: 238

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Gly Pro Gln Gly Arg Ser Pro Ser
                165                 170                 175

Tyr Ala Ser

<210> SEQ ID NO 239
<211> LENGTH: 179
<212> TYPE: PRT
<213> ORGANISM: Artificial Sequence
<220> FEATURE:
<223> OTHER INFORMATION: FGF21 M196 deleted, S201 deleted

<400> SEQUENCE: 239

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

```
Pro Glu Ser Leu Leu Gln Leu Lys Ala Leu Lys Pro Gly Val Ile Gln
     50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
             100                 105                 110

Gly Leu Pro Leu His Leu Pro Gly Asn Lys Ser Pro His Arg Asp Pro
         115                 120                 125

Ala Pro Arg Gly Pro Ala Arg Phe Leu Pro Leu Pro Gly Leu Pro Pro
     130                 135                 140

Ala Pro Pro Glu Pro Pro Gly Ile Leu Ala Pro Gln Pro Pro Asp Val
145                 150                 155                 160

Gly Ser Ser Asp Pro Leu Ser Val Gly Pro Gln Gly Arg Ser Pro Ser
                 165                 170                 175

Tyr Ala Ser

<210> SEQ ID NO 240
<211> LENGTH: 179
<212> TYPE: PRT
<213> ORGANISM: Artificial Sequence
<220> FEATURE:
<223> OTHER INFORMATION: FGF21 M196-V197 deleted

<400> SEQUENCE: 240

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
             20                  25                  30

Leu Glu Ile Arg Glu Asp Gly Thr Val Gly Gly Ala Ala Asp Gln Ser
         35                  40                  45

Pro Glu Ser Leu Leu Gln Leu Lys Ala Leu Lys Pro Gly Val Ile Gln
     50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
             100                 105                 110

Gly Leu Pro Leu His Leu Pro Gly Asn Lys Ser Pro His Arg Asp Pro
         115                 120                 125

Ala Pro Arg Gly Pro Ala Arg Phe Leu Pro Leu Pro Gly Leu Pro Pro
     130                 135                 140

Ala Pro Pro Glu Pro Pro Gly Ile Leu Ala Pro Gln Pro Pro Asp Val
145                 150                 155                 160

Gly Ser Ser Asp Pro Leu Ser Gly Pro Ser Gln Gly Arg Ser Pro Ser
                 165                 170                 175

Tyr Ala Ser

<210> SEQ ID NO 241
<211> LENGTH: 179
<212> TYPE: PRT
<213> ORGANISM: Artificial Sequence
<220> FEATURE:
<223> OTHER INFORMATION: FGF21 V197-G198 deleted
```

<400> SEQUENCE: 241

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Pro Ser Gln Gly Arg Ser Pro Ser
                165                 170                 175

Tyr Ala Ser
```

<210> SEQ ID NO 242
<211> LENGTH: 179
<212> TYPE: PRT
<213> ORGANISM: Artificial Sequence
<220> FEATURE:
<223> OTHER INFORMATION: FGF21 S195-M196 deleted

<400> SEQUENCE: 242

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160
```

```
Gly Ser Ser Asp Pro Leu Val Gly Pro Ser Gln Gly Arg Ser Pro Ser
                165                 170                 175

Tyr Ala Ser

<210> SEQ ID NO 243
<211> LENGTH: 179
<212> TYPE: PRT
<213> ORGANISM: Artificial Sequence
<220> FEATURE:
<223> OTHER INFORMATION: FGF21 G198 deleted, S200 deleted

<400> SEQUENCE: 243

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Pro Gln Gly Arg Ser Pro Ser
                165                 170                 175

Tyr Ala Ser

<210> SEQ ID NO 244
<211> LENGTH: 181
<212> TYPE: PRT
<213> ORGANISM: Artificial Sequence
<220> FEATURE:
<223> OTHER INFORMATION: FGF21 H60C, S79C

<400> SEQUENCE: 244

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala Cys
            20                  25                  30

Leu Glu Ile Arg Glu Asp Gly Thr Val Gly Gly Ala Ala Asp Gln Ser
        35                  40                  45

Pro Glu Cys Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95
```

```
Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 245
<211> LENGTH: 181
<212> TYPE: PRT
<213> ORGANISM: Artificial Sequence
<220> FEATURE:
<223> OTHER INFORMATION: FGF21 H145C, L165C

<400> SEQUENCE: 245

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu Cys Leu Pro Gly Asn Lys Ser Pro His Arg Asp Pro
            115                 120                 125

Ala Pro Arg Gly Pro Ala Arg Phe Cys Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 246
<211> LENGTH: 181
<212> TYPE: PRT
<213> ORGANISM: Artificial Sequence
<220> FEATURE:
<223> OTHER INFORMATION: FGF21 A59C, G71C

<400> SEQUENCE: 246

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30
```

Leu Glu Ile Arg Glu Asp Gly Thr Val Gly Cys Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 247
<211> LENGTH: 181
<212> TYPE: PRT
<213> ORGANISM: Artificial Sequence
<220> FEATURE:
<223> OTHER INFORMATION: FGF21 H60C, A72C

<400> SEQUENCE: 247

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala Cys
            20                  25                  30

Leu Glu Ile Arg Glu Asp Gly Thr Val Gly Gly Cys Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 248

```
<211> LENGTH: 181
<212> TYPE: PRT
<213> ORGANISM: Artificial Sequence
<220> FEATURE:
<223> OTHER INFORMATION: FGF21 I63C, G112C

<400> SEQUENCE: 248

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Cys Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Cys Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 249
<211> LENGTH: 181
<212> TYPE: PRT
<213> ORGANISM: Artificial Sequence
<220> FEATURE:
<223> OTHER INFORMATION: FGF21 L49C, L170C

<400> SEQUENCE: 249

His Pro Ile Pro Asp Ser Ser Pro Leu Leu Gln Phe Gly Gly Gln Val
1               5                   10                  15

Arg Gln Arg Tyr Cys Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125
```

```
Ala Pro Arg Gly Pro Ala Arg Phe Leu Pro Leu Pro Gly Cys Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 250
<211> LENGTH: 181
<212> TYPE: PRT
<213> ORGANISM: Artificial Sequence
<220> FEATURE:
<223> OTHER INFORMATION: FGF21 T51C, L167C

<400> SEQUENCE: 250

His Pro Ile Pro Asp Ser Ser Pro Leu Leu Gln Phe Gly Gly Gln Val
1               5                   10                  15

Arg Gln Arg Tyr Leu Tyr Cys Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Cys Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 251
<211> LENGTH: 181
<212> TYPE: PRT
<213> ORGANISM: Artificial Sequence
<220> FEATURE:
<223> OTHER INFORMATION: FGF21 H140C, L142C

<400> SEQUENCE: 251

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Ala His
            20                  25                  30

Leu Glu Ile Arg Glu Asp Gly Thr Val Gly Gly Ala Ala Asp Gln Ser
        35                  40                  45
```

```
Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala Cys
                100                 105                 110

Gly Cys Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 252
<211> LENGTH: 181
<212> TYPE: PRT
<213> ORGANISM: Artificial Sequence
<220> FEATURE:
<223> OTHER INFORMATION: FGF21 D130C, Y132C

<400> SEQUENCE: 252

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                 20                  25                  30

Leu Glu Ile Arg Glu Asp Gly Thr Val Gly Gly Ala Ala Asp Gln Ser
             35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Cys Gly Cys Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 253
<211> LENGTH: 181
<212> TYPE: PRT
<213> ORGANISM: Artificial Sequence
```

<220> FEATURE:
<223> OTHER INFORMATION: FGF21 S137C, H140C

<400> SEQUENCE: 253

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Cys Glu Ala Cys
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 254
<211> LENGTH: 181
<212> TYPE: PRT
<213> ORGANISM: Artificial Sequence
<220> FEATURE:
<223> OTHER INFORMATION: FGF21 S76C, S79C

<400> SEQUENCE: 254

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Cys
        35                  40                  45

Pro Glu Cys Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175

Pro Ser Tyr Ala Ser
            180

<210> SEQ ID NO 255
<211> LENGTH: 181
<212> TYPE: PRT
<213> ORGANISM: Artificial Sequence
<220> FEATURE:
<223> OTHER INFORMATION: FGF21 G108C, L142C

<400> SEQUENCE: 255

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Cys
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Cys Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175

Pro Ser Tyr Ala Ser
            180

<210> SEQ ID NO 256
<211> LENGTH: 181
<212> TYPE: PRT
<213> ORGANISM: Artificial Sequence
<220> FEATURE:
<223> OTHER INFORMATION: FGF21 A72C, S79C

<400> SEQUENCE: 256

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Cys Ala Asp Gln Ser
        35                  40                  45

Pro Glu Cys Leu Leu Gln Leu Lys Ala Leu Lys Pro Gly Val Ile Gln
    50                  55                  60

```
Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
             100                 105                 110

Gly Leu Pro Leu His Leu Pro Gly Asn Lys Ser Pro His Arg Asp Pro
         115                 120                 125

Ala Pro Arg Gly Pro Ala Arg Phe Leu Pro Leu Pro Gly Leu Pro Pro
     130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                 165                 170                 175

Pro Ser Tyr Ala Ser
             180

<210> SEQ ID NO 257
<211> LENGTH: 181
<212> TYPE: PRT
<213> ORGANISM: Artificial Sequence
<220> FEATURE:
<223> OTHER INFORMATION: FGF21 H60C, S79C, H145C, L165C

<400> SEQUENCE: 257

His Pro Ile Pro Asp Ser Ser Pro Leu Leu Gln Phe Gly Gly Gln Val
  1               5                  10                  15

Arg Gln Arg Tyr Leu Tyr Thr Asp Asp Ala Gln Gln Thr Glu Ala Cys
                 20                  25                  30

Leu Glu Ile Arg Glu Asp Gly Thr Val Gly Gly Ala Ala Asp Gln Ser
             35                  40                  45

Pro Glu Cys Leu Leu Gln Leu Lys Ala Leu Lys Pro Gly Val Ile Gln
         50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
             100                 105                 110

Gly Leu Pro Leu Cys Leu Pro Gly Asn Lys Ser Pro His Arg Asp Pro
         115                 120                 125

Ala Pro Arg Gly Pro Ala Arg Phe Cys Pro Leu Pro Gly Leu Pro Pro
     130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                 165                 170                 175

Pro Ser Tyr Ala Ser
             180

<210> SEQ ID NO 258
<211> LENGTH: 181
<212> TYPE: PRT
<213> ORGANISM: Artificial Sequence
<220> FEATURE:
<223> OTHER INFORMATION: FGF21 A72C, S79C, G108C, L142C
```

```
<400> SEQUENCE: 258

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Cys Ala Asp Gln Ser
        35                  40                  45

Pro Glu Cys Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Cys
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Cys Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 259
<211> LENGTH: 181
<212> TYPE: PRT
<213> ORGANISM: Artificial Sequence
<220> FEATURE:
<223> OTHER INFORMATION: FGF21 R47C, P174C

<400> SEQUENCE: 259

His Pro Ile Pro Asp Ser Ser Pro Leu Leu Gln Phe Gly Gly Gln Val
1               5                   10                  15

Arg Gln Cys Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Cys Pro Glu Pro Pro Gly Ile Leu Ala Pro Gln Pro Pro Asp Val
145                 150                 155                 160
```

```
Gly Ser Ser Asp Pro Leu Ser Met Val Gly Pro Ser Gln Gly Arg Ser
                165                 170                 175

Pro Ser Tyr Ala Ser
            180

<210> SEQ ID NO 260
<211> LENGTH: 181
<212> TYPE: PRT
<213> ORGANISM: Artificial Sequence
<220> FEATURE:
<223> OTHER INFORMATION: FGF21 M196C, R203C

<400> SEQUENCE: 260

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Cys Val Gly Pro Ser Gln Gly Cys Ser
                165                 170                 175

Pro Ser Tyr Ala Ser
            180

<210> SEQ ID NO 261
<211> LENGTH: 181
<212> TYPE: PRT
<213> ORGANISM: Artificial Sequence
<220> FEATURE:
<223> OTHER INFORMATION: FGF21 D107C, D155C

<400> SEQUENCE: 261

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Cys Gly
65                  70                  75                  80
```

```
Ala Leu Tyr Gly Ser Leu His Phe Asp Pro Glu Ala Cys Ser Phe Arg
            85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Cys Pro
            115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175

Pro Ser Tyr Ala Ser
            180

<210> SEQ ID NO 262
<211> LENGTH: 181
<212> TYPE: PRT
<213> ORGANISM: Artificial Sequence
<220> FEATURE:
<223> OTHER INFORMATION: FGF21 Q55C, G148C

<400> SEQUENCE: 262

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
            85                  90                  95

Glu Leu Leu Glu Asp Gly Tyr Asn Val Tyr Gln Ser Glu Ala His
            100                 105                 110

Gly Leu Pro Leu His Leu Pro Cys Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175

Pro Ser Tyr Ala Ser
            180

<210> SEQ ID NO 263
<211> LENGTH: 174
<212> TYPE: PRT
<213> ORGANISM: Artificial Sequence
<220> FEATURE:
<223> OTHER INFORMATION: FGF21 Q55C, G148C, N149-R159 deleted and
      replaced by GSGS (SEQ ID NO: 161)

<400> SEQUENCE: 263
```

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Cys Gly Ser Gly Ser Gly Pro Ala Arg
            115                 120                 125

Phe Leu Pro Leu Pro Gly Leu Pro Pro Ala Pro Glu Pro Pro Gly
130                 135                 140

Ile Leu Ala Pro Gln Pro Pro Asp Val Gly Ser Ser Asp Pro Leu Ser
145                 150                 155                 160

Met Val Gly Pro Ser Gln Gly Arg Ser Pro Ser Tyr Ala Ser
                165                 170
```

<210> SEQ ID NO 264
<211> LENGTH: 176
<212> TYPE: PRT
<213> ORGANISM: Artificial Sequence
<220> FEATURE:
<223> OTHER INFORMATION: FGF21 Q55C, G148C, N149-R159 deleted and
      replaced by GGSGGS (SEQ ID NO: 162)

<400> SEQUENCE: 264

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Cys Gly Gly Ser Gly Gly Ser Gly Pro
            115                 120                 125

Ala Arg Phe Leu Pro Leu Pro Gly Leu Pro Pro Ala Pro Glu Pro
130                 135                 140

Pro Gly Ile Leu Ala Pro Gln Pro Pro Asp Val Gly Ser Ser Asp Pro
145                 150                 155                 160

Leu Ser Met Val Gly Pro Ser Gln Gly Arg Ser Pro Ser Tyr Ala Ser
                165                 170                 175
```

<210> SEQ ID NO 265

```
<211> LENGTH: 181
<212> TYPE: PRT
<213> ORGANISM: Artificial Sequence
<220> FEATURE:
<223> OTHER INFORMATION: FGF21 Q55G, Q56C, L146C

<400> SEQUENCE: 265

His Pro Ile Pro Asp Ser Ser Pro Leu Leu Gln Phe Gly Gly Gln Val
  1               5                  10                  15

Arg Gln Arg Tyr Leu Tyr Thr Asp Asp Ala Gly Cys Thr Glu Ala His
             20                  25                  30

Leu Glu Ile Arg Glu Asp Gly Thr Val Gly Gly Ala Ala Asp Gln Ser
         35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Cys Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 266
<211> LENGTH: 172
<212> TYPE: PRT
<213> ORGANISM: Artificial Sequence
<220> FEATURE:
<223> OTHER INFORMATION: FGF21 Q55G, Q56C, L146C, P147-R159 deleted and
      replaced by GSGS (SEQ ID NO: 161)

<400> SEQUENCE: 266

His Pro Ile Pro Asp Ser Ser Pro Leu Leu Gln Phe Gly Gly Gln Val
  1               5                  10                  15

Arg Gln Arg Tyr Leu Tyr Thr Asp Asp Ala Gly Cys Thr Glu Ala His
             20                  25                  30

Leu Glu Ile Arg Glu Asp Gly Thr Val Gly Gly Ala Ala Asp Gln Ser
         35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Cys Gly Ser Gly Ser Gly Pro Ala Arg Phe Leu
        115                 120                 125
```

```
Pro Leu Pro Gly Leu Pro Ala Pro Pro Glu Pro Pro Gly Ile Leu
        130                 135                 140

Ala Pro Gln Pro Pro Asp Val Gly Ser Ser Asp Pro Leu Ser Met Val
145                 150                 155                 160

Gly Pro Ser Gln Gly Arg Ser Pro Ser Tyr Ala Ser
                165                 170
```

<210> SEQ ID NO 267
<211> LENGTH: 174
<212> TYPE: PRT
<213> ORGANISM: Artificial Sequence
<220> FEATURE:
<223> OTHER INFORMATION: FGF21 Q55G, Q56C, L146C, P147-R159 deleted and
      replaced by GGSGGS (SEQ ID NO: 162)

<400> SEQUENCE: 267

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gly Cys Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Cys Gly Gly Ser Gly Gly Ser Gly Pro Ala Arg
        115                 120                 125

Phe Leu Pro Leu Pro Gly Leu Pro Pro Ala Pro Pro Glu Pro Pro Gly
    130                 135                 140

Ile Leu Ala Pro Gln Pro Pro Asp Val Gly Ser Ser Asp Pro Leu Ser
145                 150                 155                 160

Met Val Gly Pro Ser Gln Gly Arg Ser Pro Ser Tyr Ala Ser
                165                 170
```

<210> SEQ ID NO 268
<211> LENGTH: 181
<212> TYPE: PRT
<213> ORGANISM: Artificial Sequence
<220> FEATURE:
<223> OTHER INFORMATION: FGF21 Q55C, P147C

<400> SEQUENCE: 268

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80
```

```
Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Cys Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 269
<211> LENGTH: 181
<212> TYPE: PRT
<213> ORGANISM: Artificial Sequence
<220> FEATURE:
<223> OTHER INFORMATION: FGF21 Q55C, N149C

<400> SEQUENCE: 269

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Cys Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 270
<211> LENGTH: 181
<212> TYPE: PRT
<213> ORGANISM: Artificial Sequence
<220> FEATURE:
<223> OTHER INFORMATION: FGF21 E62C, E78C
```

<400> SEQUENCE: 270

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Cys Ile Arg Glu Asp Gly Thr Val Gly Gly Ala Ala Asp Gln Ser
        35                  40                  45

Pro Cys Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 271
<211> LENGTH: 181
<212> TYPE: PRT
<213> ORGANISM: Artificial Sequence
<220> FEATURE:
<223> OTHER INFORMATION: FGF21 E62C, S79C

<400> SEQUENCE: 271

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Cys Ile Arg Glu Asp Gly Thr Val Gly Gly Ala Ala Asp Gln Ser
        35                  40                  45

Pro Glu Cys Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

```
Gly Ser Ser Asp Pro Leu Ser Met Val Gly Pro Ser Gln Gly Arg Ser
                165                 170                 175

Pro Ser Tyr Ala Ser
            180

<210> SEQ ID NO 272
<211> LENGTH: 181
<212> TYPE: PRT
<213> ORGANISM: Artificial Sequence
<220> FEATURE:
<223> OTHER INFORMATION: FGF21 R100C, L114C

<400> SEQUENCE: 272

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Cys Phe Leu Cys Gln Arg Pro Asp Gly
65                  70                  75                  80

Ala Leu Tyr Gly Ser Cys His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 273
<211> LENGTH: 181
<212> TYPE: PRT
<213> ORGANISM: Artificial Sequence
<220> FEATURE:
<223> OTHER INFORMATION: FGF21 L102C, G112C

<400> SEQUENCE: 273

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Cys Cys Gln Arg Pro Asp Gly
65                  70                  75                  80

Ala Leu Tyr Cys Ser Leu His Phe Asp Pro Glu Ala Cys Ser Phe Arg
                85                  90                  95
```

```
Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 274
<211> LENGTH: 181
<212> TYPE: PRT
<213> ORGANISM: Artificial Sequence
<220> FEATURE:
<223> OTHER INFORMATION: FGF21 A59C, A73C

<400> SEQUENCE: 274

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Gly Ala Cys Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 275
<211> LENGTH: 181
<212> TYPE: PRT
<213> ORGANISM: Artificial Sequence
<220> FEATURE:
<223> OTHER INFORMATION: FGF21 E62C, A72C

<400> SEQUENCE: 275

His Pro Ile Pro Asp Ser Ser Pro Leu Leu Gln Phe Gly Gly Gln Val
1               5                   10                  15
```

```
Arg Gln Arg Tyr Leu Tyr Thr Asp Asp Ala Gln Gln Thr Glu Ala His
            20                  25                  30

Leu Cys Ile Arg Glu Asp Gly Thr Val Gly Gly Cys Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 276
<211> LENGTH: 181
<212> TYPE: PRT
<213> ORGANISM: Artificial Sequence
<220> FEATURE:
<223> OTHER INFORMATION: FGF21 Q104C, S137C

<400> SEQUENCE: 276

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Cys Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Cys Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 277
<211> LENGTH: 181
<212> TYPE: PRT
<213> ORGANISM: Artificial Sequence
<220> FEATURE:
<223> OTHER INFORMATION: FGF21 Q104C, H140C

<400> SEQUENCE: 277

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Cys Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala Cys
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 278
<211> LENGTH: 181
<212> TYPE: PRT
<213> ORGANISM: Artificial Sequence
<220> FEATURE:
<223> OTHER INFORMATION: FGF21 A54C, P161C

<400> SEQUENCE: 278

His Pro Ile Pro Asp Ser Ser Pro Leu Leu Gln Phe Gly Gly Gln Val
1               5                   10                  15

Arg Gln Arg Tyr Leu Tyr Thr Asp Asp Cys Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

```
Gly Leu Pro Leu His Leu Pro Gly Asn Lys Ser Pro His Arg Asp Pro
        115                 120                 125

Ala Pro Arg Gly Cys Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175

Pro Ser Tyr Ala Ser
            180

<210> SEQ ID NO 279
<211> LENGTH: 181
<212> TYPE: PRT
<213> ORGANISM: Artificial Sequence
<220> FEATURE:
<223> OTHER INFORMATION: FGF21 Q56C, L146C

<400> SEQUENCE: 279

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Cys Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Cys His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
            165                 170                 175

Pro Ser Tyr Ala Ser
            180

<210> SEQ ID NO 280
<211> LENGTH: 181
<212> TYPE: PRT
<213> ORGANISM: Artificial Sequence
<220> FEATURE:
<223> OTHER INFORMATION: FGF21 I63C, T98C

<400> SEQUENCE: 280

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30
```

```
Leu Glu Cys Arg Glu Asp Gly Thr Val Gly Ala Ala Asp Gln Ser
        35                  40                  45

Pro Glu Ser Leu Leu Gln Leu Lys Ala Leu Lys Pro Gly Val Ile Gln
 50                  55                  60

Ile Leu Gly Val Lys Cys Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
                115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
                180

<210> SEQ ID NO 281
<211> LENGTH: 181
<212> TYPE: PRT
<213> ORGANISM: Artificial Sequence
<220> FEATURE:
<223> OTHER INFORMATION: FGF21 G67C, R100C

<400> SEQUENCE: 281

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                 20                  25                  30

Leu Glu Ile Arg Glu Asp Cys Thr Val Gly Gly Ala Ala Asp Gln Ser
        35                  40                  45

Pro Glu Ser Leu Leu Gln Leu Lys Ala Leu Lys Pro Gly Val Ile Gln
 50                  55                  60

Ile Leu Gly Val Lys Thr Ser Cys Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
                115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
                180

<210> SEQ ID NO 282
```

<211> LENGTH: 181
<212> TYPE: PRT
<213> ORGANISM: Artificial Sequence
<220> FEATURE:
<223> OTHER INFORMATION: FGF21 V69C, L110C

<400> SEQUENCE: 282

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Cys Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Cys Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 283
<211> LENGTH: 181
<212> TYPE: PRT
<213> ORGANISM: Artificial Sequence
<220> FEATURE:
<223> OTHER INFORMATION: FGF21 A120C, A139C

<400> SEQUENCE: 283

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Cys Cys Ser Phe Arg
                85                  90                  95

Glu Leu Leu Leu Glu Asp Gly Tyr Asn Val Tyr Gln Ser Glu Cys His
            100                 105                 110

Gly Leu Pro Leu His Leu Pro Gly Asn Lys Ser Pro His Arg Asp Pro
        115                 120                 125
```

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 284
<211> LENGTH: 181
<212> TYPE: PRT
<213> ORGANISM: Artificial Sequence
<220> FEATURE:
<223> OTHER INFORMATION: FGF21 R124C, Q136C

<400> SEQUENCE: 284

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Cys
                85                  90                  95

Glu Leu Leu Leu Glu Asp Gly Tyr Asn Val Tyr Cys Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 285
<211> LENGTH: 181
<212> TYPE: PRT
<213> ORGANISM: Artificial Sequence
<220> FEATURE:
<223> OTHER INFORMATION: FGF21 P143C, A162C

<400> SEQUENCE: 285

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

```
Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                    100                 105                 110

Gly Leu Cys Leu His Leu Pro Gly Asn Lys Ser Pro His Arg Asp Pro
            115                 120                 125

Ala Pro Arg Gly Pro Cys Arg Phe Leu Pro Leu Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 286
<211> LENGTH: 181
<212> TYPE: PRT
<213> ORGANISM: Artificial Sequence
<220> FEATURE:
<223> OTHER INFORMATION: FGF21 P77C, K97C

<400> SEQUENCE: 286

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Cys Glu Ser Leu Leu Gln Leu Lys Ala Leu Lys Pro Gly Val Ile Gln
    50                  55                  60

Ile Leu Gly Val Cys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                    100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 287
<211> LENGTH: 181
<212> TYPE: PRT
<213> ORGANISM: Artificial Sequence
```

<220> FEATURE:
<223> OTHER INFORMATION: FGF21 E78C, T98C

<400> SEQUENCE: 287

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Cys Ser Leu Leu Gln Leu Lys Ala Leu Lys Pro Gly Val Ile Gln
50                  55                  60

Ile Leu Gly Val Lys Cys Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 288
<211> LENGTH: 181
<212> TYPE: PRT
<213> ORGANISM: Artificial Sequence
<220> FEATURE:
<223> OTHER INFORMATION: FGF21 L80C, V96C

<400> SEQUENCE: 288

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Cys Leu Gln Leu Lys Ala Leu Lys Pro Gly Val Ile Gln
50                  55                  60

Ile Leu Gly Cys Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

-continued

Ala Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 289
<211> LENGTH: 181
<212> TYPE: PRT
<213> ORGANISM: Artificial Sequence
<220> FEATURE:
<223> OTHER INFORMATION: FGF21 H145C, P161C

<400> SEQUENCE: 289

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu Cys Leu Pro Gly Asn Lys Ser Pro His Arg Asp Pro
        115                 120                 125

Ala Pro Arg Gly Cys Ala Arg Phe Leu Pro Leu Pro Gly Leu Pro Pro
    130                 135                 140

Ala Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 290
<211> LENGTH: 181
<212> TYPE: PRT
<213> ORGANISM: Artificial Sequence
<220> FEATURE:
<223> OTHER INFORMATION: FGF21 L81C, G95C

<400> SEQUENCE: 290

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Cys Gln Leu Lys Ala Leu Lys Pro Gly Val Ile Gln
    50                  55                  60

```
Ile Leu Cys Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
             100                 105                 110

Gly Leu Pro Leu His Leu Pro Gly Asn Lys Ser Pro His Arg Asp Pro
         115                 120                 125

Ala Pro Arg Gly Pro Ala Arg Phe Leu Pro Leu Pro Gly Leu Pro Pro
     130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                 165                 170                 175

Pro Ser Tyr Ala Ser
             180

<210> SEQ ID NO 291
<211> LENGTH: 181
<212> TYPE: PRT
<213> ORGANISM: Artificial Sequence
<220> FEATURE:
<223> OTHER INFORMATION: FGF21 Q82C, L94C

<400> SEQUENCE: 291

His Pro Ile Pro Asp Ser Ser Pro Leu Leu Gln Phe Gly Gly Gln Val
  1               5                  10                  15

Arg Gln Arg Tyr Leu Tyr Thr Asp Asp Ala Gln Gln Thr Glu Ala His
             20                  25                  30

Leu Glu Ile Arg Glu Asp Gly Thr Val Gly Gly Ala Ala Asp Gln Ser
         35                  40                  45

Pro Glu Ser Leu Leu Cys Leu Lys Ala Leu Lys Pro Gly Val Ile Gln
     50                  55                  60

Ile Cys Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
             100                 105                 110

Gly Leu Pro Leu His Leu Pro Gly Asn Lys Ser Pro His Arg Asp Pro
         115                 120                 125

Ala Pro Arg Gly Pro Ala Arg Phe Leu Pro Leu Pro Gly Leu Pro Pro
     130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                 165                 170                 175

Pro Ser Tyr Ala Ser
             180

<210> SEQ ID NO 292
<211> LENGTH: 181
<212> TYPE: PRT
<213> ORGANISM: Artificial Sequence
<220> FEATURE:
<223> OTHER INFORMATION: FGF21 L83C, I91C
```

```
<400> SEQUENCE: 292

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Cys Lys Ala Leu Lys Pro Gly Val Cys Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 293
<211> LENGTH: 181
<212> TYPE: PRT
<213> ORGANISM: Artificial Sequence
<220> FEATURE:
<223> OTHER INFORMATION: FGF21 D155L

<400> SEQUENCE: 293

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Leu Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160
```

```
Gly Ser Ser Asp Pro Leu Ser Met Val Gly Pro Ser Gln Gly Arg Ser
                165                 170                 175

Pro Ser Tyr Ala Ser
            180

<210> SEQ ID NO 294
<211> LENGTH: 181
<212> TYPE: PRT
<213> ORGANISM: Artificial Sequence
<220> FEATURE:
<223> OTHER INFORMATION: FGF21 D155K

<400> SEQUENCE: 294

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Lys Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 295
<211> LENGTH: 181
<212> TYPE: PRT
<213> ORGANISM: Artificial Sequence
<220> FEATURE:
<223> OTHER INFORMATION: FGF21 D155Y

<400> SEQUENCE: 295

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80
```

```
Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Tyr Pro
        115                 120                 125

Ala Pro Arg Gly Pro Ala Arg Phe Leu Pro Leu Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 296
<211> LENGTH: 181
<212> TYPE: PRT
<213> ORGANISM: Artificial Sequence
<220> FEATURE:
<223> OTHER INFORMATION: FGF21 D155P

<400> SEQUENCE: 296

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Pro Pro
        115                 120                 125

Ala Pro Arg Gly Pro Ala Arg Phe Leu Pro Leu Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 297
<211> LENGTH: 181
<212> TYPE: PRT
<213> ORGANISM: Artificial Sequence
<220> FEATURE:
<223> OTHER INFORMATION: FGF21 D155E
```

<400> SEQUENCE: 297

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Glu Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 298
<211> LENGTH: 181
<212> TYPE: PRT
<213> ORGANISM: Artificial Sequence
<220> FEATURE:
<223> OTHER INFORMATION: FGF21 D155N

<400> SEQUENCE: 298

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asn Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160
```

```
Gly Ser Ser Asp Pro Leu Ser Met Val Gly Pro Ser Gln Gly Arg Ser
                165                 170                 175

Pro Ser Tyr Ala Ser
            180

<210> SEQ ID NO 299
<211> LENGTH: 181
<212> TYPE: PRT
<213> ORGANISM: Artificial Sequence
<220> FEATURE:
<223> OTHER INFORMATION: FGF21 R154Q, D155L

<400> SEQUENCE: 299

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Gln Leu Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 300
<211> LENGTH: 181
<212> TYPE: PRT
<213> ORGANISM: Artificial Sequence
<220> FEATURE:
<223> OTHER INFORMATION: FGF21 R154Q, D155K

<400> SEQUENCE: 300

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95
```

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Gln Lys Pro
        115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 301
<211> LENGTH: 181
<212> TYPE: PRT
<213> ORGANISM: Artificial Sequence
<220> FEATURE:
<223> OTHER INFORMATION: FGF21 H153Q, R154Q, D155N, A157V, R159K

<400> SEQUENCE: 301

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro Gln Gln Asn Pro
        115                 120                 125

Val Pro Lys Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 302
<211> LENGTH: 181
<212> TYPE: PRT
<213> ORGANISM: Artificial Sequence
<220> FEATURE:
<223> OTHER INFORMATION: FGF21 P152A, H153K, R154K, D155E, P156A, A157S,
      R159Q

<400> SEQUENCE: 302

His Pro Ile Pro Asp Ser Ser Pro Leu Leu Gln Phe Gly Gly Gln Val
1               5                   10                  15

```
Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Ala Lys Lys Glu Ala
            115                 120                 125

Ser Pro Gln Gly Pro Ala Arg Phe Leu Pro Leu Pro Gly Leu Pro Pro
 130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
                180

<210> SEQ ID NO 303
<211> LENGTH: 181
<212> TYPE: PRT
<213> ORGANISM: Artificial Sequence
<220> FEATURE:
<223> OTHER INFORMATION: FGF21 H153Y, R154K, D155N, P156K, A157G

<400> SEQUENCE: 303

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro Tyr Lys Asn Lys
            115                 120                 125

Gly Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
                180
```

```
<210> SEQ ID NO 304
<211> LENGTH: 179
<212> TYPE: PRT
<213> ORGANISM: Artificial Sequence
<220> FEATURE:
<223> OTHER INFORMATION: FGF21 P152-H153 deleted

<400> SEQUENCE: 304

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Arg Asp Pro Ala Pro
        115                 120                 125

Arg Gly Pro Ala Arg Phe Leu Pro Leu Pro Gly Leu Pro Pro Ala Pro
    130                 135                 140

Pro Glu Pro Pro Gly Ile Leu Ala Pro Gln Pro Pro Asp Val Gly Ser
145                 150                 155                 160

Ser Asp Pro Leu Ser Met Val Gly Pro Ser Gln Gly Arg Ser Pro Ser
                165                 170                 175

Tyr Ala Ser

<210> SEQ ID NO 305
<211> LENGTH: 170
<212> TYPE: PRT
<213> ORGANISM: Artificial Sequence
<220> FEATURE:
<223> OTHER INFORMATION: FGF21 N149-R163 deleted and replaced by GSGS
      (SEQ ID NO: 161)

<400> SEQUENCE: 305

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gly Ser Gly Ser Phe Leu Pro Leu
        115                 120                 125
```

```
Pro Gly Leu Pro Pro Ala Pro Pro Glu Pro Pro Gly Ile Leu Ala Pro
        130                 135                 140

Gln Pro Pro Asp Val Gly Ser Ser Asp Pro Leu Ser Met Val Gly Pro
145                 150                 155                 160

Ser Gln Gly Arg Ser Pro Ser Tyr Ala Ser
                165                 170

<210> SEQ ID NO 306
<211> LENGTH: 172
<212> TYPE: PRT
<213> ORGANISM: Artificial Sequence
<220> FEATURE:
<223> OTHER INFORMATION: FGF21 N149-A162 deleted and replaced by GSHSG
      (SEQ ID NO: 163)

<400> SEQUENCE: 306

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gly Ser His Ser Gly Arg Phe Leu
        115                 120                 125

Pro Leu Pro Gly Leu Pro Pro Ala Pro Pro Glu Pro Pro Gly Ile Leu
    130                 135                 140

Ala Pro Gln Pro Pro Asp Val Gly Ser Ser Asp Pro Leu Ser Met Val
145                 150                 155                 160

Gly Pro Ser Gln Gly Arg Ser Pro Ser Tyr Ala Ser
                165                 170

<210> SEQ ID NO 307
<211> LENGTH: 173
<212> TYPE: PRT
<213> ORGANISM: Artificial Sequence
<220> FEATURE:
<223> OTHER INFORMATION: FGF21 N149-A162 deleted and replaced by GSHSGS
      (SEQ ID NO: 165)

<400> SEQUENCE: 307

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80
```

```
Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gly Ser His Ser Gly Ser Arg Phe
        115                 120                 125

Leu Pro Leu Pro Gly Leu Pro Pro Ala Pro Pro Glu Pro Pro Gly Ile
    130                 135                 140

Leu Ala Pro Gln Pro Pro Asp Val Gly Ser Ser Asp Pro Leu Ser Met
145                 150                 155                 160

Val Gly Pro Ser Gln Gly Arg Ser Pro Ser Tyr Ala Ser
                165                 170

<210> SEQ ID NO 308
<211> LENGTH: 181
<212> TYPE: PRT
<213> ORGANISM: Artificial Sequence
<220> FEATURE:
<223> OTHER INFORMATION: FGF21 K150H

<400> SEQUENCE: 308

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn His Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 309
<211> LENGTH: 181
<212> TYPE: PRT
<213> ORGANISM: Artificial Sequence
<220> FEATURE:
<223> OTHER INFORMATION: FGF21 K150H, P152L

<400> SEQUENCE: 309

His Pro Ile Pro Asp Ser Ser Pro Leu Leu Gln Phe Gly Gly Gln Val
1               5                   10                  15
```

```
Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
               100                 105                 110

Gly Leu Pro Leu His Leu Pro Gly Asn His Ser Leu His Arg Asp Pro
           115                 120                 125

Ala Pro Arg Gly Pro Ala Arg Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 310
<211> LENGTH: 181
<212> TYPE: PRT
<213> ORGANISM: Artificial Sequence
<220> FEATURE:
<223> OTHER INFORMATION: FGF21 R163H

<400> SEQUENCE: 310

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
               100                 105                 110

Gly Leu Pro Leu His Leu Pro Gly Asn Lys Ser Pro His Arg Asp Pro
           115                 120                 125

Ala Pro Arg Gly Pro Ala His Phe Leu Pro Leu Pro Gly Leu Pro Pro
130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 311
<211> LENGTH: 181
<212> TYPE: PRT
<213> ORGANISM: Artificial Sequence
<220> FEATURE:
<223> OTHER INFORMATION: FGF21 P158H, R159H

<400> SEQUENCE: 311

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala His His Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 312
<211> LENGTH: 178
<212> TYPE: PRT
<213> ORGANISM: Artificial Sequence
<220> FEATURE:
<223> OTHER INFORMATION: FGF21 N149-D155 deleted and replaced by GSGS
      (SEQ ID NO: 161)

<400> SEQUENCE: 312

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110
```

Gly Leu Pro Leu His Leu Pro Gly Gly Ser Gly Ser Pro Ala Pro Arg
            115                 120                 125

Gly Pro Ala Arg Phe Leu Pro Leu Pro Gly Leu Pro Pro Ala Pro Pro
130                 135                 140

Glu Pro Pro Gly Ile Leu Ala Pro Gln Pro Pro Asp Val Gly Ser Ser
145                 150                 155                 160

Asp Pro Leu Ser Met Val Gly Pro Ser Gln Gly Arg Ser Pro Ser Tyr
                165                 170                 175

Ala Ser

<210> SEQ ID NO 313
<211> LENGTH: 179
<212> TYPE: PRT
<213> ORGANISM: Artificial Sequence
<220> FEATURE:
<223> OTHER INFORMATION: FGF21 N149-D155 deleted and replaced by GSHSG
      (SEQ ID NO: 163)

<400> SEQUENCE: 313

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Gly Ser His Ser Gly Pro Ala Pro
        115                 120                 125

Arg Gly Pro Ala Arg Phe Leu Pro Leu Pro Gly Leu Pro Pro Ala Pro
    130                 135                 140

Pro Glu Pro Pro Gly Ile Leu Ala Pro Gln Pro Pro Asp Val Gly Ser
145                 150                 155                 160

Ser Asp Pro Leu Ser Met Val Gly Pro Ser Gln Gly Arg Ser Pro Ser
                165                 170                 175

Tyr Ala Ser

<210> SEQ ID NO 314
<211> LENGTH: 178
<212> TYPE: PRT
<213> ORGANISM: Artificial Sequence
<220> FEATURE:
<223> OTHER INFORMATION: FGF21 N149-D155 deleted and replaced by ATTS
      (SEQ ID NO: 164)

<400> SEQUENCE: 314

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

```
Pro Glu Ser Leu Leu Gln Leu Lys Ala Leu Lys Pro Gly Val Ile Gln
     50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Ala Thr Thr Ser Pro Ala Pro Arg
            115                 120                 125

Gly Pro Ala Arg Phe Leu Pro Leu Pro Gly Leu Pro Pro Ala Pro Pro
            130                 135                 140

Glu Pro Pro Gly Ile Leu Ala Pro Gln Pro Pro Asp Val Gly Ser Ser
145                 150                 155                 160

Asp Pro Leu Ser Met Val Gly Pro Ser Gln Gly Arg Ser Pro Ser Tyr
                165                 170                 175

Ala Ser

<210> SEQ ID NO 315
<211> LENGTH: 178
<212> TYPE: PRT
<213> ORGANISM: Artificial Sequence
<220> FEATURE:
<223> OTHER INFORMATION: FGF21 R159-R163 deleted and replaced by GA

<400> SEQUENCE: 315

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
         35                  40                  45

Pro Glu Ser Leu Leu Gln Leu Lys Ala Leu Lys Pro Gly Val Ile Gln
     50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Gly Ala Phe Leu Pro Leu Pro Gly Leu Pro Pro Ala Pro Pro
            130                 135                 140

Glu Pro Pro Gly Ile Leu Ala Pro Gln Pro Pro Asp Val Gly Ser Ser
145                 150                 155                 160

Asp Pro Leu Ser Met Val Gly Pro Ser Gln Gly Arg Ser Pro Ser Tyr
                165                 170                 175

Ala Ser

<210> SEQ ID NO 316
<211> LENGTH: 178
<212> TYPE: PRT
<213> ORGANISM: Artificial Sequence
<220> FEATURE:
<223> OTHER INFORMATION: FGF21 R159-R163 deleted and replaced by GY
```

<400> SEQUENCE: 316

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Gly Tyr Phe Leu Pro Leu Pro Gly Leu Pro Pro Ala Pro Pro
    130                 135                 140

Glu Pro Pro Gly Ile Leu Ala Pro Gln Pro Pro Asp Val Gly Ser Ser
145                 150                 155                 160

Asp Pro Leu Ser Met Val Gly Pro Ser Gln Gly Arg Ser Pro Ser Tyr
                165                 170                 175

Ala Ser
```

<210> SEQ ID NO 317
<211> LENGTH: 178
<212> TYPE: PRT
<213> ORGANISM: Artificial Sequence
<220> FEATURE:
<223> OTHER INFORMATION: FGF21 R159-R163 deleted and replaced by HH

<400> SEQUENCE: 317

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro His His Phe Leu Pro Leu Pro Gly Leu Pro Pro Ala Pro Pro
    130                 135                 140

Glu Pro Pro Gly Ile Leu Ala Pro Gln Pro Pro Asp Val Gly Ser Ser
145                 150                 155                 160
```

Asp Pro Leu Ser Met Val Gly Pro Ser Gln Gly Arg Ser Pro Ser Tyr
            165                 170                 175

Ala Ser

<210> SEQ ID NO 318
<211> LENGTH: 178
<212> TYPE: PRT
<213> ORGANISM: Artificial Sequence
<220> FEATURE:
<223> OTHER INFORMATION: FGF21 R159-R163 deleted and replaced by GE

<400> SEQUENCE: 318

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Gly Glu Phe Leu Pro Leu Pro Gly Leu Pro Pro Ala Pro Pro
    130                 135                 140

Glu Pro Pro Gly Ile Leu Ala Pro Gln Pro Pro Asp Val Gly Ser Ser
145                 150                 155                 160

Asp Pro Leu Ser Met Val Gly Pro Ser Gln Gly Arg Ser Pro Ser Tyr
                165                 170                 175

Ala Ser

<210> SEQ ID NO 319
<211> LENGTH: 178
<212> TYPE: PRT
<213> ORGANISM: Artificial Sequence
<220> FEATURE:
<223> OTHER INFORMATION: FGF21 R159-R163 deleted and replaced by HE

<400> SEQUENCE: 319

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

```
Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro His Glu Phe Leu Pro Leu Pro Gly Leu Pro Pro Ala Pro Pro
        130                 135                 140

Glu Pro Pro Gly Ile Leu Ala Pro Gln Pro Pro Asp Val Gly Ser Ser
145                 150                 155                 160

Asp Pro Leu Ser Met Val Gly Pro Ser Gln Gly Arg Ser Pro Ser Tyr
                165                 170                 175

Ala Ser
```

```
<210> SEQ ID NO 320
<211> LENGTH: 181
<212> TYPE: PRT
<213> ORGANISM: Artificial Sequence
<220> FEATURE:
<223> OTHER INFORMATION: FGF21 A162Y

<400> SEQUENCE: 320

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Tyr Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

```
<210> SEQ ID NO 321
<211> LENGTH: 181
<212> TYPE: PRT
<213> ORGANISM: Artificial Sequence
<220> FEATURE:
<223> OTHER INFORMATION: FGF21 R159H

<400> SEQUENCE: 321

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30
```

```
Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro His Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 322
<211> LENGTH: 181
<212> TYPE: PRT
<213> ORGANISM: Artificial Sequence
<220> FEATURE:
<223> OTHER INFORMATION: FGF21 S200M

<400> SEQUENCE: 322

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Met Gln Gly Arg Ser
                165                 170                 175

Pro Ser Tyr Ala Ser
            180

<210> SEQ ID NO 323
<211> LENGTH: 181
```

```
<212> TYPE: PRT
<213> ORGANISM: Artificial Sequence
<220> FEATURE:
<223> OTHER INFORMATION: FGF21 G202T

<400> SEQUENCE: 323

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Thr Arg Ser
                165                 170                 175

Pro Ser Tyr Ala Ser
            180

<210> SEQ ID NO 324
<211> LENGTH: 181
<212> TYPE: PRT
<213> ORGANISM: Artificial Sequence
<220> FEATURE:
<223> OTHER INFORMATION: FGF21 R203E

<400> SEQUENCE: 324

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140
```

```
Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Glu Ser
                165                 170                 175

Pro Ser Tyr Ala Ser
            180

<210> SEQ ID NO 325
<211> LENGTH: 181
<212> TYPE: PRT
<213> ORGANISM: Artificial Sequence
<220> FEATURE:
<223> OTHER INFORMATION: FGF21 R203H

<400> SEQUENCE: 325

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly His Ser
                165                 170                 175

Pro Ser Tyr Ala Ser
            180

<210> SEQ ID NO 326
<211> LENGTH: 179
<212> TYPE: PRT
<213> ORGANISM: Artificial Sequence
<220> FEATURE:
<223> OTHER INFORMATION: FGF21 G202-R203 deleted

<400> SEQUENCE: 326

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60
```

-continued

```
Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Ser Pro Ser
                165                 170                 175

Tyr Ala Ser

<210> SEQ ID NO 327
<211> LENGTH: 198
<212> TYPE: PRT
<213> ORGANISM: Artificial Sequence
<220> FEATURE:
<223> OTHER INFORMATION: FGF21 PLSMVGPSQGRSPSYAS (SEQ ID NO: 169)
      inserted after S209

<400> SEQUENCE: 327

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser Pro Leu Ser Met Val Gly Pro Ser Gln Gly Arg
            180                 185                 190

Ser Pro Ser Tyr Ala Ser
        195

<210> SEQ ID NO 328
<211> LENGTH: 197
<212> TYPE: PRT
<213> ORGANISM: Artificial Sequence
```

```
<220> FEATURE:
<223> OTHER INFORMATION: FGF21 P199 deleted, PLSMVGSQGRSPSYAS (SEQ ID
      NO: 170) inserted after S209

<400> SEQUENCE: 328

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser Pro Leu Ser Met Val Gly Ser Gln Gly Arg Ser
            180                 185                 190

Pro Ser Tyr Ala Ser
            195
```

FGF21 VARIANTS

CROSS-REFERENCE TO RELATED APPLICATIONS

This application is a 35 U.S.C. § 371 filing of International Patent Application No. PCT/EP2016/079551, filed Dec. 2, 2016, which claims priority to European Patent Application No. 15306913.3, filed Dec. 2, 2015, the entire contents of which are incorporated herein by reference.

TECHNICAL FIELD OF THE INVENTION

The present invention relates to polypeptide variants of human fibroblast growth factor 21 (FGF21) and fusion molecules thereof, as well as to nucleic acid molecules encoding the same. It further relates to their use as medicaments, in particular for the treatment of obesity, overweight, metabolic syndrome, diabetes mellitus, hyperglycemia, dyslipidemia, non-alcoholic steatohepatitis (NASH) and/or atherosclerosis.

BACKGROUND OF THE INVENTION

Fibroblast growth factors (FGFs) are polypeptides widely expressed in developing and adult tissues. The FGF family currently consists of twenty-two members, FGF1 to FGF23 (one of them being referred to as FGF15/19). The members of the FGF family are highly conserved in both gene structure and amino acid sequence between vertebrate species. There are 18 mammalian fibroblast growth factors (FGF1-FGF10 and FGF16-FGF23) which are grouped into 6 subfamilies based on differences in sequence homology and phylogeny. The numbered 'FGFs' that are unassigned to subfamilies—the FGF homologous factors (previously known as FGF11-FGF14)—have high sequence identity with the FGF family but do not activate FGF receptors (FGFRs) and are therefore not generally considered members of the FGF family. While most of FGFs act as local regulators of cell growth and differentiation, recent studies indicated that FGF19 subfamily members including FGF15/19, FGF21 and FGF23 exert important metabolic effects by an endocrine fashion. The members of the FGF19 subfamily regulate diverse physiological processes that are not affected by classical FGFs. The wide variety of metabolic activities of these endocrine factors include the regulation of the bile acid, carbohydrate and lipid metabolism as well as phosphate, calcium and vitamin D homeostasis.

FGF21 was originally isolated from mouse embryos. FGF21 mRNA was most abundantly expressed in the liver, and to lesser extent in the thymus. Human FGF21 is highly similar (approximately 81% amino acid identity) to mouse FGF21. Among human FGF family members, FGF21 is the most similar (approximately 30% amino acid identity) to FGF19. FGF21 does not exhibit the proliferative and tumorigenic effects that are typical for a majority of the members of the FGF family.

FGF21 is a metabolic regulator produced primarily by the liver that exerts potent antidiabetic and lipid-lowering effects in animal models of obesity and type 2 diabetes mellitus. This hormone contributes to body weight regulation and is involved in the response to nutritional deprivation and ketogenic state in mice. The principal sites of metabolic actions of FGF21 are adipose tissue, liver and pancreas. Experimental studies have shown improvements in diabetes compensation and dyslipidemia after FGF21 administration in diabetic mice and primates. FGF21 has been shown to stimulate glucose uptake in mouse 3T3-L1 adipocytes in the presence and absence of insulin, and to decrease fed and fasting blood glucose, triglycerides, and glucagon levels in ob/ob and db/db mice and 8 week old ZDF rats in a dose dependent manner, thus, providing the basis for the use of FGF21 as a therapy for treating diabetes and obesity).

The administration of FGF21 to obese leptin-deficient ob/ob and leptin receptor-deficient db/db mice and obese ZDF rats significantly lowered blood glucose and triglycerides, decreased fasting insulin levels and improved glucose clearance during an oral glucose tolerance test. FGF21 did not affect food intake or body weight/composition of diabetic or lean mice and rats over the course of 2 weeks of administration. Importantly, FGF21 did not induce mitogenicity, hypoglycemia, or weight gain at any dose tested in diabetic or healthy animals or when overexpressed in transgenic mice. FGF21-overexpressing transgenic mice were resistant to diet-induced obesity.

The administration of FGF21 to diabetic rhesus monkeys for 6 weeks reduced fasting plasma glucose, fructosamine, triglyceride, insulin and glucagon levels. Importantly, hypoglycemia was not observed during the study despite of significant glucose-lowering effects. FGF21 administration also significantly lowered LDL-cholesterol and increased HDL-cholesterol and, in contrast to mice, slightly but significantly decreased body weight.

SUMMARY OF THE INVENTION

A problem associated with the use of human wild-type FGF21 as a therapeutic in the treatment of diabetes, obesity, metabolic syndrome and other indications is its limited half-life in vivo. In mice FGF21 has a half-life below 1 hour and in cynomolgus monkeys (*Macaca fascicularis*) around 2-4 hours only. Therefore, in developing an FGF21 protein for use as a therapeutic there is a need for variants with improved pharmaceutical properties over human wild-type FGF21, in particular increased stability against proteases and/or thermal degradation and/or increased potency/efficacy. To achieve this goal, FGF21 variants were designed to identify FGF21 polypeptides having enhanced stability.

In a first aspect, the present invention relates to a variant of human fibroblast growth factor 21 (FGF21) comprising the amino acid sequence of SEQ ID NO: 171,
wherein
    amino acids 1-28 are deleted;
    Xaa55 is Q or another amino acid, such as G or C;
    Xaa147 is P or C, or deleted;
    Xaa148 is G or C, or deleted;
    Xaa149 is N or C, or deleted;
    Xaa150 is K or another amino acid, such as H, or deleted;
    Xaa151 is S or deleted;
    Xaa152 is P or another amino acid, such as A or L, or deleted;
    Xaa153 is H or another amino acid, such as Q, Y or K, or deleted;
    Xaa154 is R or another amino acid, such as Q or K, or deleted;
    Xaa155 is D or another amino acid, such as L, K, Y, P, E, N or C, or deleted;
    Xaa156 is P or another amino acid, such as A or K, or deleted;
    Xaa157 is A or another amino acid, such as V, G or S, or deleted;
    Xaa158 is P or another amino acid, such as H, or deleted;
    Xaa159 is R or another amino acid, such as H, K or Q, or deleted;

Xaa160 is G or deleted;
Xaa161 is P or C, or deleted;
Xaa162 is A or another amino acid, such as C or Y, or deleted;
Xaa163 is R or another amino acid, such as H, or deleted;
Xaa184 is Q or deleted;
Xaa185 is P or deleted;
Xaa186 is P or deleted;
Xaa187 is D or deleted;
Xaa188 is V or deleted;
Xaa189 is G or deleted;
Xaa190 is S or deleted;
Xaa191 is S or deleted;
Xaa192 is D or deleted;
Xaa193 is P or deleted;
Xaa194 is L or deleted;
Xaa195 is S or C, or deleted;
Xaa196 is M or another amino acid, such as P, V or C, or deleted;
Xaa197 is V or another amino acid, such as E, D, G or M, or deleted;
Xaa198 is G or another amino acid, such as E, D, R, K, Y, P or V, or deleted;
Xaa199 is P or another amino acid, such as S, Q, R, T, G, F, L, D or M, or deleted;
Xaa200 is S or another amino acid, such as Q, M, C, P, N or H, or deleted;
Xaa201 is Q or another amino acid, such as P or S, or deleted;
Xaa202 is G or another amino acid, such as T, or deleted;
Xaa203 is R or another amino acid, such as E, H or C, or deleted;
Xaa204 is S or deleted;
Xaa205 is P or deleted;
Xaa206 is S or deleted; and
Xaa207 is Y or deleted;
wherein, optionally, SEQ ID NO: 171 comprises a substitution of at least one of the following amino acids with C: R47, L49, T51, A54, Q56, A59, H60, E62, I63, G67, V69, G71, A72, A73, S76, P77, E78, S79, L80, L81, Q82, L83, I91, L94, G95, V96, K97, T98, R100, L102, Q104, D107, G108, L110, G112, L114, A120, R124, D130, Y132, Q136, S137, A139, H140, L142, P143, H145, L146, L165, L167, L170, P174;
with the proviso that the variant of human FGF21 is not mature human wild-type FGF21 (SEQ ID NO: 2) and comprises 0, 2, 4, 6 or 8 additional cysteines as compared to mature human wild-type FGF21 (SEQ ID NO: 2),
wherein, optionally, SEQ ID NO: 171 further comprises the mutation G141S and/or the mutation P174L.

In one embodiment,
Xaa147 to Xaa159 are deleted and replaced by a protease resistant peptide linker, such as the peptide linker of SEQ ID NO: 161 or SEQ ID NO: 162;
Xaa149 to Xaa155 are deleted and replaced by a protease resistant peptide linker, such as the peptide linker of SEQ ID NO: 161, SEQ ID NO: 163 or SEQ ID NO: 164;
Xaa149 to Xaa159 are deleted and replaced by a protease resistant peptide linker, such as the peptide linker of SEQ ID NO: 161 or SEQ ID NO: 162;
Xaa149 to Xaa162 are deleted and replaced by a protease resistant peptide linker, such as the peptide linker of SEQ ID NO: 163 or SEQ ID NO: 165;
Xaa149 to Xaa163 are deleted and replaced by a protease resistant peptide linker, such as the peptide linker of SEQ ID NO: 161;
Xaa159 to Xaa163 are deleted and replaced by a protease resistant peptide linker, such as GA, GY, HH, GE or HE;
Xaa197 to Xaa203 are deleted and replaced by a protease resistant peptide linker, such as the peptide linker of SEQ ID NO: 166 or SEQ ID NO: 167;
a protease resistant peptide linker, such as the peptide linker of SEQ ID NO: 168, is inserted between Xaa198 and Xaa199; and/or
the amino acid sequence of SEQ ID NO: 169 or SEQ ID NO: 170 is added after S209 of SEQ ID NO: 171.

In one embodiment, the variant of human FGF21 has at least 90% or at least 91% or at least 92% or at least 93% or at least 94% or at least 95% or at least 96% or at least 97% or at least 98% sequence identity with mature human wild-type FGF21 (SEQ ID NO: 2).

In one embodiment,
Xaa55 is Q or C;
Xaa147 is P or C;
Xaa148 is G or C;
Xaa149 is N or C;
Xaa150 is K;
Xaa151 is S;
Xaa152 is P;
Xaa153 is H;
Xaa154 is R;
Xaa155 is D or C;
Xaa156 is P;
Xaa157 is A;
Xaa158 is P;
Xaa159 is R;
Xaa160 is G;
Xaa161 is P or C;
Xaa162 is A or C;
Xaa163 is R;
Xaa184 is Q;
Xaa185 is P;
Xaa186 is P;
Xaa187 is D;
Xaa188 is V;
Xaa189 is G;
Xaa190 is S;
Xaa191 is S;
Xaa192 is D;
Xaa193 is P;
Xaa194 is L;
Xaa195 is S or C;
Xaa196 is M or another amino acid, such as P, V or C, or deleted;
Xaa197 is V or another amino acid, such as E, D, G or M, or deleted;
Xaa198 is G or another amino acid, such as E, D, R, K, Y, P or V, or deleted;
Xaa199 is P or another amino acid, such as S, Q, R, T, G, F, L, D or M, or deleted;
Xaa200 is S or another amino acid, such as Q, M, C, P, N or H, or deleted;
Xaa201 is Q or another amino acid, such as P or S, or deleted;
Xaa202 is G or another amino acid, such as T, or deleted;
Xaa203 is R or another amino acid, such as E, H or C, or deleted;
Xaa204 is S;
Xaa205 is P;
Xaa206 is S; and
Xaa207 is Y;

wherein, optionally, SEQ ID NO: 171 comprises a substitution of at least one of the following amino acids with C: R47, L49, T51, A54, Q56, A59, H60, E62, I63, G67, V69, G71, A72, A73, S76, P77, E78, S79, L80, L81, Q82, L83, I91, L94, G95, V96, K97, T98, R100, L102, Q104, D107, G108, L110, G112, L114, A120, R124, D130, Y132, Q136, S137, A139, H140, L142, P143, H145, L146, L165, L167, L170, P174.

In one embodiment, the variant comprises the amino acid sequence of SEQ ID NO: 175 (wherein the variables are as defined herein),
wherein, optionally, SEQ ID NO: 175 comprises a substitution of at least one of the following amino acids with C: R47, L49, T51, A54, Q56, A59, H60, E62, I63, G67, V69, G71, A72, A73, S76, P77, E78, S79, L80, L81, Q82, L83, I91, L94, G95, V96, K97, T98, R100, L102, Q104, D107, G108, L110, G112, L114, A120, R124, D130, Y132, Q136, S137, A139, H140, L142, P143, H145, L146, L165, L167, L170, P174;
with the proviso that SEQ ID NO: 175 is not mature human wild-type FGF21 (SEQ ID NO: 2) and comprises 0, 2, 4, 6 or 8 additional cysteines as compared to mature human wild-type FGF21 (SEQ ID NO: 2),
wherein, optionally, SEQ ID NO: 175 further comprises the mutation G141S and/or the mutation P174L.

In one embodiment,
Xaa55 is Q or C;
Xaa147 is P or C;
Xaa148 is G;
Xaa149 is N or C;
Xaa155 is D or C;
Xaa161 is P;
Xaa162 is A;
Xaa195 is S;
Xaa196 is M;
Xaa197 is V;
Xaa198 is G or another amino acid, such as E, D, R, K, Y, P or V, or deleted;
Xaa199 is P or another amino acid, such as S, Q, R, T, G, F, L, D or M, or deleted;
Xaa200 is S;
Xaa201 is Q;
Xaa202 is G; and
Xaa203 is R;
wherein, optionally, SEQ ID NO: 171 comprises a substitution of at least one of the following amino acids with C: R47, A59, H60, G71, S76, S79, D107, G108, L142, P174.

In one embodiment, the variant comprises the amino acid sequence of SEQ ID NO: 176 (wherein the variables are as defined herein),
wherein, optionally, SEQ ID NO: 176 comprises a substitution of at least one of the following amino acids with C: R47, A59, H60, G71, S76, S79, D107, G108, L142, P174;
with the proviso that SEQ ID NO: 176 is not mature human wild-type FGF21 (SEQ ID NO: 2) and comprises 0, 2, 4, 6 or 8 additional cysteines as compared to mature human wild-type FGF21 (SEQ ID NO: 2),
wherein, optionally, SEQ ID NO: 176 further comprises the mutation G141S and/or the mutation P174L.

In one embodiment, Xaa198 is G, R, K or Y.
In one embodiment, Xaa199 is P or deleted.
In one embodiment, SEQ ID NO: 171, 175 or 176 comprises a substitution of the following amino acids with C:
R47 and P174;
Xaa55 and Xaa147;
Xaa55 and Xaa149;
A59 and G71;
H60 and S79;
S76 and S79;
D107 and Xaa155; and/or
G108 and L142.

In one embodiment, SEQ ID NO: 171, 175 or 176 comprises a substitution of the following amino acids with C:
Xaa55 and Xaa147;
Xaa55 and Xaa149;
A59 and G71;
S76 and S79;
D107 and Xaa155; or
G108 and L142.

In one embodiment, SEQ ID NO: 171, 175 or 176 comprises a substitution of Xaa55 and Xaa147 with C. In another embodiment, SEQ ID NO: 171, 175 or 176 comprises a substitution of Xaa55 and Xaa149 with C.

In one embodiment,
Xaa55 is C, Xaa147 is C, Xaa149 is N, Xaa155 is D, Xaa198 is G, and Xaa199 is deleted;
Xaa55 is C, Xaa147 is C, Xaa149 is N, Xaa155 is D, Xaa198 is Y, and Xaa199 is P;
Xaa55 is C, Xaa147 is P, Xaa149 is C, Xaa155 is D, Xaa198 is G, and Xaa199 is deleted;
Xaa55 is C, Xaa147 is P, Xaa149 is C, Xaa155 is D, Xaa198 is Y, and Xaa199 is P;
Xaa55 is Q, Xaa147 is P, Xaa149 is N, Xaa155 is D, Xaa198 is G, and Xaa199 is deleted;
Xaa55 is Q, Xaa147 is P, Xaa149 is N, Xaa155 is D, Xaa198 is R, and Xaa199 is P;
Xaa55 is Q, Xaa147 is P, Xaa149 is N, Xaa155 is D, Xaa198 is K, and Xaa199 is P;
Xaa55 is Q, Xaa147 is P, Xaa149 is N, Xaa155 is D, Xaa198 is Y, and Xaa199 is P;
Xaa55 is C, Xaa147 is C, Xaa149 is N, Xaa155 is D, Xaa198 is G, and Xaa199 is P;
Xaa55 is C, Xaa147 is P, Xaa149 is C, Xaa155 is D, Xaa198 is G, and Xaa199 is P;
Xaa55 is Q, Xaa147 is P, Xaa149 is N, Xaa155 is D, Xaa198 is G, and Xaa199 is deleted, wherein SEQ ID NO: 171, 175 or 176 comprises the substitution of A59 and G71 with C;
Xaa55 is Q, Xaa147 is P, Xaa149 is N, Xaa155 is D, Xaa198 is Y, and Xaa199 is P, wherein SEQ ID NO: 171, 175 or 176 comprises the substitution of A59 and G71 with C;
Xaa55 is Q, Xaa147 is P, Xaa149 is N, Xaa155 is D, Xaa198 is G, and Xaa199 is deleted, wherein SEQ ID NO: 171, 175 or 176 comprises the substitution of S76 and S79 with C;
Xaa55 is Q, Xaa147 is P, Xaa149 is N, Xaa155 is D, Xaa198 is Y, and Xaa199 is P, wherein SEQ ID NO: 171, 175 or 176 comprises the substitution of S76 and S79 with C;
Xaa55 is Q, Xaa147 is P, Xaa149 is N, Xaa155 is D, Xaa198 is G, and Xaa199 is deleted, wherein SEQ ID NO: 171, 175 or 176 comprises the substitution of G108 and L142 with C;
Xaa55 is Q, Xaa147 is P, Xaa149 is N, Xaa155 is D, Xaa198 is Y, and Xaa199 is P, wherein SEQ ID NO: 171, 175 or 176 comprises the substitution of G108 and L142 with C;
Xaa55 is Q, Xaa147 is P, Xaa149 is N, Xaa155 is C, Xaa198 is G, and Xaa199 is deleted, wherein SEQ ID NO: 171, 175 or 176 comprises the substitution of D107 with C; or Xaa55 is Q, Xaa147 is P, Xaa149 is N, Xaa155 is C, Xaa198 is Y, and Xaa199 is P, wherein SEQ ID NO: 171, 175 or 176 comprises the substitution of D107 with C.

In one embodiment, the variant further comprises at least one additional amino acid at its N-terminus.

In one embodiment, the at least one additional amino acid is selected from the group consisting of G, A, N and C.

In a second aspect, the present invention relates to a variant of human FGF21 comprising or consisting of an amino acid sequence according to one of SEQ ID NOs: 1 to 3, 172, 173 and 174,
wherein the amino acid sequence comprises at least one of the following mutations:
Q55G, K150H, P152A, P152L, P152 deleted, H153Q, H153Y, H153K, H153 deleted, R154Q, R154K, D155L, D155K, D155Y, D155P, D155E, D155N, P156A, P156K, A157V, A157G, A157S, P158H, R159H, R159K, R159Q, A162Y, R163H, Q184 deleted, P185 deleted, P186 deleted, D187 deleted, V188 deleted, G189 deleted, S190 deleted, S191 deleted, D192 deleted, P193 deleted, L194 deleted, S195 deleted, M196 deleted, M196P, M196V, V197E, V197D, V197 deleted, V197G, V197M, G198E, G198D, G198R, G198K, G198Y, G198P, G198V, G198 deleted, P199S, P199Q, P199 deleted, P199R, P199T, P199G, P199F, P199L, P199D, P199M, S200Q, S200M, S200P, S200N, S200H, S200 deleted, Q201P, Q201S, Q201 deleted, G202T, G202 deleted, R203E, R203H, R203 deleted, S204 deleted, P205 deleted, S206 deleted, Y207 deleted, P147-R159 replaced by GSGS (SEQ ID NO: 161), P147-R159 replaced by GGSGGS (SEQ ID NO: 162), N149-D155 replaced by GSGS (SEQ ID NO: 161), N149-D155 replaced by GSHSG (SEQ ID NO: 163), N149-D155 replaced by ATTS (SEQ ID NO: 164), N149-R159 replaced by GSGS (SEQ ID NO: 161), N149-R159 replaced by GGSGGS (SEQ ID NO: 162), N149-A162 replaced by GSHSG (SEQ ID NO: 163), N149-A162 replaced by GSHSGS (SEQ ID NO: 165), N149-R163 replaced by GSGS (SEQ ID NO: 161), R159-R163 replaced by GA, GY, HH, GE or HE, V197-R203 replaced by GHRSHLQTVF (SEQ ID NO: 166), V197-R203 replaced by GLNSMV (SEQ ID NO: 167), GGGGS (SEQ ID NO: 168) inserted between G198 and P199, PLSMVGPSQGRSPSYAS (SEQ ID NO: 169) or PLSMVGSQGRSPSYAS (SEQ ID NO: 170) added after S209;
and/or
wherein the amino acid sequence comprises a substitution of two, four, six or eight of the following amino acids with C:
R47, L49, T51, A54, Q55, Q56, A59, H60, E62, I63, G67, V69, G71, A72, A73, S76, P77, E78, S79, L80, L81, Q82, L83, I91, L94, G95, V96, K97, T98, R100, L102, Q104, D107, G108, L110, G112, L114, A120, R124, D130, Y132, Q136, S137, A139, H140, L142, P143, H145, L146, P147, G148, N149, D155, P161, A162, L165, L167, L170, P174, S195, M196, S200, R203;
wherein the numbering of the amino acids is in accordance with SEQ ID NO: 1.

In one embodiment, the amino acid sequence comprises at least one of the following mutations:
K150H, P152A, P152L, P152 deleted, H153Q, H153Y, H153K, H153 deleted, R154Q, R154K, D155L, D155K, D155Y, D155P, D155E, D155N, P156A, P156K, A157V, A157G, A157S, P158H, R159H, R159K, R159Q, A162Y, R163H, M196 deleted, M196P, M196V, V197E, V197D, V197 deleted, V197G, V197M, G198E, G198D, G198R, G198K, G198Y, G198P, G198V, G198 deleted, P199S, P199Q, P199 deleted, P199R, P199T, P199G, P199F, P199L, P199D, P199M, S200Q, S200M, S200P, S200N, S200H, S200 deleted, Q201P, Q201S, Q201 deleted, G202T, G202 deleted, R203E, R203H, R203 deleted;
and/or
the amino acid sequence comprises a substitution of two, four, six or eight of the following amino acids with C:
R47, L49, T51, A54, Q55, Q56, A59, H60, E62, I63, G67, V69, G71, A72, A73, S76, P77, E78, S79, L80, L81, Q82, L83, I91, L94, G95, V96, K97, T98, R100, L102, Q104, D107, G108, L110, G112, L114, A120, R124, D130, Y132, Q136, S137, A139, H140, L142, P143, H145, L146, P147, G148, N149, D155, P161, A162, L165, L167, L170, P174, S195, M196, S200, R203.

In one embodiment, the amino acid sequence comprises at least one of the following mutations:
M196 deleted, M196P, M196V, V197E, V197D, V197 deleted, V197G, V197M, G198E, G198D, G198R, G198K, G198Y, G198P, G198V, G198 deleted, P199S, P199Q, P199 deleted, P199R, P199T, P199G, P199F, P199L, P199D, P199M, S200Q, S200M, S200P, S200N, S200H, S200 deleted, Q201P, Q201S, Q201 deleted, G202T, G202 deleted, R203E, R203H, R203 deleted;
and/or
the amino acid sequence comprises a substitution of two, four, six or eight of the following amino acids with C:
R47, L49, T51, A54, Q55, Q56, A59, H60, E62, I63, G67, V69, G71, A72, A73, S76, P77, E78, S79, L80, L81, Q82, L83, I91, L94, G95, V96, K97, T98, R100, L102, Q104, D107, G108, L110, G112, L114, A120, R124, D130, Y132, Q136, S137, A139, H140, L142, P143, H145, L146, P147, G148, N149, D155, P161, A162, L165, L167, L170, P174.

In one embodiment, the amino acid sequence comprises a substitution of the following amino acids with C:
R47 and P174;
Q55 and P147;
Q55 and N149;
A59 and G71;
H60 and S79;
S76 and S79;
D107 and D155; and/or
G108 and L142.

In one embodiment, the amino acid sequence comprises a mutation selected from the group consisting of G198R, G198K, G198Y and P199 deleted;
and/or
the amino acid sequence comprises a substitution of the following amino acids with C:
Q55 and P147;
Q55 and N149;
A59 and G71;
S76 and S79;
D107 and D155; or
G108 and L142.

In one embodiment, the amino acid sequence comprises a substitution of Q55 and P147 with C.

In another embodiment, the amino acid sequence comprises a substitution of Q55 and N149 with C.

In one embodiment, the amino acid sequence comprises at least one further mutation (e.g., 1, 2, 3, 4 or 5 further mutation(s)) at another site of one of SEQ ID NOs: 1 to 3, 172, 173 and 174.

In one embodiment, the amino acid sequence has at least 90% or at least 91% or at least 92% or at least 93% or at least 94% or at least 95% or at least 96% or at least 97% or at least 98% sequence identity with one of SEQ ID NOs: 1 to 3, 172, 173 and 174.

In a third aspect, the present invention relates to a variant of human FGF21 comprising or consisting of an amino acid sequence according to one of SEQ ID NOs: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327 and 328, wherein, optionally, the variant further comprises the mutation G141S and/or the mutation P174L, wherein the numbering of the amino acids is in accordance with SEQ ID NO: 1.

In one embodiment, the variant according to the first, second and third aspect has an increased proteolytic stability in human and/or murine blood plasma as compared to mature human wild-type FGF21 (SEQ ID NO: 2).

In one embodiment, the variant has an increased thermal stability as compared to mature human wild-type FGF21 (SEQ ID NO: 2).

In one embodiment, the variant induces phosphorylation of the mitogen-activated protein kinase (MAPK) ERK1/2.

In one embodiment, the variant induces phosphorylation of the mitogen-activated protein kinase (MAPK) ERK1/2 with an EC50 of 100 nmol/L or lower, or 90 nmol/L or lower, or 80 nmol/L or lower, or 70 nmol/L or lower, or 60 nmol/L or lower, or 50 nmol/L or lower, or 40 nmol/L or lower, or 30 nmol/L or lower, or 20 nmol/L or lower, or 15 nmol/L or lower, or 12 nmol/L or lower, or 11 nmol/L or lower, or 10 nmol/L or lower, or 9 nmol/L or lower, or 8 nmol/L or lower, or 7 nmol/L or lower, or 6 nmol/L or lower, or 5 nmol/L or lower, or 4 nmol/L or lower, or 3 nmol/L or lower, or 2 nmol/L or lower, e.g., as determined in an In-Cell Western (ICW) assay, such as in a mammalian cell culture.

In one embodiment, the variant further comprises at least one label or tag allowing the detection and/or isolation of the variant.

In one embodiment, the variant is fused or conjugated to a half-life extension module.

In one embodiment, the half-life extension module is selected from the group consisting of a polymer (e.g., polyethylene glycol (PEG), hydroxyethyl starch (HES), hyaluronic acid, polysialic acid), an unstructured (poly-)peptide chain (e.g., PAS, XTEN), an elastin-like polypeptide (ELP), a serum protein (e.g., albumin), a serum protein binding molecule (e.g., an albumin binding domain (ABD), an albumin binding fatty acid), an antibody, an immunoglobulin, an Fc region/domain of an immunoglobulin and an immunoglobulin binding domain.

In another aspect, the present invention relates to a fusion molecule comprising a variant of human FGF21 as defined above and at least one other active pharmaceutical ingredient.

In another aspect, the present invention relates to a nucleic acid molecule encoding a variant of human FGF21 as defined above or a fusion molecule as defined above.

In one embodiment, the nucleic acid molecule is contained in a vector or is integrated into a genome.

In another aspect, the present invention relates to a host cell containing a nucleic acid molecule as defined above.

In another aspect, the present invention relates to a method of producing a variant of human FGF21 as defined above or a fusion molecule as defined above, comprising cultivating a host cell as defined above and isolating the variant or fusion molecule from the culture medium.

In another aspect, the present invention relates to a pharmaceutical composition comprising a variant of human FGF21 as defined above or a fusion molecule as defined above or a nucleic acid molecule as defined above or a host cell as defined above, together with a pharmaceutically acceptable carrier and/or excipient.

In one embodiment, the pharmaceutical composition further comprises at least one other active pharmaceutical ingredient.

In another aspect, the present invention relates to a combination of a variant of human FGF21 as defined above with at least one other active pharmaceutical ingredient.

In one embodiment, the at least one other active pharmaceutical ingredient comprised in the fusion molecule or the pharmaceutical composition or the combination as defined above is selected from the group consisting of insulin and insulin derivatives, GLP-1, GLP-1 analogues and GLP-1 receptor agonists, polymer bound GLP-1 and GLP-1 analogues, dual GLP-1/GIP agonists, dual GLP-1/glucagon receptor agonists, PYY3-36 or analogues thereof, pancreatic polypeptide or analogues thereof, glucagon receptor agonists or antagonists, GIP receptor agonists or antagonists, ghrelin antagonists or inverse agonists, xenin and analogues thereof, peptides (specifically) binding to one of the aforementioned receptors (e.g., GLP-1 receptor, GIP receptor, glucagon receptor), DDP-IV inhibitors, SGLT-2 inhibitors, dual SGLT-2/SGLT-1 inhibitors, biguanides, thiazolidinediones, PPAR agonists, PPAR modulators, sulfonylureas, meglitinides, alpha-glucosidase inhibitors, amylin and amylin analogues, GPR119 agonists, GPR40 agonists, GPR120 agonists, GPR142 agonists, TGR5 agonists, AMPK stimulants, AMPK activators, inhibitors of 11-beta-HSD, activators of glucokinase, inhibitors of DGAT, inhibitors of protein tyrosine phosphatase 1, inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase, CCR-2 antagonists, modulators of glucose transporter-4, somatostatin receptor 3 agonists, HMG-CoA-reductase inhibitors, fibrates, nicotinic acid and derivatives thereof, nicotinic acid receptor 1 agonists, ACAT inhibitors, cholesterol absorption inhibitors, bile acid-binding substances, BAT inhibitors, MTP inhibitors, modulators of PCSK9, LDL receptor up-regulators (liver selective thyroid hormone receptor beta agonists), HDL-raising compounds, lipid metabolism modulators, PLA2 inhibitors, ApoA-1 enhancers, cholesterol synthesis inhibitors, omega-3 fatty acids and derivatives thereof, active substances for the treatment of obesity, CB1 receptor antagonists, MCH-1 antagonists, MC4 receptor agonists and partial agonists, NPY5 or NPY2 antagonists, NPY4 agonists, beta-3 adrenergic receptor agonists, leptin or leptin mimetics, 5HT2c receptor agonists, lipase inhibitors, angiogenesis inhibitors, H3 antagonists, AgRP inhibitors, triple monoamine uptake inhibitors, MetAP2 inhibitors, antisense oligonucleotides against production of fibroblast growth factor receptor 4 or prohibitin targeting peptide-1, drugs for influencing high blood pressure, chronic heart failure or atherosclerosis, angiotensin II receptor antagonists, dual angiotensin receptor blockers (ARB), angiotensin converting enzyme (ACE) inhibitors, angiotensin converting enzyme 2 (ACE-2) activators, renin inhibitors, prorenin inhibitors, endothelin converting enzyme (ECE) inhibitors, endothelin receptor blockers, endothelin antagonists, diuretics, aldosterone antagonists, aldosterone synthase inhibitors, alpha-blockers, antagonists of the alpha-2 adrenergic receptor, beta-blockers, mixed alpha-/beta-blockers, calcium antagonists/calcium channel blockers (CBBs), dual mineralocorticoid/CCBs, centrally acting antihypertensives, inhibitors of neutral endopeptidase, aminopeptidase-A inhibitors, vasopeptide inhibitors, dual vasopeptide inhibitors, neprilysin-ACE inhibitors, neprilysin-ECE inhibitors, dual-acting Angiotensin (AT) receptor-neprilysin inhibitors, dual AT1/endothelin-1 (ETA) antagonists, advanced glycation end-product breakers, recombinant renalase, blood pressure vaccines, anti-RAAS vaccines, AT1- or AT2-vaccines, modulators of genetic polymorphisms with antihypertensive response and thrombocyte aggregation inhibitors.

In one embodiment, the at least one other active pharmaceutical ingredient is a glucagon-like peptide-1 (GLP-1) receptor agonist.

In another aspect, the present invention relates to a kit comprising a variant of human FGF21 as defined above or a fusion molecule as defined above or a nucleic acid molecule as defined above or a host cell as defined above or a pharmaceutical composition as defined above.

In another aspect, the present invention relates to a variant of human FGF21 as defined above or a fusion molecule as defined above or a nucleic acid molecule as defined above or a host cell as defined above or a pharmaceutical composition as defined above for use as a medicament.

In another aspect, the present invention relates to a variant of human FGF21 as defined above or a fusion molecule as defined above or a nucleic acid molecule as defined above or a host cell as defined above or a pharmaceutical composition as defined above for use in the treatment of a disease or disorder selected from the group consisting of obesity, overweight, metabolic syndrome, diabetes mellitus, hyperglycemia, dyslipidemia, non-alcoholic steatohepatitis (NASH) and atherosclerosis.

In another aspect, the present invention relates to the use of a variant of human FGF21 as defined above or a fusion molecule as defined above or a nucleic acid molecule as defined above or a host cell as defined above or a pharmaceutical composition as defined above in the manufacture of a medicament for the treatment of a disease or disorder selected from the group consisting of obesity, metabolic syndrome, diabetes mellitus, hyperglycemia, dyslipidemia, non-alcoholic steatohepatitis (NASH) and atherosclerosis.

In another aspect, the present invention relates to a method of treating a disease or disorder selected from the group consisting of obesity, metabolic syndrome, diabetes mellitus, hyperglycemia, dyslipidemia, non-alcoholic steatohepatitis (NASH) and atherosclerosis, the method comprising administering a variant of human FGF21 as defined above or a fusion molecule as defined above or a nucleic acid molecule as defined above or a host cell as defined above or a pharmaceutical composition as defined above to a subject in need thereof.

In one embodiment, the disease or disorder is diabetes mellitus.

DESCRIPTION OF THE FIGURES

FIG. 3A: GHRSHLQTVF (SEQ ID NO: 166); GLNSMV (SEQ ID NO: 167).

FIGS. 6A-6C shows structural details of computational and experimental models of human FGF21. (FIG. 6A) Superposition of computational models represented as backbone structures based on different experimental homologous structures of FGF19 and FGF23, white (BL 2P23): model created with BioLuminate based on the structure of FGF19 (PDB code 2P23); light gray (SM 1PWA): model created using the Swiss-Model server based on the structure of FGF19 (PDB code 1PWA); dark gray (SM 2P23): model created using the Swiss-Model server based on the structure of FGF19 (PDB code 2P23); black (SM 2P39): model created using the Swiss-Model server based on the structure of FGF23 (PDB code 2P39). Particularly the loop region around residues 150-158 (encircled) is significantly different in these models due to the structural differences of the underlying experimental data. (FIG. 6B) Superposition, shown as a cartoon, of molecule A and molecule B present in the X-ray crystal structure of FGF21 Q55C, N149C (SEQ ID NO: 158). The engineered disulfide bond between cysteines 149 and 55 that stabilize the conformation, thereby increasing the thermal stability, is highlighted. (FIG. 6C) 2mFo-dFc electron density around the engineered C55-C149 disulfide link in molecule B. The contour level is 16. Between C149 and P156, the electron density is discontinuous, suggesting significant disorder.

DETAILED DESCRIPTION OF THE INVENTION

Figure 1A:
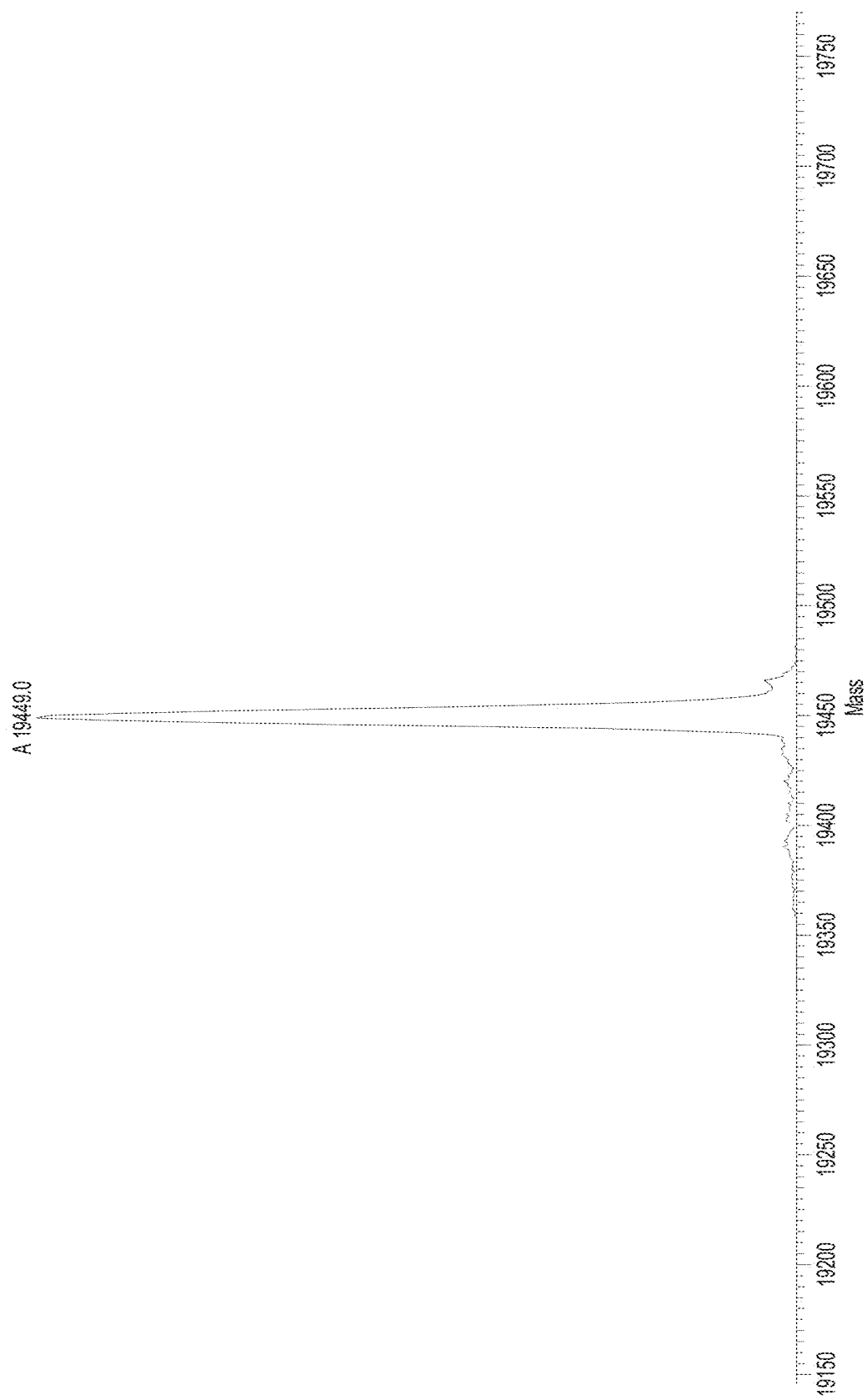
FIGS. 1A-1L show mass spectra and deconvolution data for FGF21 of SEQ ID NO: 3 and its metabolites. Mass spectra (FIG. 1A) and deconvolution (FIG. 1B) of the sequence of amino acids [1-182] of SEQ ID NO: 3; Mass spectra (FIG. 1C) and deconvolution (FIG. 1D) of the sequence of amino acids [1-172] of SEQ ID NO: 3 in human plasma (also found in rat and murine plasma); RT: 33.6 min; the multicharged masses labelled with C were deconvoluted to 18,429 Da; Mass spectra (FIG. 1E) and deconvolution (FIG. 1F) of the sequence of amino acids [132-182] of SEQ ID NO: 3 in human plasma (also found in rat plasma); RT: 30.4 min; the multicharged masses labelled with F were deconvoluted to 5,113.67 Da; Mass spectra (FIG. 1G) and deconvolution (FIG. 1H) of the proposed sequences of amino acids [129-182], [125-177], [126-178] or [124-176] of SEQ ID NO: 3 in human plasma; RT: 30.8 min; the multicharged masses labelled with E were deconvoluted to 5,379 Da; Mass spectra (FIG. 1I) and deconvolution (FIG. 1J) of the proposed sequence of amino acids [136-182] of SEQ ID NO: 3 in human plasma; RT: 31.3 min; the multicharged masses labelled with B were deconvoluted to 4,732.41 Da; Mass spectra (FIG. 1K) and deconvolution (FIG. 1L) of the proposed sequence of amino acids [53-129] or [21-98] of SEQ ID NO: 3 in murine plasma; RT: 32.5; the multicharged masses labelled with A were deconvoluted to 8,564.67 Da.
Figure 1A:
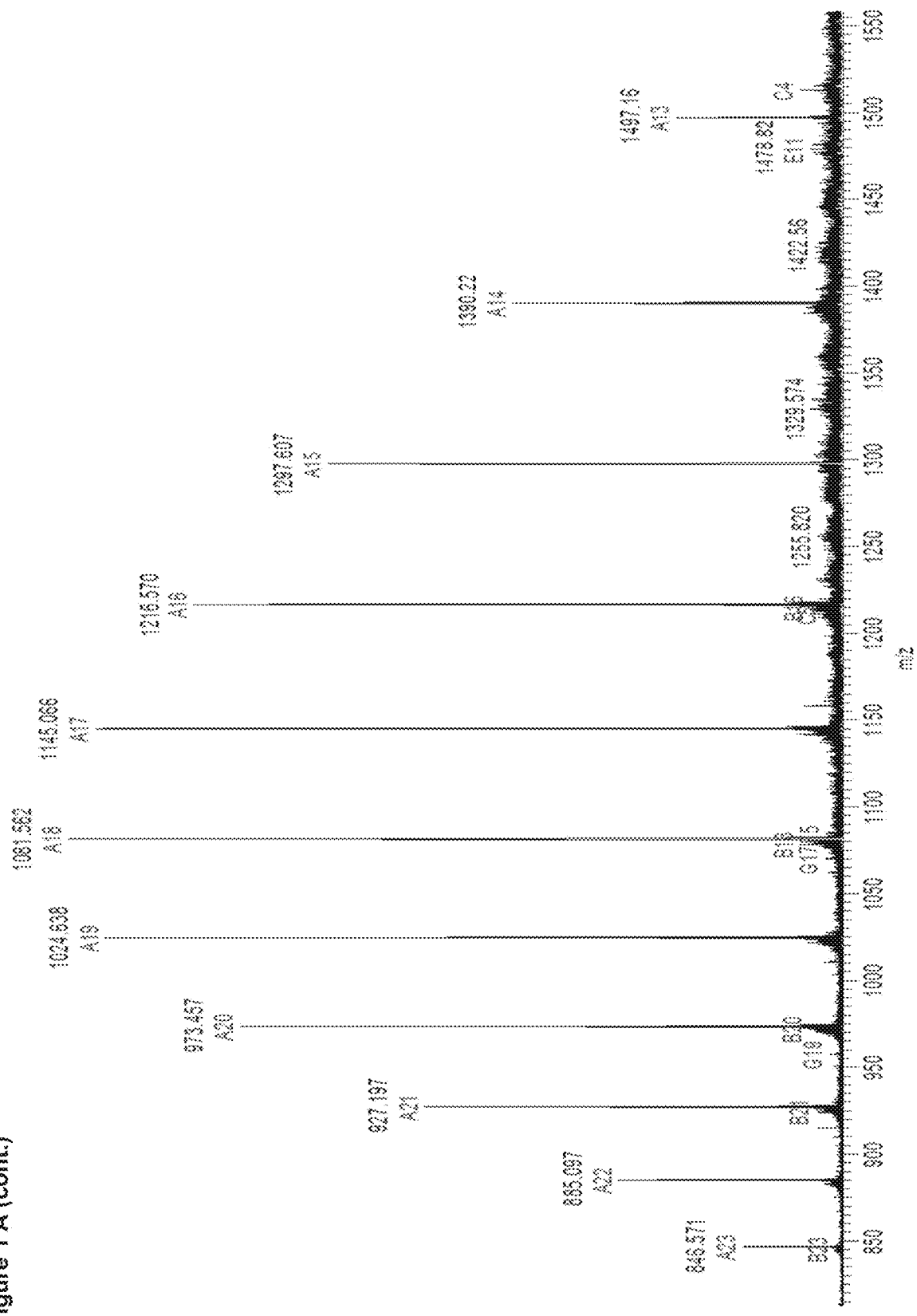
Figure 1B:
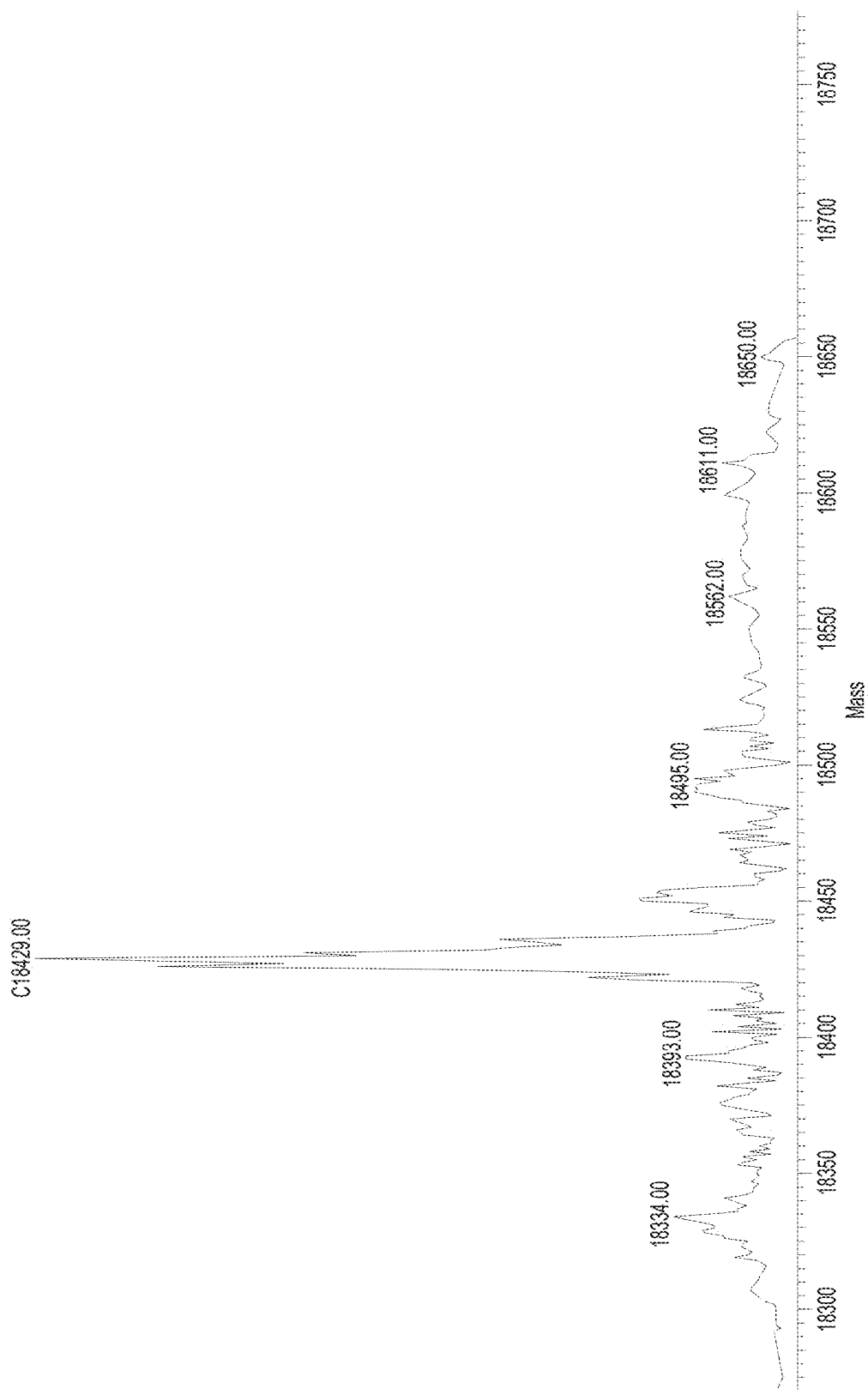
Figure 1:
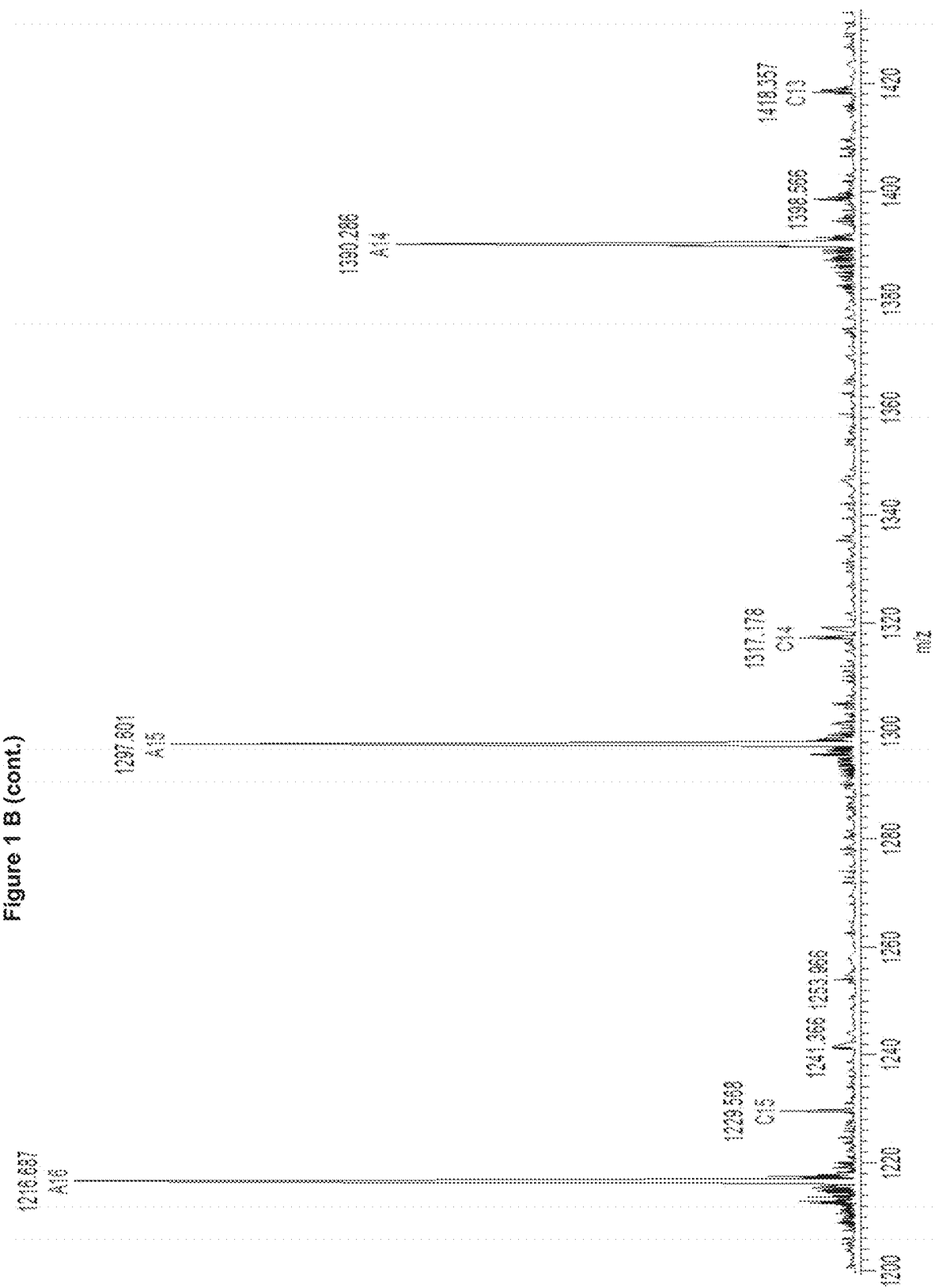
Figure 1:
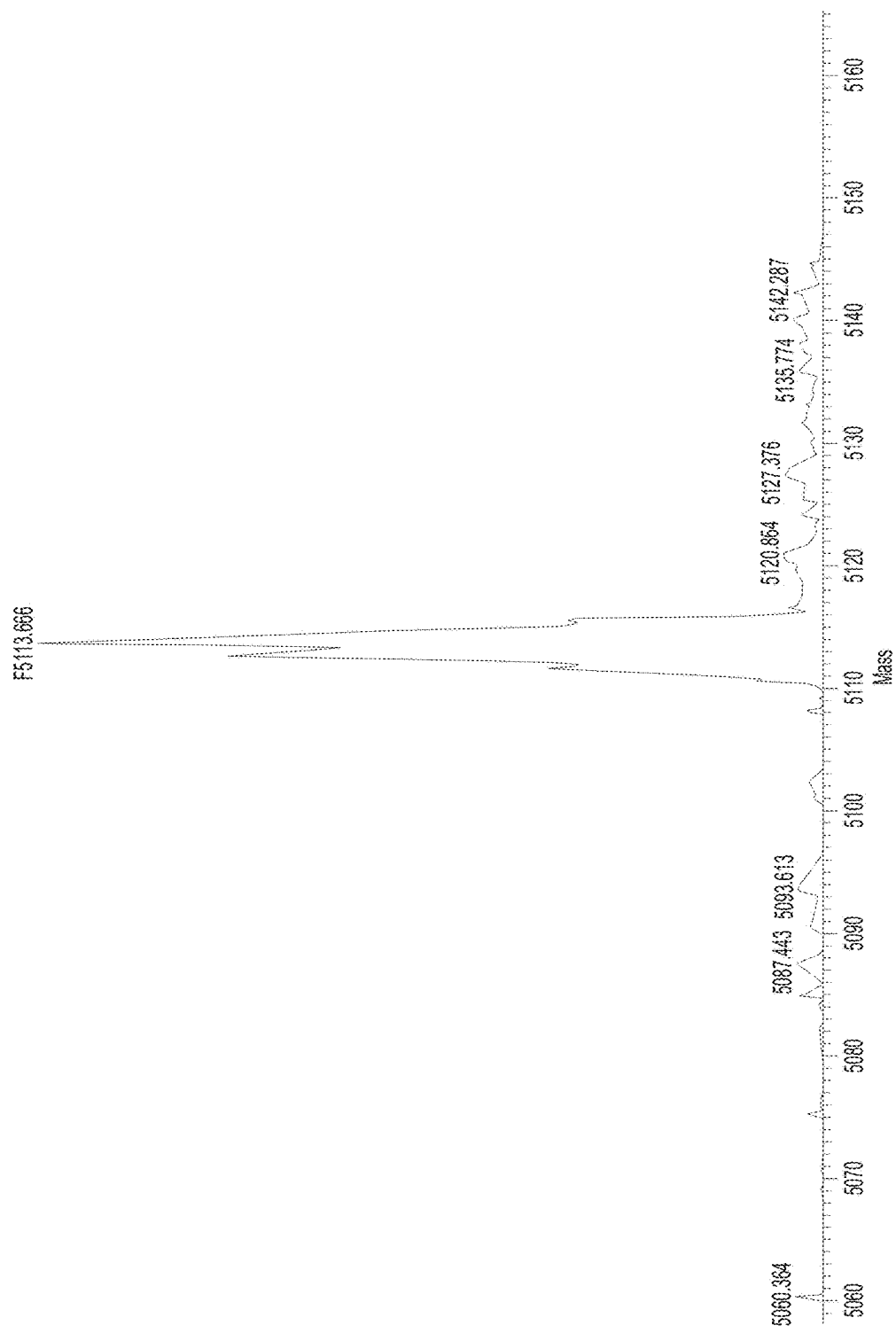
Figure 1:
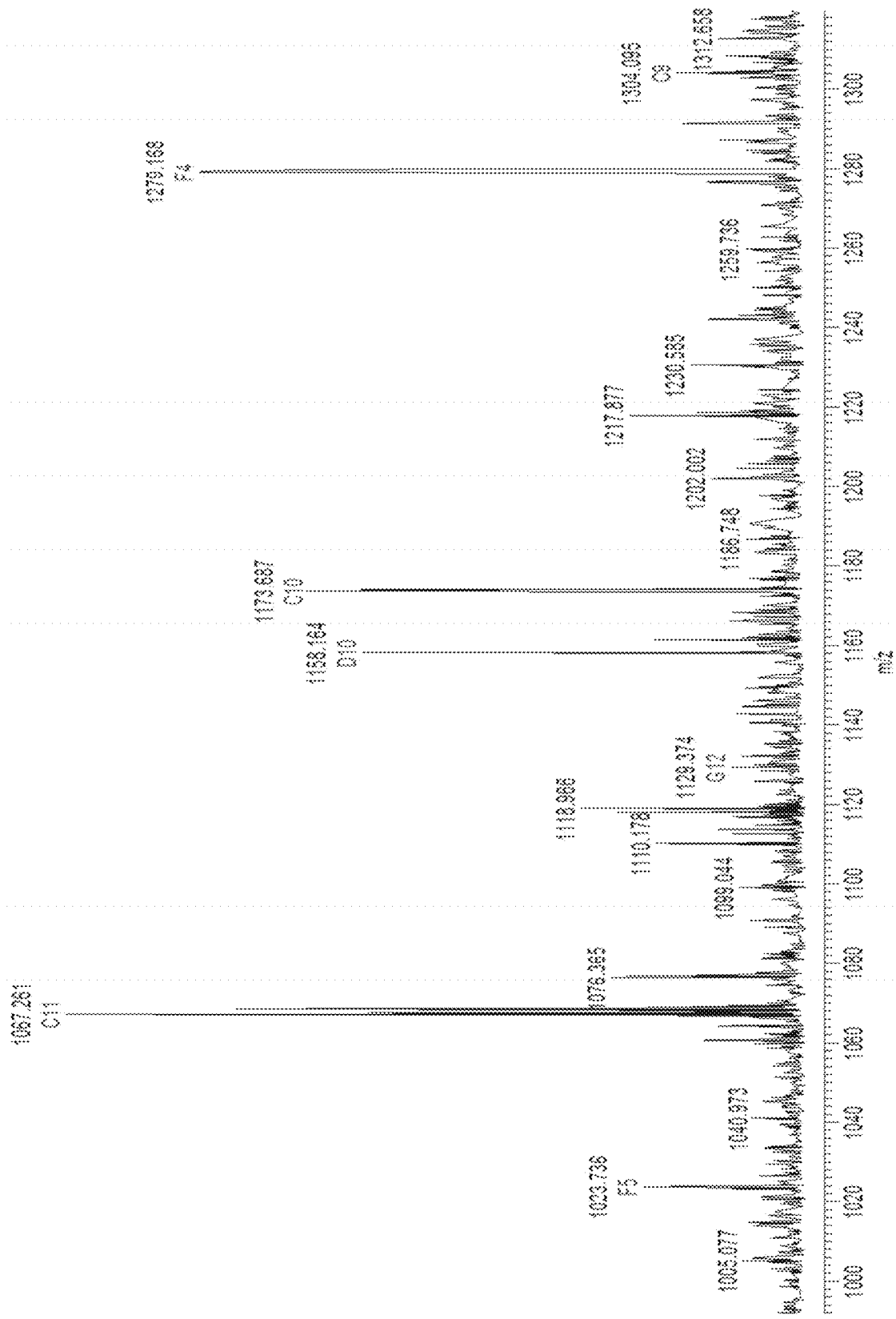
Figure 1:
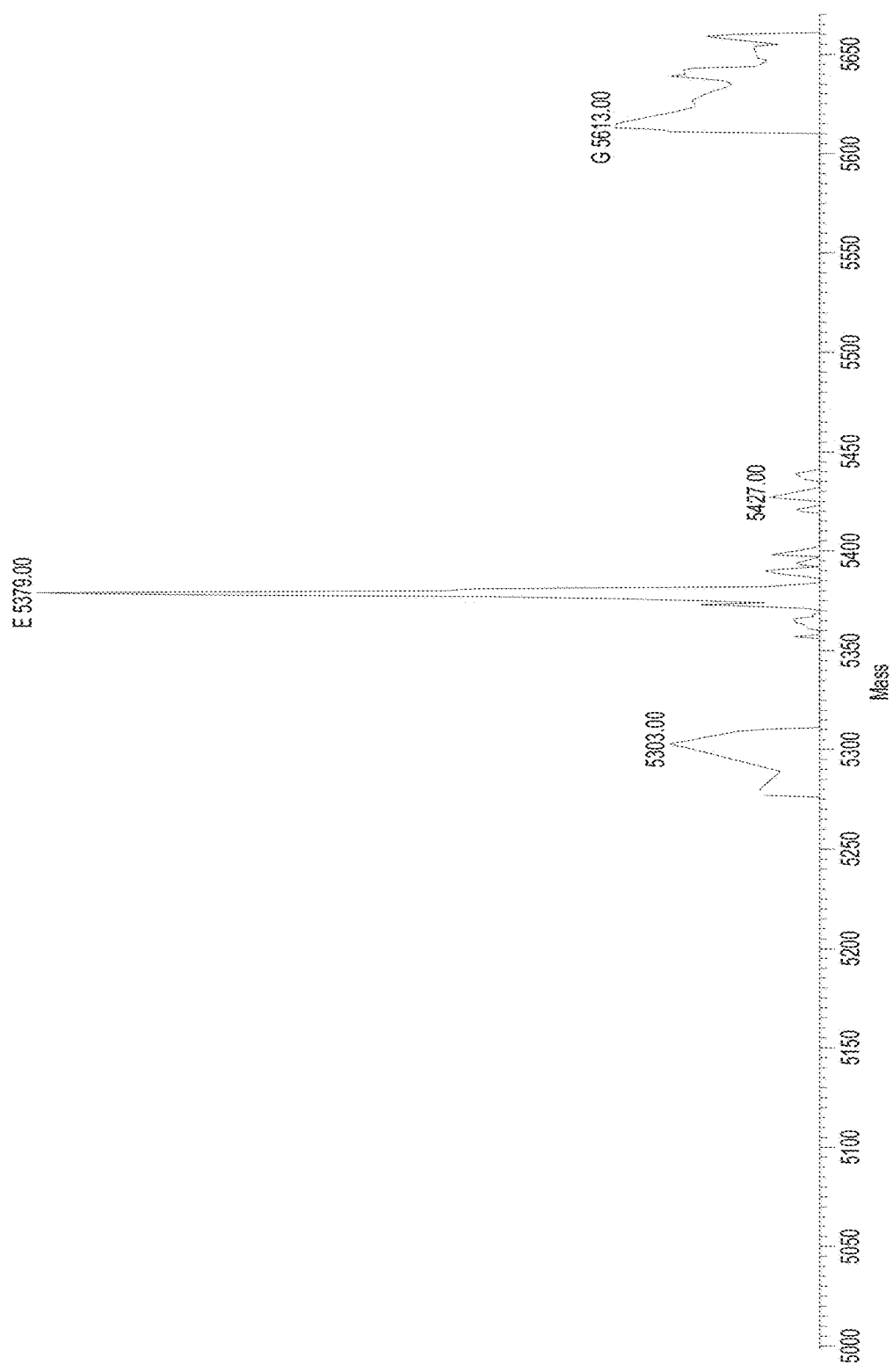
Figure 1:
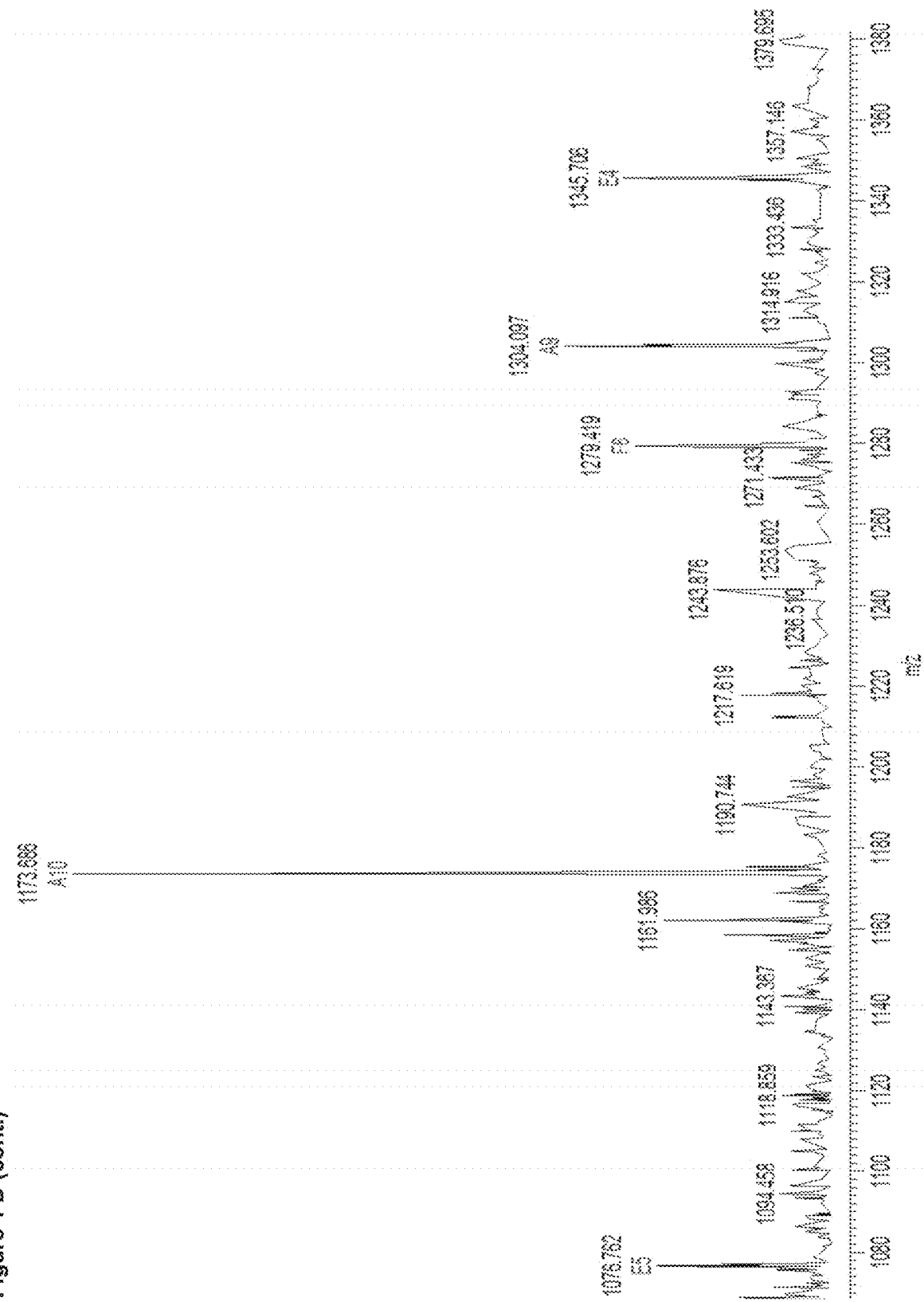
Figure 1E:
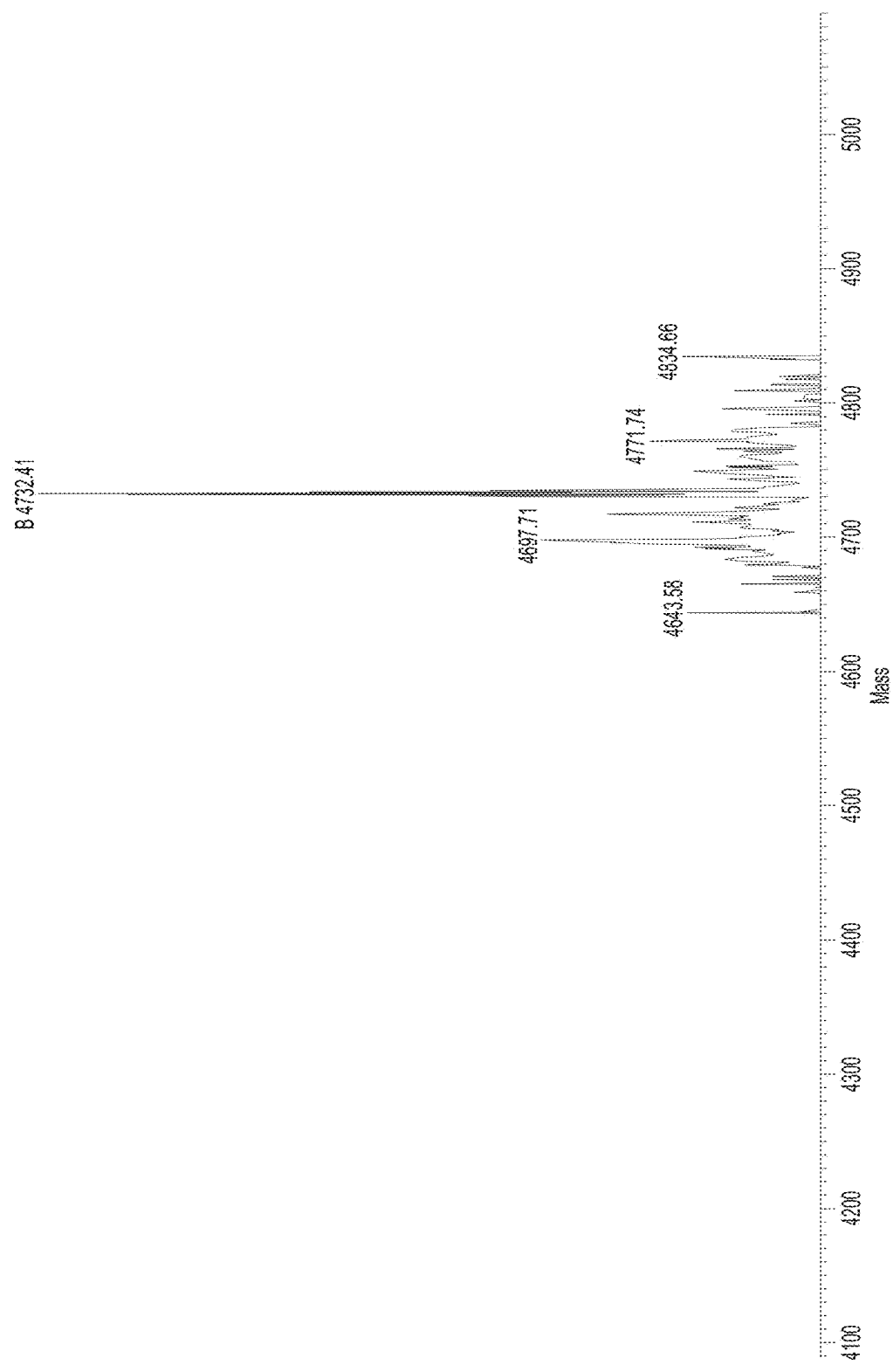
Figure 1:
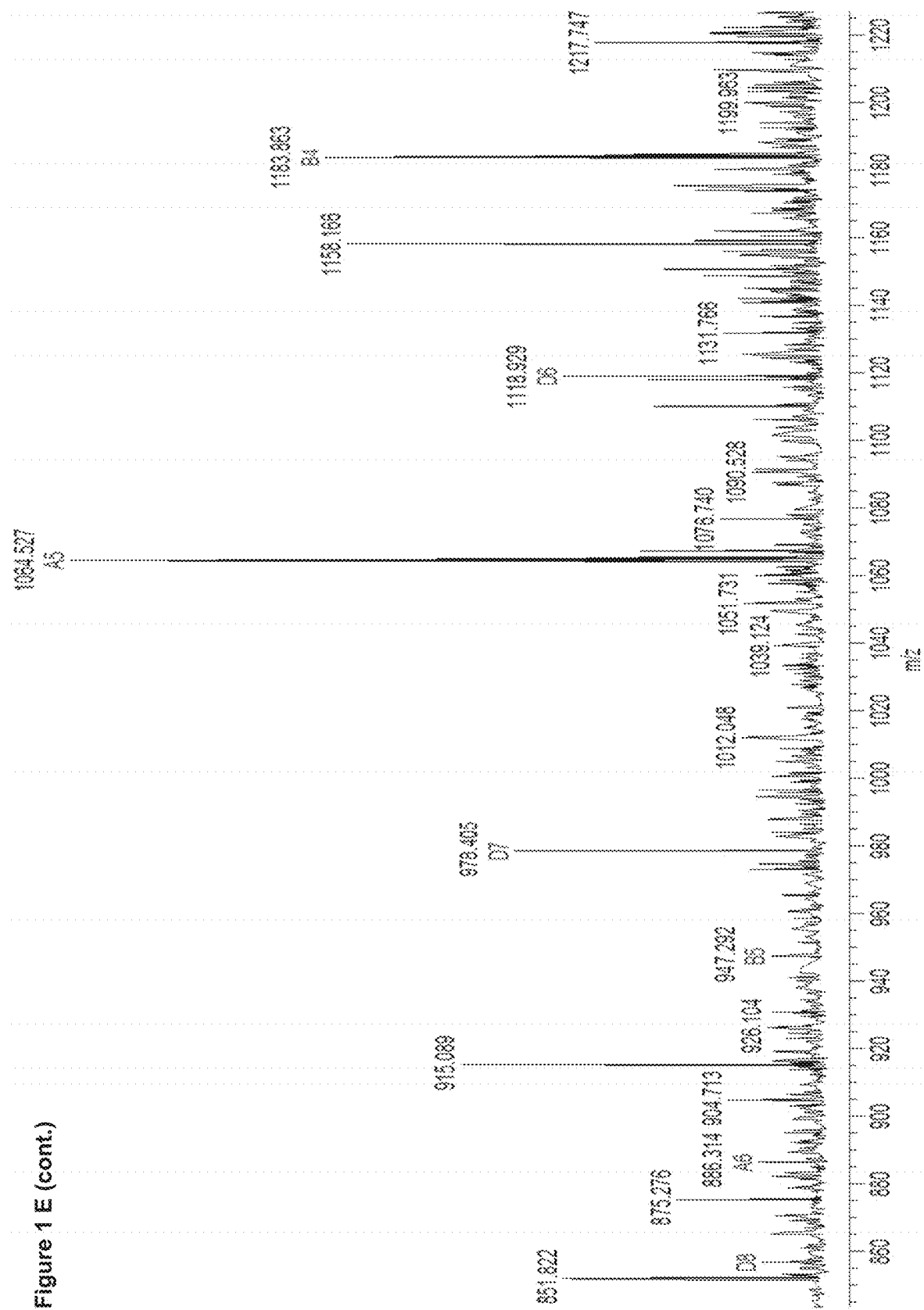
Figure 1F:
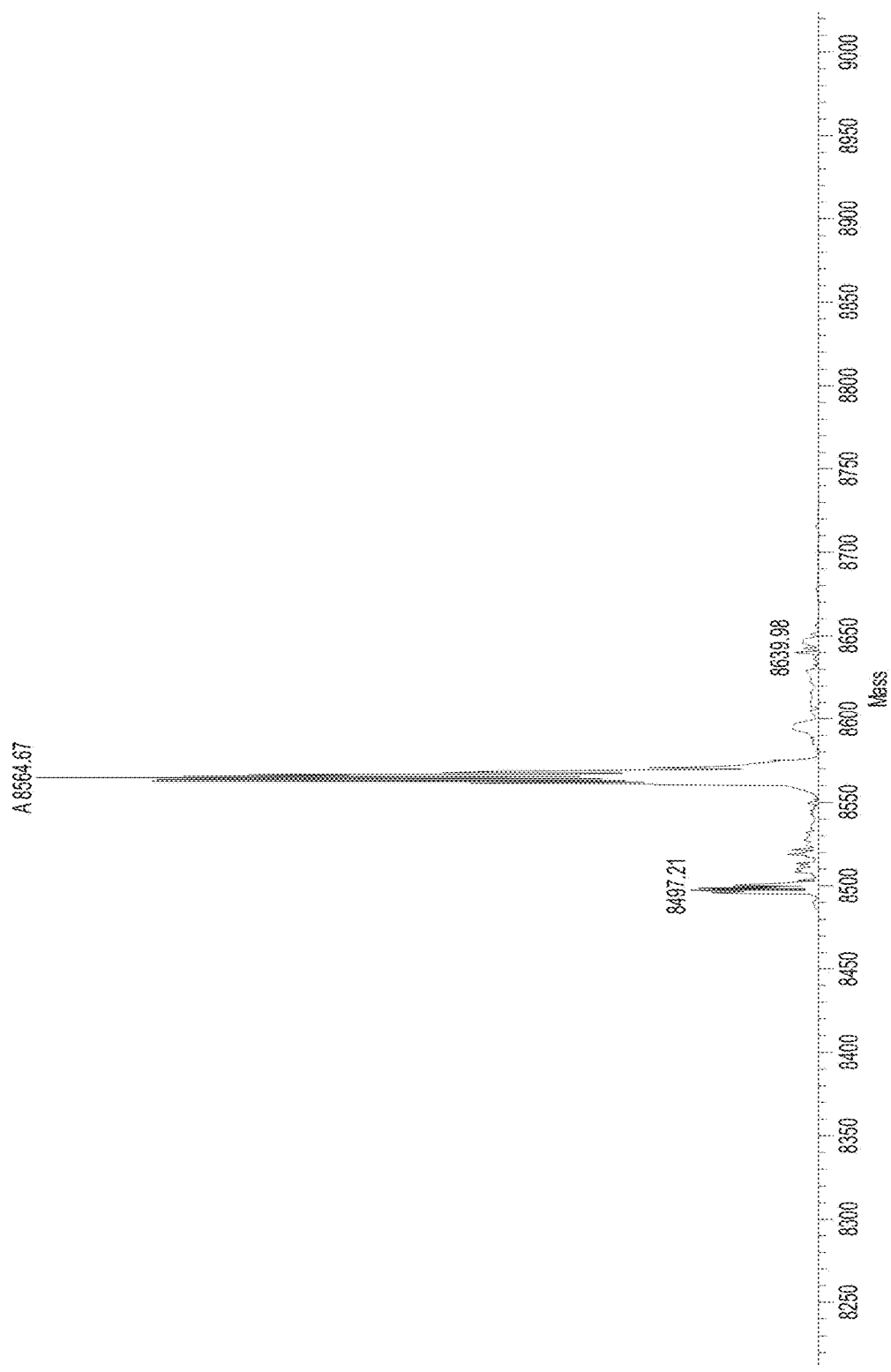
Figure 1F:
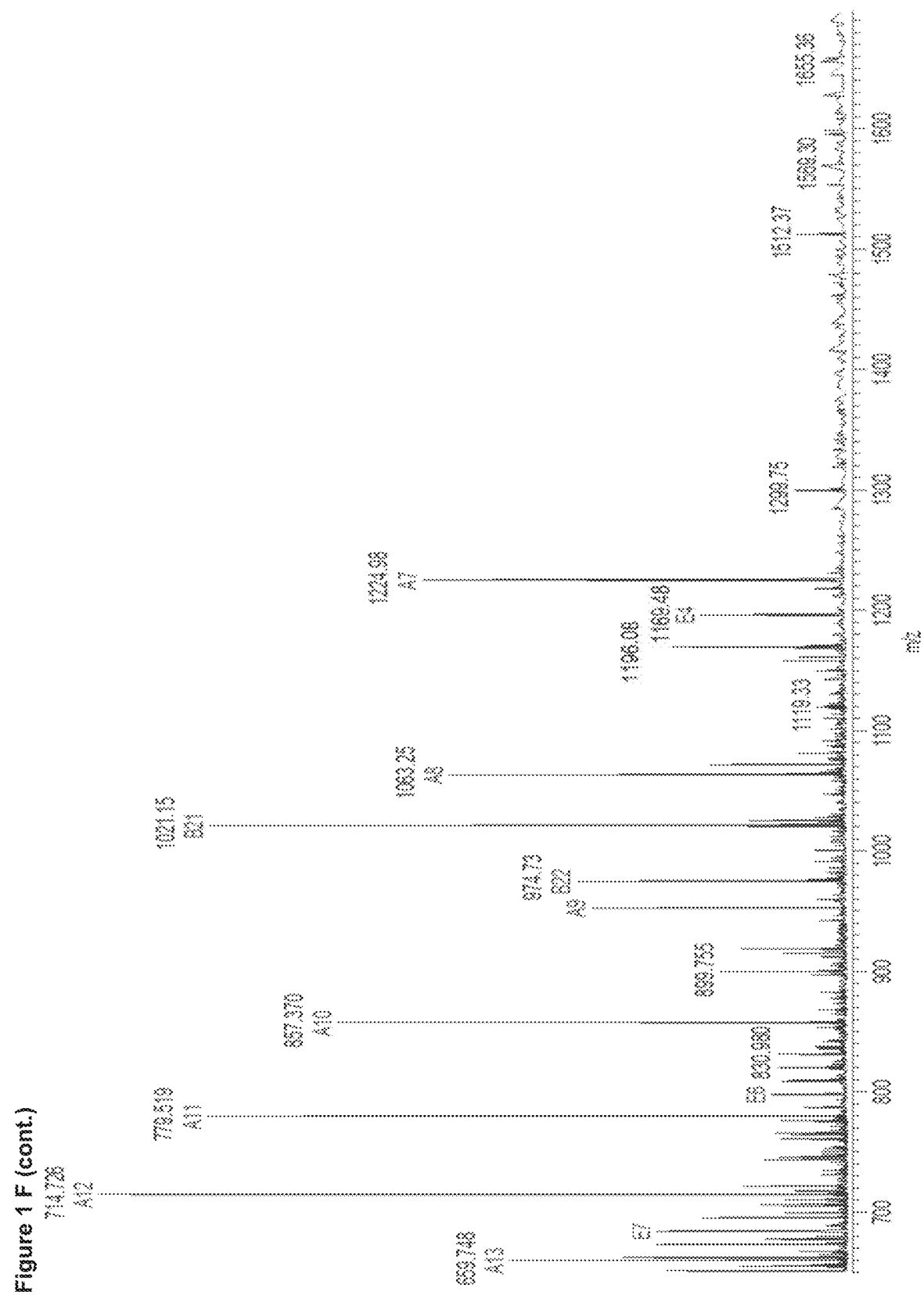
Figure 1H:
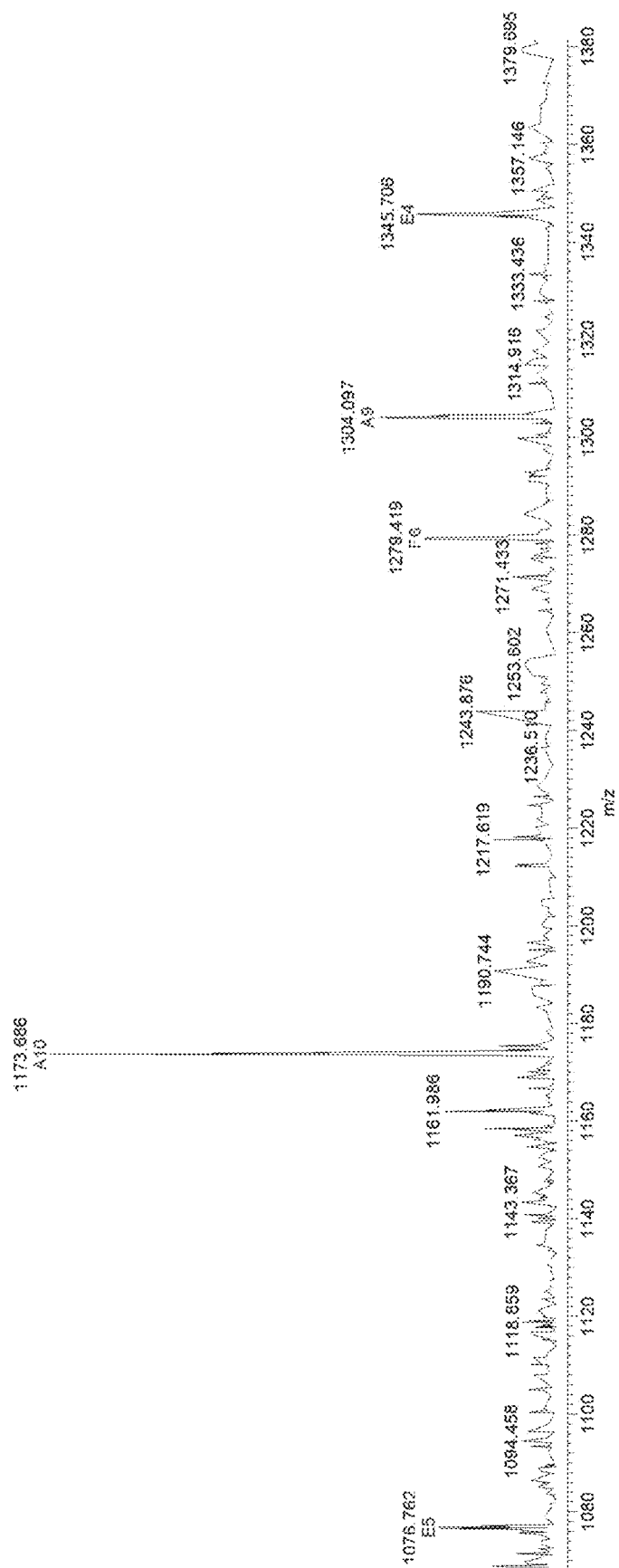
Figure 1J:
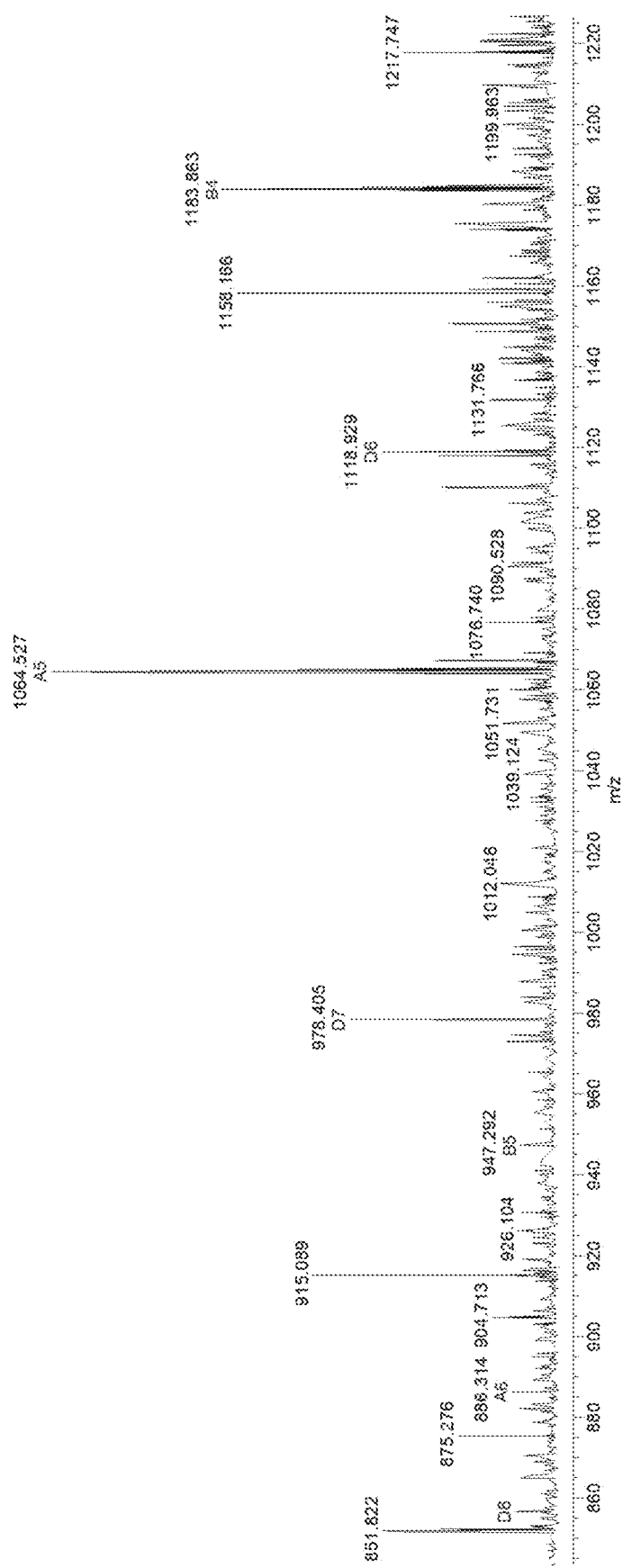
Figure 1L:
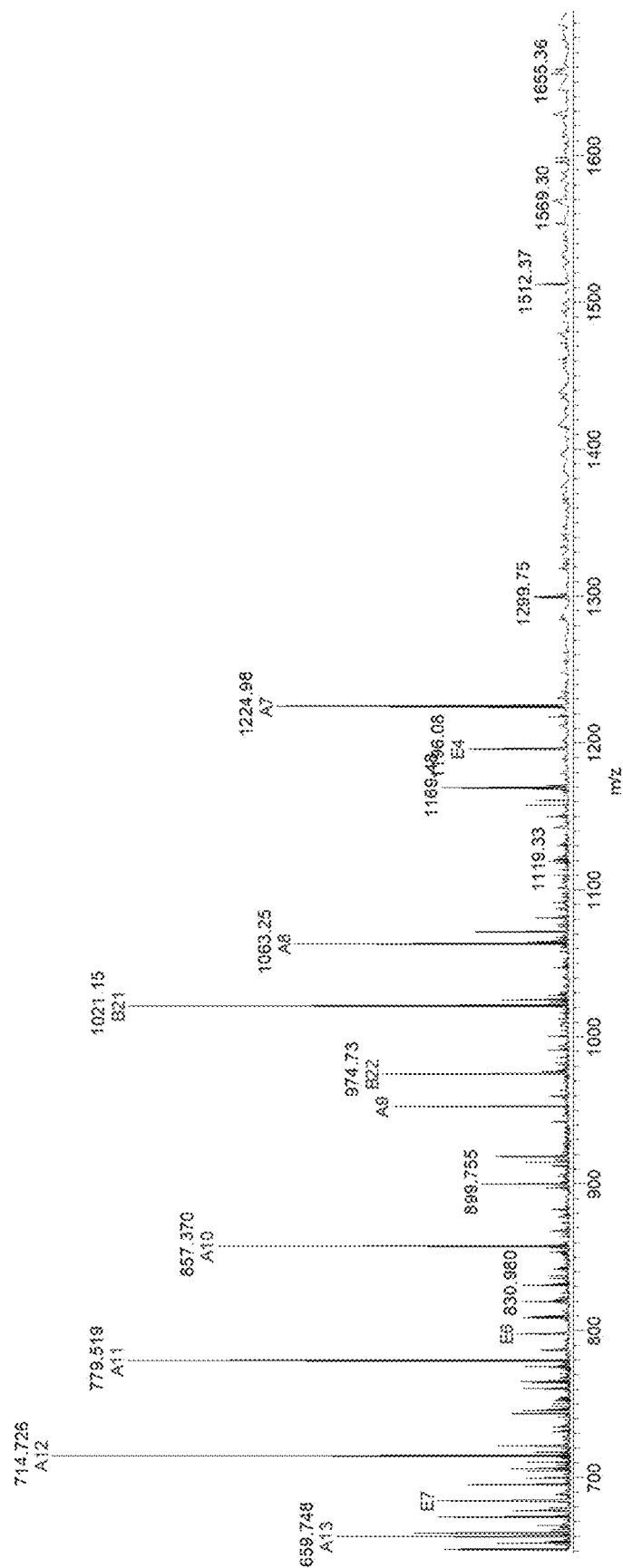

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, certain elements of the present invention will be described. These elements may be listed with specific embodiments, however, it should be understood that they may be combined in any manner and in any number to create additional embodiments. The variously described examples and embodiments should not be construed to limit the present invention to only the explicitly described embodiments. This description should be understood to support and encompass embodiments which combine the explicitly described embodiments with any number of the disclosed elements. Furthermore, any permutations and combinations of all described elements in this application should be considered disclosed by the description of the present application unless the context indicates otherwise.

The terms used herein are defined generally as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (Sambrook, J. et al. (2001) Molecular Cloning: A Laboratory Manual, 3rd Ed., Cold Spring Harbor Laboratory Press, Cold Spring Harbor, N.Y.).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "human fibroblast growth factor 21 (FGF21)", as used herein, refers to human wild-type FGF21 with the amino acid sequence of SEQ ID NO: 1 (also referred to as "full-length human wild-type FGF21") or to naturally occurring variants thereof. The term "mature human wild-type FGF21" refers to human wild-type FGF21 lacking the natural signal sequence (also referred to as signal peptide), i.e., amino acids 1 to 28 (M1 to A28) of SEQ ID NO: 1, and is represented by SEQ ID NO: 2. Unless indicated otherwise, the numbering of particular amino acid residues in the FGF21 (poly-)peptides disclosed herein is in accordance with SEQ ID NO: 1.

The term "naturally occurring" when used in connection with biological materials, such as nucleic acid molecules, (poly-)peptides, host cells, and the like, refers to materials which are found in nature and are not manipulated by man.

In data bases open to the public like The Universal Protein Resource (UniProt, online database available at uniprot.org) some naturally occurring variants of human FGF21 are described. Under the UniProtKB accession number Q9NSA1 two human FGF21 variants are listed: FGF21 G141→S (VAR_055375, SEQ ID NO: 172) and FGF21 L174→P (VAR_049064). The incidence for a proline at position 174 is more common than a leucine according to data bases like ExAC browser (P=73% versus L=27%; The Exome Aggregation Consortium; online available at exac.broadinstitute.org/variant/19-49261368-T-C) and AMP (Accelerating Medicines Partnership; online available at type2diabetesgenetics.org/variantInfo/variantInfo/rs739320). Thus, human FGF21 with P174 is referred to herein as human wild-type FGF21 (see SEQ ID NO: 1), whereas human FGF21 with L174 is included herein as a naturally occurring variant (see SEQ ID NO: 173). The mutation at position 174 has no impact on type 2 diabetes occurrence according to AMP. In addition, the mutation of L174 to P has no impact on the in vitro activity of FGF21 as assessed via In-Cell Western (described in Example 3). The EC50 of G-FGF21 with a proline in position 174 (SEQ ID NO: 3) is 0.24 nmol/L versus 0.21 nmol/L for G-FGF21 with a leucine in position 174 (SEQ ID NO: 174). The FGF21 variant G141→S (VAR_055375, SEQ ID NO: 172) is very rare with an allele frequency below 0.1% (online available at exac.broadinstitute.org/variant/19-49261268-G-A) and was not further characterized in vitro.

A "variant of human fibroblast growth factor 21 (FGF21)" (also referred to as "FGF21 variant" or "FGF21 analogue") in accordance with the present invention is a polypeptide which has a molecular structure which formally can be derived from the structure of human wild-type FGF21 or a naturally occurring variant thereof by deleting and/or substituting at least one amino acid residue in the naturally occurring human FGF21 (e.g., of SEQ ID NO: 1 or 2) and/or adding at least one amino acid residue.

In one embodiment, the variant of human FGF21 is a biologically active variant of human FGF21. The term "biologically active variant of human FGF21" refers to any variant that possesses an activity of the human wild-type FGF21 polypeptide, such as the ability to lower blood glucose, insulin, triglyceride, or cholesterol, reduce body weight, and/or to improve glucose tolerance, energy expenditure, or insulin sensitivity. Variants possessing a somewhat decreased level of FGF21 activity relative to the human wild-type FGF21 polypeptide can nonetheless be considered to be biologically active variants of human FGF21.

In some embodiments, a particular amino acid of the human wild-type FGF21 amino acid sequence (e.g., that of SEQ ID NO: 1 or 2) may be substituted by another amino acid. The term "another amino acid", as used herein, typically relates to an amino acid which contributes to an increased stability, e.g., proteolytic and/or thermal stability, of the variant as compared to the human wild-type FGF21 (e.g., SEQ ID NO: 1 or 2). This may be achieved, for example, by the prevention of protease cleavage at or in proximity to the substituted amino acid or by formation of one or more additional disulfide bridges.

The term "amino acid" or "amino acid residue", as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

When used in connection with amino acids, the term "naturally occurring" refers to the 20 conventional amino acids (i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y)), as well as selenocysteine, pyrrolysine (PYL), and pyrroline-carboxylysine (PCL).

The term "unnatural amino acid", as used herein, is meant to refer to amino acids that are not naturally encoded or found in the genetic code of any organism. They may, for example, be purely synthetic compounds. Examples of unnatural amino acids include, but are not limited to, hydroxyproline, gamma-carboxyglutamate, 0-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, D-ornithine, D-arginine, p-aminophenylalanine, pentylglycine, pipecolic acid and thioproline.

The term "amino acid analogue", as used herein, refers to compounds that have the same basic chemical structure as a naturally occurring amino acid. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(betamethylester), N-ethylglycine, alanine carboxamide, homoserine, norleucine and methionine methyl sulfonium.

The term "amino acid mimetics", as used herein, refers to chemical compounds that have a structure that is different from the general chemical structure of an amino acid, but functions in a manner similar to a naturally occurring amino acid.

The term "peptide", as used herein, refers to a polymeric form of amino acids of any length, for example, comprising two or more, or 3 or more, or 4 or more, or 6 or more, or 8 or more, or 9 or more, or 10 or more, or 13 or more, or 16 or more, or 21 or more amino acids joined covalently by peptide bonds. The term "polypeptide" refers to large peptides, e.g., to peptides with more than 100 amino acid residues. The terms "polypeptide" and "protein" are used interchangeably herein.

In some embodiments, the variant comprises at least one additional amino acid at its N-terminus. In one embodiment, the at least one additional amino acid is selected from naturally occurring amino acids except proline, unnatural amino acids, amino acid analogues and amino acid mimetics. In one embodiment, the at least one additional amino acid is selected from the group consisting of G, A, N and C. In a particular embodiment, the at least one additional amino acid is G.

In some embodiments, the amino acid sequence of the variant according to the present invention has at least 90% or at least 91% or at least 92% or at least 93% or at least 94% or at least 95% or at least 96% or at least 97% or at least 98% sequence identity with one of SEQ ID NOs: 1 to 3, 172, 173 and 174, e.g., with mature human wild-type FGF21 (SEQ ID NO: 2).

"Sequence identity" between two amino acid sequences indicates the percentage of amino acids that are identical between the sequences. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The FGF21 variants featured in the invention typically have an increased proteolytic stability in human and/or murine blood plasma as compared to mature human wild-type FGF21 (SEQ ID NO: 2).

The term "proteolytic stability" refers to the ability of a (poly-)peptide to withstand proteolysis catalyzed by proteases. Examples of such proteases are serine proteases, threonine proteases, cysteine proteases, aspartate proteases and/or glutamic acid proteases. Examples of serine proteases are trypsin, chymotrypsin, plasmin, thrombin, granzyme and/or kallikreine. Examples of cysteine proteases are cathepsin K, caspase and/or calpain. According to the EC numbering such proteases are, e.g., classified according to the enzymatic activity as serine carboxypeptidases (EC 3.4.16), serine endopeptidases (EC 3.4.21), threonine endopeptidases (EC 3.4.25), cysteine carboxypeptidases (EC 3.4.18), cysteine endopeptidases (EC 3.4.22) or aspartate endopeptidases (EC 3.4.23). The term "proteolytic stability" may refer to in vitro or in vivo proteolytic stability. Means and methods to measure proteolytic stability of a given (poly-)peptide are known to a person skilled in the art. In one embodiment, proteolytic stability is measured with a sandwich immunoassay, e.g., essentially as described in Example 2.

The term "protease resistant peptide linker", as used herein, refers to a peptide linker which has a low susceptibility to or withstands proteolysis catalyzed by proteases, e.g., proteases as described above. Such linker may have a length of 1 to 20 or 1 to 15 or 1 to 12 or 1 to 10 amino acids. In some embodiments, the linker may consist of as few as two amino acids (e.g., GA, GY, HH, GE or HE). In particular embodiments, the protease resistant peptide linker is of the peptide linker of SEQ ID NO:161, SEQ ID NO:162, SEQ ID NO:163, SEQ ID NO:164, SEQ ID NO:165, SEQ ID NO:166, SEQ ID NO:167, or SEQ ID NO:168.

The FGF21 variants featured in the invention will typically have an increased thermal stability as compared to mature human wild-type FGF21 (SEQ ID NO: 2).

The term "thermal stability" refers to the ability of a (poly-)peptide to resist irreversible change in its chemical or physical structure at higher temperatures, e.g., above 40° C. In particular embodiments, an increased thermal stability refers to an increased melting temperature ($T_M$) of the variant. Means and methods to measure thermal stability of a given (poly-)peptide are known to a person skilled in the art. In one embodiment, the thermal stability (e.g., $T_M$) is measured in a physiological buffer, such as PBS. In one embodiment, thermal stability (e.g., $T_M$) is measured with a thermal shift assay, e.g., essentially as described in Example 5.

In one embodiment, the melting temperature ($T_M$) of the variant is increased by at least 2° C., at least 4° C., at least 6° C., at least 8° C., at least 10° C., at least 12° C., at least 14° C., at least 16° C., at least 18° C. or at least 20° C. as compared to mature human wild-type FGF21 (SEQ ID NO: 2). In one embodiment, TM is increased by at least 18° C., e.g., between 18° C. and 30° C. or between 18° C. and 25° C., as compared to mature human wild-type FGF21 (SEQ ID NO: 2).

The biological function or activity of a FGF21 variant is usually measured and/or compared with human wild-type FGF21, e.g., mature human wild-type FGF21 (SEQ ID NO: 2), in a FGF21 activity assay generally known to a person skilled in the art. An FGF21 activity assay is, e.g., a "glucose uptake assay" as described in Kharitonenkov A. et al. (2005) J Clin Invest 115: 1627-1635. Alternatively, cellular assays, e.g., autophosporylation assays, such as an In-Cell Western (ICW) assay, can be used to measure the efficacy of the FGF21 variant to activate the FGF21 receptor of the FGF receptor:KLB complex or to stimulate the downstream intracellular signal transduction.

The term "In-Cell Western (ICW) assay", as used herein, refers to an immunocytochemical assay, more particularly a quantitative immunofluorescence assay, usually performed in microplates (e.g., in a 96- or 384-well format). It combines the specificity of Western blotting with the reproducibility and throughput of ELISA (see, for example, Aguilar H. N. et al. (2010) PLoS ONE 5(4): e9965). Appropriate ICW assay systems are commercially available (e.g., from LI-COR Biosciences, USA). In one embodiment, the ICW assay is performed essentially as described in Example 3 or 4.

Typically, the FGF21 variants will induce phosphorylation of the mitogen-activated protein kinase (MAPK) ERK1/2. In one embodiment, the variants induce phosphorylation of the mitogen-activated protein kinase (MAPK) ERK1/2 with an EC50 of 100 nmol/L or lower, or 90 nmol/L or lower, or 80 nmol/L or lower, or 70 nmol/L or lower, or 60 nmol/L or lower, or 50 nmol/L or lower, or 40 nmol/L or lower, or 30 nmol/L or lower, or 20 nmol/L or lower, or 15 nmol/L or lower, or 12 nmol/L or lower, or 11 nmol/L or lower, or 10 nmol/L or lower, or 9 nmol/L or lower, or 8 nmol/L or lower, or 7 nmol/L or lower, or 6 nmol/L or lower, or 5 nmol/L or lower, or 4 nmol/L or lower, or 3 nmol/L or lower, or 2 nmol/L or lower, e.g., as determined in an In-Cell Western (ICW) assay.

A "label or tag allowing the detection and/or isolation of the variant" is meant to include any labels/tags known in the art for these purposes. Exemplary tags include affinity tags, such as chitin binding protein (CBP), maltose binding protein (MBP), glutathione-S-transferase (GST) and a His-tag, such as a histidine-rich sequence (e.g., SEQ ID NO: 5 or 6) or poly(His) (e.g., $His_6$); solubilization tags, such as thioredoxin (TRX) and poly(NANP); chromatography tags, such as a FLAG-tag; epitope tags, such as V5-tag, myc-tag and HA-tag; and fluorescent or luminescent labels or tags, such as fluorescent proteins (e.g., GFP, YFP, RFP etc.), fluorescent dyes and luciferase.

The amino acid sequence of a (poly)peptide label or tag may be introduced at any position within the amino acid sequence of the variant, and may, for example, take the shape of a loop within the encoded protein structure, or it may be N-terminally or C-terminally fused. In one embodiment, the label or tag is N-terminally fused. The label or tag may further contain a cleavage site (e.g., a TEV protease-cleavage site) that allows a removal of the label or tag from the variant. Similarly, non-peptidic labels or tags, e.g., fluorescent dyes, may be conjugated to the variant at any suitable site.

An FGF21 variant featured in the invention may also comprise an amino acid sequence for facilitating secretion of the molecule, such as an N-terminal secretion signal. In some embodiments, the secretion signal is a signal sequence that allows a sufficient passage through the secretory pathway and/or secretion into the extracellular environment. In some embodiments, the secretion signal sequence is cleavable and is removed from the variant. In one embodiment, the signal sequence is different from the natural signal sequence of human FGF21. The secretion signal sequence will be suitable for use in the cell or organism in which the variant is produced. In one embodiment, the secretion signal sequence comprises or consists of the amino acid sequence of SEQ ID NO: 4.

An FGF21 variant featured in the invention may further comprise a binding domain which serves, e.g., to enhance selectivity for a specific cell type or tissue. This can be achieved, e.g., by providing a binding domain that binds to a specific antigen expressed on the surface of said cell type or tissue.

An FGF21 variant may also be fused or conjugated to a half-life extension module. "Half-life" relates to the period of time which is needed to eliminate half of the activity, amount, or number of molecules, e.g., in vivo. Such modules are known to a person skilled in the art and include, for example, polymers (e.g., polyethylene glycol (PEG), hydroxyethyl starch (HES), hyaluronic acid, polysialic acid), unstructured (poly-)peptide chains, elastin-like polypeptides (ELPs), serum proteins (e.g., albumin, such as human serum albumin (HAS)), serum protein binding molecules (e.g., an albumin binding domain (ABD), an albumin binding fatty acid), antibodies, immunoglobulins, Fc regions/domains of immunoglobulins and immunoglobulin binding domains.

The term "unstructured (poly-)peptide chain", as used herein, refers to a (poly-)peptide chain which lacks a fixed or ordered three-dimensional structure and is typically hydrophilic. Unstructured (poly-)peptide chains that extend the (in vivo) half-life of peptides and proteins they are fused to are known to a person skilled in the art and include, for example, XTEN (Schellenberger V. et al. (2009) Nat Biotechnol. 27(12): 1186-90) and PAS sequences (Schlapschy M. et al. (2013) Protein Eng Des Sel. 26(8): 489-501).

The term "fused to", as used herein, refers, in particular, to genetic fusion, e.g., by recombinant DNA technology. The amino acid sequence of a (poly)peptide half-life extension module may be introduced at any position within the amino acid sequence of the variant, and may, for example, take the shape of a loop within the encoded protein structure, or it may be N-terminally or C-terminally fused.

The term "conjugated to", as used herein, refers, in particular, to chemical and/or enzymatic conjugation resulting in a stable covalent link between a (poly-)peptide and another molecule, e.g., the variant and the half-life extension module. Such conjugation may occur at the N- or C-terminus or at particular side chains of a (poly-)peptide, e.g., at lysine, cysteine, tyrosine or unnatural amino acid residues.

The term "fusion molecule" generally refers to molecules created by joining, in particular covalently linking, two or more distinct molecules (e.g., proteins and/or peptides) resulting in a single molecule with functional properties derived from each of the original molecules. In the case of proteins and/or peptides, the fusion molecule is referred to as "fusion protein". Fusion molecules may be generated by genetic fusion (e.g., by recombinant DNA technology) or by chemical and/or enzymatic conjugation. The two or more distinct molecules may also be linked by suitable linker molecules, e.g., peptide linkers or non-peptidic polymers, such as polyethylene glycol (PEG). Peptide linkers may further comprise specific protease cleavage sites.

According to the present invention, the fusion molecule comprises at least one other active pharmaceutical ingredient in addition to the FGF21 variant.

The term "active pharmaceutical ingredient" (API), us used herein, includes any pharmaceutically active chemical or biological compound and any pharmaceutically acceptable salt thereof and any mixture thereof, that provides some pharmacologic effect and is used for treating or preventing a condition, e.g., a disease or disorder as defined herein. Exemplary pharmaceutically acceptable salts include hydrochloric, sulfuric, nitric, phosphoric, hydrobromic, maleric, malic, ascorbic, citric, tartaric, pamoic, lauric, stearic, palmitic, oleic, myristic, lauryl sulfuric, naphthalinesulfonic, linoleic, linolenic acid, and the like. As used herein, the terms "active pharmaceutical ingredient", "active agent", "active ingredient", "active substance", "therapeutically active compound" and "drug" are meant to be synonyms, i.e., have identical meaning.

In accordance with the present invention, an active pharmaceutical ingredient is optionally selected from:
all drugs mentioned in the Rote Liste 2014, e.g. all antidiabetics mentioned in the Rote Liste 2014, chapter 12, all weight-reducing agents or appetite suppressants mentioned in the Rote Liste 2014, chapter 06, all lipid-lowering agents mentioned in the Rote Liste 2014, chapter 58, all antihypertensives mentioned in the Rote Liste 2014 chapter 17, all nephroprotectives mentioned in the Rote Liste, or all diuretics mentioned in the Rote Liste 2014, chapter 36;
insulin and insulin derivatives, for example: insulin glargine (e.g. Lantus®), higher than 100 U/mL concentrated insulin glargine, e.g. 270-330 U/mL of insulin glargine or 300 U/mL of insulin glargine (as disclosed in EP 2387989), insulin glulisine (e.g. Apidra®), insulin detemir (e.g. Levemir®), insulin lispro (e.g. Humalog®, Liprolog®), insulin degludec (e.g. DegludecPlus®, IdegLira (NN9068)), insulin aspart and aspart formulations (e.g. NovoLog®), basal insulin and analogues (e.g. LY2605541, LY2963016, NN1436), PEGylated insulin lispro (e.g. LY-275585), long-acting insulins (e.g. NN1436, Insumera (PE0139), AB-101, AB-102, Sensulin LLC), intermediate-acting insulins (e.g. Humulin® N, Novolin® N), fast-acting and short-acting insulins (e.g. Humulin® R, Novolin® R, Linjeta® (VIAject®), PH20 insulin, NN1218, HinsBet®), premixed insulins, SuliXen®, NN1045, insulin plus Symlin®, PE-0139, ACP-002 hydrogel insulin, and oral, inhalable, transdermal and buccal or sublingual insulins (e.g. Exubera®, Nasulin®, Afrezza®, insulin tregopil, TPM-02 insulin, Capsulin®, Oral-lyn®, Cobalamin® oral insulin, ORMD-0801, Oshadi oral insulin, NN1953, NN1954, NN1956, VIAtab®). also suitable are those insulin derivatives which are bonded to albumin or another protein by a bifunctional linker;
glucagon-like-peptide 1 (GLP-1), GLP-1 analogues, and GLP-1 receptor agonists, for example: GLP-1(7-37), GLP-1(7-36)amide, lixisenatide (e.g. Lyxumia®), exenatide (e.g. exendin-4, rExendin-4, Byetta®, Bydureon®, exenatide NexP), exenatide-LAR, liraglutide (e.g. Victoza®), semaglutide, taspoglutide, albiglutide, dulaglutide, albugon, oxyntomodulin, geniproside, ACP-003, CJC-1131, CJC-1134-PC, GSK-2374697, PB-1023, TTP-054, langlenatide (HM-11260C), CM-3, GLP-1 Eligen, AB-201, ORMD-0901, NN9924, NN9926, NN9927, Nodexen, Viador-GLP-1, CVX-096, ZYOG-1, ZYD-1, ZP-3022, CAM-2036, DA-3091, DA-15864, ARI-2651, ARI-2255, exenatide-XTEN (VRS-859), exenatide-XTEN+ Glucagon-XTEN (VRS-859+AMX-808) and polymer-bound GLP-1 and GLP-1 analogues;

dual GLP-1/GIP agonists (e.g. RG-7697 (MAR-701), MAR-709, BHM081, BHM089, BHM098); dual GLP-1/glucagon receptor agonists (e.g. BHM-034, OAP-189 (PF-05212389, TKS-1225), TT-401/402, ZP2929, LAPS-HMOXM25, MOD-6030);

dual GLP-1/gastrin agonists (e.g. ZP-3022);

gastrointestinal peptides such as peptide YY 3-36 (PYY3-36) or analogues thereof and pancreatic polypeptide (PP) or analogues thereof;

glucagon receptor agonists or antagonists, glucose-dependent insulinotropic polypeptide (GIP) receptor agonists or antagonists, ghrelin antagonists or inverse agonists, xenin and analogues thereof;

dipeptidyl peptidase-IV (DPP-4) inhibitors, for example: alogliptin (e.g. Nesina®, Kazano®), linagliptin (e.g. Ondero®, Trajenta®, Tradjenta®, Trayenta®), saxagliptin (e.g. Onglyza® Komboglyze XR®), sitagliptin (e.g. Januvia®, Xelevia®, Tesavel®, Janumet®, Velmetia®, Juvisync®, Janumet XR®), anagliptin, teneligliptin (e.g. Tenelia®), trelagliptin, vildagliptin (e.g. Galvus®, Galvumet®), gemigliptin, omarigliptin, evogliptin, dutogliptin, DA-1229, MK-3102, KM-223, KRP-104, PBL-1427, Pinoxacin hydrochloride, and Ari-2243;

sodium-dependent glucose transporter 2 (SGLT-2) inhibitors, for example: canagliflozin, dapagliflozin, remogliflozin, remogliflozin etabonate, sergliflozin, empagliflozin, ipragliflozin, tofogliflozin, luseogliflozin, ertugliflozin, EGT-0001442, LIK-066, SBM-TFC-039, and KGA-3235 (DSP-3235);

dual inhibitors of SGLT-2 and SGLT-1 (e.g. LX-4211, LIK066).

SGLT-1 inhibitors (e.g. LX-2761, KGA-3235) or SGLT-1 inhibitors in combination with anti-obesity drugs such as ileal bile acid transfer (IBAT) inhibitors (e.g. GSK-1614235+GSK-2330672);

biguanides (e.g. metformin, buformin, phenformin);

thiazolidinediones (e.g. pioglitazone, rosiglitazone), glitazone analogues (e.g. lobeglitazone);

peroxisome proliferator-activated receptors (PPAR-)(alpha, gamma or alpha/gamma) agonists or modulators (e.g. saroglitazar (e.g. Lipaglyn®), GFT-505), or PPAR gamma partial agonists (e.g. Int-131);

sulfonylureas (e.g. tolbutamide, glibenclamide, glimepiride, Amaryl®, glipizide) and meglitinides (e.g. nateglinide, repaglinide, mitiglinide);

alpha-glucosidase inhibitors (e.g. acarbose, miglitol, voglibose);

amylin and amylin analogues (e.g. pramlintide, Symlin®);

G-protein coupled receptor 119 (GPR119) agonists (e.g. GSK-1292263, PSN-821, MBX-2982, APD-597, ARRY-981, ZYG-19, DS-8500, HM-47000, YH-Chem1);

GPR40 agonists (e.g. TUG-424, P-1736, P-11187, JTT-851, GW9508, CNX-011-67, AM-1638, AM-5262);

GPR120 agonists and GPR142 agonists;

systemic or low-absorbable TGR5 (GPBAR1=G-protein-coupled bile acid receptor 1) agonists (e.g. INT-777, XL-475, SB756050);

diabetes immunotherapeutics, for example: oral C—C chemokine receptor type 2 (CCR-2) antagonists (e.g. CCX-140, JNJ-41443532), interleukin 1 beta (IL-1B) antagonists (e.g. AC-201), or oral monoclonal antibodies (MoA) (e.g. methalozamide, VVP808, PAZ-320, P-1736, PF-05175157, PF-04937319);

anti-inflammatory agents for the treatment of the metabolic syndrome and diabetes, for example: nuclear factor kappa B inhibitors (e.g. Triolex®);

adenosine monophosphate-activated protein kinase (AMPK) stimulants, for example: Imeglimin (PXL-008), Debio-0930 (MT-63-78), R-118;

inhibitors of 11-beta-hydroxysteroid dehydrogenase 1 (11-beta-HSD-1) (e.g. LY2523199, BMS770767, RG-4929, BMS816336, AZD-8329, HSD-016, BI-135585);

activators of glucokinase (e.g. PF-04991532, TTP-399 (GK1-399), GKM-001 (ADV-1002401), ARRY-403 (AMG-151), TAK-329, TMG-123, ZYGK1);

inhibitors of diacylglycerol O-acyltransferase (DGAT) (e.g. pradigastat (LCQ-908)), inhibitors of protein tyrosine phosphatase 1 (e.g. trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase;

modulators of glucose transporter-4, somatostatin receptor 3 agonists (e.g. MK-4256);

one or more lipid lowering agents are also suitable as combination partners, for example: 3-hydroxy-3-methylglutaryl-coenzym-A-reductase (HMG-CoA-reductase) inhibitors such as simvastatin (e.g. Zocor®, Inegy®, Simcor®), atorvastatin (e.g. Sortis®, Caduet®), rosuvastatin (e.g. Crestor®), pravastatin (e.g. Lipostat®, Selipran®), fluvastatin (e.g. Lescol®), pitavastatin (e.g. Livazo®, Livalo®), lovastatin (e.g. Mevacor®, Advicor®), mevastatin (e.g. Compactin®), rivastatin, cerivastatin (Lipobayl, fibrates such as bezafibrate (e.g. Cedur® retard), ciprofibrate (e.g. Hyperlipen®), fenofibrate (e.g. Antara®, Lipofen®, Lipanthyl®), gemfibrozil (e.g. Lopid®, Gevilon®), etofibrate, simfibrate, ronifibrate, clinofibrate, clofibride, nicotinic acid and derivatives thereof (e.g. niacin, including slow release formulations of niacin), nicotinic acid receptor 1 agonists (e.g. GSK-256073), PPAR-delta agonists, acetyl-CoA-acetyltransferase (ACAT) inhibitors (e.g. avasimibe), cholesterol absorption inhibitors (e.g. ezetimibe, Ezetrol®, Zetia®, Liptruzet®, Vytorin®, S-556971), bile acid-binding substances (e.g. cholestyramine, colesevelam), ileal bile acid transport (IBAT) inhibitors (e.g. GSK-2330672, LUM-002), microsomal triglyceride transfer protein (MTP) inhibitors (e.g. lomitapide (AEGR-733), SLx-4090, granotapide), modulators of proprotein convertase subtilisin/kexin type 9 (PCSK9) (e.g. alirocumab (REGN727/SAR236553), AMG-145, LGT-209, PF-04950615, MPSK3169A, LY3015014, ALD-306, ALN-PCS, BMS-962476, SPC5001, ISIS-394814, 1B20, LGT-210, 1D05, BMS-PCSK9Rx-2, SX-PCK9, RG7652), LDL receptor up-regulators, for example liver selective thyroid hormone receptor beta agonists (e.g. eprotirome (KB-2115), MB07811, sobetirome (QRX-431), VIA-3196, ZYT1), HDL-raising compounds such as: cholesteryl ester transfer protein (CETP) inhibitors (e.g. anacetrapib (MK0859), dalcetrapib, evacetrapib, JTT-302, DRL-17822, TA-8995, R-1658, LY-2484595, DS-1442), or dual CETP/PCSK9 inhibitors (e.g. K-312), ATP-binding cassette (ABC1) regulators, lipid metabolism modulators (e.g. BMS-823778, TAP-301, DRL-21994, DRL-21995), phospholipase A2 (PLA2) inhibitors (e.g. darapladib, Tyrisa®, varespladib, rilapladib), ApoA-1 enhancers (e.g.

RVX-208, CER-001, MDCO-216, CSL-112), cholesterol synthesis inhibitors (e.g. ETC-1002), lipid metabolism modulators (e.g. BMS-823778, TAP-301, DRL-21994, DRL-21995) and omega-3 fatty acids and derivatives thereof (e.g. icosapent ethyl (AMR101), Epanova®, AKR-063, NKPL-66, PRC-4016, CAT-2003);

bromocriptine (e.g. Cycloset®, Parlodel®), phentermine and phentermine formulations or combinations (e.g. Adipex-P, Ionamin, Qsymia®), benzphetamine (e.g. Didrex®), diethylpropion (e.g. Tenuate®), phendimetrazin (e.g. Adipost®, Bontril®), bupropion and combinations (e.g. Zyban®, Wellbutrin XL®, Contrave®, Empatic®), sibutramine (e.g. Reductil®, Meridia®), topiramat (e.g. Topamax®), zonisamid (e.g. Zonegran®), tesofensine, opioid antagonists such as naltrexone (e.g. Naltrexin®, naltrexone+bupropion), cannabinoid receptor 1 (CB1) antagonists (e.g. TM-38837), melanin-concentrating hormone (MCH-1) antagonists (e.g. BMS-830216, ALB-127158(a)), MC4 receptor agonists and partial agonists (e.g. AZD-2820, RM-493), neuropeptide Y5 (NPY5) or NPY2 antagonists (e.g. velneperit, S-234462), NPY4 agonists (e.g. PP-1420), beta-3-adrenergic receptor agonists, leptin or leptin mimetics, agonists of the 5-hydroxytryptamine 2c (5HT2c) receptor (e.g. lorcaserin, Belviq®), pramlintide/metreleptin, lipase inhibitors such as cetilistat (e.g. Cametor®), orlistat (e.g. Xenical®, Calobalin®), angiogenesis inhibitors (e.g. ALS-L1023), betahistidin and histamine H3 antagonists (e.g. HPP-404), AgRP (agouti related protein) inhibitors (e.g. TTP-435), serotonin re-uptake inhibitors such as fluoxetine (e.g. Fluctine®), duloxetine (e.g. Cymbalta®), dual or triple monoamine uptake inhibitors (dopamine, norepinephrine and serotonin re-uptake) such as sertraline (e.g. Zoloft®), tesofensine, methionine aminopeptidase 2 (MetAP2) inhibitors (e.g. beloranib), and antisense oligonucleotides against production of fibroblast growth factor receptor 4 (FGFR4) (e.g. ISIS-FGFR4Rx) or prohibitin targeting peptide-1 (e.g. Adipotide®);

nitric oxide donors, AT1 antagonists or angiotensin II (AT2) receptor antagonists such as telmisartan (e.g. Kinzal®, Micardis®), candesartan (e.g. Atacand®, Blopress®), valsartan (e.g. Diovan®, Co-Diovan®), losartan (e.g. Cosaar®), eprosartan (e.g. Teveten®), irbesartan (e.g. Aprovel®, CoAprovel®), olmesartan (e.g. Votum®, Olmetec®), tasosartan, azilsartan (e.g. Edarbi®), dual angiotensin receptor blockers (dual ARBs), angiotensin converting enzyme (ACE) inhibitors, ACE-2 activators, renin inhibitors, prorenin inhibitors, endothelin converting enzyme (ECE) inhibitors, endothelin receptor (ET1/ETA) blockers, endothelin antagonists, diuretics, aldosterone antagonists, aldosterone synthase inhibitors, alpha-blockers, antagonists of the alpha-2 adrenergic receptor, beta-blockers, mixed alpha-/beta-blockers, calcium antagonists, calcium channel blockers (CCBs), nasal formulations of the calcium channel blocker diltiazem (e.g. CP-404), dual mineralocorticoid/CCBs, centrally acting antihypertensives, inhibitors of neutral endopeptidase, aminopeptidase-A inhibitors, vasopeptide inhibitors, dual vasopeptide inhibitors such as neprilysin-ACE inhibitors or neprilysin-ECE inhibitors, dual-acting AT receptor-neprilysin inhibitors, dual AT1/ETA antagonists, advanced glycation end-product (AGE) breakers, recombinant renalase, blood pressure vaccines such as anti-RAAS (renin-angiotensin-aldosteron-system) vaccines, AT1- or AT2-vaccines, drugs based on hypertension pharmacogenomics such as modulators of genetic polymorphisms with antihypertensive response, thrombocyte aggregation inhibitors, and others or combinations thereof are suitable.

A "nucleic acid molecule" is deoxyribonucleic acid (DNA) or ribonucleic acid (RNA). A nucleic acid molecule may be in the form of a molecule which is single-stranded or double-stranded and linear or covalently closed to form a circle.

The term "DNA" relates to a molecule which comprises deoxyribonucleotide residues and s typically entirely or substantially composed of deoxyribonucleotide residues. "Deoxyribonucleotide" relates to a nucleotide which lacks a hydroxyl group at the 2'-position of a beta-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogues or analogues of naturally-occurring DNA. When used in connection with nucleotides, the term "naturally occurring" refers to the bases adenine (A), cytosine (C), guanine (G), thymine (T), and uracil (U).

The term "RNA" relates to a molecule which comprises ribonucleotide residues and is typically entirely or substantially composed of ribonucleotide residues. "Ribonucleotide" relates to a nucleotide with a hydroxyl group at the 2'-position of a beta-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogues or analogues of naturally-occurring RNA. According to the invention, "RNA" refers to single-stranded RNA or double stranded RNA. In one embodiment, the RNA is mRNA, e.g., in vitro transcribed RNA (IVT RNA) or synthetic RNA. The RNA may also be modified, e.g., with one or more modifications increasing the stability (e.g., the half-life) of the RNA. Such modifications are known to a person skilled in the art and include, for example, 5'-caps or 5'cap analogues The nucleic acid molecule according to the present invention may be contained/comprised in a vector. The term "vector", as used herein, includes all vectors known to the skilled person, including plasmid vectors, cosmid vectors, phage vectors, such as lambda phage, viral vectors, such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

Alternatively, the nucleic acid molecule according to the present invention may be integrated into a genome, e.g., the genome of a host cell. Means and methods to integrate a particular nucleic acid molecule into a genome are known to a person skilled in the art.

The term "cell" or "host cell" typically relates to an intact cell, i.e., a cell with an intact membrane that has not released its normal intracellular components such as enzymes, organelles, or genetic material. An intact cell is typically a viable cell, i.e. a living cell capable of carrying out its normal metabolic functions. The term typically relates to any cell which can be transfected or transformed with an exogenous nucleic acid. The cell when transfected or transformed with an exogenous nucleic acid and transferred to a recipient can typically express the nucleic acid in the recipient. The term "cell" includes prokaryotic cells, such as bacterial cells, and eukaryotic cells, such as yeast cells, fungal cells or mammalian cells. Suitable bacterial cells include cells from gram-negative bacterial strains, such as strains of *Escherichia coli*, *Proteus*, and *Pseudomonas*, and gram-positive bacterial strains, such as strains of *Bacillus*, *Streptomyces*, *Staphylococcus*, and *Lactococcus*. Suitable fungal cells include cells from the species of *Trichoderma*, *Neurospora*, and *Aspergillus*. Suitable yeast cells include cells from the species of *Saccharomyces* (for example, *Saccharomyces cerevisiae*), *Schizosaccharomyces* (for example, *Schizosaccharomyces pombe*), *Pichia* (for example, *Pichia pastoris* and *Pichia methanolica*), and *Hansenula*. Suitable mammalian cells include for example CHO cells, BHK cells, HeLa cells, COS cells, HEK293 and the like. In one embodiment, HEK293 cells are used. However, amphibian cells, insect cells, plant cells, and any other cells used in the art for the expression of heterologous proteins can be used as well. Mammalian cells, such as mammalian adipocyte cells, are particularly useful for adoptive transfer, including cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR). The "cell" or "host cell" may be isolated or part of a tissue or organism, in particular a "non-human organism".

The term "non-human organism", as used herein, is meant to include non-human primates or other animals, in particular mammals, such as cows, horses, pigs, sheep, goats, dogs, cats, rabbits or rodents, such as mice, rats, guinea pigs and hamsters.

A pharmaceutical composition featured in the invention typically contains a therapeutically effective amount of a variant of human FGF21, optionally as part of a fusion molecule, the nucleic acid molecule or the host cell as described herein (also referred to herein as "agents") to generate the desired reaction or the desired effect.

A pharmaceutical composition in accordance with the present invention may further comprise at least one other active pharmaceutical ingredient, e.g., at least one other active pharmaceutical ingredient as defined above.

A pharmaceutical composition in accordance with the present invention is typically a sterile composition. Pharmaceutical compositions are usually provided in a uniform dosage form and may be prepared in a manner known per se. A pharmaceutical composition may, e.g., be in the form of a solution or suspension.

A pharmaceutical composition may further comprise one or more carriers and/or excipients, all of which are pharmaceutically acceptable. The term "pharmaceutically acceptable", as used herein, refers to the non-toxicity of a material which, does not interact with the action of the active agent of the pharmaceutical composition.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a subject.

Possible carrier substances for parenteral administration are, e.g., sterile water, Ringer's solution, Lactated Ringer's solution, physiological saline, bacteriostatic saline (e.g., saline containing 0.9% benzyl alcohol), phosphate-buffered saline (PBS), Hank's solution, polyalkylene glycols, hydrogenated naphthalenes and, in particular, biocompatible lactide polymers, lactide/glycolide copolymers or polyoxyethylene/polyoxy-propylene copolymers.

The term "excipient", as used herein, is intended to include all substances which may be present in a pharmaceutical composition and which are not active ingredients, such as salts, binders (e.g., lactose, dextrose, sucrose, trehalose, sorbitol, mannitol), lubricants, thickeners, surface active agents, preservatives, emulsifiers, buffer substances, flavouring agents, or colorants.

Salts, which are not pharmaceutically acceptable, may be used for preparing pharmaceutically acceptable salts and are included in the invention. Pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts. Salts may be added to adjust the ionic strength or tonicity.

Suitable preservatives for use in a pharmaceutical composition include antioxidants, citric acid, sodium citrate, benzalkonium chloride, chlorobutanol, cysteine, methionine, parabens and thimerosal.

Suitable buffer substances for use in a pharmaceutical composition include acetic acid in a salt, citric acid in a salt, boric acid in a salt and phosphoric acid in a salt.

The pharmaceutical composition may also be formulated as a stable lyophilized product that is reconstituted with an appropriate diluent, which, optionally, comprises one or more excipients as defined above.

As used herein, the term "kit of parts (in short: kit)" refers to an article of manufacture comprising one or more containers and, optionally, a data carrier. Said one or more containers may be filled with one or more of the above mentioned (re-)agents. Additional containers may be included in the kit that contain, e.g., diluents, buffers and further reagents. Said data carrier may be a non-electronical data carrier, e.g., a graphical data carrier such as an information leaflet, an information sheet, a bar code or an access code, or an electronical data carrier such as a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the FGF21 variants featured in the invention.

The agents and compositions described herein may be administered via any conventional route, e.g., orally, pulmonary, by inhalation or parenterally, including by injection or infusion. In one embodiment, parenteral administration is used, e.g., intravenously, intraarterially, subcutaneously, intradermally or intramuscularly. The agents and compositions described herein may also be administered through sustained release administration.

Pharmaceutical compositions suitable for parenteral administration usually comprise a sterile aqueous or non-aqueous preparation of the active compound, which is typically isotonic to the blood of the recipient. Examples of compatible carriers/solvents/diluents are sterile water, Ringer's solution, Lactated Ringer's solution, physiological saline, bacteriostatic saline (e.g., saline containing 0.9% benzyl alcohol), phosphate-buffered saline (PBS) and Hank's solution. In addition, usually sterile, fixed oils may be used as solution or suspension medium.

The agents and compositions described herein are usually administered in therapeutically effective amounts. A "therapeutically effective amount" refers to the amount, which achieves a desired therapeutic reaction or a desired therapeutic effect alone or together with further doses, typically without causing unacceptable side-effects. In the case of treatment of a particular disease or of a particular condition, the desired reaction typically relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. An effective amount of an agent or composition described herein will depend on the condition to be treated, the severeness of the disease, the individual parameters of the subject, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a subject is insufficient with an initial dose, higher doses (or effectively higher doses achieved by a different, more localized route of administration) may be used.

The present invention also provides a combination of a variant of human FGF21 of the present invention with at least one other active pharmaceutical ingredient.

In one embodiment, the combination of the variant of human FGF21 of the present invention with at least one other active pharmaceutical ingredient can be applied either by separate administration of the active pharmaceutical ingredient to the patient or in the form of combination products in which a plurality of active pharmaceutical ingredients are present in one pharmaceutical composition. When administered separately, administration may occur simultaneously or sequentially, in any order. The amount of the FGF21 variant and the other active pharmaceutical ingredient(s) and the relative timings of administration will be selected in order to achieve the desired combined therapeutic effect. The administration of the combination may be concomitantly in: (1) a unitary pharmaceutical composition including all active pharmaceutical ingredient; or (2) separate pharmaceutical compositions each including at least one of the active pharmaceutical ingredient. Alternatively, the combination may be administered separately in a sequential manner wherein one treatment agent is administered first and the other second or vice versa. Such sequential administration may be close in time or remote in time.

According to the invention, the term "disease or disorder" refers to any pathological or unhealthy state, in particular obesity, overweight, metabolic syndrome, diabetes mellitus, hyperglycemia, dyslipidemia, non-alcoholic steatohepatitis (NASH) and/or atherosclerosis.

The term "obesity" refers to a medical condition in which excess body fat has accumulated to the extent that it may have a negative effect on health. In terms of a human (adult) subject, obesity can be defined as a body mass index (BMI) greater than or equal to 30 kg/m$^2$ (BMI≥30 kg/m$^2$).

The term "overweight" refers to a medical condition in which the amount of body fat is higher than is optimally healthy. In terms of a human (adult) subject, obesity can be defined as a body mass index (BMI) greater than or equal to 25 kg/m$^2$ (e.g., 25 kg/m$^2$≤BMI<30 kg/m$^2$).

The BMI is a simple index of weight-for-height that is commonly used to classify overweight and obesity in adults. It is defined as a person's weight in kilograms divided by the square of his/her height in meters (kg/m$^2$).

"Metabolic syndrome" can be defined as a clustering of at least three of the following medical conditions: abdominal (central) obesity (e.g., defined as waist circumference ≥94 cm for Europid men and ≥80 cm for Europid women, with ethnicity specific values for other groups), elevated blood pressure (e.g., 130/85 mmHg or higher), elevated fasting plasma glucose (e.g., at least 100 mg/dL), high serum triglycerides (e.g., at least 150 mg/dL), and low high-density lipoprotein (HDL) levels (e.g., less than 40 mg/dL for males and less than 50 mg/dL for females).

"Diabetes mellitus" (also simply referred to as "diabetes") refers to a group of metabolic diseases characterized by high levels of blood glucose resulting from defects in insulin production, insulin action, or both. In one embodiment, diabetes mellitus is selected from the group consisting of type 1 diabetes mellitus, type 2 diabetes mellitus, gestational diabetes mellitus, late onset autoimmune diabetes in the adult (LADA), maturity onset diabetes of the young (MODY) and other types of diabetes resulting from specific genetic conditions, drugs, malnutrition, infections and other illnesses.

The current WHO diagnostic criteria for diabetes mellitus are as follows: fasting plasma glucose ≥7.0 mmol/l (126 mg/dL) or 2-h plasma glucose ≥11.1 mmol/l (200 mg/dL).

"Type 1 diabetes mellitus" (also known as "insulin-dependent diabetes (IDDM)" or "juvenile diabetes") is a condition characterized by high blood glucose levels caused by total lack of insulin. This occurs when the body's immune system attacks the insulin producing beta cells in the pancreas and destroys them. The pancreas then produces little or no insulin. Pancreatic removal or disease may also lead to loss of insulin-producing beta cells. Type 1 diabetes mellitus accounts for between 5% and 10% of cases of diabetes.

"Type 2 diabetes mellitus" (also known as "non-insulin-dependent diabetes (NIDDM)" or "adult-onset diabetes") is a condition characterized by excess glucose production in spite of the availability of insulin, and circulating glucose levels remain excessively high as a result of inadequate glucose clearance (insulin action). Type 2 diabetes mellitus may account for about 90% to 95% of all diagnosed cases of diabetes.

"Gestational diabetes" is a condition in which women without previously diagnosed diabetes exhibit high blood glucose levels during pregnancy (especially during the third trimester). Gestational diabetes affects 3-10% of pregnancies, depending on the population studied.

"Late onset autoimmune diabetes in the adult (LADA)" (also referred to as "slow onset type 1 diabetes") is a form of type 1 diabetes mellitus that occurs in adults, often with a slower course of onset.

"Maturity onset diabetes of the young (MODY)" refers to a hereditary form of diabetes caused by mutations in an autosomal dominant gene disrupting insulin production.

The term "hyperglycemia" refers to an excess of sugar (glucose) in the blood.

The term "dyslipidemia" refers to a disorder of lipoprotein metabolism, including lipoprotein overproduction ("hyperlipidemia") or deficiency ("hypolipidemia"). Dyslipidemias may be manifested by elevation of the total cholesterol, low-density lipoprotein (LDL) cholesterol and/or triglyceride concentrations, and/or a decrease in high-density lipoprotein (HDL) cholesterol concentration in the blood.

Non-alcoholic steatohepatitis (NASH) is a liver disease characterized by an accumulation of fat (lipid droplets), along with inflammation and degeneration of hepatocytes. Once installed, the disease is accompanied with a high risk of cirrhosis, a state where the liver functions are altered and can progress to liver insufficiency. Thereafter, NASH often progresses to liver cancer.

"Atherosclerosis" is a vascular disease characterized by irregularly distributed lipid deposits called plaque in the intima of large and medium-sized arteries that may cause narrowing of arterial lumens and proceed to fibrosis and calcification. Lesions are usually focal and progress slowly and intermittently. Occasionally plaque rupture occurs leading to obstruction of blood flow resulting in tissue death distal to the obstruction. Limitation of blood flow accounts for most clinical manifestations, which vary with the distribution and severity of the obstruction.

The term "medicament", as used herein, refers to a substance/composition used in therapy, i.e., in the treatment of a disease or disorder.

By "treat" is meant to administer a compound or composition or a combination of compounds or compositions to a subject in order to prevent or eliminate a disease or disorder; arrest or slow a disease or disorder in a subject; inhibit or slow the development of a new disease or disorder in a subject; decrease the frequency or severity of symptoms and/or recurrences in a subject who currently has or who previously has had a disease or disorder; and/or prolong, i.e., increase, the lifespan of the subject.

In particular, the term "treating/treatment of a disease or disorder" includes curing, shortening the duration, ameliorating, preventing, slowing down or inhibiting progression or worsening, or preventing or delaying the onset of a disease or disorder or the symptoms thereof.

The term "subject" means according to the invention a subject for treatment, in particular a diseased subject (also referred to as "patient"), including human beings, non-human primates or other animals, in particular mammals, such as cows, horses, pigs, sheep, goats, dogs, cats, rabbits or rodents, such as mice, rats, guinea pigs and hamsters. In one embodiment, the subject/patient is a human being.

FURTHER REFERENCES

Tomlinson E. et al. (2002) Endocrinology 143: 1741-1747;
Holt J. A. et al. (2003) Genes Dev 17: 1581-1591;
Shimada T. et al. (2004) J Bone Miner Res 19: 429-435;
Inagaki T. et al. (2005) Cell Metab 5: 415-425;
Lundasen T. et al. (2006) J Intern Med 260: 530-536;
Nishimura T. et al. (2000) Biochim Biophys Acta 1492: 203-206;
Kharitonenkov A. et al. (2005) J Clin Invest 115: 1627-1635;
Kharitonenkov A. et al. (2007) Endocrinology 148: 774-781;
Huang X. et al. (2006) Mol Carcinog 45: 934-942;
Wente W. et al. (2006) Diabetes 55: 2470-2478;
Ornitz D. M. et al. (2001) Genome Biol 2: REVIEWS3005;
Nicholes K. et al. (2002) Am J Pathol 160: 2295-2307:
Eswarakumar V. P. et al. (2005) Cytokine Growth Factor Rev 16: 139-149;
Dostalova I. et al. (2009) Physiol Res 58: 1-7;
WO 2003/011213 A2 and US 2004/0259780 A1;
WO 2005/061712 A1 and US 2007/0142278 A1;
WO 2006/028595 A2 and US 2008/0103096 A1;
WO 2006/028714 A1 and US 2007/0299007 A1;
WO 2006/065582 A2 and US 2007/0293430 A1;
WO 2008/121563 A2 and US 2008/0255045 A1.

EXAMPLES

Example 1: Expression of FGF21 Variants in HEK293 Cells or in *Escherichia coli* (*E. coli*)

The FGF21 variants were produced by transient transfection of HEK293 cells or in *E. coli*.

(a) Expression of FGF21 Variants in HEK293 Cells

The DNA sequence of the FGF21 variants was N-terminally fused to an IL2 signal sequence (SEQ ID NO: 4) followed by a Histidine-rich sequence (His-tag) and a TEV protease-cleavage site (SEQ ID NO: 5 or 6). The signal sequence was required for secretion of the desired proteins into the culture medium. The desired proteins were purified from the culture supernatant using immobilized metal-ion affinity chromatography (IMAC) (cOmplete His-Tag Purification Column, Roche). After elution from the IMAC-column, the N-terminal His-tag was optionally cleaved by addition of TEV protease. After His-tag cleavage, the cleavage reaction solution was passed a second time over an Immobilized-Metal Affinity Column (IMAC-column) (cOmplete His-Tag Purification Column, Roche), collecting the (His-tag-free) flow-through fraction. The protein was further purified using a gelfiltration column with phosphate buffered saline (PBS, Gibco) as running buffer. Fractions containing the desired proteins were collected, pooled, concentrated and stored at −80° C. until further usage.

(b) Expression of FGF21 Variants in *E. coli*

The FGF21 proteins of SEQ ID NO: 2 (mature human wild-type FGF21, i.e. without signal sequence; also referred to as FGF21 H29-S209) and SEQ ID NO: 3 (mature human wild-type FGF21 with an additional N-terminal G; also referred to as G+FGF21 H29-S209 or G-FGF21 H29-S209 or simply G-FGF21) as well as the proteins of SEQ ID NOs: 124 through SEQ ID NO:157 and SEQ ID NO: 174 were expressed in *E. coli*. The DNA sequences of the FGF21 proteins were N-terminally fused to a Histidine-rich sequence (His-tag) and a TEV or SUMO protease-cleavage site (SEQ ID NO: 6 or 7). The desired proteins were purified using immobilized metal-ion affinity chromatography (IMAC) (His Trap HP, GE Healthcare) followed by cleavage of the N-terminal His-tag by addition of TEV or SUMO protease. After His-tag cleavage, the cleavage reaction solution was purified using an ion exchange column, followed by a gelfiltration step using phosphate buffered saline (PBS, Gibco) as running buffer. Fractions containing the desired proteins were collected, pooled, concentrated and stored at −80° C. until further usage.

Example 2: Stability Measurement of FGF21 Variants in Human and Murine Plasma

In vivo pharmacokinetic (PK) analysis of mature human wild-type FGF21 in mice and rat revealed a half-life of less than 1 hour due to a rapid clearance via the kidney (Kharitonenkov A. et al. (2007) Endocrinology 148(2): 774-781; Stein S. et al. (2009) Diabetes Care 32(1): 126-8; Lin Z. et al. (2011) PLoS ONE 6(4): e18398). In addition, FGF21 was also found to be susceptible to in vivo proteolytic degradation. This degradation negatively affects the therapeutic potential of FGF21 significantly (Table 1) (Hecht R. et al. (2012) PLoS ONE 7(11): e49345; Micanovic R. et al. (2009) J Cell Physiol. 219(2): 227-34; Yie J. et al. (2012) Chem Biol Drug Des. 79(4): 398-410).

TABLE 1

Loss of C-terminal amino acids of FGF21 decreases its in vitro activity.

| Protein | Mw (kDa) | pFGFR ICW | |
|---|---|---|---|
| | | EC50 (nmol/L) | Emax (%) |
| FGF21, mature human wild-type (H29-S209) | 19.393 | 4.49 | 146 |
| FGF21 truncated C-terminus delta15 amino acids (H29-L194) | 17.973 | inactive | inactive |
| FGF21 truncated C-terminus delta33 amino acids (H29-E176) | 16.234 | inactive | inactive |

To learn more about the metabolic stability of human FGF21 and to identify metabolites formed by proteolytic degradation in blood the protein was analysed as described subsequently. In detail, 15 µmol/L of human wild-type FGF21 (SEQ ID NO: 3) was incubated in vitro in human, mouse, and rat lithium heparin plasma at 37° C. for 60 minutes. At the end of incubation, samples were worked up with Norgen Serum Depletion Kit (Norgen Biotek, Thorold, ON, Canada, #17300) according to the procedure described by the manufacturer. Major serum proteins including albumin, alpha-antitrypsin, transferrin and haptoglobin were depleted from plasma samples. At 4° C. 500 µL plasma samples were applied to the activated spin column and centrifuged in a benchtop microcentrifuge at 6,700×g for one minute, wherein the flow-through was discarded. The column was washed two times by addition of 500 µL Wash Buffer and centrifugation for one minute. Two times 100 µL Elution Buffer were added to the column and centrifuged for one minute to elute bound proteins.

Metabolites were identified by liquid chromatography-mass spectrometry (LC-MS) experiments on an ion trap mass spectrometer within the mass range from m/z 650 to m/z 1700 in the positive ionization mode with accurate mass measurement (Thermo-Fisher LTQ-Orbitrap, NanoLC 1D Ultra, AS2 Autosampler). The HPLC conditions used for metabolite identification were the following: column Vydac MS C4 300 A, 5 µm, 150 mm×75 µm (Grace, Lokeren, Belgium); mobile phase: eluent A 0.1% Formic acid solution with 2% (v/v) of acetonitrile and eluent B Acetonitrile+0.1% Formic acid; run time 75 min; flow rate: 280 nL/min. Multi charged masses were deconvoluted by Magtran software (Zhongqi Zhang), and the protein sequence of the formed metabolite was elucidated by GPMAW program (Lighthouse Data, Odense, Denmark).

Incubation of FGF21 of SEQ ID NO: 3 for 1 hour as described above in blood plasma resulted in a rapid cleavage, and several metabolites could be detected which are listed in Table 2. A cleavage product corresponding to the amino acid sequence from position 29 to position 199 of human wild-type FGF21 (SEQ ID NO: 1) was formed in the plasma of all species investigated. This metabolite can be described as human-FGF21-des-decapeptide, having a molecular weight of 18428.56 Da. Mass spectra and deconvolution of human FGF21 of SEQ ID NO: 3 and its cleavage products are presented in FIGS. 1A-1F.

TABLE 2

Metabolites of human FGF21 identified in plasma of human, rat, and mice after 1 hour incubation (numbering of the amino acids refers to human wild-type FGF21 of SEQ ID NO: 1).

| Input | Found | Dev. | from | to |
|---|---|---|---|---|
| Human | | | | |
| 18429 | 18428.56 | 24 | H29 | P199 |
| 19392 | 19392.55 | 28 | H29 | S209 |
| 5113.7 | 5113.76 | 12 | R159 | S209 |
| 5379 | 5379.07 | 13 | P156 | S209 |
| 5379 | 5379.08 | 14 | P152 | S204 |
| 5379 | 5379.08 | 14 | H153 | P205 |
| 5379 | 5379.08 | 14 | S151 | R203 |
| 4732.4 | 4732.33 | 15 | R163 | S209 |
| Rat | | | | |
| 18428 | 18428.56 | 30 | H29 | P199 |
| 5113.7 | 5113.76 | 12 | R159 | S209 |
| Mouse | | | | |
| 18427 | 18428.56 | 85 | H29 | P199 |
| 8564.67 | 8564.73 | 7 | L80 | P156 |
| 8564.67 | 8564.46 | 25 | Y48 | E125 |
| 8564.67 | 8565.54 | 102 | Y111 | S190 |
| 8564.67 | 8565.64 | 113 | V90 | P166 |

The in vitro stability of mature human wild-type FGF21 (SEQ ID NO: 2) and various FGF21 variants was analyzed by incubating the proteins for up to 24 hours at 37° C. in human or mouse blood plasma, and analysis of the remaining intact, full length FGF21 protein using a sandwich immunoassay. In detail, mature human FGF21 (SEQ ID NO: 2) or variants were added to blood samples (K2EDTA plasma, mixture of several healthy human donors) at a concentration of 100 ng/mL and incubated for up to 24 hours at 37° C. After 0, 1, 8, and/or 24 hours, samples were taken, and incubation was stopped by adding 2× concentrated protease inhibitor (Protease Inhibitor Cocktail Tablets, Roche). The samples were then transferred to −80° C. until further processing. Subsequently, the amount of remaining intact, full length FGF21 protein was assessed using Human Intact FGF21 ELISA (F2131-K01, Eagle Biosciences, Nashua, N.H., USA). The assay utilizes the sandwich technique with the two selected antibodies specifically binding to the N-terminus of mature human FGF21 (aa1-7) and the C-terminus (aa175-181) as described by the vendor which corresponds to amino aa29-35 and aa203-209 of full-length human wild-type FGF21 (SEQ ID NO: 1). The concentration of each individual sample at start of the incubation was used as internal reference and correlated to concentrations measured at later time points.

Figure 2:
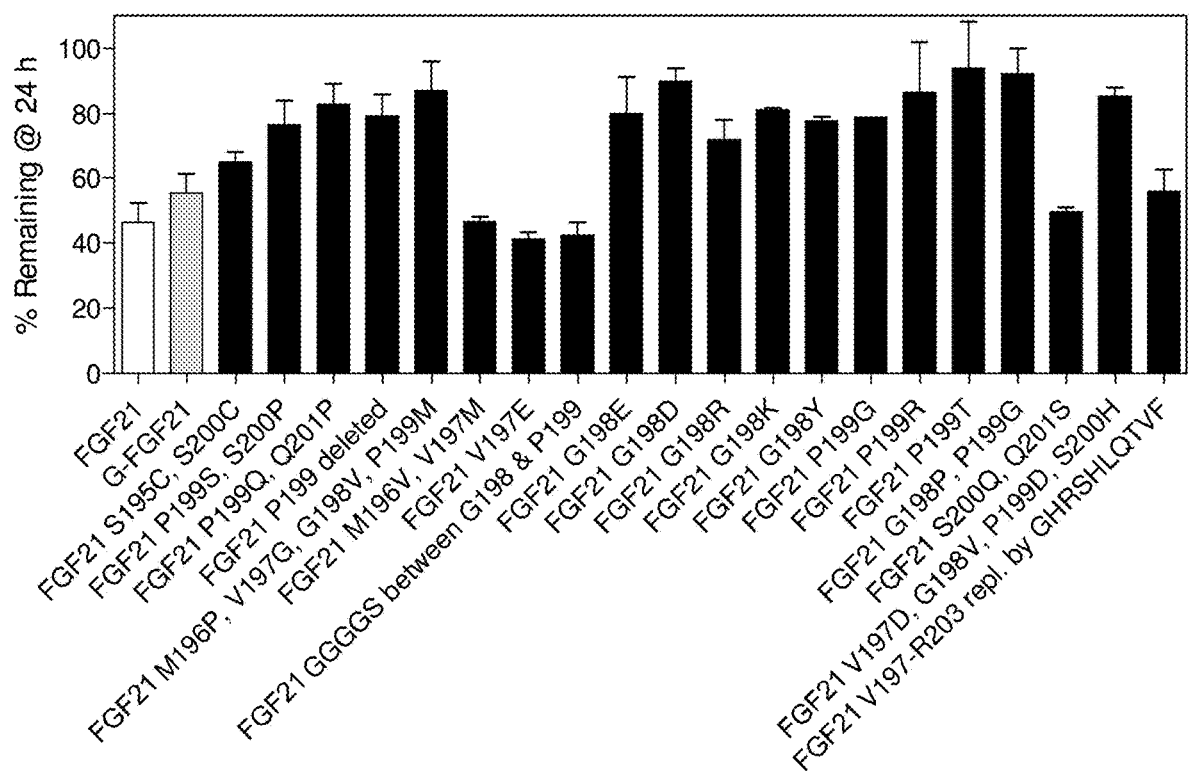
FIG. 2 shows an analysis of the stability of mature human FGF21 (SEQ ID NO: 2) and FGF21 variants in human plasma. The proteins were incubated in plasma for 24 hours at 37° C., and remaining FGF21 amounts were measured using an ELISA recognizing intact mature FGF21. Amounts at the start of the incubation were set as 100%. Data are mean+SD. Corresponding SEQ ID NOs are shown in Table 3. GGGGS (SEQ ID NO: 168); GHRSHLQTVF (SEQ ID NO: 166).

The results of the tested recombinant FGF21 variants for stability in human and murine plasma are summarized in Table 3, and representative results are shown in FIG. 2.

TABLE 3

Influence of FGF21 mutations on its stability against proteolysis (numbering of the amino acids refers to human wild-type FGF21 of SEQ ID NO: 1).

| Protein/Mutation | Stability against Proteolysis |
|---|---|
| FGF21, human (SEQ ID NO: 2) | Reference |
| G-FGF21 (SEQ ID NO: 3) | Reference |
| FGF21 V197D, G198V, P199D, S200H (SEQ ID NO: 26) | increased |
| FGF21 V197-R203 deleted and replaced by GHRSHLQTVF (SEQ ID NO: 27) | not increased |
| FGF21 P199S, S200P (SEQ ID NO: 9) | increased |
| FGF21 P199Q, Q201P (SEQ ID NO: 10) | increased |
| FGF21 P199 deleted (SEQ ID NO: 11) | increased |
| FGF21 M196P, V197G, G198V, P199M (SEQ ID NO: 12) | increased |
| FGF21 M196V, V197M (SEQ ID NO: 13) | not increased |
| FGF21 V197E (SEQ ID NO: 14) | not increased |
| FGF21 G198E (SEQ ID NO: 16) | increased |
| FGF21 G198D (SEQ ID NO: 17) | increased |
| FGF21 G198R (SEQ ID NO: 18) | increased |
| FGF21 G198K (SEQ ID NO: 19) | increased |
| FGF21 G198Y (SEQ ID NO: 20) | increased |
| FGF21 P199G (SEQ ID NO: 21) | increased |
| FGF21 P199T (SEQ ID NO: 23) | increased |
| FGF21 G198P, P199G (SEQ ID NO: 24) | increased |
| FGF21 S200Q, Q201S (SEQ ID NO: 25) | not increased |
| FGF21 S195C, S200C (SEQ ID NO: 8) | not increased |
| FGF21 GGGGS inserted between G198 and P199 (SEQ ID NO: 15) | not increased |
| FGF21 P199R (SEQ ID NO: 22) | increased |

Example 3: In Vitro Cellular Assay for Human FGF21 Receptor Efficacy in CHO Cells (in-Cell Western)

Figure 3A:
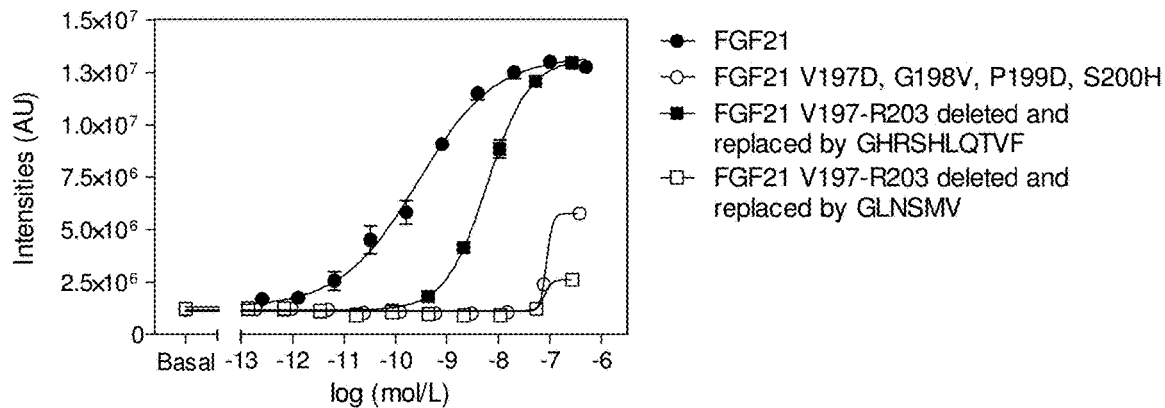
FIGS. 3A-3W show dose-response curves of ERK1/2-phosphorylation in CHO cells overexpressing human FGFR1c and beta-klotho after stimulus with mature human FGF21 (SEQ ID NO: 2) or various FGF21 variants measured via In-Cell Western (FIGS. 3A to 3W). Corresponding SEQ ID NOs are shown in Table 4.
Figure 3B:
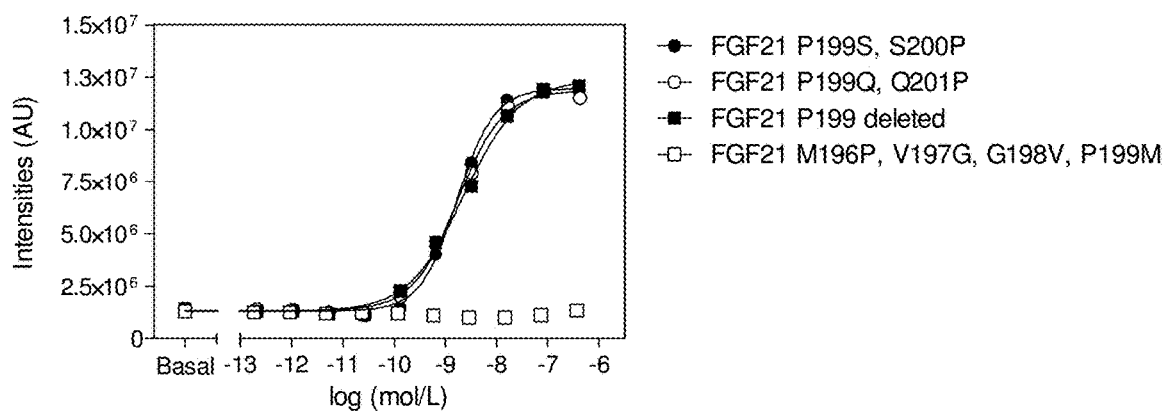
FIG. 3J: GSGS (SEQ ID NO: 161).
FIG. 3O: PLSMVGPSQGRSPSYAS (SEQ ID NO: 169).
Figure 3C:
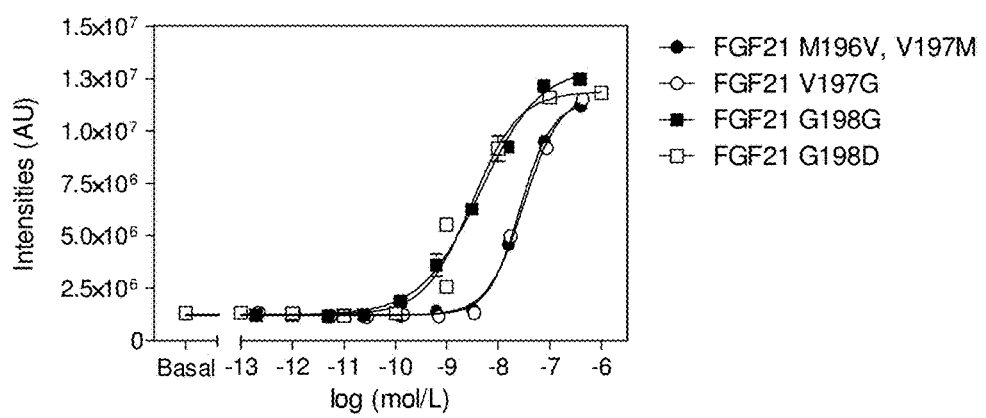
Figure 3D:
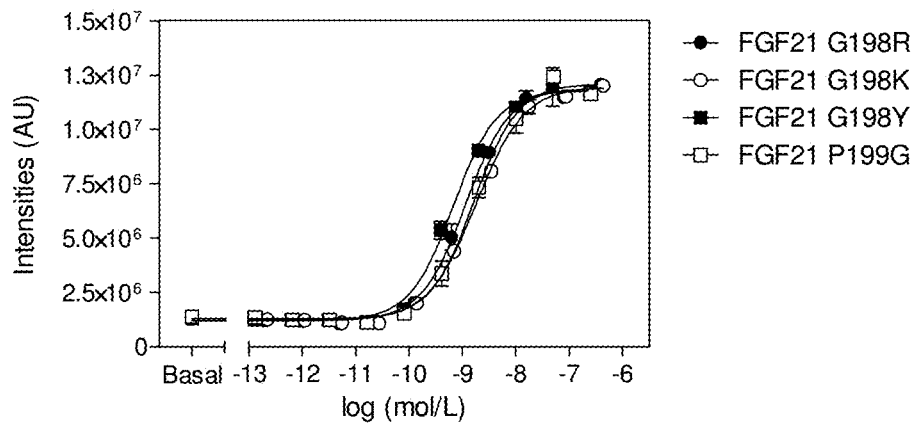
Figure 3E:
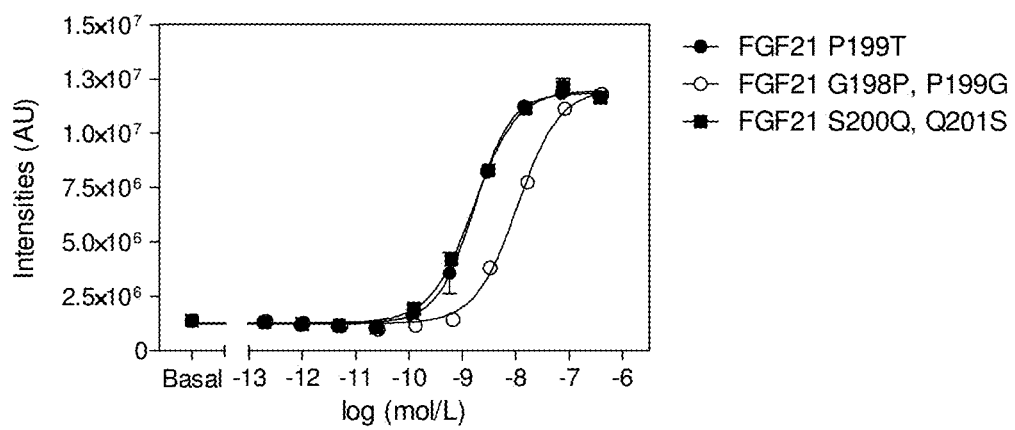
Figure 3F:
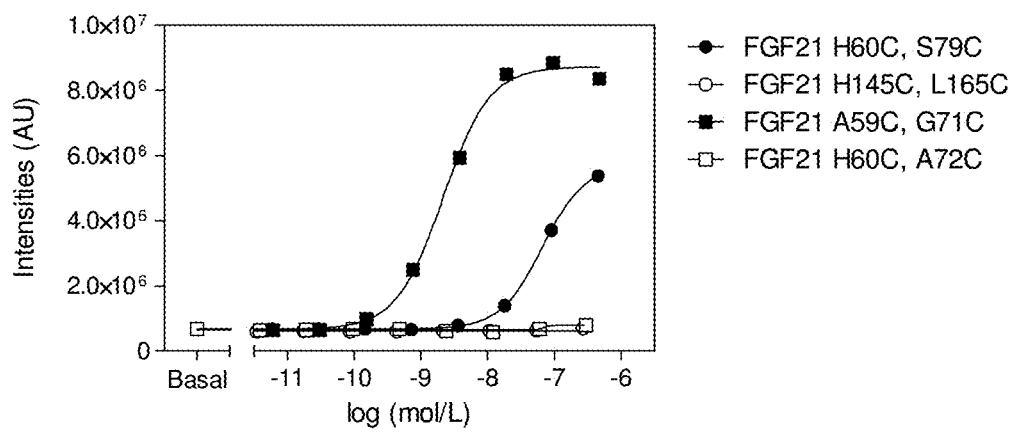
Figure 3G:
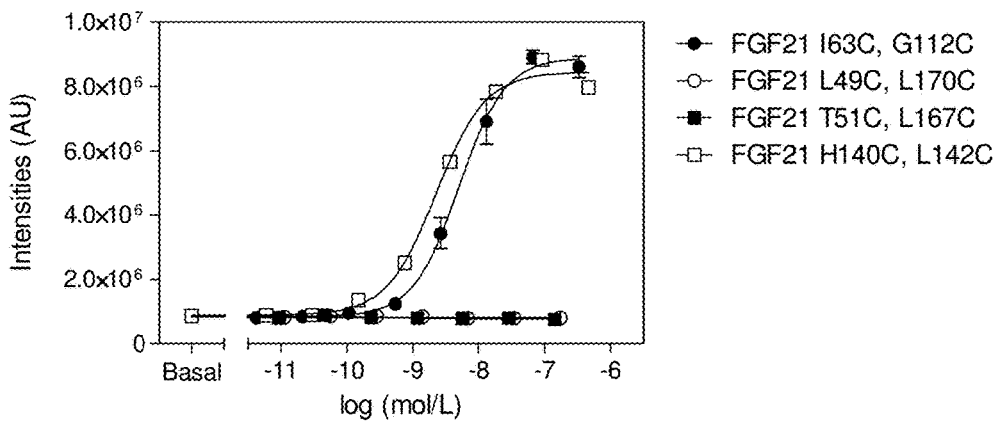
Figure 3H:
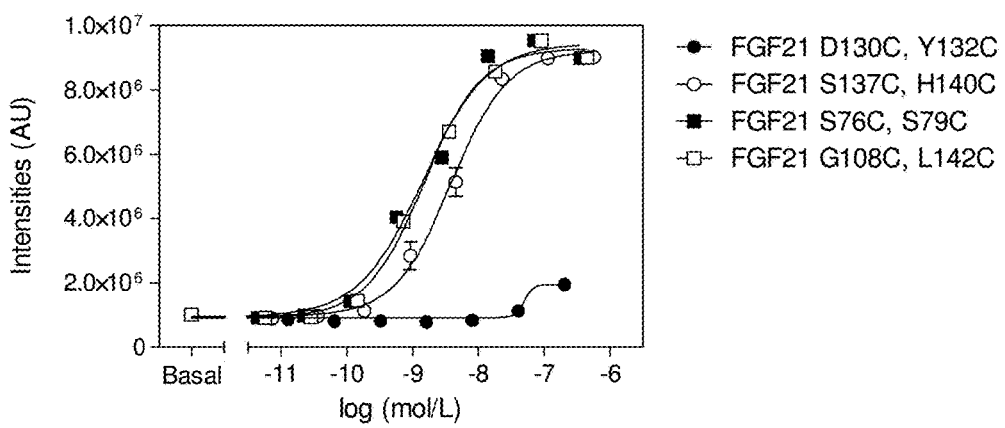
Figure 3I:
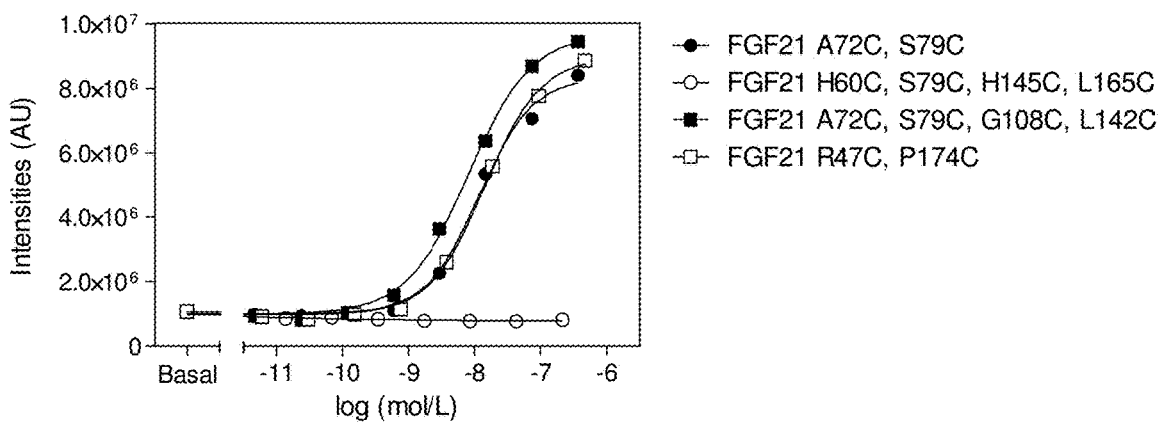
Figure 3J:
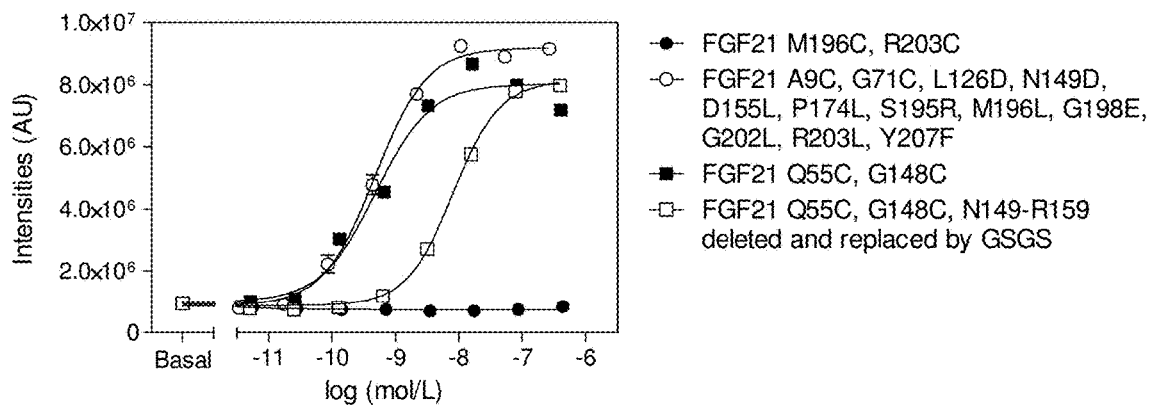
Figure 3K:
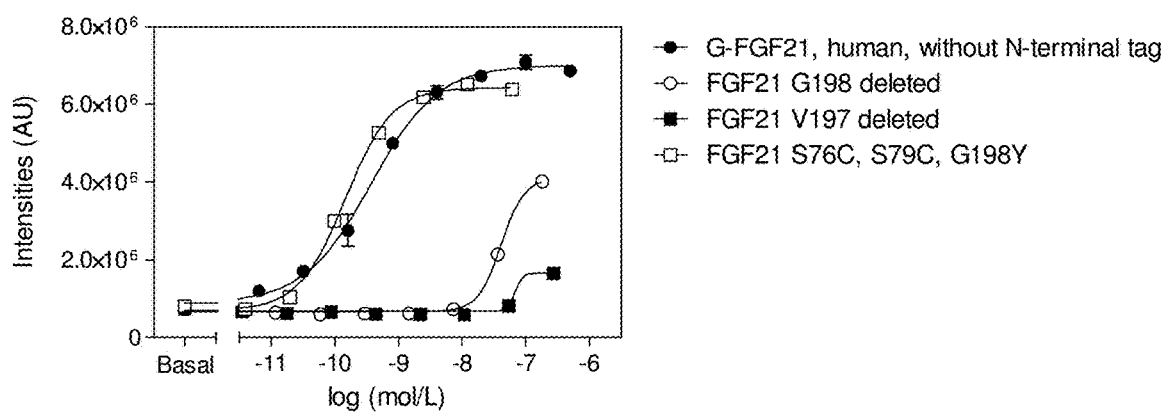
Figure 3L:
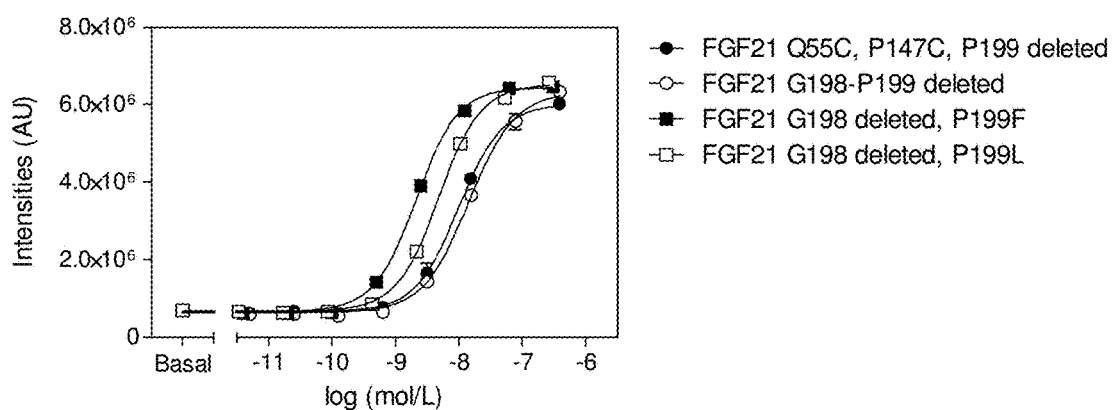
Figure 3M:
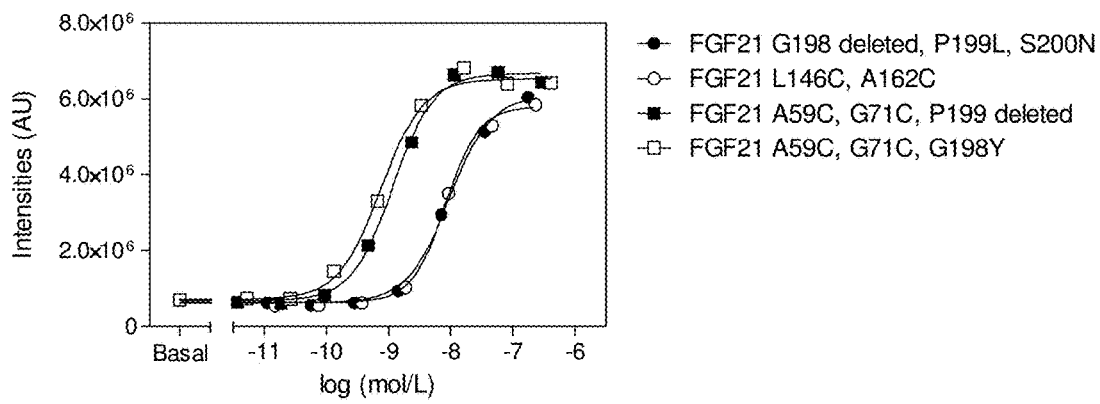
Figure 3N:
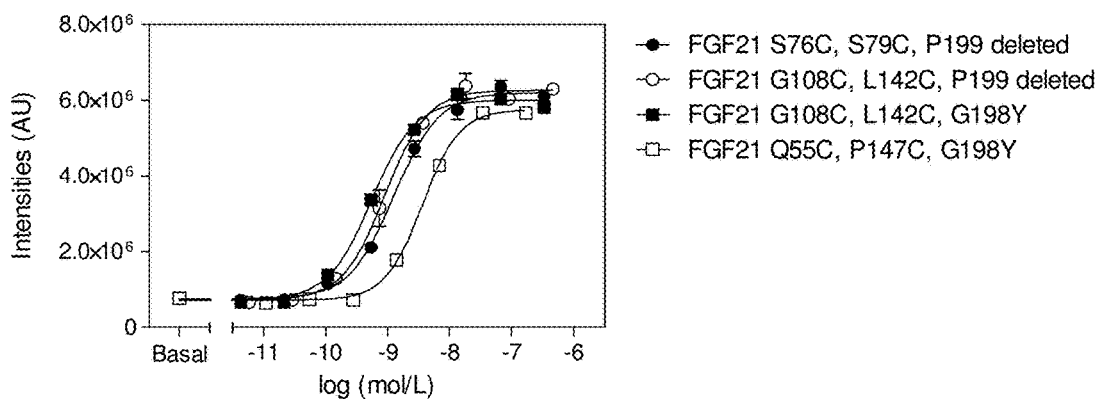
Figure 3O:
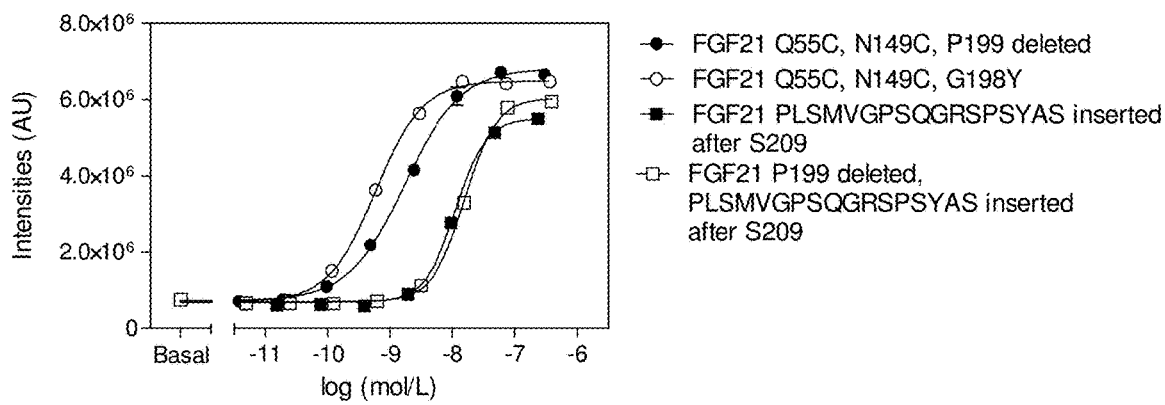
Figure 3P:
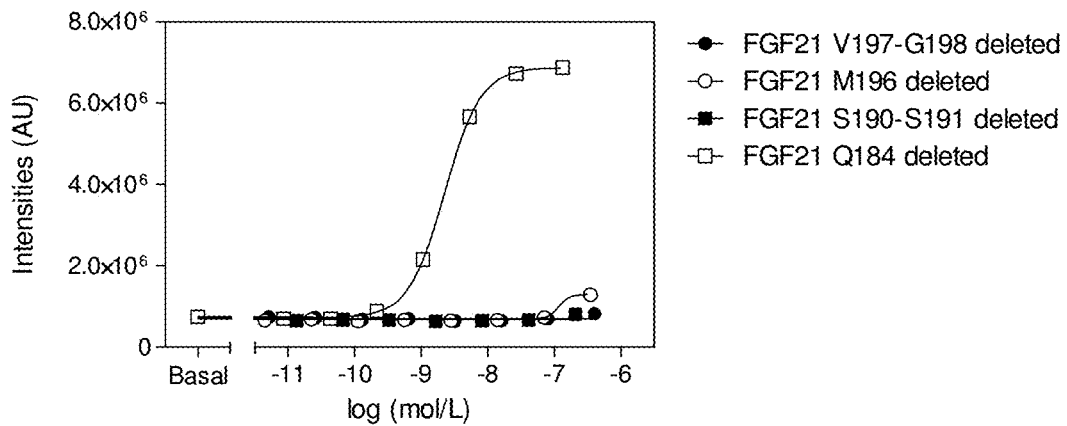
Figure 3Q:
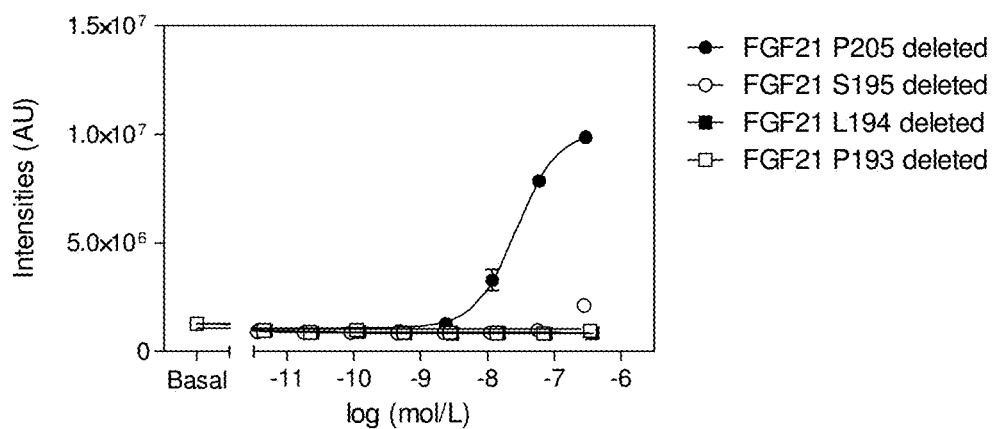
Figure 3R:
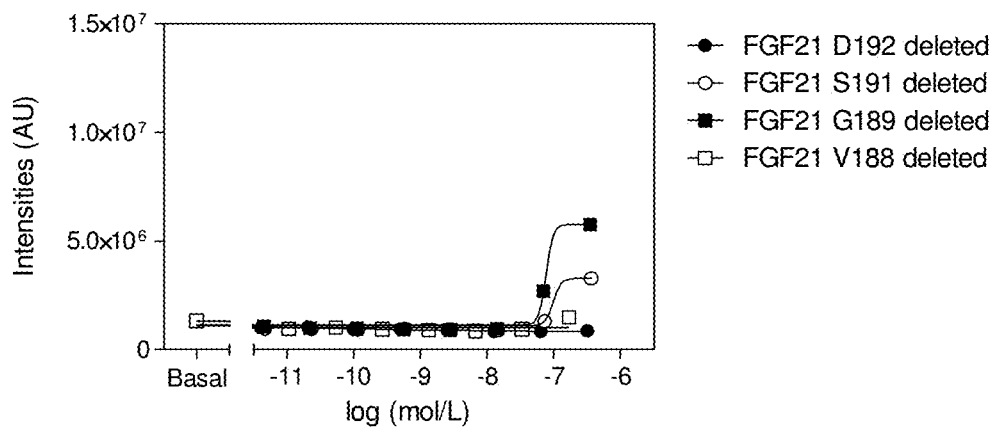
Figure 3S:
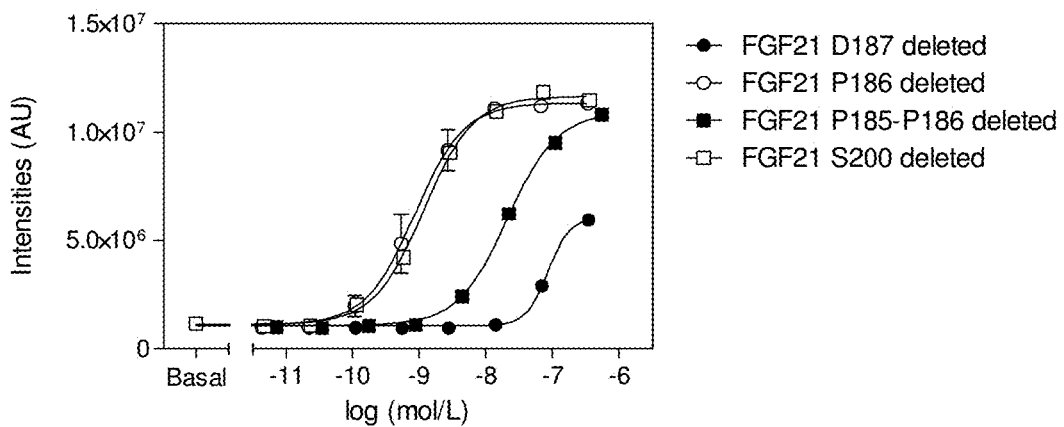
Figure 3T:
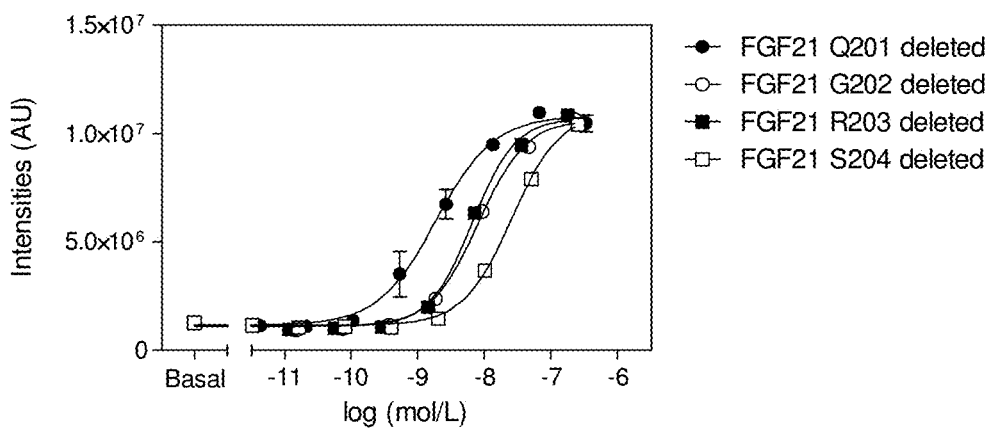
Figure 3U:
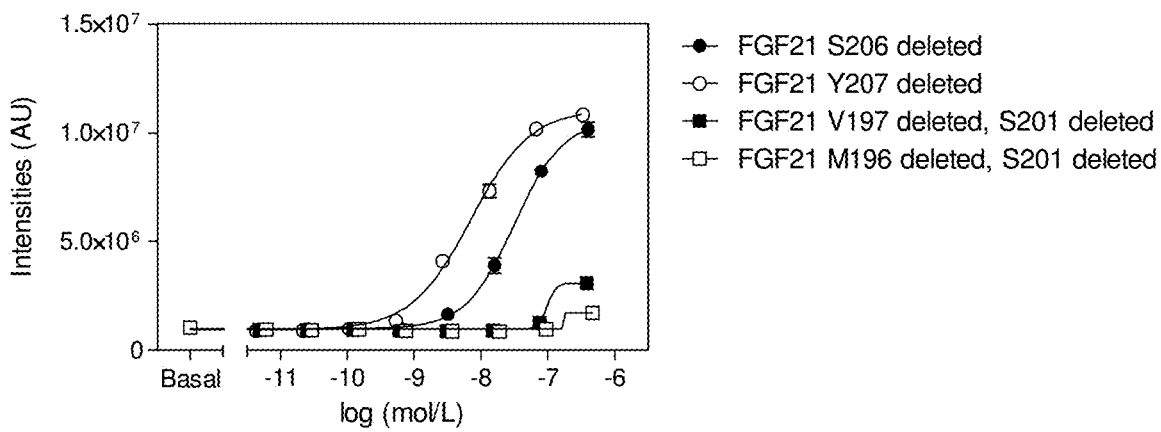
Figure 3V:
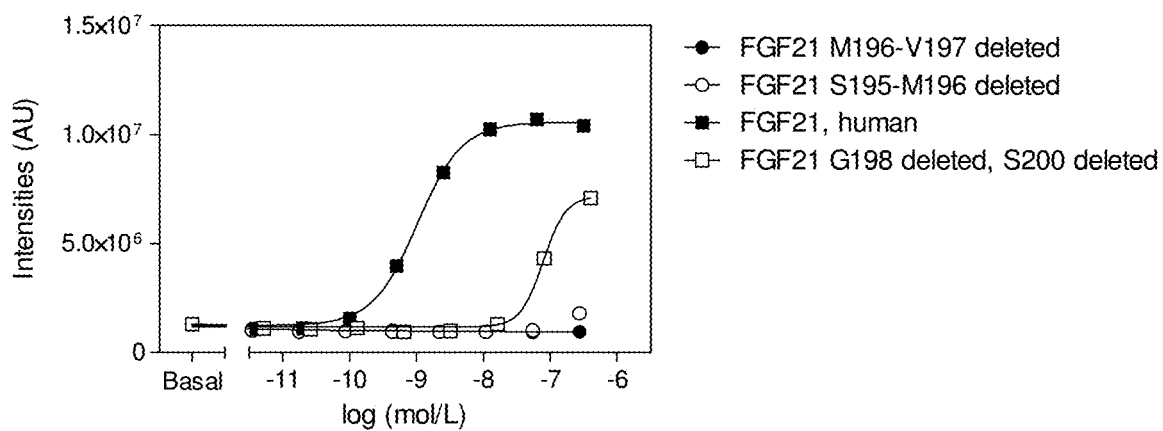
Figure 3W:
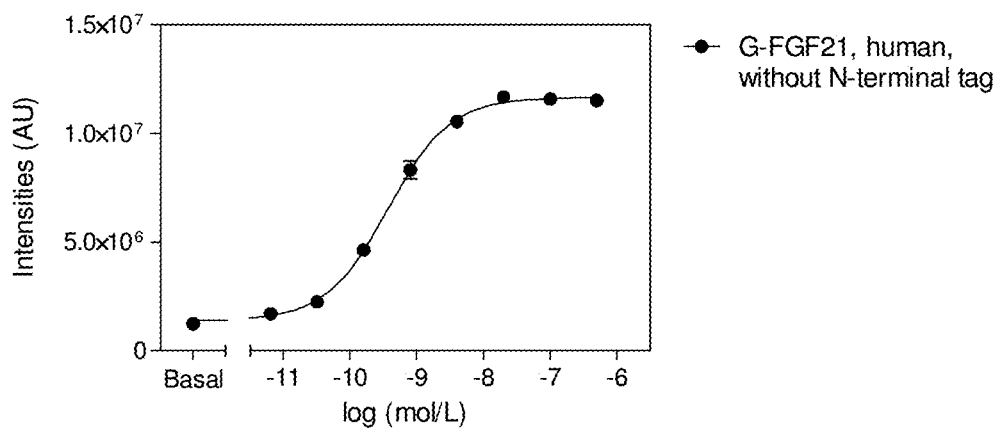

The cellular in vitro efficacy of mature human FGF21 (SEQ ID NO: 2) or FGF21 variants was measured using a specific and highly sensitive In-Cell Western (ICW) assay. The ICW assay is an immunocytochemical assay usually performed in microplate format. CHO Flp-In cells (Invitrogen, Darmstadt, Germany) stably expressing the human FGFR1c together with human beta-Klotho (KLB) were used for a FGF21 receptor autophosphorylation assay using In-Cell Western (Aguilar H. N. et al. (2010) PLoS ONE 5(4): e9965). In order to determine the receptor autophosphorylation level or downstream activation of the MAP kinase ERK1/2, $2 \times 10^4$ cells/well were seeded into 96-well plates and grown for 48 h. Cells were serum starved with serum-free medium Ham's F-12 Nutrient Mix with GlutaMAX (Gibco, Darmstadt, Germany) for 3-4 h. The cells were subsequently treated with increasing concentrations of either mature human FGF21 (SEQ ID NO: 2), the indicated FGF21 variant, or other peptides for 5 min at 37° C. After incubation, the medium was discarded, and the cells were fixed in 3.7% freshly prepared para-formaldehyde for 20 min. Cells were permeabilized with 0.1% Triton-X-100 in PBS for 20 min. Blocking was performed with Odyssey blocking buffer (LICOR, Bad Homburg, Germany) for 2 h at room temperature. As primary antibody, anti-pFGFR Tyr653/654 (New England Biolabs, Frankfurt, Germany) or anti-pERK Phospho-p44/42 MAP Kinase Thr202/Tyr204 (Cell Signaling) was added and incubated overnight at 4° C. After incubation of the primary antibody, cells were washed with PBS plus 0.1% Tween20. The secondary anti-Mouse 800CW antibody (LICOR, Bad Homburg, Germany) was incubated for 1 h at room temperature. Subsequently, cells were washed again with PBS plus 0.1% Tween20, and infrared dye signals were quantified with an Odyssey imager (LICOR, Bad Homburg, Germany). Results were normalized by quantification of DNA with TO-PRO3 dye (Invitrogen, Karlsruhe, Germany). Data were obtained as arbitrary units (AU), and EC50 values were obtained from dose-response curves and are summarized in Table 4. FIGS. 3A-3W show the results from an ICW with CHO cells overexpressing human FGFR1c plus KLB.

TABLE 4

EC50-values of mature human FGF21 (SEQ ID NO: 2) and FGF21 variants measured via ICW pERK in CHO cells. Unless otherwise specified, tested FGF21 proteins were purified by using an N-terminal tag (SEQ ID NO: 5 or 6), i.e. unless otherwise specified the FGF21 proteins carried an N-terminal tag when determining the EC50-values. The numbering of the amino acids refers to human wild-type FGF21 of SEQ ID NO: 1.

| Protein/Mutation | pERK ICW EC50 (nmol/L) |
|---|---|
| FGF21, human (SEQ ID NO: 2), without N-terminal tag | 0.17 |
| G-FGF21 (SEQ ID NO: 3), without N-terminal tag | 0.24 |
| FGF21, human (SEQ ID NO: 2) | 1.03 |
| FGF21 V197D, G198V, P199D, S200H (SEQ ID NO: 26) | 85.84 |
| FGF21 V197-R203 deleted and replaced by GHRSHLQTVF(SEQ ID NO: 27) | 6.08 |
| FGF21 V197-R203 deleted and replaced by GLNSMV(SEQ ID NO: 28) | 78.10 |
| FGF21 P199S, S200P (SEQ ID NO: 9) | 1.72 |
| FGF21 P199Q, Q201P (SEQ ID NO: 10) | 1.76 |
| FGF21 P199 deleted (SEQ ID NO: 11) | 2.31 |
| FGF21 M196P, V197G, G198V, P199M (SEQ ID NO: 12) | inactive |
| FGF21 M196V, V197M (SEQ ID NO: 13) | 26.73 |
| FGF21 V197E (SEQ ID NO: 14) | 31.45 |
| FGF21 G198E (SEQ ID NO: 16) | 4.53 |
| FGF21 G198D (SEQ ID NO: 17) | 4.94 |
| FGF21 G198R (SEQ ID NO: 18) | 1.15 |
| FGF21 G198K (SEQ ID NO: 19) | 1.81 |
| FGF21 G198Y (SEQ ID NO: 20) | 0.68 |
| FGF21 P199G (SEQ ID NO: 21) | 1.65 |
| FGF21 P199T (SEQ ID NO: 23) | 1.66 |
| FGF21 G198P, P199G (SEQ ID NO: 24) | 10.75 |
| FGF21 S200Q, Q201S (SEQ ID NO: 25) | 1.62 |
| FGF21 H60C, S79C (SEQ ID NO: 75) | 67.06 |
| FGF21 H145C, L165C (SEQ ID NO: 76) | inactive |
| FGF21 A59C, G71C (SEQ ID NO: 77) | 2.15 |
| FGF21 H60C, A72C (SEQ ID NO: 78) | inactive |
| FGF21 I63C, G112C (SEQ ID NO: 79) | 5.05 |
| FGF21 L49C, L170C (SEQ ID NO: 80) | inactive |
| FGF21 T51C, L167C (SEQ ID NO: 81) | inactive |
| FGF21 H140C, L142C (SEQ ID NO: 82) | 2.27 |
| FGF21 D130C, Y132C (SEQ ID NO: 83) | 49.39 |
| FGF21 S137C, H140C (SEQ ID NO: 84) | 3.87 |
| FGF21 S76C, S79C (SEQ ID NO: 85) | 1.44 |
| FGF21 G108C, L142C (SEQ ID NO: 86) | 1.48 |
| FGF21 A72C, S79C (SEQ ID NO: 87) | 11.85 |
| FGF21 H60C, S79C, H145C, L165C (SEQ ID NO: 88) | inactive |
| FGF21 A72C, S79C, G108C, L142C (SEQ ID NO: 89) | 8.24 |
| FGF21 R47C, P174C (SEQ ID NO: 90) | 14.53 |
| FGF21 M196C, R203C (SEQ ID NO: 91) | inactive |
| FGF21 Q55C, G148C (SEQ ID NO: 93) | 0.48 |
| FGF21 Q55C, G148C, N149-R159 deleted and replaced by GSGS (SEQ ID NO: 94) | 8.19 |

TABLE 4-continued

EC50-values of mature human FGF21 (SEQ ID NO: 2) and FGF21 variants measured via ICW pERK in CHO cells. Unless otherwise specified, tested FGF21 proteins were purified by using an N-terminal tag (SEQ ID NO: 5 or 6), i.e. unless otherwise specified the FGF21 proteins carried an N-terminal tag when determining the EC50-values. The numbering of the amino acids refers to human wild-type FGF21 of SEQ ID NO: 1.

| Protein/Mutation | pERK ICW EC50 (nmol/L) |
|---|---|
| FGF21 Q55C, G148C, N149-R159 deleted and replaced by GGSGGS (SEQ ID NO: 95) | 7.27 |
| FGF21 Q55G, Q56C, L146C (SEQ ID NO: 96) | 163.20 |
| FGF21 Q55G, Q56C, L146C, P147-R159 deleted and replaced by GSGS (SEQ ID NO: 97) | 113.90 |
| FGF21 Q55G, Q56C, L146C, P147-R159 deleted and replaced by GGSGGS (SEQ ID NO: 98) | 155.20 |
| FGF21 R124C, Q136C (SEQ ID NO: 115) | 22.59 |
| FGF21 P143C, A162C (SEQ ID NO: 116) | 17.58 |
| FGF21 P77C, K97C (SEQ ID NO: 117) | 8.76 |
| FGF21 E78C, T98C (SEQ ID NO: 118) | 9.22 |
| FGF21 L80C, V96C (SEQ ID NO: 119) | 17.85 |
| FGF21 S195C, S200C (SEQ ID NO: 8) | 10.79 |
| FGF21 GGGGS inserted between G198 and P199 (SEQ ID NO: 15) | 3.07 |
| FGF21 P199R (SEQ ID NO: 22) | 0.95 |
| FGF21 A59C, A73C (SEQ ID NO: 105) | 19.21 |
| FGF21 Q56C, L146C (SEQ ID NO: 110) | inactive |
| FGF21 H145C, P161C (SEQ ID NO: 120) | 6.51 |
| FGF21 E62C, E78C (SEQ ID NO: 101) | 2.44 |
| FGF21 E62C, S79C (SEQ ID NO: 102) | 0.55 |
| FGF21 R100C, L114C (SEQ ID NO: 103) | 48.22 |
| FGF21 L102C, G112C (SEQ ID NO: 104) | inactive |
| FGF21 E62C, A72C (SEQ ID NO: 106) | 2.03 |
| FGF21 Q104C, S137C (SEQ ID NO: 107) | 1.83 |
| FGF21 Q104C, H140C (SEQ ID NO: 108) | 21.85 |
| FGF21 A54C, P161C (SEQ ID NO: 109) | 6.38 |
| FGF21 I63C, T98C (SEQ ID NO: 111) | 87.58 |
| FGF21 G67C, R100C (SEQ ID NO: 112) | 23.32 |
| FGF21 V69C, L110C (SEQ ID NO: 113) | 11.70 |
| FGF21 A120C, A139C (SEQ ID NO: 114) | 22.00 |
| FGF21 L81C, G95C (SEQ ID NO: 121) | 46.46 |
| FGF21 Q82C, L94C (SEQ ID NO: 122) | 5.57 |
| FGF21 L83C, I91C (SEQ ID NO: 123) | inactive |
| FGF21 D155L (SEQ ID NO: 124) | 0.11 |
| FGF21 D155K (SEQ ID NO: 125) | 0.06 |
| FGF21 D155Y (SEQ ID NO: 126) | 0.07 |
| FGF21 D155P (SEQ ID NO: 127) | 0.08 |
| FGF21 D155E (SEQ ID NO: 128) | 0.13 |
| FGF21 D155N (SEQ ID NO: 129) | 0.06 |
| FGF21 R154Q, D155L (SEQ ID NO: 130) | 0.14 |
| FGF21 R154Q, D155K (SEQ ID NO: 131) | 0.39 |
| FGF21 H153Q, R154Q, D155N, A157V, R159K (SEQ ID NO: 132) | 0.23 |
| FGF21 P152A, H153K, R154Q, D155E, P156A, A157S, R159Q (SEQ ID NO: 133) | 0.24 |
| FGF21 H153Y, R154K, D155N, P156K, A157G (SEQ ID NO: 134) | 0.05 |
| FGF21 P152-H153 deleted (SEQ ID NO: 135) | 0.21 |
| FGF21 N149-R163 deleted and replaced by GSGS (SEQ ID NO: 136) | 3.69 |
| FGF21 N149-A162 deleted and replaced by GSHSG (SEQ ID NO: 137) | 0.57 |
| FGF21 N149-A162 deleted and replaced by GSHSGS (SEQ ID NO: 138) | 0.19 |
| FGF21 K150H (SEQ ID NO: 139) | 0.15 |
| FGF21 K150H, P152L (SEQ ID NO: 140) | 0.13 |
| FGF21 R163H (SEQ ID NO: 141) | 0.39 |
| FGF21 P158H, R159H (SEQ ID NO: 142) | 0.84 |
| FGF21 N149-D155 deleted and replaced by GSGS (SEQ ID NO: 143) | 0.28 |
| FGF21 N149-D155 deleted and replaced by GSHSG (SEQ ID NO: 144) | 0.10 |
| FGF21 N149-D155 deleted and replaced by ATTS (SEQ ID NO: 145) | 0.02 |
| FGF21 R159-R163 deleted and replaced by HE (SEQ ID NO: 150) | 0.98 |
| FGF21 A162Y (SEQ ID NO: 151) | 0.08 |
| FGF21 R159H (SEQ ID NO: 152) | 0.17 |
| FGF21 S200M (SEQ ID NO: 153) | 0.17 |
| FGF21 G202T (SEQ ID NO: 154) | 0.01 |
| FGF21 G202-R203 deleted (SEQ ID NO: 157) | 1.63 |
| FGF21 G198 deleted (SEQ ID NO: 29) | 41.65 |
| FGF21 V197 deleted (SEQ ID NO: 34) | 68.8 |
| FGF21 S76C, S79C, G198Y (SEQ ID NO: 39) | 0.15 |
| FGF21 Q55C, P147C, P199 deleted (SEQ ID NO: 44) | 10.03 |
| FGF21 G198-P199 deleted (SEQ ID NO: 30) | 14.47 |
| FGF21 G198 deleted, P199F (SEQ ID NO: 31) | 2.10 |
| FGF21 G198 deleted, P199L (SEQ ID NO: 32) | 4.80 |
| FGF21 G198 deleted, P199L, S200N (SEQ ID NO: 33) | 9.44 |
| FGF21 L146C, A162C (SEQ ID NO: 35) | 8.28 |
| FGF21 A59C, G71C, P199 deleted (SEQ ID NO: 36) | 1.16 |
| FGF21 A59C, G71C, G198Y (SEQ ID NO: 37) | 0.75 |
| FGF21 S76C, S79C, P199 deleted (SEQ ID NO: 38) | 1.25 |
| FGF21 G108C, L142C, P199 deleted (SEQ ID NO: 40) | 0.90 |
| FGF21 G108C, L142C, G198Y (SEQ ID NO: 41) | 0.55 |
| FGF21 Q55C, P147C, G198Y (SEQ ID NO: 45) | 3.60 |
| FGF21 Q55C, N149C, P199 deleted (SEQ ID NO: 46) | 1.70 |
| FGF21 Q55C, N149C, G198Y (SEQ ID NO: 47) | 0.58 |
| FGF21 PLSMVGPSQGRSPSYAS inserted after S209 (SEQ ID NO: 159) | 11.26 |
| FGF21 P199 deleted, PLSMVGPSQGRSPSYAS inserted after S209 (SEQ ID NO: 160) | 15.73 |
| FGF21 V197-G198 deleted (SEQ ID NO: 72) | inactive |
| FGF21 M196 deleted (SEQ ID NO: 48) | inactive |
| FGF21 S190-S191 deleted (SEQ ID NO: 54) | inactive |
| FGF21 Q184 deleted (SEQ ID NO: 60) | 2.26 |
| FGF21 P205 deleted (SEQ ID NO: 66) | 27.38 |
| FGF21 S195 deleted (SEQ ID NO: 49) | inactive |
| FGF21 L194 deleted (SEQ ID NO: 50) | inactive |
| FGF21 P193 deleted (SEQ ID NO: 51) | inactive |
| FGF21 D192 deleted (SEQ ID NO: 52) | inactive |
| FGF21 S191 deleted (SEQ ID NO: 53) | 97.28 |
| FGF21 G189 deleted (SEQ ID NO: 55) | 76.16 |
| FGF21 V188 deleted (SEQ ID NO: 56) | inactive |
| FGF21 D187 deleted (SEQ ID NO: 57) | 86.1 |
| FGF21 P186 deleted (SEQ ID NO: 58) | 0.87 |
| FGF21 P185-P186 deleted (SEQ ID NO: 59) | 21.09 |
| FGF21 S200 deleted (SEQ ID NO: 61) | 1.17 |
| FGF21 Q201 deleted (SEQ ID NO: 62) | 1.91 |
| FGF21 G202 deleted (SEQ ID NO: 63) | 8.18 |
| FGF21 R203 deleted (SEQ ID NO: 64) | 6.69 |
| FGF21 S204 deleted (SEQ ID NO: 65) | 25.67 |
| FGF21 S206 deleted (SEQ ID NO: 67) | 31.89 |
| FGF21 Y207 deleted (SEQ ID NO: 68) | 7.14 |
| FGF21 V197 deleted, S201 deleted (SEQ ID NO: 69) | 98.7 |
| FGF21 M196 deleted, S201 deleted (SEQ ID NO: 70) | 165.3 |
| FGF21 M196-V197 deleted (SEQ ID NO: 71) | inactive |
| FGF21 S195-M196 deleted (SEQ ID NO: 73) | inactive |
| FGF21 G198 deleted, S200 deleted (SEQ ID NO: 74) | 77.77 |

Figure 4A:
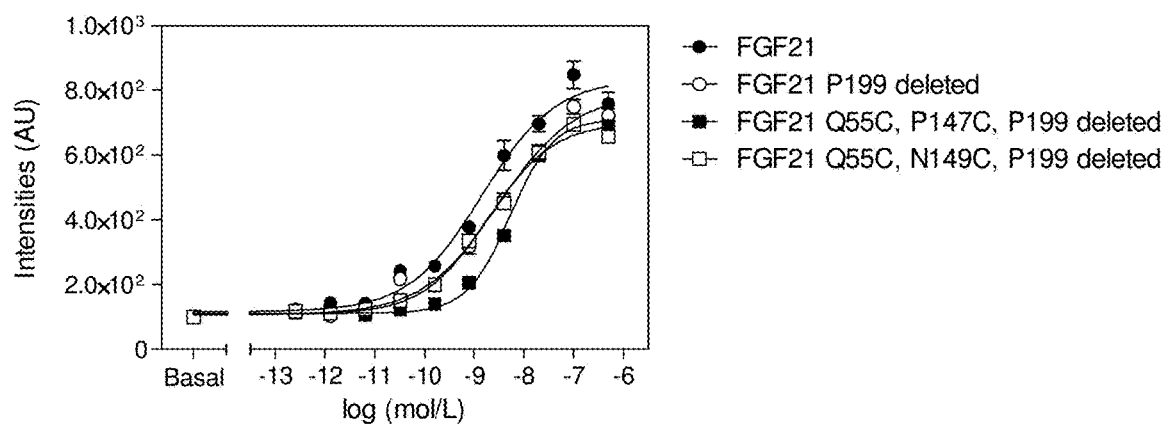
FIGS. 4A-4B show dose-response curves of ERK1/2-phosphorylation in primary human subcutaneous adipocytes after stimulus with mature human FGF21 (SEQ ID NO: 2) or various FGF21 variants measured via In-Cell Western (FIGS. 4A and 4B). Corresponding SEQ ID NOs are shown in Table 5.
Figure 4B:
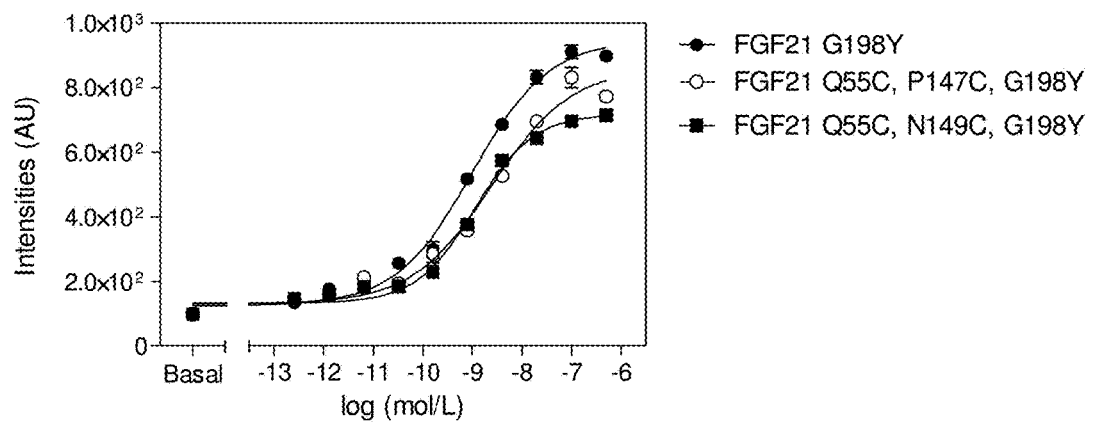

Example 4: In Vitro Activity Measurements of FGF21 Variants with Primary Human Adipocytes The cellular in vitro efficacy of human FGF21 (SEQ ID NO: 2) or FGF21 variants was also measured with human primary subcutaneous adipocytes using In-Cell Western (ICW) assay (Aguilar H. N. et al. (2010) PLoS ONE 5(4): e9965). Briefly, $2.8 \times 10^4$ human preadipocytes (PromoCell, Heidelberg, Germany) were seeded into each well of 96-well plates and differentiated to mature adipocytes (Hemmrich K. et al. (2005) Differentiation 73(1): 28-35; Lee M. J. (2014) Methods Enzymol. 538: 49-65). Prior to stimulation of the MAP kinase ERK1/2 activation, cells were serum starved with serum-free medium (DMEM 1 g/l/Ham's F-10 Medium (1:1, v/v) (PAN-Biotech, Aidenbach, Germany), 15 mmol/L Hepes, pH 7.4, 33 µmol/L biotin, 17 µmol/L pantothenate) for 3-4 h. The cells were subsequently treated with increasing concentrations of either mature human FGF21 (SEQ ID NO: 2), the indicated FGF21 variant, or other peptides for 5 min at 37° C. After incubation, the medium was discarded, and the cells were fixed in 3.7% freshly prepared paraformaldehyde for 20 min. Cells were permeabilized with 0.1% Triton-X-100 in PBS for 20 min. Blocking was performed with Odyssey blocking buffer (LICOR, Bad Homburg, Germany) for 2 h at room temperature. As primary antibody, anti-pERK Phospho-p44/42 MAP Kinase Thr202/Tyr204 (Cell Signaling) was added and incubated overnight at 4° C. After incubation of the primary antibody, cells were washed with PBS plus 0.1% Tween20. The secondary anti-Mouse 800CW antibody (LICOR, Bad Homburg, Germany) was incubated for 1 h at room temperature. Subsequently, cells were washed again with PBS plus 0.1% Tween20, and infrared dye signals were quantified with an Odyssey imager (LICOR, Bad Homburg, Germany). Results were normalized by quantification of DNA with TO-PRO3 dye (Invitrogen, Karlsruhe, Germany). Data were obtained as arbitrary units (AU), and EC50 values were obtained from dose-response curves as shown in FIGS. 4A and 4B. EC50 values are summarized in Table 5.

TABLE 5

EC50-values of mature human FGF21 (SEQ ID NO: 2) and FGF21 variants measured via ICW pERK in primary human adipocytes. The numbering of the amino acids refers to human wild-type FGF21 of SEQ ID NO: 1.

| Protein/Mutation | pERK ICW EC50 (nmol/L) |
|---|---|
| FGF21, human (SEQ ID NO: 2) | 1.55 |
| FGF21 P199 deleted (SEQ ID NO: 11) | 3.47 |
| FGF21 Q55C, P147C, P199 deleted (SEQ ID NO: 44) | 5.32 |
| FGF21 Q55C, N149C, P199 deleted (SEQ ID NO: 46) | 1.42 |
| FGF21 G198Y (SEQ ID NO: 20) | 1.03 |
| FGF21 Q55C, P147C, G198Y (SEQ ID NO: 45) | 2.55 |
| FGF21 Q55C, N149C, G198Y (SEQ ID NO: 47) | 1.18 |

Example 5: Analyzing Thermal Stability of Human FGF21 and FGF21 Variants

To analyze the impact of mutations in FGF21 on thermostability, a thermal shift assay was applied in imitation of differential scanning fluorimetry (DSF or ThermoFluor™) assays used for searching stabilizing ligands (Ahmad S. et al. (2012) Protein Science 21: 433-446; Pantoliano et al. (2001) J. Biomol. Screen 6: 429-440; Niesen et al. (2007) Nat. Protoc. 2: 2212-21). This assay is based on the observation that hydrophobic fluorescent dyes, such as Sypro™ Orange (Life Technologies, cat. No. S6651), increase their fluorescence when they bind to hydrophobic patches on a protein. Such hydrophobic patches are exposed in proteins when they unfold upon heating, so that the increase in fluorescence can be used as a measure for the degree of unfolding and, hence, for the thermostability of the proteins.

Figure 5:
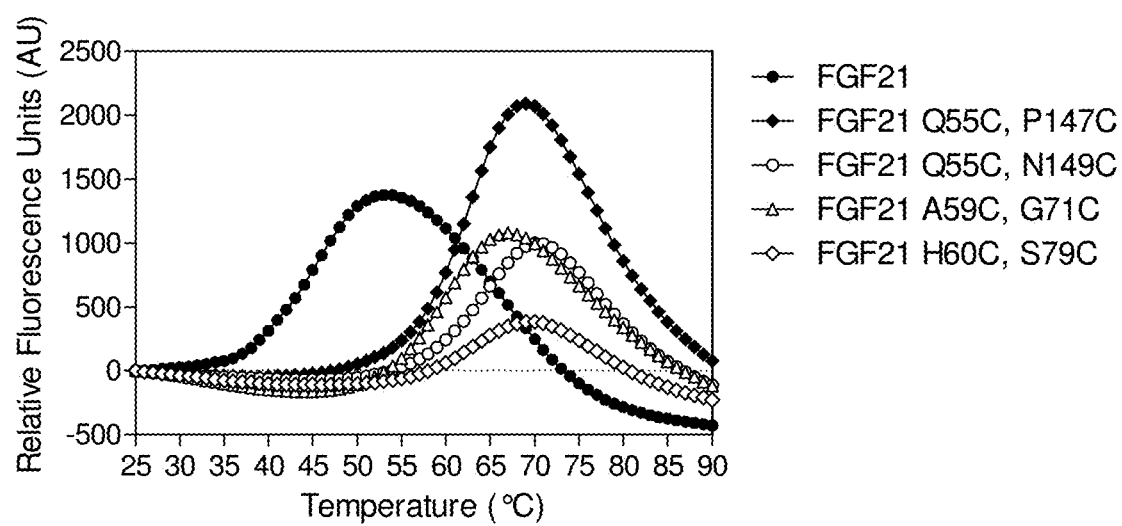
FIG. 5 shows an analysis of the thermal stability of human FGF21 (SEQ ID NO: 3) and FGF21 variants analyzed via differential scanning fluorimetry (DSF). Exemplary melting curves from the ThermoFluor™ experiment for human FGF21 (SEQ ID NO: 3) and selected FGF21 variants are shown. Relative fluorescence units normalized at 25° C. are plotted against temperature (° C.). Corresponding SEQ ID NOs are shown in Table 6.

FGF21 variants were tested by mixing a solution of the protein in PBS (Gibco) with a 160× solution of Sypro™ Orange (diluted in water from a 5000× DMSO stock as provided by the supplier). The sample volume was adjusted to 20 µl with PBS. Typical conditions contained 0.8 mg/ml FGF21 variant protein and 8× Sypro™ Orange in the final mixture, but protein concentrations could be varied between 0.4 mg/ml and 1.2 mg/ml. Samples were dispensed in 96-well PCR plates (BioRad Semi-Skirt 96 white) and shortly centrifuged to remove air bubbles. Plates were inserted in a BioRad iQ5 real-time PCR instrument and subjected to a thermal gradient from 10 to 90° C. at a ramp speed of 1° C./min. For excitation and quantification of fluorescence, filters for wavelengths of 485 nm and 575 nm were chosen. Biorad iQ5 Standard Edition software (v. 2.0.148.60623) was used for data processing. In curves of fluorescence intensity against temperature, the inflection point was chosen as the measure for the melting temperature ($T_M$). Human FGF21 (SEQ ID NO: 3) was included on every plate as a reference. FIG. 5 is showing representative melting curves of selected FGF21 variants and Table 6 is listing the differences in $T_M$ values with respect to human FGF21 (SEQ ID NO: 3).

TABLE 6

Melting point differences (deltaTm) of FGF21 variants with respect to human FGF21 of SEQ ID NO: 3. Values in brackets represent data from curves with initial high fluorescence and are less reliable. "n.d.": not determinable. Tested variants may carry an N-terminal His-tag (SEQ ID NO: 5 or 6). The tag may also be removed by protease-cleavage. The numbering of the amino acids refers to human wild-type FGF21 of SEQ ID NO: 1.

| Protein/Mutation | SEQ ID NO | deltaTm (° C.) |
|---|---|---|
| FGF21, human | 3 | 0 |
| FGF21 D155L | 124 | 0 |
| FGF21 D155K | 125 | −1.3 |
| FGF21 D155Y | 126 | −0.7 |
| FGF21 D155P | 127 | 0 |
| FGF21 D155E | 128 | 0 |
| FGF21 D155N | 129 | −1 |
| FGF21 R154Q, D155L | 130 | −1 |
| FGF21 R154Q, D155K | 131 | −1.7 |
| FGF21 H153Q, R154Q, D155N, A157V, R159K | 132 | −2.3 |
| FGF21 P152A, H153K, R154K, D155E, P156A, A157S, R159Q | 133 | −2.7 |
| FGF21 H153Y, R154K, D155N, P156K, A157G | 134 | 2.3 |
| FGF21 P152-H153 deleted | 135 | 0.3 |
| FGF21 N149-R163 deleted and replaced by GSGS (SEQ ID NO: 161) | 136 | −3 |
| FGF21 N149-A162 deleted and replaced by GSHSG (SEQ ID NO: 163) | 137 | 9.4 |
| FGF21 N149-A162 deleted and replaced by GSHSGS (SEQ ID NO: 165) | 138 | 2.3 |
| FGF21 K150H | 139 | 0.7 |
| FGF21 K150H, P152L | 140 | 0.7 |
| FGF21 R163H | 141 | −10.1 |
| FGF21 P158H, R159H | 142 | 0.7 |
| FGF21 N149-D155 deleted and replaced by GSGS (SEQ ID NO: 161) | 143 | 2.9 |
| FGF21 N149-D155 deleted and replaced by GSHSG (SEQ ID NO: 163) | 144 | 3.6 |
| FGF21 N149-D155 deleted and replaced by ATTS (SEQ ID NO: 164) | 145 | 2.6 |
| FGF21 R159-R163 deleted and replaced by GA | 146 | −13 |
| FGF21 R159-R163 deleted and replaced by GY | 147 | −17.5 |
| FGF21 R159-R163 deleted and replaced by HH | 148 | 12.5 |
| FGF21 R159-R163 deleted and replaced by GE | 149 | −14.5 |
| FGF21 R159-R163 deleted and replaced by HE | 150 | −16.4 |
| FGF21 A162Y | 151 | 1 |
| FGF21 R159H | 152 | 0 |
| FGF21 S200M | 153 | 0.7 |
| FGF21 G202T | 154 | 0.3 |

TABLE 6-continued

Melting point differences (deltaTm) of FGF21 variants with respect to human FGF21 of SEQ ID NO: 3. Values in brackets represent data from curves with initial high fluorescence and are less reliable. "n.d.": not determinable. Tested variants may carry an N-terminal His-tag (SEQ ID NO: 5 or 6). The tag may also be removed by protease-cleavage. The numbering of the amino acids refers to human wild-type FGF21 of SEQ ID NO: 1.

| Protein/Mutation | SEQ ID NO | deltaTm (° C.) |
|---|---|---|
| FGF21 R203E | 155 | −1.5 |
| FGF21 R203H | 156 | −1 |
| FGF21 G202-R203 deleted | 157 | 1.7 |
| FGF21 G108C, L142C | 86 | [14] |
| FGF21 M196C, R203C | 91 | [−1] |
| FGF21 S76C, S79C | 85 | 8 |
| FGF21 H140C, L142C | 82 | [−10] |
| FGF21 Q55C, P147C | 99 | 20 |
| FGF21 Q55C, N149C | 100 | 22 |
| FGF21 R47C, P174C | 90 | 7.5 |
| FGF21 A59C, G71C | 77 | 23.5 |
| FGF21 H60C, S79C | 75 | 19.9 |
| FGF21 H145C, L165C | 76 | −8.5 |
| FGF21 H60C, A72C | 78 | n.d. |
| FGF21 I63C, G112C | 79 | n.d. |
| FGF21 L49C, L170C | 80 | n.d. |
| FGF21 T51C, L167C | 81 | n.d. |
| FGF21 D130C, Y132C | 83 | n.d. |
| FGF21 S137C, H140C | 84 | n.d. |
| FGF21 A72C, S79C | 87 | n.d. |
| FGF21 H60C, S79C, H145C, L165C | 88 | n.d. |
| FGF21 A72C, S79C, G108C, L142C | 89 | n.d. |
| FGF21 M196C, R203C | 91 | n.d. |
| FGF21 Q55C, G148C, N149-R159 deleted and replaced by GSGS (SEQ ID NO: 161) | 94 | n.d. |
| FGF21 Q55C, N149C, G198Y | 47 | 21.9 |
| FGF21 Q55C, N149C, P199 deleted | 46 | 22.2 |
| FGF21 Q55C, P147C, G198Y | 45 | 20.7 |
| FGF21 Q55C, P147C, P199 deleted | 44 | 21.1 |
| FGF21 Q55C, G148C, N149-R159 deleted and replaced by GGSGGS (SEQ ID NO: 162) | 95 | n.d. |
| FGF21 Q55G, Q56C, L146C | 96 | n.d. |
| FGF21 Q55G, Q56C, L146C, P147-R159 deleted and replaced by GSGS (SEQ ID NO: 161) | 97 | n.d. |
| FGF21 Q55G, Q56C, L146C, P147-R159 deleted and replaced by GGSGGS (SEQ ID NO: 162) | 98 | n.d. |
| FGF21 R124C, Q136C | 115 | n.d. |
| FGF21 P143C, A162C | 116 | n.d. |
| FGF21 P77C, K97C | 117 | n.d. |
| FGF21 L80C, V96C | 119 | n.d. |
| FGF21 S195C, S200C | 8 | n.d. |
| FGF21 GGGGS (SEQ ID NO: 168) inserted between G198 and P199 | 15 | n.d. |
| FGF21 A59C, A73C | 105 | n.d. |
| FGF21 Q56C, L146C | 110 | n.d. |

Example 6: Design of Thermostable Variants and X-Ray Crystal Structure of FGF21 Q55C, N149C (SEQ ID NO: 158)

Figure 6A:
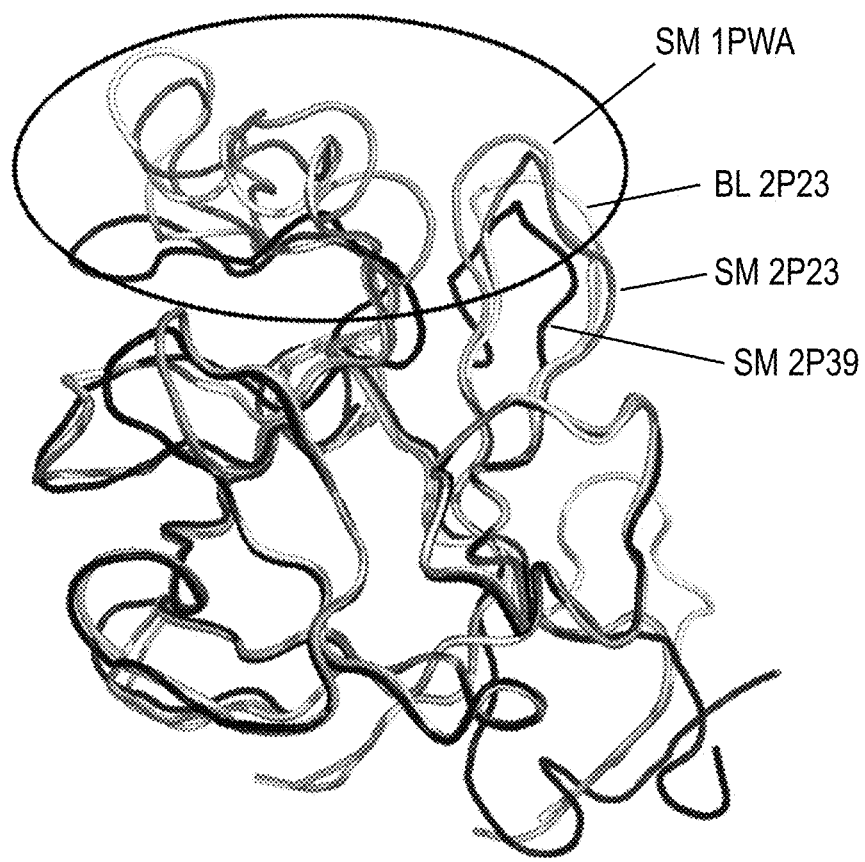
Figure 6A:
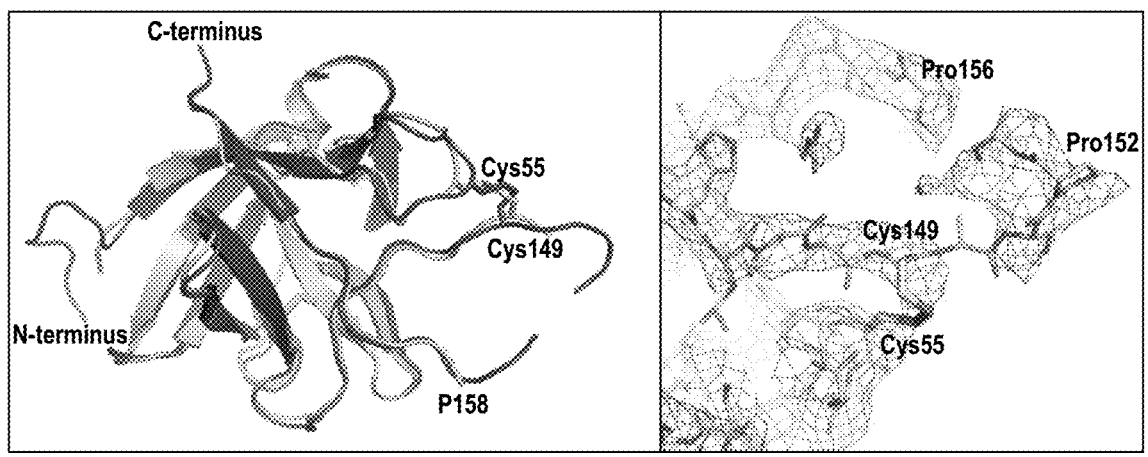

Since in public data bases like RCSB Protein Data Bank (PDB) no structure of FGF21 was deposited, different homology models of human FGF21 (SEQ ID NO: 2) were created using the SWISS-MODEL homology modeling server (Kiefer et al. (2009) Nucleic Acids Res. 37: D387-D392) or the software program BioLuminate (BioLuminate, version 1.0, Schrödinger, LLC, New York, N.Y., 2012). These models are based on the published crystal structures of FGF19 (Goetz et al. (2007) Mol. Cell. Biol. 27: 3417-3428; PDB code 2P23; Harmer (2004) Biochemistry 43: 629-640; PDB code 1PWA) and FGF23 (Goetz et al. (2007) Mol. Cell. Biol. 27: 3417-3428; PDB code 2P39) (FIGS. 6A-6C). The different models were subjected to further analysis using BioLuminate to generate a list of potential sites for introducing disulfide bridges. Potential positions were inspected visually in the model structures using the software program PYMOL (The PyMOL Molecular Graphics System, Version 1.7 Schrödinger, LLC) for the final selection of candidates for expression and experimental testing.

To crystallize human FGF21, a modified and truncated variant (human FGF21 S34-E176, Q55C, N149C; SEQ ID NO: 158) was expressed and purified as described above (Example 1). Crystals were grown by hanging-drop vapor diffusion. The protein was concentrated to 12 mg/mL in 50 mmol/L Tris, pH 8.0, 0.5 mol/L NaCl. The reservoir solution contained 2 mol/L $NH_4SO_4$ in 100 mmol/L Tris, pH 8.5. 100 nL protein solution was mixed with 100 nL reservoir solution and equilibrated at 20° C. Crystals appeared within two weeks. Cryoprotection was achieved by soaking crystals in the reservoir solution supplemented with 20 to 25% (vol/vol) ethylene glycol before flash freezing in liquid nitrogen.

X-ray diffraction data were collected at beamline PX-III of the Swiss Light Source (SLS) in Viligen, Switzerland, and processed with XDS (Kabsch W. (2010) Acta Crystallogr. D66: 125-132) and scaled with Aimless (Evans P. R. (2006) Acta Crystallogr. D62: 72-82) as implemented in autoProc (Vonrhein C. et al. (2011) Acta Crystallogr. D67: 293-302). The crystal was of space group $P4_132$ and contained two FGF21 Q55C, N149C molecules in the asymmetric unit. The unit cell dimensions of this crystal were as follows: a=b=c=136.7 Å. The crystal diffracted to 2.97 Å resolution and the Rmerge was 10.5%.

The structure was determined by molecular replacement using the program Phaser (McCoy A. J. et al. (2007) J. Appl. Crystallogr. 40: 658-674). The crystal structures of FGF19 (Protein Data Bank code 1pwa), FGF23 (Protein Data Bank code 2p39), and FGF9 (Protein Data Bank code 2P39) were superimposed, and all loops that differed more than ~5 Å were removed. The resulting ensemble was used as a search model and resulted in an unambiguous solution. Phaser placed three FGF-ensembles. However, the electron density for the third ensemble was extremely weak, and this ensemble was deleted. Model building was done with Coot (Emsley P. et al. (2010) Acta Crystallogr. D66: 486-501) and refinement was done with Buster (Bricogne G. et al. (2011) Cambridge, United Kingdom: Global Phasing Ltd.) and Refmac5 (Murshudov G. N. et al. (2011) Acta Crystallogr. D67: 355-367). The final Rfactor was 25.5% and the free Rfactor was 28.6%. These Rfactors were relatively high and may indicate a certain amount of disorder in the crystals.

In the final model for the FGF21 Q55C, N149C (SEQ ID NO: 158), molecule A contained the residues G42-K150 and P158-G169; molecule B contained the residues P36-H154 and P156-L170. In both molecules, the loop between P150 and R159 was significantly disordered which is an indication for high flexibility in this region.

It may be assumed that such a highly flexible loop represents a starting point for thermal unfolding of the protein. Hence, stabilization of this region by a disulfide bond may explain the significant increase in thermal stability of about 20° C. as assessed for the FGF21 variant H29-S209 Q55C, N149C (SEQ ID NO: 100) or the neighboring variant H29-S209 Q55C, P147C (SEQ ID NO: 99).

TABLE 7

List of Sequences.

| SEQ ID NO | Description | Sequence |
|---|---|---|
| 1 | full-length human wild-type FGF21 (including signal sequence Met1-Ala28) | MDSDETGFEH SGLWVSVLAG LLLGACQAHP IPDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH GLPLHLPGNK SPHRDPAPRG PARFLPLPGL PPAPPEPPGI LAPQPPDVGS SDPLSMVGPS QGRSPSYAS |
| 2 | mature human wild-type FGF21 (without signal sequence Met1-Ala28) | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 3 | mature human wild-type FGF21 with additional N-terminal G (G-FGF21) | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 4 | IL2 signal sequence | MYRMQLLSCI ALLSLALVTN S |
| 5 | Histidine-rich presequence a (His-tag + TEV cleavage site) | DIQTGGSHAH GHGHAHGHGG SGENLYFQ |
| 6 | Histidine-rich presequence b (His-tag + TEV cleavage site) | MGHHHHHHHH GGGENLYFQG |
| 7 | Histidine-rich presequence c (His-tag) + SUMO-tag | MGHHHHHHGS LQDSEVNQEA KPEVKPEVKP ETHINLKVSD GSSEIFFKIK KTTPLRRLME AFAKRQGKEM DSLRFLYDGI RIQADQAPED LDMEDNDIIE AHREQIGG |
| 8 | G-FGF21 S195C, S200C | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLCMV GPCQGRSPSY AS |
| 9 | G-FGF21 P199S, S200P | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GSPQGRSPSY AS |
| 10 | G-FGF21 P199Q, Q201P | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GQSPGRSPSY AS |
| 11 | G-FGF21 P199 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GSQGRSPSYA S |
| 12 | G-FGF21 M196P, V197G, G198V, P199M | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSPG VMSQGRSPSY AS |
| 13 | G-FGF21 M196V, V197M | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSVM GPSQGRSPSY AS |
| 14 | G-FGF21 V197E | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSME GPSQGRSPSY AS |
| 15 | G-FGF21 GGGGS (SEQ ID NO: 168) | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP |

TABLE 7-continued

List of Sequences.

| SEQ ID NO | Description | Sequence |
|---|---|---|
| | inserted between G198 and P199 | PGILAPQPPD VGSSDPLSMV GGGGGSPSQG RSPSYAS |
| 16 | G-FGF21 G198E | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV EPSQGRSPSY AS |
| 17 | G-FGF21 G198D | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV DPSQGRSPSY AS |
| 18 | G-FGF21 G198R | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV RPSQGRSPSY AS |
| 19 | G-FGF21 G198K | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV KPSQGRSPSY AS |
| 20 | G-FGF21 G198Y | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV YPSQGRSPSY AS |
| 21 | G-FGF21 P199G | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GGSQGRSPSY AS |
| 22 | G-FGF21 P199R | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GRSQGRSPSY AS |
| 23 | G-FGF21 P199T | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GTSQGRSPSY AS |
| 24 | G-FGF21 G198P, P199G | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV PGSQGRSPSY AS |
| 25 | G-FGF21 S200Q, Q201S | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPQSGRSPSY AS |
| 26 | G-FGF21 V197D, G198V, P199D, S200H | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMD VDHQGRSPSY AS |
| 27 | G-FGF21 V197-R203 deleted and replaced by GHRSHLQTVF (SEQ ID NO: 166) | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMG HRSHLQTVFS PSYAS |
| 28 | G-FGF21 V197-R203 deleted and replaced by GLNSMV (SEQ ID NO: 167) | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMG LNSMVSPSYA S |

TABLE 7-continued

List of Sequences.

| SEQ ID NO | Description | Sequence |
|---|---|---|
| 29 | G-FGF21 G198 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV PSQGRSPSYA S |
| 30 | G-FGF21 G198-P199 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV SQGRSPSYAS |
| 31 | G-FGF21 G198 deleted, P199F | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV FSQGRSPSYA S |
| 32 | G-FGF21 G198 deleted, P199L | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV LSQGRSPSYA S |
| 33 | G-FGF21 G198 deleted, P199L, S200N | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV LNQGRSPSYA S |
| 34 | G-FGF21 V197 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMG PSQGRSPSYA S |
| 35 | G-FGF21 L146C, A162C | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHCP GNKSPHRDPA PRGPCRFLPL PGLPPAPPEP PGILAPQPPD VGSSDPLSMV GPSQGRSPSY AS |
| 36 | G-FGF21 A59C, G71C, P199 deleted | GHPIPDSSPL LQFGGQVRQR YLYTDDAQQT ECHLEIREDG TVGCAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GSQGRSPSYA S |
| 37 | G-FGF21 A59C, G71C, G198Y | GHPIPDSSPL LQFGGQVRQR YLYTDDAQQT ECHLEIREDG TVGCAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV YPSQGRSPSY AS |
| 38 | G-FGF21 S76C, S79C, P199 deleted | GHPIPDSSPL LQFGGQVRQR YLYTDDAQQT EAHLEIREDG TVGGAADQCP ECLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GSQGRSPSYA S |
| 39 | G-FGF21 S76C, S79C, G198Y | GHPIPDSSPL LQFGGQVRQR YLYTDDAQQT EAHLEIREDG TVGGAADQCP ECLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV YPSQGRSPSY AS |
| 40 | G-FGF21 G108C, L142C, P199 deleted | GHPIPDSSPL LQFGGQVRQR YLYTDDAQQT EAHLEIREDG TVGGAADQSP ESLLQLKALK PGVIQILGVK TSRFLCQRPD CALYGSLHFD PEACSFRELL LEDGYNVYQS EAHGCPLHLP GNKSPHRDPA PRGPARFLPL PGLPPAPPEP PGILAPQPPD VGSSDPLSMV GSQGRSPSYA S |
| 41 | G-FGF21 G108C, L142C, G198Y | GHPIPDSSPL LQFGGQVRQR YLYTDDAQQT EAHLEIREDG TVGGAADQSP ESLLQLKALK PGVIQILGVK TSRFLCQRPD CALYGSLHFD PEACSFRELL LEDGYNVYQS EAHGCPLHLP GNKSPHRDPA PRGPARFLPL PGLPPAPPEP PGILAPQPPD VGSSDPLSMV YPSQGRSPSY AS |
| 42 | G-FGF21 D107C, D155C, P199 deleted | GHPIPDSSPL LQFGGQVRQR YLYTDDAQQT EAHLEIREDG TVGGAADQSP ESLLQLKALK PGVIQILGVK TSRFLCQRPC GALYGSLHFD PEACSFRELL LEDGYNVYQS EAHGLPLHLP GNKSPHRCPA PRGPARFLPL PGLPPAPPEP PGILAPQPPD VGSSDPLSMV GSQGRSPSYA S |

TABLE 7-continued

List of Sequences.

| SEQ ID NO | Description | Sequence |
|---|---|---|
| 43 | G-FGF21 D107C, D155C, G198Y | GHPIPDSSPL LQFGGQVRQR YLYTDDAQQT EAHLEIREDG TVGGAADQSP ESLLQLKALK PGVIQILGVK TSRFLCQRPC GALYGSLHFD PEACSFRELL LEDGYNVYQS EAHGLPLHLP GNKSPHRCPA PRGPARFLPL PGLPPAPPEP PGILAPQPPD VGSSDPLSMV YPSQGRSPSY AS |
| 44 | G-FGF21 Q55C, P147C, P199 deleted | GHPIPDSSPL LQFGGQVRQR YLYTDDACQT EAHLEIREDG TVGGAADQSP ESLLQLKALK PGVIQILGVK TSRFLCQRPD GALYGSLHFD PEACSFRELL LEDGYNVYQS EAHGLPLHLC GNKSPHRDPA PRGPARFLPL PGLPPAPPEP PGILAPQPPD VGSSDPLSMV GSQGRSPSYA S |
| 45 | G-FGF21 Q55C, P147C, G198Y | GHPIPDSSPL LQFGGQVRQR YLYTDDACQT EAHLEIREDG TVGGAADQSP ESLLQLKALK PGVIQILGVK TSRFLCQRPD GALYGSLHFD PEACSFRELL LEDGYNVYQS EAHGLPLHLC GNKSPHRDPA PRGPARFLPL PGLPPAPPEP PGILAPQPPD VGSSDPLSMV YPSQGRSPSY AS |
| 46 | G-FGF21 Q55C, N149C, P199 deleted | GHPIPDSSPL LQFGGQVRQR YLYTDDACQT EAHLEIREDG TVGGAADQSP ESLLQLKALK PGVIQILGVK TSRFLCQRPD GALYGSLHFD PEACSFRELL LEDGYNVYQS EAHGLPLHLP GCKSPHRDPA PRGPARFLPL PGLPPAPPEP PGILAPQPPD VGSSDPLSMV GSQGRSPSYA S |
| 47 | G-FGF21 Q55C, N149C, G198Y | GHPIPDSSPL LQFGGQVRQR YLYTDDACQT EAHLEIREDG TVGGAADQSP ESLLQLKALK PGVIQILGVK TSRFLCQRPD GALYGSLHFD PEACSFRELL LEDGYNVYQS EAHGLPLHLP GCKSPHRDPA PRGPARFLPL PGLPPAPPEP PGILAPQPPD VGSSDPLSMV YPSQGRSPSY AS |
| 48 | G-FGF21 M196 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSVG PSQGRSPSYA S |
| 49 | G-FGF21 S195 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLMVG PSQGRSPSYA S |
| 50 | G-FGF21 L194 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPSMVG PSQGRSPSYA S |
| 51 | G-FGF21 P193 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDLSMVG PSQGRSPSYA S |
| 52 | G-FGF21 D192 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSPLSMVG PSQGRSPSYA S |
| 53 | G-FGF21 S191 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSDPLSMVG PSQGRSPSYA S |
| 54 | G-FGF21 S190-S191 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGDPLSMVGP SQGRSPSYAS |
| 55 | G-FGF21 G189 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VSSDPLSMVG PSQGRSPSYA S |
| 56 | G-FGF21 V188 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD GSSDPLSMVG PSQGRSPSYA S |

TABLE 7-continued

List of Sequences.

| SEQ ID NO | Description | Sequence |
|---|---|---|
| 57 | G-FGF21 D187 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPV GSSDPLSMVG PSQGRSPSYA S |
| 58 | G-FGF21 P186 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPDV GSSDPLSMVG PSQGRSPSYA S |
| 59 | G-FGF21 P185-P186 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQDVG SSDPLSMVGP SQGRSPSYAS |
| 60 | G-FGF21 Q184 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPPPDV GSSDPLSMVG PSQGRSPSYA S |
| 61 | G-FGF21 S200 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPQGRSPSYA S |
| 62 | G-FGF21 Q201 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSGRSPSYA S |
| 63 | G-FGF21 G202 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQRSPSYA S |
| 64 | G-FGF21 R203 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGSPSYA S |
| 65 | G-FGF21 S204 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRPSYA S |
| 66 | G-FGF21 P205 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSSYA S |
| 67 | G-FGF21 S206 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPYA S |
| 68 | G-FGF21 Y207 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSA S |
| 69 | G-FGF21 V197 deleted, S201 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMG PQGRSPSYAS |
| 70 | G-FGF21 M196 deleted, S201 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSVG PQGRSPSYAS |
| 71 | G-FGF21 M196-V197 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL |

TABLE 7-continued

List of Sequences.

| SEQ ID NO | Description | Sequence |
|---|---|---|
| | | LEDGYNVYQS EAHGLPLHLP GNKSPHRDPA PRGPARFLPL PGLPPAPPEP PGILAPQPPD VGSSDPLSGP SQGRSPSYAS |
| 72 | G-FGF21 V197-G198 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMP SQGRSPSYAS |
| 73 | G-FGF21 S195-M196 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLVGP SQGRSPSYAS |
| 74 | G-FGF21 G198 deleted, S200 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV PQGRSPSYAS |
| 75 | G-FGF21 H60C, S79C | GHPIPDSSPL LQFGGQVRQR YLYTDDAQQT EACLEIREDG TVGGAADQSP ECLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 76 | G-FGF21 H145C, L165C | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLCLP GNKSPHRDPA PRGPARFCPL PGLPPAPPEP PGILAPQPPD VGSSDPLSMV GPSQGRSPSY AS |
| 77 | G-FGF21 A59C, G71C | GHPIPDSSPL LQFGGQVRQR YLYTDDAQQT ECHLEIREDG TVGCAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 78 | G-FGF21 H60C, A72C | GHPIPDSSPL LQFGGQVRQR YLYTDDAQQT EACLEIREDG TVGGCADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 79 | G-FGF21 I63C, G112C | GHPIPDSSPL LQFGGQVRQR YLYTDDAQQT EAHLECREDG TVGGAADQSP ESLLQLKALK PGVIQILGVK TSRFLCQRPD GALYCSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 80 | G-FGF21 L49C, L170C | GHPIPDSSPL LQFGGQVRQR YCYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGCPPAPPEP PGILAPQPPD VGSSDPLSMV GPSQGRSPSY AS |
| 81 | G-FGF21 T51C, L167C | GHPIPDSSPL LQFGGQVRQR YLYCDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPC PGLPPAPPEP PGILAPQPPD VGSSDPLSMV GPSQGRSPSY AS |
| 82 | G-FGF21 H140C, L142C | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EACGCPLHLP GNKSPHRDPA PRGPARFLPL PGLPPAPPEP PGILAPQPPD VGSSDPLSMV GPSQGRSPSY AS |
| 83 | G-FGF21 D130C, Y132C | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LECGCNVYQS EAHGLPLHLP GNKSPHRDPA PRGPARFLPL PGLPPAPPEP PGILAPQPPD VGSSDPLSMV GPSQGRSPSY AS |
| 84 | G-FGF21 S137C, H140C | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQC EACGLPLHLPGNKSPHRDPAP RGPARFLPLP GLPPAPPEPP GILAPQPPDV GSSDPLSMVG PSQGRSPSYA S |
| 85 | G-FGF21 S76C, S79C | GHPIPDSSPL LQFGGQVRQR YLYTDDAQQT EAHLEIREDG TVGGAADQCP ECLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |

TABLE 7-continued

List of Sequences.

| SEQ ID NO | Description | Sequence |
|---|---|---|
| 86 | G-FGF21 G108C, L142C | GHPIPDSSPL LQFGGQVRQR YLYTDDAQQT EAHLEIREDG TVGGAADQSP ESLLQLKALK PGVIQILGVK TSRFLCQRPD CALYGSLHFD PEACSFRELL LEDGYNVYQS EAHGCPLHLP GNKSPHRDPA PRGPARFLPL PGLPPAPPEP PGILAPQPPD VGSSDPLSMV GPSQGRSPSY AS |
| 87 | G-FGF21 A72C, S79C | GHPIPDSSPL LQFGGQVRQR YLYTDDAQQT EAHLEIREDG TVGGCADQSP ECLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 88 | G-FGF21 H60C, S79C, H145C, L165C | GHPIPDSSPL LQFGGQVRQR YLYTDDAQQT EACLEIREDG TVGGAADQSP ECLLQLKALK PGVIQILGVK TSRFLCQRPD GALYGSLHFD PEACSFRELL LEDGYNVYQS EAHGLPLCLP GNKSPHRDPA PRGPARFCPL PGLPPAPPEP PGILAPQPPD VGSSDPLSMV GPSQGRSPSY AS |
| 89 | G-FGF21 A72C, S79C, G108C, L142C | GHPIPDSSPL LQFGGQVRQR YLYTDDAQQT EAHLEIREDG TVGGCADQSP ECLLQLKALK PGVIQILGVK TSRFLCQRPD CALYGSLHFD PEACSFRELL LEDGYNVYQS EAHGCPLHLP GNKSPHRDPA PRGPARFLPL PGLPPAPPEP PGILAPQPPD VGSSDPLSMV GPSQGRSPSY AS |
| 90 | G-FGF21 R47C, P174C | GHPIPDSSPL LQFGGQVRQC YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPACPEP PGILAPQPPD VGSSDPLSMV GPSQGRSPSY AS |
| 91 | G-FGF21 M196C, R203C | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSCV GPSQGCSPSY AS |
| 92 | G-FGF21 D107C, D155C | GHPIPDSSPL LQFGGQVRQR YLYTDDAQQT EAHLEIREDG TVGGAADQSP ESLLQLKALK PGVIQILGVK TSRFLCQRPC GALYGSLHFD PEACSFRELL LEDGYNVYQS EAHGLPLHLP GNKSPHRCPA PRGPARFLPL PGLPPAPPEP PGILAPQPPD VGSSDPLSMV GPSQGRSPSY AS |
| 93 | G-FGF21 Q55C, G148C | GHPIPDSSPL LQFGGQVRQR YLYTDDACQT EAHLEIREDG TVGGAADQSP ESLLQLKALK PGVIQILGVK TSRFLCQRPD GALYGSLHFD PEACSFRELL LEDGYNVYQS EAHGLPLHLP CNKSPHRDPA PRGPARFLPL PGLPPAPPEP PGILAPQPPD VGSSDPLSMV GPSQGRSPSY AS |
| 94 | G-FGF21 Q55C, G148C, N149-R159 deleted and replaced by GSGS (SEQ ID NO: 161) | GHPIPDSSPL LQFGGQVRQR YLYTDDACQT EAHLEIREDG TVGGAADQSP ESLLQLKALK PGVIQILGVK TSRFLCQRPD GALYGSLHFD PEACSFRELL LEDGYNVYQS EAHGLPLHLP CGSGSGPARF LPLPGLPPAP PEPPGILAPQ PPDVGSSDPL SMVGPSQGRS PSYAS |
| 95 | G-FGF21 Q55C, G148C, N149-R159 deleted and replaced by GGSGGS (SEQ ID NO: 162) | GHPIPDSSPL LQFGGQVRQR YLYTDDACQT EAHLEIREDG TVGGAADQSP ESLLQLKALK PGVIQILGVK TSRFLCQRPD GALYGSLHFD PEACSFRELL LEDGYNVYQS EAHGLPLHLP CGGSGGSGPA RFLPLPGLPP APPEPPGILA PQPPDVGSSD PLSMVGPSQG RSPSYAS |
| 96 | G-FGF21 Q55G, Q56C, L146C | GHPIPDSSPL LQFGGQVRQR YLYTDDAGCT EAHLEIREDG TVGGAADQSP ESLLQLKALK PGVIQILGVK TSRFLCQRPD GALYGSLHFD PEACSFRELL LEDGYNVYQS EAHGLPLHCP GNKSPHRDPA PRGPARFLPL PGLPPAPPEP PGILAPQPPD VGSSDPLSMV GPSQGRSPSY AS |
| 97 | G-FGF21 Q55G, Q56C, L146C, P147-R159 deleted and replaced by GSGS (SEQ ID NO: 161) | GHPIPDSSPL LQFGGQVRQR YLYTDDAGCT EAHLEIREDG TVGGAADQSP ESLLQLKALK PGVIQILGVK TSRFLCQRPD GALYGSLHFD PEACSFRELL LEDGYNVYQS EAHGLPLHCG SGSGPARFLP LPGLPPAPPE PPGILAPQPP DVGSSDPLSM VGPSQGRSPS YAS |
| 98 | G-FGF21 Q55G, Q56C, L146C, | GHPIPDSSPL LQFGGQVRQR YLYTDDAGCT EAHLEIREDG TVGGAADQSP ESLLQLKALK PGVIQILGVK TSRFLCQRPD GALYGSLHFD PEACSFRELL |

TABLE 7-continued

List of Sequences.

| SEQ ID NO | Description | Sequence |
|---|---|---|
| | P147-R159 deleted and replaced by GGSGGS (SEQ ID NO: 162) | LEDGYNVYQS EAHGLPLHCG GSGGSGPARF LPLPGLPPAP PEPPGILAPQ PPDVGSSDPL SMVGPSQGRS PSYAS |
| 99 | G-FGF21 Q55C, P147C | GHPIPDSSPL LQFGGQVRQR YLYTDDACQT EAHLEIREDG TVGGAADQSP ESLLQLKALK PGVIQILGVK TSRFLCQRPD GALYGSLHFD PEACSFRELL LEDGYNVYQS EAHGLPLHLC GNKSPHRDPA PRGPARFLPL PGLPPAPPEP PGILAPQPPD VGSSDPLSMV GPSQGRSPSY AS |
| 100 | G-FGF21 Q55C, N149C | GHPIPDSSPL LQFGGQVRQR YLYTDDACQT EAHLEIREDG TVGGAADQSP ESLLQLKALK PGVIQILGVK TSRFLCQRPD GALYGSLHFD PEACSFRELL LEDGYNVYQS EAHGLPLHLP GCKSPHRDPA PRGPARFLPL PGLPPAPPEP PGILAPQPPD VGSSDPLSMV GPSQGRSPSY AS |
| 101 | G-FGF21 E62C, E78C | GHPIPDSSPL LQFGGQVRQR YLYTDDAQQT EAHLCIREDG TVGGAADQSP CSLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 102 | G-FGF21 E62C, S79C | GHPIPDSSPL LQFGGQVRQR YLYTDDAQQT EAHLCIREDG TVGGAADQSP ECLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 103 | G-FGF21 R100C, L114C | GHPIPDSSPL LQFGGQVRQR YLYTDDAQQT EAHLEIREDG TVGGAADQSP ESLLQLKALK PGVIQILGVK TSCFLCQRPD GALYGSCHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 104 | G-FGF21 L102C, G112C | GHPIPDSSPL LQFGGQVRQR YLYTDDAQQT EAHLEIREDG TVGGAADQSP ESLLQLKALK PGVIQILGVK TSRFCCQRPD GALYCSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 105 | G-FGF21 A59C, A73C | GHPIPDSSPL LQFGGQVRQR YLYTDDAQQT ECHLEIREDG TVGGACDQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 106 | G-FGF21 E62C, A72C | GHPIPDSSPL LQFGGQVRQR YLYTDDAQQT EAHLCIREDG TVGGCADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 107 | G-FGF21 Q104C, S137C | GHPIPDSSPL LQFGGQVRQR YLYTDDAQQT EAHLEIREDG TVGGAADQSP ESLLQLKALK PGVIQILGVK TSRFLCCRPD GALYGSLHFD PEACSFRELL LEDGYNVYQC EAHGLPLHLP GNKSPHRDPA PRGPARFLPL PGLPPAPPEP PGILAPQPPD VGSSDPLSMV GPSQGRSPSY AS |
| 108 | G-FGF21 Q104C, H140C | GHPIPDSSPL LQFGGQVRQR YLYTDDAQQT EAHLEIREDG TVGGAADQSP ESLLQLKALK PGVIQILGVK TSRFLCCRPD GALYGSLHFD PEACSFRELL LEDGYNVYQS EACGLPLHLP GNKSPHRDPA PRGPARFLPL PGLPPAPPEP PGILAPQPPD VGSSDPLSMV GPSQGRSPSY AS |
| 109 | G-FGF21 A54C, P161C | GHPIPDSSPL LQFGGQVRQR YLYTDCQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGCARFLPL PGLPPAPPEP PGILAPQPPD VGSSDPLSMV GPSQGRSPSY AS |
| 110 | G-FGF21 56C, L146C | GHPIPDSSPL LQFGGQVRQR YLYTDDACQT EAHLEIREDG TVGGAADQSP ESLLQLKALK PGVIQILGVK TSRFLCQRPD GALYGSLHFD PEACSFRELL LEDGYNVYQS EAHGLPCHLP GNKSPHRDPA PRGPARFLPL PGLPPAPPEP PGILAPQPPD VGSSDPLSMV GPSQGRSPSY AS |
| 111 | G-FGF21 I63C, T98C | GHPIPDSSPL LQFGGQVRQR YLYTDDAQQT EAHLECREDG TVGGAADQSP ESLLQLKALK PGVIQILGVK CSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 112 | G-FGF21 G67C, R100C | GHPIPDSSPL LQFGGQVRQR YLYTDDAQQT EAHLEIREDC TVGGAADQSP ESLLQLKALK PGVIQILGVK TSCFLCQRPD GALYGSLHFD PEACSFRELL |

TABLE 7-continued

List of Sequences.

| SEQ ID NO | Description | Sequence |
|---|---|---|
| | | LEDGYNVYQS EAHGLPLHLP GNKSPHRDPA PRGPARFLPL PGLPPAPPEP PGILAPQPPD VGSSDPLSMV GPSQGRSPSY AS |
| 113 | G-FGF21 V69C, L110C | GHPIPDSSPL LQFGGQVRQR YLYTDDAQQT EAHLEIREDG TCGGAADQSP ESLLQLKALK PGVIQILGVK TSRFLCQRPD GACYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 114 | G-FGF21 A120C, A139C | GHPIPDSSPL LQFGGQVRQR YLYTDDAQQT EAHLEIREDG TVGGAADQSP ESLLQLKALK PGVIQILGVK TSRFLCQRPD GALYGSLHFD PECCSFRELL LEDGYNVYQS ECHGLPLHLP GNKSPHRDPA PRGPARFLPL PGLPPAPPEP PGILAPQPPD VGSSDPLSMV GPSQGRSPSY AS |
| 115 | G-FGF21 R124C, Q136C | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFCELL LEDGYNVYCS EAHGLPLHLP GNKSPHRDPA PRGPARFLPL PGLPPAPPEP PGILAPQPPD VGSSDPLSMV GPSQGRSPSY AS |
| 116 | G-FGF21 P143C, A162C | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLCLHLP GNKSPHRDPA PRGPCRFLPL PGLPPAPPEP PGILAPQPPD VGSSDPLSMV GPSQGRSPSY AS |
| 117 | G-FGF21 P77C, K97C | GHPIPDSSPL LQFGGQVRQR YLYTDDAQQT EAHLEIREDG TVGGAADQSC ESLLQLKALK PGVIQILGVC TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 118 | G-FGF21 E78C, T98C | GHPIPDSSPL LQFGGQVRQR YLYTDDAQQT EAHLEIREDG TVGGAADQSP CSLLQLKALK PGVIQILGVK CSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 119 | G-FGF21 L80C, V96C | GHPIPDSSPL LQFGGQVRQR YLYTDDAQQT EAHLEIREDG TVGGAADQSP ESCLQLKALK PGVIQILGCK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 120 | G-FGF21 H145C, P161C | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLCLP GNKSPHRDPA PRGCARFLPL PGLPPAPPEP PGILAPQPPD VGSSDPLSMV GPSQGRSPSY AS |
| 121 | G-FGF21 L81C, G95C | GHPIPDSSPL LQFGGQVRQR YLYTDDAQQT EAHLEIREDG TVGGAADQSP ESLCQLKALK PGVIQILCVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 122 | G-FGF21 Q82C, L94C | GHPIPDSSPL LQFGGQVRQR YLYTDDAQQT EAHLEIREDG TVGGAADQSP ESLLCLKALK PGVIQICGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 123 | G-FGF21 L83C, I91C | GHPIPDSSPL LQFGGQVRQR YLYTDDAQQT EAHLEIREDG TVGGAADQSP ESLLQCKALK PGVCQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY AS |
| 124 | G-FGF21 D155L | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRLPA PRGPARFLPL PGLPPAPPEP PGILAPQPPD VGSSDPLSMV GPSQGRSPSY AS |
| 125 | G-FGF21 D155K | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRKPA PRGPARFLPL PGLPPAPPEP PGILAPQPPD VGSSDPLSMV GPSQGRSPSY AS |
| 126 | G-FGF21 D155Y | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRYPA PRGPARFLPL PGLPPAPPEP PGILAPQPPD VGSSDPLSMV GPSQGRSPSY AS |
| 127 | G-FGF21 D155P | GHPIPDSSPL LQFGGQVRQR YLYTDDAQQT EAHLEIREDG TVGGAADQSP |

TABLE 7-continued

List of Sequences.

| SEQ ID NO | Description | Sequence |
|---|---|---|
| | | ESLLQLKALK PGVIQILGVK TSRFLCQRPD GALYGSLHFD PEACSFRELL<br>LEDGYNVYQS EAHGLPLHLP GNKSPHRPPA PRGPARFLPL PGLPPAPPEP<br>PGILAPQPPD VGSSDPLSMV GPSQGRSPSY AS |
| 128 | G-FGF21 D155E | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GNKSPHREPA PRGPARFLPL PGLPPAPPEP<br>PGILAPQPPD VGSSDPLSMV GPSQGRSPSY AS |
| 129 | G-FGF21 D155N | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GNKSPHRNPA PRGPARFLPL PGLPPAPPEP<br>PGILAPQPPD VGSSDPLSMV GPSQGRSPSY AS |
| 130 | G-FGF21 R154Q, D155L | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GNKSPHQLPA PRGPARFLPL PGLPPAPPEP<br>PGILAPQPPD VGSSDPLSMV GPSQGRSPSY AS |
| 131 | G-FGF21 R154Q, D155K | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GNKSPHQKPA PRGPARFLPL PGLPPAPPEP<br>PGILAPQPPD VGSSDPLSMV GPSQGRSPSY AS |
| 132 | G-FGF21 H153Q, R154Q, D155N, A157V, R159K | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GNKSPQQNPV PKGPARFLPL PGLPPAPPEP<br>PGILAPQPPD VGSSDPLSMV GPSQGRSPSYAS |
| 133 | G-FGF21 P152A, H153K, R154K, D155E, P156A, A157S, R159Q | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GNKSAKKEAS PQGPARFLPL PGLPPAPPEP<br>PGILAPQPPD VGSSDPLSMV GPSQGRSPSY AS |
| 134 | G-FGF21 H153Y, R154K D155N, P156K, A157G | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GNKSPYKNKG PRGPARFLPL PGLPPAPPEP<br>PGILAPQPPD VGSSDPLSMV GPSQGRSPSY AS |
| 135 | G-FGF21 P152-H153 deleted | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GNKSRDPAPR GPARFLPLPG LPPAPPEPPG<br>ILAPQPPDVG SSDPLSMVGP SQGRSPSYAS |
| 136 | G-FGF21 N149-R163 deleted and replaced by GSGS (SEQ ID NO: 161) | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GGSGSFLPLP GLPPAPPEPP GILAPQPPDV<br>GSSDPLSMVG PSQGRSPSYA S |
| 137 | G-FGF21 N149-A162 deleted and replaced by GSHSG (SEQ ID NO: 163) | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GGSHSGRFLP LPGLPPAPPE PPGILAPQPP<br>DVGSSDPLSM VGPSQGRSPS YAS |
| 138 | G-FGF21 N149-A162 deleted and replaced by GSHSGS (SEQ ID NO: 165) | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GGSHSGSRFL PLPGLPPAPP EPPGILAPQP<br>PDVGSSDPLS MVGPSQGRSP SYAS |
| 139 | G-FGF21 K150H | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GNHSPHRDPA PRGPARFLPL PGLPPAPPEP<br>PGILAPQPPD VGSSDPLSMV GPSQGRSPSY AS |
| 140 | G-FGF21 K150H, P152L | GHPIPDSSPL LQFGGQVRQR YLYTDDAQQT EAHLEIREDG TVGGAADQSP<br>ESLLQLKALK PGVIQILGVK TSRFLCQRPD GALYGSLHFD PEACSFRELL<br>LEDGYNVYQS EAHGLPLHLP GNHSLHRDPA PRGPARFLPL PGLPPAPPEP<br>PGILAPQPPD VGSSDPLSMV GPSQGRSPSY AS |

TABLE 7-continued

List of Sequences.

| SEQ ID NO | Description | Sequence |
|---|---|---|
| 141 | G-FGF21 R163H | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPAHFLPL PGLPPAPPEP PGILAPQPPD VGSSDPLSMV GPSQGRSPSY AS |
| 142 | G-FGF21 P158H, R159H | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA HHGPARFLPL PGLPPAPPEP PGILAPQPPD VGSSDPLSMV GPSQGRSPSY AS |
| 143 | G-FGF21 N149-D155 deleted and replaced by GSGS (SEQ ID NO: 161) | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GGSGSPAPRG PARFLPLPGL PPAPPEPPGI LAPQPPDVGS SDPLSMVGPS QGRSPSYAS |
| 144 | G-FGF21 N149-D155 deleted and replaced by GSHSG (SEQ ID NO: 163) | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GGSHSGPAPR GPARFLPLPG LPPAPPEPP GILAPQPPDVG SSDPLSMVG PSQGRSPSY AS |
| 145 | G-FGF21 N149-D155 deleted and replaced by ATTS (SEQ ID NO: 164) | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GATTSPAPRG PARFLPLPGL PPAPPEPPGI LAPQPPDVGS SDPLSMVGPS QGRSPSYAS |
| 146 | G-FGF21 R159-R163 deleted and replaced by GA | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PGAFLPLPGL PPAPPEPPGI LAPQPPDVGS SDPLSMVGPS QGRSPSYAS |
| 147 | G-FGF21 R159-R163 deleted and replaced by GY | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PGYFLPLPGL PPAPPEPPGI LAPQPPDVGS SDPLSMVGPS QGRSPSYAS |
| 148 | G-FGF21 R159-R163 deleted and replaced by HH | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PHHFLPLPGL PPAPPEPPGI LAPQPPDVGS SDPLSMVGPS QGRSPSYAS |
| 149 | G-FGF21 R159-R163 deleted and replaced by GE | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPAPGEFLPLPGLPPAPPEPPGILA PQPPDVGSSD PLSMVGPSQG RSPSYAS |
| 150 | G-FGF21 R159-R163 deleted and replaced by HE | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PHEFLPLPGL PPAPPEPPGI LAPQPPDVGS SDPLSMVGPS QGRSPSYAS |
| 151 | G-FGF21 A162Y | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPYRFLPL PGLPPAPPEP PGILAPQPPD VGSSDPLSMV GPSQGRSPSY AS |
| 152 | G-FGF21 R159H | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PHGPARFLPL PGLPPAPPEP PGILAPQPPD VGSSDPLSMV GPSQGRSPSY AS |
| 153 | G-FGF21 S200M | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPMQGRSPSY AS |
| 154 | G-FGF21 G202T | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQTRSPSY AS |

TABLE 7-continued

List of Sequences.

| SEQ ID NO | Description | Sequence |
|---|---|---|
| 155 | G-FGF21 R203E | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGESPSY AS |
| 156 | G-FGF21 R203H | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGHSPSY AS |
| 157 | G-FGF21 G202-R203 deleted | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQSPSYAS |
| 158 | FGF21 (S34-E176), Q55C, N149C | SSPLLQFGGQ VRQRYLYTDD ACQTEAHLEI REDGTVGGAA DQSPESLLQL KALKPGVIQI LGVKTSRFLC QRPDGALYGS LHFDPEACSF RELLLEDGYN VYQSEAHGLP LHLPGCKSPH RDPAPRGPAR FLPLPGLPPA PPE |
| 159 | G-FGF21 PLSMVGPSQG RSPSYAS (SEQ ID NO: 169) inserted after S209 | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY ASPLSMVGPS QGRSPSYAS |
| 160 | G-FGF21 P199 deleted, PLSMVGSQGR SPSYAS (SEQ ID NO: 170) inserted after S209 | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPAPPEP PGILAPQPPD VGSSDPLSMV GPSQGRSPSY ASPLSMVGSQ GRSPSYAS |
| 161 | Linker | GSGS |
| 162 | linker | GGSGGS |
| 163 | linker | GSHSG |
| 164 | linker | ATTS |
| 165 | linker | GSHSGS |
| 166 | linker | GHRSHLQTVF |
| 167 | linker | GLNSMV |
| 168 | linker | GGGGS |
| 169 | C-terminal extension | PLSMVGPSQG RSPSYAS |
| 170 | C-terminal extension | PLSMVGSQGR SPSYAS |
| 171 | FGF21 variant, consensus sequence1 | MDSDETGFEH SGLWVSVLAG LLLGACQAHP IPDSSPLLQF GGQVRQRYLY TDDAX$^{55}$QTEAH LEIREDGTVG GAADQSPESL LQLKALKPGV IQILGVKTSR FLCQRPDGAL YGSLHFDPEA CSFRELLLED GYNVYQSEAH GLPLHLX$^{147}$X$^{148}$X$^{149}$X$^{150}$X$^{151}$X$^{152}$X$^{153}$X$^{154}$X$^{155}$X$^{156}$X$^{157}$X$^{158}$X$^{159}$X$^{160}$X$^{161}$X$^{162}$X$^{163}$FLPLPGL PPAPPEPPGI LAPX$^{184}$X$^{185}$X$^{186}$X$^{187}$X$^{188}$X$^{189}$X$^{190}$X$^{191}$X$^{192}$X$^{193}$X$^{194}$X$^{195}$X$^{196}$X$^{197}$X$^{198}$X$^{199}$X$^{200}$ X$^{201}$X$^{202}$X$^{203}$X$^{204}$X$^{205}$X$^{206}$X$^{207}$AS |
| 172 | FGF21 S141, natural variant | MDSDETGFEH SGLWVSVLAG LLLGACQAHP IPDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH SLPLHLPGNK SPHRDPAPRG PARFLPLPGL PPAPPEPPGI LAPQPPDVGS SDPLSMVGPS QGRSPSYAS |
| 173 | FGF21 L174 natural variant | MDSDETGFEH SGLWVSVLAG LLLGACQAHP IPDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH GLPLHLPGNK SPHRDPAPRG PARFLPLPGL PPALPEPPGI LAPQPPDVGS SDPLSMVGPS QGRSPSYAS |

TABLE 7-continued

List of Sequences.

| SEQ ID NO | Description | Sequence |
|---|---|---|
| 174 | mature human wild-type FGF21 variant L174 with additional N-terminal G (G-FGF21) | GHPIPDSSPL LQFGGQVRQR YLYTDDAQQT EAHLEIREDG TVGGAADQSP ESLLQLKALK PGVIQILGVK TSRFLCQRPD GALYGSLHFD PEACSFRELL LEDGYNVYQS EAHGLPLHLP GNKSPHRDPA PRGPARFLPL PGLPPALPEP PGILAPQPPD VGSSDPLSMV GPSQGRSPSY AS |
| 175 | FGF21 variant, consensus sequence II | HPIPDSSPLL QFGGQVRQRY LYTDDAX$^{55}$QTE AHLEIREDGT VGGAADQSPE SLLQLKALKP GVIQILGVKT SRFLCQRPDG ALYGSLHFDP EACSFRELLL EDGYNVYQSE AHGLPLHLX$^{147}$X$^{148}$ X$^{149}$KSPHRX$^{155}$PAP RGX$^{161}$X$^{162}$RFLPLP GLPPAPPEPP GILAPQPPDV GSSDPLX$^{195}$X$^{196}$X$^{197}$X$^{198}$ X$^{199}$X$^{200}$X$^{201}$X$^{202}$X$^{203}$SPSYA S |
| 176 | FGF21 variant, consensus sequence III | HPIPDSSPLL QFGGQVRQRY LYTDDAX$^{55}$QTE AHLEIREDGT VGGAADQSPE SLLQLKALKP GVIQILGVKT SRFLCQRPDG ALYGSLHFDP EACSFRELLL EDGYNVYQSE AHGLPLHLX$^{147}$G X$^{149}$KSPHRX$^{155}$PAP RGPARFLPLP GLPPAPPEPP GILAPQPPDV GSSDPLSMVX$^{198}$ X$^{199}$SQGRSPSYA S |
| 177 | FGF21 S195C, S200C | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLCMVG PCQGRSPSYA S |
| 178 | FGF21 P199S, S200P | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG SPQGRSPSYA S |
| 179 | FGF21 P199Q, Q201P | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG QSPGRSPSYA S |
| 180 | FGF21 P199 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG SQGRSPSYAS |
| 181 | FGF21 M196P, V197G, G198V, P199M | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSPGV MSQGRSPSYA S |
| 182 | FGF21 M196V, V197M | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSVMG PSQGRSPSYA S |
| 183 | FGF21 V197E | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMEG PSQGRSPSYA S |
| 184 | FGF21 GGGGS (SEQ ID NO: 168) inserted between G198 and P199 | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG GGGGSPSQGR SPSYAS |
| 185 | FGF21 G198E | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVE PSQGRSPSYA S |
| 186 | FGF21 G198D | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVD PSQGRSPSYA S |
| 187 | FGF21 G198R | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVR PSQGRSPSYA S |

TABLE 7-continued

List of Sequences.

| SEQ ID NO | Description | Sequence |
|---|---|---|
| 188 | FGF21 G198K | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVK PSQGRSPSYA S |
| 189 | FGF21 G198Y | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVY PSQGRSPSYA S |
| 190 | FGF21 P199G | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVG GSQGRSPSYA S |
| 191 | FGF21 P199R | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVG RSQGRSPSYA S |
| 192 | FGF21 P199T | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVG TSQGRSPSYA S |
| 193 | FGF21 G198P, P199G | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVP GSQGRSPSYA S |
| 194 | FGF21 S200Q, Q201S | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVG PQSGRSPSYA S |
| 195 | FGF21 V197D, G198V, P199D, S200H | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMDV DHQGRSPSYA S |
| 196 | FGF21 V197-R203 deleted and replaced by GHRSHLQTVF (SEQ ID NO: 166) | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMGH RSHLQTVFSP SYAS |
| 197 | FGF21 V197-R203 deleted and replaced by GLNSMV (SEQ ID NO: 167) | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMGL NSMVSPSYAS |
| 198 | FGF21 G198 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVP SQGRSPSYAS |
| 199 | FGF21 G198-P199 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVS QGRSPSYAS |
| 200 | FGF21 G198 deleted, P199F | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVF SQGRSPSYAS |
| 201 | FGF21 G198 deleted, P199L | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL |

TABLE 7-continued

List of Sequences.

| SEQ ID NO | Description | Sequence |
|---|---|---|
| | | EDGYNVYQSE AHGLPLHLPG NKSPHRDPAP RGPARFLPLP GLPPAPPEPP GILAPQPPDV GSSDPLSMVL SQGRSPSYAS |
| 202 | FGF21 G198 deleted P199L, S200N | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVL NQGRSPSYAS |
| 203 | FGF21 V197 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMGP SQGRSPSYAS |
| 204 | FGF21 L146C, A162C | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHCPG NKSPHRDPAP RGPCRFLPLP GLPPAPPEPP GILAPQPPDV GSSDPLSMVG PSQGRSPSYA S |
| 205 | FGF21 A59C, G71C, P199 deleted | HPIPDSSPLL QFGGQVRQRY LYTDDAQQTE CHLEIREDGT VGCAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG SQGRSPSYAS |
| 206 | FGF21 A59C, G710, G198Y | HPIPDSSPLL QFGGQVRQRY LYTDDAQQTE CHLEIREDGT VGCAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVY PSQGRSPSYA S |
| 207 | FGF21 S76C, S79C, P199 deleted | HPIPDSSPLL QFGGQVRQRY LYTDDAQQTE AHLEIREDGT VGGAADQCPE CLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG SQGRSPSYAS |
| 208 | FGF21 S76C, S79C, G198Y | HPIPDSSPLL QFGGQVRQRY LYTDDAQQTE AHLEIREDGT VGGAADQCPE CLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVY PSQGRSPSYA S |
| 209 | FGF21 G108C, L142C, P199 deleted | HPIPDSSPLL QFGGQVRQRY LYTDDAQQTE AHLEIREDGT VGGAADQSPE SLLQLKALKP GVIQILGVKT SRFLCQRPDC ALYGSLHFDP EACSFRELLL EDGYNVYQSE AHGCPLHLPG NKSPHRDPAP RGPARFLPLP GLPPAPPEPP GILAPQPPDV GSSDPLSMVG SQGRSPSYAS |
| 210 | FGF21 G108C, L142C, G198Y | HPIPDSSPLL QFGGQVRQRY LYTDDAQQTE AHLEIREDGT VGGAADQSPE SLLQLKALKP GVIQILGVKT SRFLCQRPDC ALYGSLHFDP EACSFRELLL EDGYNVYQSE AHGCPLHLPG NKSPHRDPAP RGPARFLPLP GLPPAPPEPP GILAPQPPDV GSSDPLSMVY PSQGRSPSYA S |
| 211 | FGF21 D107C, D155C, P199 deleted | HPIPDSSPLL QFGGQVRQRY LYTDDAQQTE AHLEIREDGT VGGAADQSPE SLLQLKALKP GVIQILGVKT SRFLCQRPCG ALYGSLHFDP EACSFRELLL EDGYNVYQSE AHGLPLHLPG NKSPHRCPAP RGPARFLPLP GLPPAPPEPP GILAPQPPDV GSSDPLSMVG SQGRSPSYAS |
| 212 | FGF21 D107C, D155C, G198Y | HPIPDSSPLL QFGGQVRQRY LYTDDAQQTE AHLEIREDGT VGGAADQSPE SLLQLKALKP GVIQILGVKT SRFLCQRPCG ALYGSLHFDP EACSFRELLL EDGYNVYQSE AHGLPLHLPG NKSPHRCPAP RGPARFLPLP GLPPAPPEPP GILAPQPPDV GSSDPLSMVY PSQGRSPSYA S |
| 213 | FGF21 Q55C, P147C, P199 deleted | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLCG NKSPHRDPAP RGPARFLPLP GLPPAPPEPP GILAPQPPDV GSSDPLSMVG SQGRSPSYAS |
| 214 | FGF21 Q55C, P147C, G198Y | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLCG NKSPHRDPAP RGPARFLPLP GLPPAPPEPP GILAPQPPDV GSSDPLSMVY PSQGRSPSYA S |
| 215 | FGF21 Q55C, N149C, P199 deleted | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLPG CKSPHRDPAP RGPARFLPLP GLPPAPPEPP GILAPQPPDV GSSDPLSMVG SQGRSPSYAS |

TABLE 7-continued

List of Sequences.

| SEQ ID NO | Description | Sequence |
|---|---|---|
| 216 | FGF21 Q55C, N14 9C, G198Y | HPIPDSSPLL QFGGQVRQRY LYTDDACQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG CKSPHRDPAP RGPARFLPLP GLPPAPPEPP<br>GILAPQPPDV GSSDPLSMVY PSQGRSPSYA        S |
| 217 | FGF21 M196 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSVGP SQGRSPSYAS |
| 218 | FGF21 S195 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLMVGP SQGRSPSYAS |
| 219 | FGF21 L194 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPSMVGP SQGRSPSYAS |
| 220 | FGF21 P193 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDLSMVGP SQGRSPSYAS |
| 221 | FGF21 D192 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSPLSMVGP SQGRSPSYAS |
| 222 | FGF21 S191 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSDPLSMVGP SQGRSPSYAS |
| 223 | FGF21 S190-S191 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GDPLSMVGPS QGRSPSYAS |
| 224 | FGF21 G189 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV SSDPLSMVGP SQGRSPSYAS |
| 225 | FGF21 V188 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDG SSDPLSMVGP SQGRSPSYAS |
| 226 | FGF21 D187 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPVG SSDPLSMVGP SQGRSPSYAS |
| 227 | FGF21 P186 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPDVG SSDPLSMVGP SQGRSPSYAS |
| 228 | FGF21 P185-P186 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQDVGS SDPLSMVGPS QGRSPSYAS |
| 229 | FGF21 Q184 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPPPDVG SSDPLSMVGP SQGRSPSYAS |
| 230 | FGF21 S200 deleted | HPIPDSSPLL QFGGQVRQRY LYTDDAQQTE AHLEIREDGT VGGAADQSPE<br>SLLQLKALKP GVIQILGVKT SRFLCQRPDG ALYGSLHFDP EACSFRELLL<br>EDGYNVYQSE AHGLPLHLPG NKSPHRDPAP RGPARFLPLP GLPPAPPEPP<br>GILAPQPPDV GSSDPLSMVG PQGRSPSYAS |

TABLE 7-continued

List of Sequences.

| SEQ ID NO | Description | Sequence |
|---|---|---|
| 231 | FGF21 Q201 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSGRSPSYAS |
| 232 | FGF21 G202 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQRSPSYAS |
| 233 | FGF21 R203 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGSPSYAS |
| 234 | FGF21 S204 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRPSYAS |
| 235 | FGF21 P205 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSSYAS |
| 236 | FGF21 S206 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPYAS |
| 237 | FGF21 Y207 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSAS |
| 238 | FGF21 V197 deleted, S201 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMGP QGRSPSYAS |
| 239 | FGF21 M196 deleted S201 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSVGP QGRSPSYAS |
| 240 | FGF21 M196-V197 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSGPS QGRSPSYAS |
| 241 | FGF21 V197-G198 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMPS QGRSPSYAS |
| 242 | FGF21 S195-M196 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLVGPS QGRSPSYAS |
| 243 | FGF21 G198 deleted, S200 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVP QGRSPSYAS |
| 244 | FGF21 H60C, S79C | HPIPDSSPLL QFGGQVRQRY LYTDDAQQTE ACLEIREDGT VGGAADQSPE CLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 245 | FGF21 H145C, L165C | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL |

TABLE 7-continued

List of Sequences.

| SEQ ID NO | Description | Sequence |
|---|---|---|
| | | EDGYNVYQSE AHGLPLCLPG NKSPHRDPAP RGPARFCPLP GLPPAPPEPP GILAPQPPDV GSSDPLSMVG PSQGRSPSYA S |
| 246 | FGF21 A59C, G71C | HPIPDSSPLL QFGGQVRQRY LYTDDAQQTE CHLEIREDGT VGCAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 247 | FGF21 H60C, A72C | HPIPDSSPLL QFGGQVRQRY LYTDDAQQTE ACLEIREDGT VGGCADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 248 | FGF21 I63C, G112C | HPIPDSSPLL QFGGQVRQRY LYTDDAQQTE AHLECREDGT VGGAADQSPE SLLQLKALKP GVIQILGVKT SRFLCQRPDG ALYCSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 249 | FGF21 L49C, L170C | HPIPDSSPLL QFGGQVRQRY CYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GCPPAPPEPP GILAPQPPDV GSSDPLSMVG PSQGRSPSYA S |
| 250 | FGF21 T51C, L167C | HPIPDSSPLL QFGGQVRQRY LYCDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPCP GLPPAPPEPP GILAPQPPDV GSSDPLSMVG PSQGRSPSYA S |
| 251 | FGF21 H140C, L142C | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE ACGCPLHLPG NKSPHRDPAP RGPARFLPLP GLPPAPPEPP GILAPQPPDV GSSDPLSMVG PSQGRSPSYA S |
| 252 | FGF21 D130C, Y132C | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL ECGCNVYQSE AHGLPLHLPG NKSPHRDPAP RGPARFLPLP GLPPAPPEPP GILAPQPPDV GSSDPLSMVG PSQGRSPSYA S |
| 253 | FGF21 S137C, H140C | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQCE ACGLPLHLPG NKSPHRDPAP RGPARFLPLP GLPPAPPEPP GILAPQPPDV GSSDPLSMVG PSQGRSPSYA S |
| 254 | FGF21 S76C, S79C | HPIPDSSPLL QFGGQVRQRY LYTDDAQQTE AHLEIREDGT VGGAADQCPE CLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 255 | FGF21 G108C, L142C | HPIPDSSPLL QFGGQVRQRY LYTDDAQQTE AHLEIREDGT VGGAADQSPE SLLQLKALKP GVIQILGVKT SRFLCQRPDC ALYGSLHFDP EACSFRELLL EDGYNVYQSE AHGCPLHLPG NKSPHRDPAP RGPARFLPLP GLPPAPPEPP GILAPQPPDV GSSDPLSMVG PSQGRSPSYA S |
| 256 | FGF21 A72C, S79C | HPIPDSSPLL QFGGQVRQRY LYTDDAQQTE AHLEIREDGT VGGCADQSPE CLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 257 | FGF21 H60C, S79C, H145C, L165C | HPIPDSSPLL QFGGQVRQRY LYTDDAQQTE ACLEIREDGT VGGAADQSPE CLLQLKALKP GVIQILGVKT SRFLCQRPDG ALYGSLHFDP EACSFRELLL EDGYNVYQSE AHGLPLCLPG NKSPHRDPAP RGPARFCPLP GLPPAPPEPP GILAPQPPDV GSSDPLSMVG PSQGRSPSYA S |
| 258 | FGF21 A72C, S79C, G108C, L142C | HPIPDSSPLL QFGGQVRQRY LYTDDAQQTE AHLEIREDGT VGGCADQSPE CLLQLKALKP GVIQILGVKT SRFLCQRPDC ALYGSLHFDP EACSFRELLL EDGYNVYQSE AHGCPLHLPG NKSPHRDPAP RGPARFLPLP GLPPAPPEPP GILAPQPPDV GSSDPLSMVG PSQGRSPSYA S |
| 259 | FGF21 R47C, P174C | HPIPDSSPLL QFGGQVRQCY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPACPEPP GILAPQPPDV GSSDPLSMVG PSQGRSPSYA S |

TABLE 7-continued

List of Sequences.

| SEQ ID NO | Description | Sequence |
|---|---|---|
| 260 | FGF21 M196C, R203C | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSCVG PSQGCSPSYA S |
| 261 | FGF21 D107C, D155C | HPIPDSSPLL QFGGQVRQRY LYTDDAQQTE AHLEIREDGT VGGAADQSPE SLLQLKALKP GVIQILGVKT SRFLCQRPCG ALYGSLHFDP EACSFRELLL EDGYNVYQSE AHGLPLHLPG NKSPHRCPAP RGPARFLPLP GLPPAPPEPP GILAPQPPDV GSSDPLSMVG PSQGRSPSYA S |
| 262 | FGF21 Q55C, G148C | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLPC NKSPHRDPAP RGPARFLPLP GLPPAPPEPP GILAPQPPDV GSSDPLSMVG PSQGRSPSYA S |
| 263 | FGF21 Q55C, G148C, N149-R159 deleted and replaced by GSGS (SEQ ID NO: 161) | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLPC GSGSGPARFL PLPGLPPAPP EPPGILAPQP PDVGSSDPLS MVGPSQGRSP SYAS |
| 264 | FGF21 Q55C, G148C, N149-R159 deleted and replaced by GGSGGS (SEQ ID NO: 162) | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLPC GGSGGSGPAR FLPLPGLPPA PPEPPGILAP QPPDVGSSDP LSMVGPSQGR SPSYAS |
| 265 | FGF21 Q55G, Q56C, L146C | HPIPDSSPLL QFGGQVRQRY LYTDDAGCTE AHLEIREDGT VGGAADQSPE SLLQLKALKP GVIQILGVKT SRFLCQRPDG ALYGSLHFDP EACSFRELLL EDGYNVYQSE AHGLPLHCPG NKSPHRDPAP RGPARFLPLP GLPPAPPEPP GILAPQPPDV GSSDPLSMVG PSQGRSPSYA S |
| 266 | FGF21 Q55G, Q56C, L146C, P147-R159 deleted and replaced by GSGS (SEQ ID NO: 161) | HPIPDSSPLL QFGGQVRQRY LYTDDAGCTE AHLEIREDGT VGGAADQSPE SLLQLKALKP GVIQILGVKT SRFLCQRPDG ALYGSLHFDP EACSFRELLL EDGYNVYQSE AHGLPLHCGS GSGPARFLPL PGLPPAPPEP PGILAPQPPD VGSSDPLSMV GPSQGRSPSY AS |
| 267 | FGF21 Q55G, Q56C, L146C, P147-R159 deleted and replaced by GGSGGS (SEQ ID NO: 162) | HPIPDSSPLL QFGGQVRQRY LYTDDAGCTE AHLEIREDGT VGGAADQSPE SLLQLKALKP GVIQILGVKT SRFLCQRPDG ALYGSLHFDP EACSFRELLL EDGYNVYQSE AHGLPLHCGG SGGSGPARFL PLPGLPPAPP EPPGILAPQP PDVGSSDPLS MVGPSQGRSP SYAS |
| 268 | FGF21 Q55C, P147C | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLCG NKSPHRDPAP RGPARFLPLP GLPPAPPEPP GILAPQPPDV GSSDPLSMVG PSQGRSPSYA S |
| 269 | FGF21 Q55C, N149C | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPLHLPG CKSPHRDPAP RGPARFLPLP GLPPAPPEPP GILAPQPPDV GSSDPLSMVG PSQGRSPSYA S |
| 270 | FGF21 E62C, E78C | HPIPDSSPLL QFGGQVRQRY LYTDDAQQTE AHLCIREDGT VGGAADQSPC SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 271 | FGF21 E62C, S79C | HPIPDSSPLL QFGGQVRQRY LYTDDAQQTE AHLCIREDGT VGGAADQSPE CLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |

TABLE 7-continued

List of Sequences.

| SEQ ID NO | Description | Sequence |
|---|---|---|
| 272 | FGF21 R100C, L114C | HPIPDSSPLL QFGGQVRQRY LYTDDAQQTE AHLEIREDGT VGGAADQSPE SLLQLKALKP GVIQILGVKT SCFLCQRPDG ALYGSCHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 273 | FGF21 L102C, G112C | HPIPDSSPLL QFGGQVRQRY LYTDDAQQTE AHLEIREDGT VGGAADQSPE SLLQLKALKP GVIQILGVKT SRFCCQRPDG ALYCSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 274 | FGF21 A59C, A73C | HPIPDSSPLL QFGGQVRQRY LYTDDAQQTE CHLEIREDGT VGGACDQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 275 | FGF21 E62C, A72C | HPIPDSSPLL QFGGQVRQRY LYTDDAQQTE AHLCIREDGT VGGCADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 276 | FGF21 Q104C, S137C | HPIPDSSPLL QFGGQVRQRY LYTDDAQQTE AHLEIREDGT VGGAADQSPE SLLQLKALKP GVIQILGVKT SRFLCCRPDG ALYGSLHFDP EACSFRELLL EDGYNVYQCE AHGLPLHLPG NKSPHRDPAP RGPARFLPLP GLPPAPPEPP GILAPQPPDV GSSDPLSMVG PSQGRSPSYA S |
| 277 | FGF21 Q104C, H140C | HPIPDSSPLL QFGGQVRQRY LYTDDAQQTE AHLEIREDGT VGGAADQSPE SLLQLKALKP GVIQILGVKT SRFLCCRPDG ALYGSLHFDP EACSFRELLL EDGYNVYQSE ACGLPLHLPG NKSPHRDPAP RGPARFLPLP GLPPAPPEPP GILAPQPPDV GSSDPLSMVG PSQGRSPSYA S |
| 278 | FGF21 A54C, P161C | HPIPDSSPLL QFGGQVRQRY LYTDDCQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGCARFLPLP GLPPAPPEPP GILAPQPPDV GSSDPLSMVG PSQGRSPSYA S |
| 279 | FGF21 Q56C, L146C | HPIPDSSPLL QFGGQVRQRY LYTDDACQTE AHLEIREDGT VGGAADQSPE SLLQLKALKP GVIQILGVKT SRFLCQRPDG ALYGSLHFDP EACSFRELLL EDGYNVYQSE AHGLPCHLPG NKSPHRDPAP RGPARFLPLP GLPPAPPEPP GILAPQPPDV GSSDPLSMVG PSQGRSPSYA S |
| 280 | FGF21 I63C, T98C | HPIPDSSPLL QFGGQVRQRY LYTDDAQQTE AHLECREDGT VGGAADQSPE SLLQLKALKP GVIQILGVKC SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 281 | FGF21 G67C, R100C | HPIPDSSPLL QFGGQVRQRY LYTDDAQQTE AHLEIREDCT VGGAADQSPE SLLQLKALKP GVIQILGVKT SCFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 282 | FGF21 V69C, L110C | HPIPDSSPLL QFGGQVRQRY LYTDDAQQTE AHLEIREDGT CGGAADQSPE SLLQLKALKP GVIQILGVKT SRFLCQRPDG ACYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 283 | FGF21 A120C, A139C | HPIPDSSPLL QFGGQVRQRY LYTDDAQQTE AHLEIREDGT VGGAADQSPE SLLQLKALKP GVIQILGVKT SRFLCQRPDG ALYGSLHFDP ECCSFRELLL EDGYNVYQSE CHGLPLHLPG NKSPHRDPAP RGPARFLPLP GLPPAPPEPP GILAPQPPDV GSSDPLSMVG PSQGRSPSYA S |
| 284 | FGF21 R124C, Q136C | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFCELLL EDGYNVYCSE AHGLPLHLPG NKSPHRDPAP RGPARFLPLP GLPPAPPEPP GILAPQPPDV GSSDPLSMVG PSQGRSPSYA S |
| 285 | FGF21 P143C, A162C | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLCLHLPG NKSPHRDPAP RGPCRFLPLP GLPPAPPEPP |

TABLE 7-continued

List of Sequences.

| SEQ ID NO | Description | Sequence |
|---|---|---|
| | | GILAPQPPDV GSSDPLSMVG PSQGRSPSYA S |
| 286 | FGF21 P77C, K97C | HPIPDSSPLL QFGGQVRQRY LYTDDAQQTE AHLEIREDGT VGGAADQSCE SLLQLKALKP GVIQILGVCT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 287 | FGF21 E78C, T98C | HPIPDSSPLL QFGGQVRQRY LYTDDAQQTE AHLEIREDGT VGGAADQSPC SLLQLKALKP GVIQILGVKC SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 288 | FGF21 L80C, V96C | HPIPDSSPLL QFGGQVRQRY LYTDDAQQTE AHLEIREDGT VGGAADQSPE SCLQLKALKP GVIQILGCKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 289 | FGF21 H145C, P161C | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLCLPG NKSPHRDPAP RGCARFLPLP GLPPAPPEPP GILAPQPPDV GSSDPLSMVG PSQGRSPSYA S |
| 290 | FGF21 L81C, G95C | HPIPDSSPLL QFGGQVRQRY LYTDDAQQTE AHLEIREDGT VGGAADQSPE SLCQLKALKP GVIQILCVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 291 | FGF21 Q82C, L94C | HPIPDSSPLL QFGGQVRQRY LYTDDAQQTE AHLEIREDGT VGGAADQSPE SLLCLKALKP GVIQICGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 292 | FGF21 L83C, I91C | HPIPDSSPLL QFGGQVRQRY LYTDDAQQTE AHLEIREDGT VGGAADQSPE SLLQCKALKP GVCQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA S |
| 293 | FGF21 D155L | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRLPAP RGPARFLPLP GLPPAPPEPP GILAPQPPDV GSSDPLSMVG PSQGRSPSYA S |
| 294 | FGF21 D155K | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRKPAP RGPARFLPLP GLPPAPPEPP GILAPQPPDV GSSDPLSMVG PSQGRSPSYA S |
| 295 | FGF21 D155Y | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRYPAP RGPARFLPLP GLPPAPPEPP GILAPQPPDV GSSDPLSMVG PSQGRSPSYA S |
| 296 | FGF21 D155P | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRPPAP RGPARFLPLP GLPPAPPEPP GILAPQPPDV GSSDPLSMVG PSQGRSPSYA S |
| 297 | FGF21 D155E | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHREPAP RGPARFLPLP GLPPAPPEPP GILAPQPPDV GSSDPLSMVG PSQGRSPSYA S |
| 298 | FGF21 D155N | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL |

TABLE 7-continued

List of Sequences.

| SEQ ID NO | Description | Sequence |
|---|---|---|
| | | EDGYNVYQSE AHGLPLHLPG NKSPHRNPAP RGPARFLPLP GLPPAPPEPP GILAPQPPDV GSSDPLSMVG PSQGRSPSYA S |
| 299 | FGF21 R154Q, D155L | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHQLPAP RGPARFLPLP GLPPAPPEPP GILAPQPPDV GSSDPLSMVG PSQGRSPSYA S |
| 300 | FGF21 R154Q, D155K | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHQKPAP RGPARFLPLP GLPPAPPEPP GILAPQPPDV GSSDPLSMVG PSQGRSPSYA S |
| 301 | FGF21 H153Q, R154Q, D155N, A157V, R159K | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPQQNPVP KGPARFLPLP GLPPAPPEPP GILAPQPPDV GSSDPLSMVG PSQGRSPSYA S |
| 302 | FGF21 P152A, H153K, R154K, D155E, P156A A157S, R159Q | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSAKKEASP QGPARFLPLP GLPPAPPEPP GILAPQPPDV GSSDPLSMVG PSQGRSPSYA S |
| 303 | FGF21 H153Y, R154K, D155N, P156K, A157G | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPYKNKGP RGPARFLPLP GLPPAPPEPP GILAPQPPDV GSSDPLSMVG PSQGRSPSYA S |
| 304 | FGF21 P152-H153 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSRDPAPRG PARFLPLPGL PPAPPEPPGI LAPQPPDVGS SDPLSMVGPS QGRSPSYAS |
| 305 | FGF21 N149-R163 deleted and replaced by GSGS (SEQ ID NO: 161) | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG GSGSFLPLPG LPPAPPEPPG ILAPQPPDVG SSDPLSMVGP SQGRSPSYAS |
| 306 | FGF21 N149-A162 deleted and replaced by GSHSG (SEQ ID NO: 163) | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG GSHSGRFLPL PGLPPAPPEP PGILAPQPPD VGSSDPLSMV GPSQGRSPSY AS |
| 307 | FGF21 N149-A162 deleted and replaced by GSHSGS (SEQ ID NO: 165) | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG GSHSGSRFLP LPGLPPAPPE PPGILAPQPP DVGSSDPLSM VGPSQGRSPS YAS |
| 308 | FGF21 K150H | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NHSPHRDPAP RGPARFLPLP GLPPAPPEPP GILAPQPPDV GSSDPLSMVG PSQGRSPSYA S |
| 309 | FGF21 K150H, P152L | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NHSLHRDPAP RGPARFLPLP GLPPAPPEPP GILAPQPPDV GSSDPLSMVG PSQGRSPSYA S |
| 310 | FGF21 R163H | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPAHFLPLP GLPPAPPEPP GILAPQPPDV GSSDPLSMVG PSQGRSPSYA S |
| 311 | FGF21 P158H, R159H | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAH HGPARFLPLP GLPPAPPEPP |

TABLE 7-continued

List of Sequences.

| SEQ ID NO | Description | Sequence |
|---|---|---|
| | | GILAPQPPDV GSSDPLSMVG PSQGRSPSYA S |
| 312 | FGF21 N149-D155 deleted and replaced by GSGS (SEQ ID NO: 161) | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG GSGSPAPRGP ARFLPLPGLP PAPPEPPGIL APQPPDVGSS DPLSMVGPSQ GRSPSYAS |
| 313 | FGF21 N149-D155 deleted and replaced by GSHSG (SEQ ID NO: 163) | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG GSHSGPAPRG PARFLPLPGL PPAPPEPPGI LAPQPPDVGS SDPLSMVGPS QGRSPSYAS |
| 314 | FGF21 N149-D155 deleted and replaced by ATTS (SEQ ID NO: 164) | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG ATTSPAPRGP ARFLPLPGLP PAPPEPPGIL APQPPDVGSS DPLSMVGPSQ GRSPSYAS |
| 315 | FGF21 R159-R163 deleted and replaced by GA | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP GAFLPLPGLP PAPPEPPGIL APQPPDVGSS DPLSMVGPSQ GRSPSYAS |
| 316 | FGF21 R159-R163 deleted and replaced by GY | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP GYFLPLPGLP PAPPEPPGIL APQPPDVGSS DPLSMVGPSQ GRSPSYAS |
| 317 | FGF21 R159-R163 deleted and replaced by HH | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP HHFLPLPGLP PAPPEPPGIL APQPPDVGSS DPLSMVGPSQ GRSPSYAS |
| 318 | FGF21 R159-R163 deleted and replaced by GE | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP GEFLPLPGLP PAPPEPPGIL APQPPDVGSS DPLSMVGPSQ GRSPSYAS |
| 319 | FGF21 R159-R163 deleted and replaced by HE | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP HEFLPLPGLP PAPPEPPGIL APQPPDVGSS DPLSMVGPSQ GRSPSYAS |
| 320 | FGF21 A162Y | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPYRFLPLP GLPPAPPEPP GILAPQPPDV GSSDPLSMVG PSQGRSPSYA S |
| 321 | FGF21 R159H | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP HGPARFLPLP GLPPAPPEPP GILAPQPPDV GSSDPLSMVG PSQGRSPSYA S |
| 322 | FGF21 S200M | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PMQGRSPSYA S |
| 323 | FGF21 G202T | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQTRSPSYA S |
| 324 | FGF21 R203E | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGESPSYA S |
| 325 | FGF21 R203H | HPIPDSSPLL QFGGQVRQRY LYTDDAQQTE AHLEIREDGT VGGAADQSPE |

TABLE 7-continued

List of Sequences.

| SEQ ID NO | Description | Sequence |
|---|---|---|
| | | SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGHSPSYA S |
| 326 | FGF21 G202-R203 deleted | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQSPSYAS |
| 327 | FGF21 PLSMVGPSQG RSPSYAS (SEQ ID NO: 169) inserted after S209 | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA SPLSMVGPSQ GRSPSYAS |
| 328 | FGF21 P199 deleted, PLSMVGSQGR SPSYAS (SEQ ID NO: 170) inserted after S209 | HPIPDSSPLL QFGGQVRQRY LYTDDAQQTE AHLEIREDGT VGGAADQSPE SLLQLKALKP GVIQILGVKT SRFLCQRPDG ALYGSLHFDP EACSFRELLL EDGYNVYQSE AHGLPLHLPG NKSPHRDPAP RGPARFLPLP GLPPAPPEPP GILAPQPPDV GSSDPLSMVG PSQGRSPSYA SPLSMVGSQG RSPSYAS |

The invention claimed is:

1. A variant of human fibroblast growth factor 21 (FGF21) comprising or consisting of the amino acid sequence of SEQ ID NO: 46 or 215.

2. The variant of human FGF21 according to claim 1, fused or conjugated to a half-life extension module, wherein the half-life extension module is selected from the group consisting of a polymer, an unstructured (poly-)peptide chain, an elastin-like polypeptide (ELP), a serum protein, a serum protein binding molecule, an antibody, an immunoglobulin, an Fc region/domain of an immunoglobulin, and an immunoglobulin binding domain.

3. A fusion molecule comprising the variant of human FGF21 according to claim 1 and at least one other active pharmaceutical ingredient.

4. The fusion molecule according to claim 3, wherein the at least one other active pharmaceutical ingredient is selected from the group consisting of insulin and insulin derivatives, GLP-1, GLP-1 analogues and GLP-1 receptor agonists, polymer bound GLP-1 and GLP-1 analogues, dual GLP-1/GIP agonists, dual GLP-1/glucagon receptor agonists, PYY3-36 or analogues thereof, pancreatic polypeptide or analogues thereof, glucagon receptor agonists or antagonists, GIP receptor agonists or antagonists, DDP-IV inhibitors, SGLT-2 inhibitors, and dual SGLT-2/SGLT-1 inhibitors.

5. A pharmaceutical composition comprising the variant of human FGF21 according to claim 1 and a pharmaceutically acceptable carrier and/or excipient.

6. A variant of human fibroblast growth factor 21 (FGF21), consisting of an amino acid sequence of SEQ ID NO: 215.

* * * * *